United States Patent

Chan Chun Kong et al.

(10) Patent No.: US 6,887,877 B2
(45) Date of Patent: May 3, 2005

(54) COMPOUNDS AND METHODS FOR THE TREATMENT OR PREVENTION OF FLAVIVIRUS INFECTIONS

(75) Inventors: Laval Chan Chun Kong, Kirkland (CA); Jean Bedard, Laval (CA); Sanjoy Kumar Das, Laval (CA); Nghe Nguyen Ba, LaPrairie (CA); Oswy Z. Pereira, Kirkland (CA); Stephen Joseph Shuttleworth, San Francisco, CA (US); Mohammad Arshad Siddiqui, Cambridge, MA (US); Wuyi Wang, Ville St-Laurent, MD (US)

(73) Assignee: ViroChem Pharma Inc., Laval (CA)

( * ) Notice: Subject to any disclaimer, the term of this patent is extended or adjusted under 35 U.S.C. 154(b) by 23 days.

(21) Appl. No.: 10/166,030

(22) Filed: Jun. 11, 2002

(65) Prior Publication Data

US 2003/0229053 A1 Dec. 11, 2003

Related U.S. Application Data

(60) Provisional application No. 60/296,732, filed on Jun. 11, 2001.

(51) Int. Cl.$^7$ .............. C07D 277/28; C07D 307/81; C07C 311/29; A61K 31/44
(52) U.S. Cl. .............. 514/254.02; 514/336; 514/366; 514/570; 514/563; 514/469; 514/406; 514/562; 514/438; 514/400; 514/378; 514/375; 514/461; 514/326; 562/450; 562/430; 548/204; 548/224; 548/247; 548/248; 548/335.5; 548/338.1; 548/370.1; 546/209; 546/281.4; 549/77; 549/469; 549/493; 544/369
(58) Field of Search .................. 549/469, 77, 493; 548/335.5, 204, 370.1, 338.1, 248, 224; 562/575, 406, 450, 430; 514/469, 365, 568, 336, 570, 563, 562, 438, 400, 378, 375, 461, 254.02, 326; 546/281.4, 209; 544/247, 369

(56) References Cited

U.S. PATENT DOCUMENTS

| 5,977,075 A | 11/1999 | Ksander et al. .............. 514/19 |
| 6,174,877 B1 | 1/2001 | Ishibashi et al. ....... 514/210.04 |

FOREIGN PATENT DOCUMENTS

| CA | 2305499 | 9/1998 |
| JP | 3-127732 | 5/1991 |
| JP | 7-48360 | 2/1995 |
| JP | 7-48360 | 6/1995 |
| JP | 2000-159610 | 6/2000 |
| RU | 2 130 023 | 5/1999 |
| WO | WO 91/12002 | 8/1991 |
| WO | WO 95/12611 | 5/1995 |
| WO | WO 96/38419 | 12/1996 |
| WO | WO 98/03166 | 1/1998 |
| WO | WO 00/03743 | 1/2000 |
| WO | WO 00/15213 | 3/2000 |
| WO | WO 00/37436 | 6/2000 |
| WO | WO 01/20995 | * 3/2001 |
| WO | WO 01-20995 | 3/2001 |

OTHER PUBLICATIONS

Douglas, Jr., Introduction to Viral Diseases, Cecil Textbook of Medicine, 20$^{th}$ Edition, vol. 2, pp. 1739–1747, 1996.*
DeFonseca et al., PubMed Abstract (Curr Opin Pediatr. 14(1):67–71), Feb. 2002.*
Sehgal et al., PubMed Abstract (Indian J. Pathol. Microbiol. 45(1):123–8), Jan. 2002.*
Fabrizi et al., PubMed Abstract (Perit Dial Int. 22(3):405–10), May 2002.*
Lindsay, PubMed Abstract (Hepatology 36(5 Suppl 1):S114–20), Nov. 2002.*
Scozzafava et al., CAPLUS Abstract 132:344757, 2000.*
Supuran et al., CAPLUS Abstract 133:177439, 2000.*
Budesinsky et al., CAPLUS Abstract 54:6563f–i, 6564a–g, 1960.*
Anette Svenson, et al., "Preparation of Fluornated Linkers: Use of $^{19}$F NMR Spectroscopy to Establish Conditions for Solid Phase Synthesis of Pilicide Libraries", *J. Comb. Chem.* 2000, vol. 2, pp. 736–748.
Gregory T Bourne et al., "A Backbone Linker for BOC-Based Peptide Synthesis and On–Resin Cyclization: Synthesis of Stylostatin 1", *J. Org. Chem. 1999*, vol. 64, pp. 3095–3101.
Carceller et al. "Novel Azo Derivatives as Prodrugs of 5–Aminosalicyclic Acid and Amino Derivatives with Potent Platelet Activating Factor Antagonist Activity", Journal of Medicinal Chemistry, 2001, vol. 44, No. 18., pp. 3001–3013.
F. Dasgupta et al., "Peptoids as Endothelin Receptor Antagonists", Bioorganic & Medicinal Chemistry Letters 11 (2001) pp. 555–557.
J. Piró et al., "Solid Phase Synthesis of Enantiomerically pure Polyhydroxyvalerolactams", Tetrahedron Letters 42 (5) (2001) pp. 871–873.

(Continued)

Primary Examiner—Deepak Rao
(74) Attorney, Agent, or Firm—Millen, White, Zelano, Branigan, P.C.

(57) ABSTRACT

The present invention provides novel compounds represented by formula I:

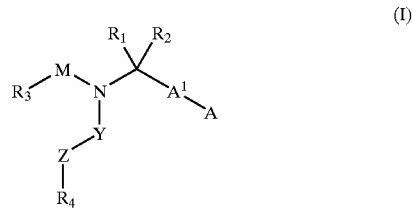

or pharmaceutically acceptable salts thereof useful for treating Flaviviridae viral infection.

96 Claims, No Drawings

OTHER PUBLICATIONS

A. Svensson, "Preparation of Fluorinated Linkers: Use of $^{19}$F NMR Spectroscopy to Establish Conditions for Solid-Phase Synthesis of Pilicide Libraries", Journal of Combinatorial Chemistry, 2000, vol. 2, No. 6, pp. 736–748.

Lin et al., "Utilization of Fukuyama's Sulfonamide Protecting Group for the Synthesis of N–substituted α–amino acids and Derivatives", Tetrahedron Letters 41 (18) (2000) pp. 3309–3313.

Turner et al., "Mitsunobu Glycosylation of Nitrobenzenesulfonamides: Novel Route to Amadon Rearrangement Products", Tetrahedron Letters 40 (38) (1999) pp. 7039–7042.

Caldarelli et al., "Synthesis of an Array of Potential Matrix Metalloproteinase Inhibitors using a Sequence of Polymer-Supported Reagents", Bioorganic & Medicinal Chemistry Letters 9 (14) (1999) pp. 2049–2052.

Donde et al., "High Enantioselection in the Rearrangement of Allylic Imidates with Ferrocenyl Oxaoline Catalysts", J. American Chemical Society, 1999, vol. 121, No. 12, pp. 2933–2934.

Wilson et al., "A Facile Rearrangement of N–Alkyl, N–(0 or p–NitrophenylSulfonamide)–α–Amino Esters", Tetrahedron Letters 55 (6) (1999) pp. 1647–1656.

Kawase et al., "A General Method for the Preparation of 5–Trifluoromethylated Oxazoles from α–Amino Acids", Chemical Pharmaceutical Bulletin 46(5) (May, 1998) pp. 749–756.

Reichwein et al., "Site–Specific N–Alkylation of Peptides on the Solid Phase", Tetrahedron Letters 39 (10) (1998) pp. 1243–1246.

Fukuyama et al., "2,4–Dinitrobenzenesulfonamides: A Simple and Practical Method for the Preparation of a Variety of Secondary Amines and Diamines", Tetrahedron Letters, vol. 38, No. 33, pp. 5831–5834 (1997).

Masami Kawase, "A Facile One–Pot Synthesis of 5–Trifluoromethyl– and 5–Perfluoroalkyloxazoles from N–Alkyl-l–N–Acylamino Acids", Heterocycles, vol. 36, No. 11, pp. 2441–2444, (1993).

Naito et al., "A New Synthesis of 2–amino–γ–Lactones Involving Photochemical Addition Reaction of Alcohols to Enamide", Heterocycles, vol. 27, No. 6, pp. 1325–1327 (1988).

Gellert et al., "Stereospecific Synthesis of Hexahydrobenzopyrroloisoquinoline and Tetrahydrobenzisoquinoline Derivatives", American Journal Chemistry, 1984, vol. 37, pp. 819–829.

Yoshioka et al., "Synthesis of Oxazolylindole Alkaloids from Tryptamine and Tryptophan by Oxidation with 2,3–Dichioro–5,6–dicyanobenzoquinone", J. Chemical Research (S), 1981, pp. 194–195.

Hitchings et al., "Degradation of the Herbicide Flampropisopropyl in Soil under Laboratory Conditions", Society of Chemical Industry, (1979) vol. 10, pp. 1–13.

Aida El Azzouny et al., "Zur Synthesis Acyclischer und Cyclischer Anthranilsäure–Phenylalanin–Peptide", Pharmazie 32, H. 6 (1977), pp. 318–323.

Bourne et al., A Backbone Linker for BOC–Based Peptide Synthesis and On–Resin Cyclization: Synthesis of Stylostatin, J. Org. Chem., 64(9), pp.: 3095–3101 (1999).

Dankwardt et al., "Solid–Phase Synthesis of N–alkyl Sulfonamides", Synlett, (1997) (7), pp. 854–856.

Xiao et al., "Diastereoselective Synthesis of Drugs: Preparation of (S,S)–2hydroxy–3–amino–4–phenylbutyric Acid", Huaxue Shijii, (1996), 18(6), pp. 324–326, 336.

Ru et al., "Diastereoselective Synthesid of (2S, 3S)–3–amino–2hydroxy–4–phenylbutyic acid: Core Unit of HIV Protease Inhibitors", Zhongguo Yigao, Gongye Zahi, (1994), 25(12), pp. 557–559.

\* cited by examiner

COMPOUNDS AND METHODS FOR THE TREATMENT OR PREVENTION OF FLAVIVIRUS INFECTIONS

This application claims the benefit of priority of U.S. Provisional Application No. 60/296,732 filed Jun. 11, 2001.

FIELD OF THE INVENTION

The present invention relates to biaryl compounds and a method for the treatment or prevention of Flavivirus infections using biaryl compounds.

BACKGROUND OF THE INVENTION

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50–60 nm. The HCV genome is a single-stranded, positive-sense RNA of about 9,600 bp coding for a polyprotein of 3009–3030 amino-acids, which is cleaved co and post-translationally by cellular and two viral proteinases into mature viral proteins (core, E1, E2, p7, NS2, NS3, NS4A, NS4B, NS5A, NS5B). It is believed that the structural proteins, E1 and E2, the major glycoproteins are embedded into a viral lipid envelope and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

The only treatment currently available for HCV infection is interferon-α (IFN-α). However, according to different clinical studies, only 70% of treated patients normalize alanine aminotransferase (ALT) levels in the serum and after discontinuation of IFN, 35% to 45% of these responders relapse. In general, only 20% to 25% of patients have long-term responses to IFN. Clinical studies have shown that combination treatment with IFN and ribavirin (RIBA) results in a superior clinical response than IFN alone. Different genotypes of HCV respond differently to IFN therapy, genotype 1b is more resistant to IFN therapy than type 2 and 3.

There is therefore a great need for the development of anti-viral agents.

SUMMARY OF THE INVENTION

The present invention provides compound of formula I:

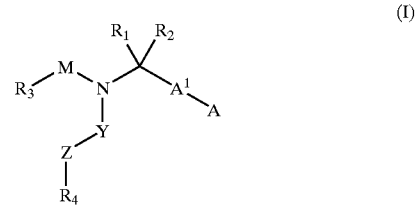

(I)

and pharmaceutically acceptable salts thereof,
wherein,
M is chosen from:

(II)

(III)

(IV)

(V)

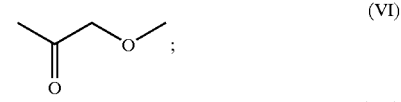

(VI)

(VII)

(VIII)

a bond;

(IX)

wherein each $R_6$ is independently chosen from H or $C_{1-6}$ alkyl;
$A^1$ is chosen from a bond, $C_{1-6}$ alkyl, $C_{2-6}$ alkenyl or $C_{2-6}$ alkynyl;
A is chosen from $COOR_5$, $CO-COOR_5$, $PO_3R_5R_5$, $SO_3R_5$, tetrazole, $CON(R_5)CH(R_5)-COOR_5$, $CONR_5R_5$, $CONR_5OH$, wherein
each $R_5$ is independently chosen from H or $C_{1-6}$ alkyl;
$R_1$, $R_2$ are independently chosen from H, $C_{1-6}$ alkyl, $C_{6-12}$ aryl, $C_{3-10}$ heterocycle, $C_{6-12}$ aralkyl or $C_{3-10}$ heteroaralkyl;
$R_3$ is chosen from $C_{6-12}$ aryl, $C_{3-10}$ heterocycle, $C_{6-12}$ aralkyl or $C_{3-10}$ heteroaralkyl;
Y is chosen from:

(X)

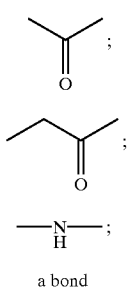

(XI)

(XII)

(XIII)

(XIV) a bond

Z is chosen from $C_{1-6}$ alkyl, $C_{2-6}$ alkenyl, $C_{2-6}$ alkynyl, $C_{6-14}$ aryl, $C_{3-10}$ heterocycle;

$R_4$ is chosen from H, halogen, CN, $NO_2$, $C_{1-6}$ alkyl, $C_{6-12}$ aryl, $C_{3-10}$ heterocycle $C_{6-12}$ aralkyl $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, $COR_7$, wherein each $R_5$ is independently chosen from H or $C_{1-6}$ alkyl, and $R_7$ is chosen from $C_{6-12}$ aryl or $C_{3-10}$ heterocycle;

with the proviso that compound of formula (I) is other than 3-[3-(2,6-Dichloro-pyridin-4-yl)-1-(4-thiophen-2-yl-benzyl)-ureido]-3-thiophen-2-yl-propionic acid; compound #1.

The compounds of the present invention are useful in therapy, particularly as antivirals.

In another aspect, there is provided a method of treating viral infections in a subject in need of such treatment comprising administering to the subject a therapeutically effective amount of a compound of formula (I) or composition of the invention.

In still another aspect, there there is provided a method of treating viral infections in a subject in need of such treatment comprising administering to the subject a combination comprising at least one compound of formula (I) and at least one further therapeutic agent.

In another aspect, there is provided a pharmaceutical formulation comprising the compound of the invention in combination with a pharmaceutically acceptable carrier or excipient.

In another aspect of the invention is the use of a compound according to formula (I), for the manufacture of a medicament for the treatment of viral infections.

DETAILED DESCRIPTION OF THE INVENTION

In one embodiment, compounds of the present invention comprise those wherein the following embodiments are present, either independently or in combination.

In a further embodiment, M is (II)

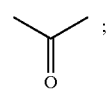

In an alternative embodiment, M is (III)

In a further embodiment, M is (VI)

In a further embodiment, M is

—$CH_2$—

In a further embodiment, M is a bond.

In a further embodiment, A is chosen from COOH or $COOCH_2CH_3$.

In a further embodiment, A is COOH.

In a further embodiment, A is $COOCH_2CH_3$.

In a further embodiment, $A^1$ is chosen from —$CH_2$, C=CH, CH—$CH_2$ or a bond.

In a further embodiment, $A^1$ is a bond.

In a further embodiment, $A^1$ is $CH_2$.

In a further embodiment, $R_2$ is H or methyl.

In a further embodiment, $R_2$ is H.

In a further embodiment, $R_2$ is methyl.

In one embodiment, $R_1$ is chosen from benzyl, thiophene, $CH_2$-thiophene, methyl, $CH_2$-imidazole, $CH_2$-cyclohexyl which can be unsubstituted or substituted by at least one substituent chosen from halogen, OH or benzyl.

In one embodiment, $R_1$ is benzyl substituted with OH.

In one embodiment, $R_1$ is benzyl substituted with Br.

In one embodiment, $R_1$ is $CH_2$-thiophene substituted with Br.

In one embodiment, $R_1$ is $CH_2$-cyclohexyl substituted with benzyl.

In a further embodiment, $R_3$ is chosen from a $C_{6-12}$ aryl or $C_{3-10}$ heterocycle.

In a further embodiment, $R_3$ is chosen from:

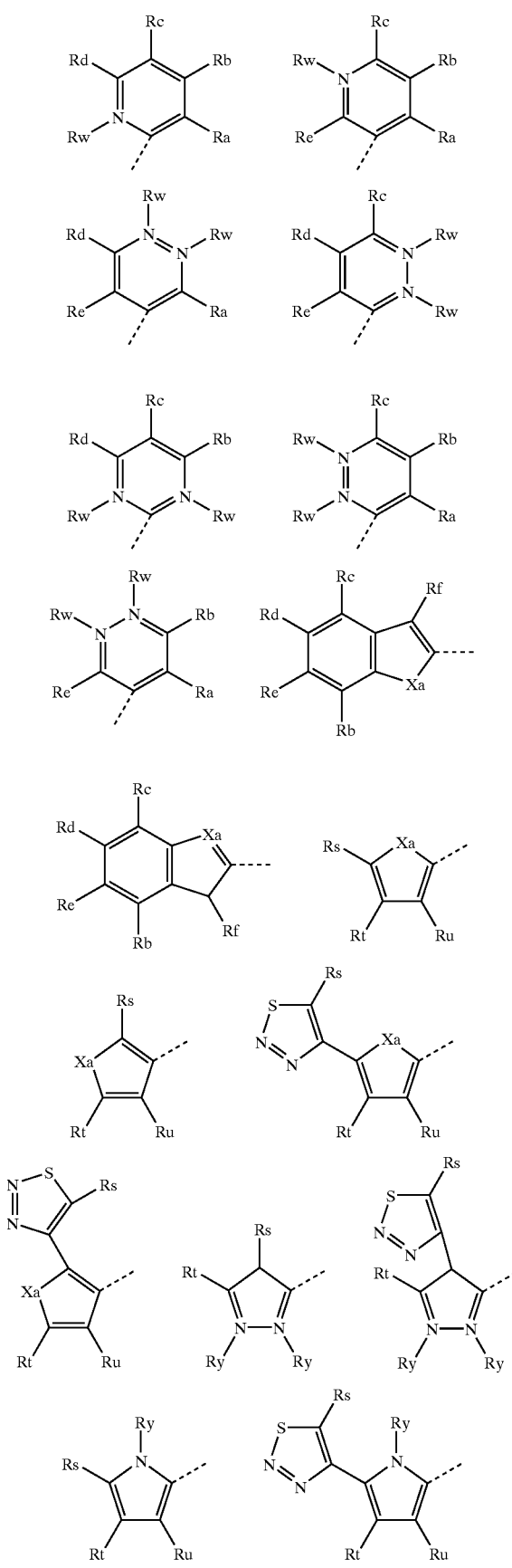

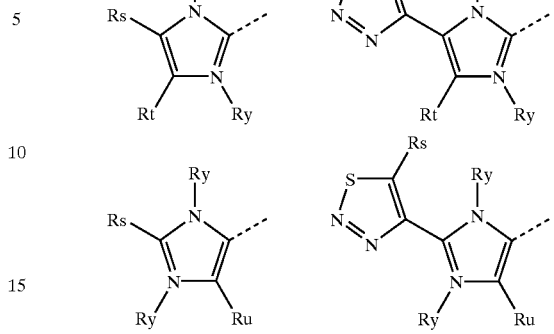

wherein:
Rw is H or methyl;
Ry is H or methyl;
Rw is H;
Rw is methyl;
Ry is H;
Ry is methyl;
And wherein, Xa is S, N, O or C.

In a further embodiment, each of Ra, Rb, Rc, Rd, Re, and Rf are independently chosen from, H, Cl, Br, I, F, $C_{1-6}$ alkyl, $C_{2-6}$ alkenyl, $OC_{1-6}$ alkyl, $CF_3$, COOH, OH, $COOC_{1-6}$ alkyl, CN, $NH_2$, $NO_2$, $NH(C_{1-6}$ alkyl), $N(C_{1-6}$ alkyl$)_2$.

In a further embodiment, each of Ra, Rb, Rc, Rd, Re, and Rf are independently chosen from, H, Cl, Br, I, F, methyl, O-methyl, vinyl, $CF_3$, COOH, $COOCH_3$, OH, CN, $NH_2$, $NO_2$, $NH(CH_3)$ or $N(CH_3)_2$.

In a further embodiment, each of Ra, Rb, Rc, Rd, Re, and Rf are independently chosen from, H, Cl, Br, I, F, methyl, O-methyl, $CF_3$, COOH, $COOCH_3$, OH, CN, $NH_2$, or $NO_2$.

In a further embodiment, each of Ra, Rb, Rc, Rd, Re, and Rf are independently chosen from, H, Cl, methyl, O-methyl, $CF_3$, COOH, $COOCH_3$, ON, $NH_2$, or $NO_2$.

In a further embodiment, each of Ra, Rb, Rc, Rd, Re, and Rf are independently chosen from, H, Cl, F, methyl, OH, $CF_3$ or O-methyl.

In one embodiment, Rf is H or methyl.
In another embodiment, Rf is H.
In another embodiment, Rf is methyl.
In a further embodiment, each of Ra, Rb, Rc, Rd and Re is independently chosen from, H or Cl.
In a further embodiment, each of Ra, Rb, Rc, Rd and Re is H.

In one embodiment:
Ra is chosen from Cl, F, methyl or O-methyl;
Rb is H;
Rc is chosen from Cl, F, methyl or O-methyl;
Rd is H;
Re is H.

In one embodiment:
Ra is Cl;
Rb is H;
Rc is Cl;
Rd is H;
Re is H.

In one embodiment:
Ra is methyl;
Rb is methyl;

Rc is O-methyl;
Rd is H;
Re is methyl.

In a further embodiment, each of Rs, Rt, Ru, are independently chosen from, H, Cl, Br, I, F, $C_{1-6}$ alkyl, $OC_{1-6}$ alkyl, $CF_3$, COOH, $COOC_{1-6}$ alkyl, CN, $NH_2$, $NO_2$, $NH(C_{1-6}$ alkyl), $N(C_{1-6}$ alkyl)$_2$.

In a further embodiment, each of Rs, Rt, Ru, are independently chosen from, H, Cl, Br, I, F, methyl, O-methyl, $CF_3$, COOH, $COOCH_3$, CN, $NH_2$, $NO_2$, $NH(CH_3)$ or $N(CH_3)_2$.

In a further embodiment, each of Rs, Rt, Ru, are independently chosen from, H, Cl, Br, I, F, methyl, O-methyl, $CF_3$, COOH, $COOCH_3$, CN, $NH_2$, or $NO_2$.

In a further embodiment, each of Rs, Rt, Ru, are independently chosen from, H, Cl, methyl, O-methyl, $CF_3$, COOH, $COOCH_3$, CN, $NH_2$, or $NO_2$.

In a further embodiment, each of Rs, Rt, Ru, are independently chosen from, H, Cl, F, methyl, $CF_3$ or O-methyl.

In a further embodiment, each of Rs, Rt, Ru, are independently chosen from, H or Cl.

In a further embodiment, each of Rs, Rt, Ru, are H.

In one embodiment:
Rs and Ru are Cl and Rt is H.
Rs is Cl, Rt and Ru are H.

In a further embodiment, Y is chosen from a bond, $—CH_2—$, CO or $—CH_3CH_2COO—$.

In a further embodiment, Y is a bond.
In a further embodiment, Y is $—CH_2$.
In a further embodiment, Y is $—CH_2CH_2COO—$.
In a further embodiment, Y is CO.

In one embodiment, Z is phenyl unsubstituted or substituted by at least one substituent chosen from halogen, $C_{3-10}$ heterocycle, $C_{3-10}$ heterocycle-$COOCH_3$, $NO_2$, CN, $CO—C_{6-12}$ aralkyl, $COOC_{1-6}$ alkyl, $C_{1-6}$ alkyl, $O—C_{1-6}$ alkyl, $C_{6-12}$ aryl, $O—C_{6-12}$ aryl, $C_{6-12}$ aralkyl, $O—C_{6-12}$ aralkyl.

In another embodiment, Z is phenyl unsubstituted or substituted by at least one substituent chosen from Br, I, F, Cl, thiophene, thiazole, benzofuran, benzooaxazole, furan-$COOCH_3$, thiophene-$COOCH_3$, $NO_2$, CN-phenyl, chlorobenzoyl, difluoro-benzoyl, CO-methyl-isoxazole substituted with chlorophenyl, dichloro-benzoyl, $CH_3$, $CF_3CH_2$, $SO_2CH_3$, $OCH_3$, $OCH_2$-fluoro-phenyl, O-chloro-phenyl, $OCH_2$-phenyl, benzyloxi.

In one embodiment, Z is furan unsubstituted or substituted by at least one substituent chosen from halogen, $C_{6-12}$ aryl, $C_{3-10}$ heterocycle.

In another embodiment, Z is furan unsubstituted or substituted by at least one substituent chosen from Br, Cl-phenyl, $CF_3CH_2$-phenyl, Br-phenyl, Cl-phenyl-$CH_2CF_3$, $NO_2$-phenyl, Cl-phenyl-Cl, Cl-phenyl-F, ethyl benzoate, benzoic acid, F-phenyl-F, tolyl, F-phenyl, benzofuran, thiazole, Cl-thiophene, methoxy-furan, pyridine.

In one embodiment, Z is thiophene unsubstituted or substituted by at least one substituent chosen from halogen, $C_{6-12}$ aryl, $C_{3-10}$ heterocycle, nitro.

In another embodiment, Z is thiophene unsubstituted or substituted by at least one substituent chosen from Br, benzoic acid, ethyl benzoate, methyl benzoate, Cl-phenyl-Cl, Cl-phenyl-F, F-phenyl-F, F-phenyl, methoxy phenyl, tolyl, CN-phenyl, methyloxi-phenyl, trifluoromethyloxi-phenyl, trifluoromethyl-phenyl, $S—CH_3$-phenyl, benzofuran, thiazole, thiphene, Cl-thiophene, pyridine, pyridinyl, $NO_2$.

In one embodiment, Z is thiazole unsubstituted or substituted by at least one substituent chosen from halogen, $C_{1-6}$ alkyl, $NR_5R_5$, $C_{3-10}$ heterocycle.

In another embodiment, Z is thiazole unsubstituted or substituted by at least one substituent chosen from Cl, $CF_3CH_2$, diethylamino, piperidine, piperazine-phenyl, piperazine-benzyl.

In another embodiment, Z is a $C_{6-12}$ aryl chosen from naphthalene, anthraquinonyl.

In another embodiment, Z is a $C_{3-10}$ heterocycle chosen from benzofuran, pyrazole, methyl oxazole, pyrrolidine, piperidine, pyridine, pyrrole, quinolinyl unsubstituted or substituted by at least one substituent chosen from chlorophenyl-ketone, dichlorophenoxy, chlorophenoxy, dichlorophenyl, COO-t-butyl, tolyl-sulfonyl, COO-benzyl, $CF_3$.

In another embodiment, Z is chosen from $C_{1-6}$ alkyl, $C_{2-6}$ alkenyl, $C_{2-6}$ alkynyl chosen from vinyl, allyl, methyl, propyl, propynyl, thiazole unsubstituted or substituted by at least one substituent chosen from benzofuran.

In one embodiment, the viral infection is chosen from Flavivirus infections.

In one embodiment, the Flavivirus infection is chosen from Hepatitis C virus (HCV), bovine viral diarrhea virus (BVDV), hog cholera virus and yellow fever virus.

In one embodiment, the Flavivirus infection is Hepatitis C virus (HCV).

In further embodiments, the present invention provides;

A method for treating or preventing a Flaviridae viral infection in a host comprising administering to the host a therapeutically effective amount of at least one compound according to formula (I).

A method for treating or preventing a Flaviridae viral infection in a host comprising administering to the host a therapeutically effective amount of at least one compound according to formula (XV):

A method for treating or preventing Flaviridae infection in a host comprising administering to the host a therapeutically effective amount of at least one compound according to formula (I) and at least one further antiviral agent.

A method for treating or preventing Flaviridae infection in a host comprising administering to the host a therapeutically effective amount of at least one compound according to formula (XV) and at least one further antiviral agent.

In one embodiment, the antiviral agent is chosen from a viral serine protease inhibitor, viral polymerase inhibitor and viral helicase inhibitor.

In one embodiment, the antiviral agent is chosen from interferon α and ribavirin.

In one embodiment, said compound of formulae (I) or (XV) and said antiviral agent are administered sequentially.

In a further embodiment, said compound of formulae (I) or (XV) and said antiviral agent are administered simultaneously.

In further embodiments, the present invention provides a method for treating or preventing a Flaviridae viral infection in a host comprising administering to the host a therapeutically effective amount of at least one compound according to formula (I) further comprising at least one additional agent chosen from immunomudulating agent, antioxydant agent, antibacterial agent or antisense agent.

In one embodiment, the additional agent is chosen from silybum marianum, interleukine-12, amantadine, ribozyme, thymosin, N-acetyl cysteine or cyclosporin.

In a further embodiment, the additionnal agent are administered sequentially.

In still a further embodiment, said compound and said additionnal agent are administered simultaneously.

In a further embodiment, the Flaviviridae infection is hepatitis C (HCV).

In further embodiments, the present invention provides;

A pharmaceutical composition for treating or preventing a Flaviviridae viral infection comprising administering at least one compound according to formula (I), together with at least one pharmaceutically acceptable carrier or excipient.

A pharmaceutical composition, further comprising one or more additional agent chosen from antiviral agent, immunomudulating agent, antioxydant agent, antibacterial agent or antisense agent.

In one embodiment, the antiviral agent is chosen from a viral serine protease inhibitor, viral polymerase inhibitor and viral helicase inhibitor.

In one embodiment, the antiviral agent is chosen from interferon α and ribavirin.

In one embodiment, the additional agent is chosen from silybum marianum, interleukine-12, amantadine, ribozyme, thymosin, N-acetyl cysteine or cyclosporin.

In one embodiment, the Flaviviridae viral infection is hepatitis C viral infection (HCV).

In one embodiment, the present invention provides the use of a compound according to formula (I) for the manufacture of a medicament for treating or preventing a viral Flaviviridae infection in a host.

In one embodiment, the Flaviviridae infection is hepatitis C viral infection (HCV).

In one embodiment, the invention provides the use of a compound according to formula (I) for use in therapy.

In one embodiment, the present invention provides the use of a compound according to formula (I) for treating or preventing Flaviviridae viral infection in a host.

In one embodiment, the invention provides the use of a compound according to formula (I) for treating or preventing Flaviviridae viral infection in a host, further comprising one or more additional agent chosen from antiviral agent, immunomudulating agent, antioxydant agent, antibacterial agent or antisense agent.

In one embodiment the antiviral agent is chosen from a viral serine protease inhibitor, viral polymerase inhibitor and viral helicase inhibitor.

In a further embodiment, the antiviral agent is chosen from interferon α and ribavirin.

In a further embodiment, the additional agent is chosen from silybum marianum, interleukine-12, amantadine, ribozyme, thymosin, N-acetyl cysteine or cyclosporin.

In still a further embodiment, the compound of formula (I) and said additionnal agent are administered sequentially.

In still a further embodiment, the compound of formula (I) and said additionnal agent are administered simultaneously.

In a further embodiment, the Flaviviridae viral infection is hepatitis C viral infection (HCV).

In one embodiment, there is provided a method for inhibiting or reducing the activity of viral polymerase in a host comprising administering a therapeutically effective amount of a compound having the formula (I):

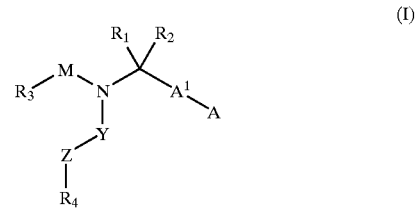
(I)

and pharmaceutically acceptable salts thereof, wherein,

M is chosen from:

(II)

(III)

(IV)

(V)

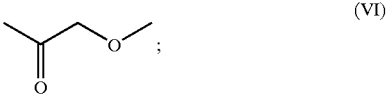
(VI)

(VII)

(VIII)

a bond;
(IX)

wherein each $R_6$ is independently chosen from H or $C_{1-6}$ alkyl;

$A^1$ is chosen from a bond, $C_{1-6}$ alkyl, $C_{2-6}$ alkenyl or $C_{2-6}$ alkynyl;

A is chosen from $COOR_5$, $CO$—$COOR_5$, $PO_3R_5R_5$, $SO_3R_5$, tetrazole, $CON(R_5)CH(R_5)$—$COOR_5$, $CONR_5R_5$, $CONR_5OH$, wherein each $R_5$ is independently chosen from H or $C_{1-6}$ alkyl;

$R_1$, $R_2$ are independently chosen from H, $C_{1-6}$ alkyl, $C_{6-12}$ aryl, $C_{3-10}$ heterocycle, $C_{6-12}$ aralkyl or $C_{3-10}$ heteroaralkyl;

$R_3$ is chosen from $C_{6-12}$ aryl, $C_{3-10}$ heterocycle, $C_{6-12}$ aralkyl or $C_{3-10}$ heteroaralkyl;

Y is selected from the group consisting of:

(X)

-continued

 (XI)

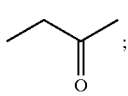 (XII)

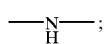 (XIII)

a bond (XIV)

Z is chosen from C$_{1-6}$ alkyl, C$_{2-6}$ alkenyl, C$_{2-6}$ alkynyl, C$_{6-14}$ aryl, C$_{3-10}$ heterocycle;

R$_4$ is chosen from H, halogen, CN, NO$_2$, C$_{1-6}$ alkyl, C$_{6-12}$ aryl, C$_{3-10}$ heterocycle, C$_{6-12}$ aralkyl, C$_{3-10}$ heteroaralkyl, NR$_5$R$_5$, SO$_2$CH$_3$, O—C$_{1-6}$ alkyl, O—C$_{6-12}$ aryl, O—C$_{6-12}$ aralkyl, COR$_7$, wherein each R$_5$ is independently chosen from H or C$_{1-6}$ alkyl, and R$_7$ is chosen from C$_{6-12}$ aryl or C$_{3-10}$ heterocycle.

In one embodiment, there is provided a method for inhibiting or reducing the activity of viral polymerase in a host comprising administering a therapeutically effective amount of a compound having the formula (XV):

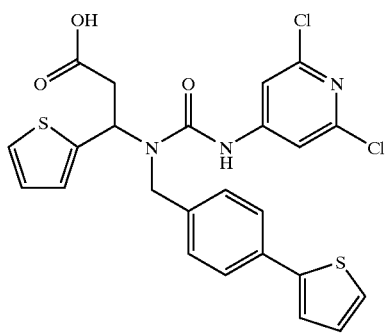

In one embodiment, there is provided a method for inhibiting or reducing the activity of viral polymerase in a host comprising administering a therapeutically effective amount of a compound having the formulae (I) or (XV), further comprising one or more viral polymerase inhibitor.

In one embodiment, the viral polymerase is a Flaviviridae viral polymerase.

In one embodiment, the viral polymerase is a RNA-dependant RNA-polymerase.

In one embodiment, the viral polymerase is HCV polymerase.

In one embodiment, the invention provides a method for inhibiting or reducing the activity of viral helicase in a host comprising administering a therapeutically effective amount of a compound having the formula (I):

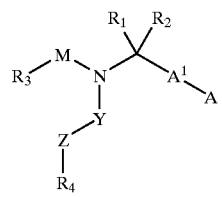 (I)

and pharmaceutically acceptable salts thereof,
wherein,
M is chosen from:

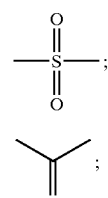 (II)

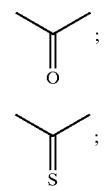 (III)

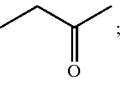 (IV)

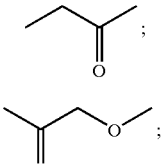 (V)

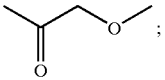 (VI)

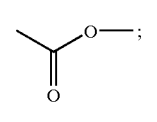 (VII)

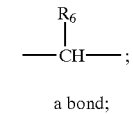 (VIII)

a bond; (IX)

wherein each R$_6$ is independently chosen from H or C$_{1-6}$ alkyl;

A$^1$ is chosen from a bond, C$_{1-6}$ alkyl, C$_{2-6}$ alkenyl or C$_{2-6}$ alkynyl;

A is chosen from COOR$_5$, CO—COOR$_5$, PO$_3$R$_5$R$_5$, SO$_3$R$_5$, tetrazole, CON(R$_5$)CH(R$_5$)—COOR$_5$, CONR$_5$R$_5$, CONR$_5$OH, wherein each R$_5$ is independently chosen from H or C$_{1-6}$ alkyl;

R$_1$, R$_2$ are independently chosen from H, C$_{1-6}$ alkyl, C$_{6-12}$ aryl, C$_{3-10}$ heterocycle, C$_{6-12}$ aralkyl or C$_{3-10}$ heteroaralkyl;

R$_3$ is chosen from C$_{6-12}$ aryl, C$_{3-10}$ heterocycle, C$_{6-12}$ aralkyl or C$_{3-10}$ heteroaralkyl;

Y is selected from the group consisting of:

—CH$_2$—; (X)

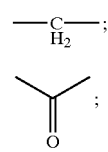 (XI)

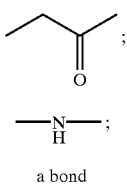
(XII)

—N—H— ;
(XIII)

a bond
(XIV)

Z is chosen from $C_{1-6}$ alkyl, $C_{2-6}$ alkenyl, $C_{2-6}$ alkynyl, $C_{6-14}$ aryl, $C_{3-10}$ heterocycle;

$R_4$ is chosen from H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, $COR_7$, wherein each $R_5$ is independently chosen from H or $C_{1-6}$ alkyl, and $R_7$ is chosen from $C_{6-12}$ aryl or $C_{3-10}$ heterocycle.

In one embodiment, the invention provides a method for inhibiting or reducing the activity of viral helicase in a host comprising administering a therapeutically effective amount of a compound having the formula (XV):

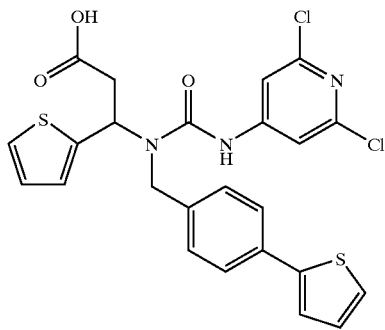

In further embodiments;
The viral helicase is a flaviviridea helicase.
The viral helicase is a HCV helicase.

In one embodiment, the invention provides the use of a compound according to formula (I) for inhibiting or reducing the activity of viral polymerase in a host.

In a further embodiment, the invention provides the use of a compound according to formula (I) for inhibiting or reducing the activity of viral polymerase in a host, further comprising one or more viral polymerase inhibitor.

In one embodiment, the viral polymerase is Flaviviridae viral polymerase.

In one embodiment, the viral polymerase is RNA-dependant RNA-polymerase.

In one embodiment, the viral polymerase is HCV polymerase. In one embodiment, the invention provides the use of a compound according to formula (I) for inhibiting or reducing the activity of viral helicase in a host.

In one embodiment, the invention provides the use of a compound according to formula (I) for inhibiting or reducing the activity of viral helicase in a host, further comprising one or more viral helicase inhibitor.

In one embodiment, the viral helicase is Flaviviridae viral helicase.

In one embodiment, the viral helicase is HCV helicase.

In one embodiment, the invention provides a combination comprising a compound according to formula (I) and one or more additionnal agent chosen from viral serine protease inhibitor, viral polymerase inhibitor and viral helicase inhibitor, immunomudulating agent, antioxydant agent, antibacterial agent or antisense agent.

In further embodiments;

The additional agent is chosen from silybum marianum, interleukine-12, amantadine, ribozyme, thymosin, N-acetyl cysteine, cyclosporin, interferon α and ribavirin.

The combination of said compound and said additionnal agent is administered sequentially.

The combination of said compound and said additionnal agent is administered simultaneously.

In another embodiment, the Flavivirus infection is Hepatitis C virus.

It will be appreciated by those skilled in the art that the compounds of formula (I) can contain a chiral centre on the general formula (I). The compounds of formula (I) thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

In accordance with the present invention, the compounds of formula (I) include:

(2s)-2-[(2,4-Dichloro-benzoyl)-(4-thiazol-2-yl-benzyl)-amino]-3-phenyl-propionic acid, compound #2

(2s)-2-[(4-Bromo-benzyl)-(2,4-dichloro-benzoyl)-amino]-3-phenyl-propionic acid, compound #3

(2s)-2-[(4-Benzofuran-2-yl-benzyl)-(2,4-dichloro-benzoyl)-amino]-3-phenyl-propionic acid, compound #4

(2s)-2-[(4-Benzofuran-2-yl-benzyl)-(4-methoxy-2,3,6-trimethyl-benzenesulfonyl)-amino]-3-phenyl-propionic acid, compound #5

(2s)-2-[(4-Benzofuran-2-yl-benzyl)-(4-methoxy-2,3,6-trimethyl-benzenesulfonyl)-amino]-3-phenyl-propionic acid, compound #6

(2s)-2-[(3-Benzofuran-2-yl-benzyl)-(4-methoxy-2,3,6-trimethyl-benzenesulfonyl)-amino]-3-phenyl-propionic acid, compound #7

3-[(4-Iodo-benzyl)-(4-methoxy-2,3,6-trimethyl-benzenesulfonyl)-amino]-3-thiophen-2-yl-propionic acid ethyl ester, compound #8

(2s)-2-[(3-Bromo-benzyl)-(2,4-dichloro-benzoyl)-amino]-3-phenyl-propionic acid, compound #9

(2s)-2-[(3-Bromo-benzyl)-(2-chloro-benzoyl)-amino]-3-phenyl-propionic acid, compound #10

(2s)-2-[(3-Benzofuran-2-yl-benzyl)-(2,4-dichloro-benzoyl)-amino]-3-phenyl-propionic acid, compound #11

(2s)-2-[(2,4-Dichloro-benzoyl)-(4-iodo-benzyl)-amino]-3-phenyl-propionic acid, compound #12

(2s)-2-[(3-Iodo-benzyl)-(4-methoxy-2,3,6-trimethyl-benzenesulfonyl)-amino]-3-phenyl-propionic acid, compound #13

(2s)-2-[(4-Bromo-benzyl)-(4-methoxy-2,3,6-trimethyl-benzenesulfonyl)-amino]-3-phenyl-propionic acid, compound #14

(2s)-2-[(3-Bromo-benzyl)-(4-chloro-benzoyl)-amino]-3-phenyl-propionic acid, compound #15

(2s)-2-[(4-Iodo-benzyl)-(4-methoxy-2,3,6-trimethyl-benzenesulfonyl)-amino]-3-phenyl-propionic acid, compound #16

(2s)-2-[(3-Bromo-benzyl)-(4-methoxy-2,3,6-trimethyl-benzenesulfonyl)-amino]-3-phenyl-propionic acid, compound #17

(2s)-5-(4-{[[(1s-1-Carboxy-2-phenyl-ethyl)-(4-methoxy-2,3,6-trimethyl-benzenesulfonyl)-amino]-methyl}-phenyl)-furan-2-carboxylic acid methyl ester, compound #18

(2s)-2-[(3-Bromo-benzyl)-(3,4-dichloro-benzoyl)-amino]-3-phenyl-propionic acid, compound #19

(2s)-2-[(3-Bromo-benzyl)-(2,4-dichloro-benzenesulfonyl)-amino]-3-phenyl-propionic acid, compound #20
(2s)-3-(1-Benzyl-1h-imidazol-4-yl)-2-[(3-bromo-benzyl)-(2,4-dichloro-benzoyl)-amino]-propionic acid, compound #21
(2s)-2-{(3-Bromo-benzyl)-[(2,4-dichloro-phenyl)-acetyl]-amino}-3-phenyl-propionic acid, compound #22
(2s)-5-(4-{[(1s-1-Carboxy-2-phenyl-ethyl)-(4-methoxy-2,3,6-trimethyl-benzenesulfonyl)-amino]-methyl}-phenyl)-thiophene-2-carboxylic acid methyl ester, compound #23
(2s)-2-[(2-Bromo-benzyl)-(4-methoxy-2,3,6-trimethyl-benzenesulfonyl)-amino]-3-phenyl-propionic acid, compound #24
(2s)-2-[(3-Bromo-benzyl)-(4-chloro-phenoxycarbonyl)-amino]-3-phenyl-propionic acid, compound #25
(2s)-2-[(4-Benzoyl-benzyl)-(4-methoxy-2,3,6-trimethyl-benzenesulfonyl)-amino]-3-phenyl-propionic acid
(2s)-Triethyl-ammonium; 2-[(3-benzofuran-2-yl-benzyl)-(4-methoxy-2,3,6-trimethyl-benzenesulfonyl)-amino]-3-phenyl-propionate, compound #26
2-[Allyl-(4-chloro-2-iodo-benzoyl)-amino]-3-phenyl-propionic acid, compound #27
(2s)-2-[(3-Bromo-benzyl)-(2,4-dimethyl-benzoyl)-amino]-3-phenyl-propionic acid, compound #28
3-(4-Benzofuran-2-yl-phenyl)-2-[(2,4-dichloro-benzoyl)-methyl-amino]-propionic acid, compound #29
(2s)-2-[(3-Bromo-benzyl)-(2,4-dichloro-benzyl)-amino]-3-phenyl-propionic acid, compound #30
(2s)-2-[(3-Benzofuran-2-yl-benzyl)-(2,4-dimethyl-benzoyl)-amino]-3-phenyl-propionic acid, compound #31
(2s)-2-[(4-Benzofuran-2-yl-benzyl)-(4-methoxy-2,3,6-trimethyl-benzenesulfonyl)-amino]-3-(4-hydroxy-phenyl)-propionic acid, compound #32
(2s)-2-[(4-Benzofuran-2-yl-benzyl)-(2,4-dichloro-benzoyl)-amino]-3-(4-hydroxy-phenyl)-propionic acid, compound #33
(2s)-2-[(3-Bromo-benzyl)-(4-chloro-2-methyl-benzoyl)-amino]-3-phenyl-propionic acid, compound #34
(2s)-2-[(3-Bromo-benzyl)-(4-chloro-2-iodo-benzoyl)-amino]-3-phenyl-propionic acid, compound #35
(2s)-2-[(3-Bromo-benzyl)-(2-bromo-4-chloro-benzoyl)-amino]-3-phenyl-propionic acid, compound #36
(2s)-2-{(3-Benzofuran-2-yl-benzyl)-[(2,4-dichloro-phenyl)-acetyl]-amino}-3-phenyl-propionic acid, compound #37
(2s)-2-[(4-Benzofuran-2-yl-benzyl)-(2,4-dichloro-phenyl)-amino]-3-phenyl-propionic acid, compound #38
(2s)-2-[(2,4-Dichloro-benzoyl)-naphthalen-2-ylmethyl-amino]-3-phenyl-propionic acid, compound #39
(2s)-2-[(2,4-Dichloro-benzoyl)-(9,10-dioxo-9,10-dihydro-anthracen-2-ylmethyl)-amino]-3-phenyl-propionic acid, compound #40
(2s)-2-[[3-(3-Chloro-benzoyl)-benzyl]-(2,4-dichloro-benzoyl)-amino]-3-phenyl-propionic acid, compound #41
(2s)-2-{(2,4-Dichloro-benzoyl)-[3-(2,4-difluoro-benzoyl)-benzyl]-amino}-3-phenyl-propionic acid, compound #42
(2s)-2-[{3-[3-(2-Chloro-phenyl)-5-methyl-isoxazole-4-carbonyl]-benzyl}-(2,4-dichloro-benzoyl)-amino]-3-phenyl-propionic acid, compound #43
(2s)-2-{(2,4-Dichloro-benzoyl)-[3-(2,4-dichloro-benzoyl)-benzyl]-amino}-3-phenyl-propionic acid, compound #44
(2s)-2-[(3-Benzooxazol-2-yl-benzyl)-(2,4-dichloro-benzoyl)-amino]-3-phenyl-propionic acid, compound #45
(2s)-2-[(3-Bromo-benzyl)-(4-chloro-2-ethyl-benzoyl)-amino]-3-phenyl-propionic acid, compound #46
(2s)-2-[(4-Benzofuran-2-yl-benzyl)-(2,4-dichloro-benzoyl)-amino]-3-cyclohexyl-propionic acid, compound #47
(2s)-2-[(3-Bromo-benzyl)-(4-chloro-2-methyl-benzoyl)-amino]-3-phenyl-propionic acid, compound #48
(2s)-2-[(3-Benzofuran-2-yl-benzyl)-(2-bromo-4-chloro-benzoyl)-amino]-3-phenyl-propionic acid, compound #49
(2s)-2-[(3-Bromo-benzyl)-(4-chloro-2-vinyl-benzoyl)-amino]-3-phenyl-propionic acid, compound #50
(2s)-2-[(2,4-Dichloro-benzoyl)-(3-fluoro-benzyl)-amino]-3-phenyl-propionic acid, compound #51
(2s)-2-[(3-Chloro-benzyl)-(2,4-dichloro-benzoyl)-amino]-3-phenyl-propionic acid, compound #52
(2S)-2-[(2,4-Dichloro-benzoyl)-(3-nitro-benzyl)-amino]-3-phenyl-propionic acid, Compound #53
(2S)-2-[(3-Cyano-benzyl)-(2,4-dichloro-benzoyl)-amino]-3-phenyl-propionic acid, compound #54
(2s)-2-{(2-Chloro-benzoyl)-[5-(3-chloro-phenyl)-furan-2-ylmethyl]-amino}-3-phenyl-propionic acid, compound #55
(2s)-2-{(2,4-Dichloro-benzoyl)-[5-(3-trifluoromethyl-phenyl)-furan-2-ylmethyl]-amino}-3-phenyl-propionic acid, compound #56
(2s)-2-[(5-Bromo-furan-2-ylmethyl)-(2,4-dichloro-benzoyl)-amino]-3-phenyl-propionic acid, compound #57
(2s)-2-[(5-Benzofuran-2-yl-furan-2-ylmethyl)-(2,4-dichloro-benzoyl)-amino]-3-phenyl-propionic acid, compound #58
(2s)-2-[[5-(4-Bromo-phenyl)-furan-2-ylmethyl]-(2,4-dichloro-benzoyl)-amino]-3-phenyl-propionic acid, compound #59
(2s)-2-[[5-(2-Chloro-phenyl)-furan-2-ylmethyl]-(2,4-dichloro-benzoyl)-amino]-3-phenyl-propionic acid, compound #60
(2s)-2-[[5-(2-Chloro-5-trifluoromethyl-phenyl)-furan-2-ylmethyl]-(2,4-dichloro-benzoyl)-amino]-3-phenyl-propionic acid, compound #61
(2s)-2-{(2,4-Dichloro-benzoyl)-[5-(2-nitro-phenyl)-furan-2-ylmethyl]-amino}-3-phenyl-propionic acid, compound #62
(3s)-3-{(2,4-Dichloro-benzoyl)-[5-(3-trifluoromethyl-phenyl)-furan-2-ylmethyl]-amino}-4-phenyl-butyric acid, compound #63
2-{(2,4-Dichloro-benzoyl)-[2-(3-nitro-phenyl)-thiazol-5-ylmethyl]-amino}-3-phenyl-propionic acid, compound #64
(2s)-2-{(2,4-Dichloro-benzoyl)-[5-(3,4-dichloro-phenyl)-furan-2-ylmethyl]-amino}-3-phenyl-propionic acid, compound #65
(2s)-2-[Benzofuran-2-ylmethyl-(2,4-dichloro-benzoyl)-amino]-3-phenyl-propionic acid, compound #66
(2s)-2-{(2,4-Dichloro-benzoyl)-[5-(2,4-dichloro-phenyl)-furan-2-ylmethyl]-amino}-3-phenyl-propionic acid, compound #67
(2s)-2-[(2-Bromo-4-chloro-benzoyl)-(5-bromo-furan-2-ylmethyl)-amino]-3-phenyl-propionic acid, compound #68
(2s)-2-[[5-(3-Chloro-4-fluoro-phenyl)-furan-2-ylmethyl]-(2,4-dichloro-benzoyl)-amino]-3-phenyl-propionic acid, compound #69
(2s)-2-[[5-(4-Chloro-3-fluoro-phenyl)-furan-2-ylmethyl]-(2,4-dichloro-benzoyl)-amino]-3-phenyl-propionic acid, compound #70
(2s)-2-[(5-Bromo-furan-2-ylmethyl)-(4-chloro-2-iodo-benzoyl)-amino]-3-phenyl-propionic acid, compound #71
(2s)-2-(5-{[(1s-1-Carboxy-2-phenyl-ethyl)-(2,4-dichloro-benzoyl)-amino]-methyl}-furan-2-yl)-benzoic acid ethyl ester, compound #72
(2s)-2-(5-{[(1-Carboxy-2-phenyl-ethyl)-(2,4-dichloro-benzoyl)-amino]-methyl}-furan-2-yl)-benzoic acid, compound #73
(2s)-2-[(2,4-Dichloro-benzoyl)-(5-thiazol-2-yl-furan-2-ylmethyl)-amino]-3-phenyl-propionic acid, compound #74

(2s)-2-[(2,4-Dichloro-benzoyl)-furan-2-ylmethyl-amino]-3-phenyl-propionic acid, compound #75

(2s)-3-(5-{[(1s-1-Carboxy-2-phenyl-ethyl)-(2,4-dichloro-benzoyl)-amino]-methyl}-furan-2-yl)-benzoic acid, compound #76

(2s)-4-(5-{[(1s-1-Carboxy-2-phenyl-ethyl)-(2,4-dichloro-benzoyl)-amino]-methyl}-furan-2-yl)-benzoic acid, compound #77

(2s)-2-{(2-Bromo-4-chloro-benzoyl)-[5-(3-trifluoromethyl-phenyl)-furan-2-ylmethyl]-amino}-3-phenyl-propionic acid, compound #78

(2s)-2-{(2,4-Dichloro-benzoyl)-[5-(3,5-difluoro-phenyl)-furan-2-ylmethyl]-amino}-3-phenyl-propionic acid, compound #79

(2s)-2-[(2,4-Dichloro-benzoyl)-(5-m-tolyl-furan-2-ylmethyl)-amino]-3-phenyl-propionic acid, compound #80

(2s)-2-{(2,4-Dichloro-benzoyl)-[5-(3-fluoro-phenyl)-furan-2-ylmethyl]-amino}-3-phenyl-propionic acid, compound #81

(2s)-2-[(5-Bromo-thiophen-2-ylmethyl)-(2,4-dichloro-benzoyl)-amino]-3-phenyl-propionic acid, compound #82

(2s)-4-(5-{[(1s-1-Carboxy-2-phenyl-ethyl)-(2,4-dichloro-benzoyl)-amino]-methyl}-thiophen-2-yl)-benzoic acid, compound #83

(2s)-4-(5-{[(1-Carboxy-2-phenyl-ethyl)-(2,4-dichloro-benzoyl)-amino]-methyl}-thiophen-2-yl)-benzoic acid methyl ester, compound #84

(2s)-2-[(5-Benzofuran-2-yl-thiophen-2-ylmethyl)-(2,4-dichloro-benzoyl)-amino]-3-phenyl-propionic acid, compound #85

2-[(2-Benzofuran-2-yl-thiazol-5-ylmethyl)-(2,4-dichloro-benzoyl)-amino]-3-phenyl-propionic acid, compound #86

(2s)-2-{(2,4-Dichloro-benzoyl)-[4-(3,4-dichloro-phenyl)-thiophen-2-ylmethyl]-amino}-3-phenyl-propionic acid, compound #87

(2s)-2-[[4-(4-Chloro-3-fluoro-phenyl)-thiophen-2-ylmethyl]-(2,4-dichloro-benzoyl)-amino]-3-phenyl-propionic acid, compound #88

(2s)-2-[[4-(3-Chloro-4-fluoro-phenyl)-thiophen-2-ylmethyl]-(2,4-dichloro-benzoyl)-amino]-3-phenyl-propionic acid, compound #89

(2s)-2-{(2,4-Dichloro-benzoyl)-[4-(2,4-dichloro-phenyl)-thiophen-2-ylmethyl]-amino}-3-phenyl-propionic acid, compound #90

(2s)-2-[[5-(3-Chloro-4-fluoro-phenyl)-thiophen-2-ylmethyl]-(2,4-dichloro-benzoyl)-amino]-3-phenyl-propionic acid, compound #91

(2s)-2-[[5-(4-chloro-3-fluoro-phenyl)-thiophen-2-ylmethyl]-(2,4-dichloro-benzoyl)-amino]-3-phenyl-propionic acid, compound #92

(2s)-2-{(2,4-Dichloro-benzoyl)-[5-(2,4-dichloro-phenyl)-thiophen-2-ylmethyl]-amino}-3-phenyl-propionic acid, compound #93

(2s)-2-[(2,4-Dichloro-benzoyl)-(5-thiazol-2-yl-thiophen-2-ylmethyl)-amino]-3-phenyl-propionic acid, compound #94

(2s)-2-{(2,4-Dichloro-benzoyl)-[5-(3,5-difluoro-phenyl)-thiophen-2-ylmethyl]-amino}-3-phenyl-propionic acid, compound #95

(2s)-2-{(2,4-Dichloro-benzoyl)-[5-(3-methoxy-phenyl)-thiophen-2-ylmethyl]-amino}-3-phenyl-propionic acid, compound #96

(2s)-2-{(2,4-Dichloro-benzoyl)-[5-(3-fluoro-phenyl)-thiophen-2-ylmethyl]-amino}-3-phenyl-propionic acid, compound #97

(2s)-2-[(2,4-Dichloro-benzoyl)-thiophen-2-ylmethyl-amino]-3-phenyl-propionic acid, compound #98

(2s)-2-[(4-Bromo-thiophen-2-ylmethyl)-(2,4-dichloro-benzoyl)-amino]-3-phenyl-propionic acid, compound #99

(2s)-2-{(2,4-Dichloro-benzoyl)-[2-(4-phenyl-piperazin-1-yl)-thiazol-5-ylmethyl]-amino}-3-phenyl-propionic acid, compound #100

(2s)-1-(5-{[(1s-1-Carboxy-2-phenyl-ethyl)-(2,4-dichloro-benzoyl)-amino]-methyl}-thiazol-2-yl)-piperidine-4-carboxylic acid, compound #101

(2s)-2-[[2-(4-Benzyl-piperazin-1-yl)-thiazol-5-ylmethyl]-(2,4-dichloro-benzoyl)-amino]-3-phenyl-propionic acid, compound #102

(2s)-2-[(2,4-Dichloro-benzoyl)-(2-piperidin-1-yl-thiazol-5-ylmethyl)-amino]-3-phenyl-propionic acid, compound #103

(2s)-2-[(2,4-Dichloro-benzoyl)-(2-diethylamino-thiazol-5-ylmethyl)-amino]-3-phenyl-propionic acid, compound #104

(2s)-2-[[2-(4-Chloro-benzoyl)-benzofuran-3-ylmethyl]-(4-methoxy-2,3,6-trimethyl-benzenesulfonyl)-amino]-3-phenyl-propionic acid, compound #105

(2s)-2-[[5-(2,4-Dichloro-phenoxy)-1-methyl-3-trifluoromethyl-1h-pyrazol-4-ylmethyl]-(4-methoxy-2,3,6-trimethyl-benzenesulfonyl)-amino]-3-phenyl-propionic acid, compound #106

(2s)-2-((2,4-Dichloro-benzoyl)-{2-[5-(2,4-dichloro-phenyl)-furan-2-yl]-2-oxo-ethyl}-amino)-3-phenyl-propionic acid, compound #107

(2s)-2-Benzyl-4-(2,4-dichloro-phenyl)-3-[3-(2,6-dichloro-phenyl)-5-methyl-isoxazol-4-ylmethyl]-4-oxo-butyric acid, compound #108

(2s)-2-[Allyl-(2,4-dichloro-benzoyl)-amino]-3-phenyl-propionic acid, compound #109

(2s)-2-[(2,4-Dichloro-benzoyl)-methyl-amino]-3-phenyl-propionic acid, compound #110

(2s)-2-[(2,4-Dichloro-benzoyl)-prop-2-ynyl-amino]-3-phenyl-propionic acid, compound #111

(2s)-2-[(2,4-Dichloro-benzoyl)-propyl-amino]-3-phenyl-propionic acid, compound #112

(2s)-2-[(3-Benzofuran-2-yl-prop-2-ynyl)-(2,4-dichloro-benzoyl)-amino]-3-phenyl-propionic acid, compound #113

(2s)-2-[(4-Benzofuran-2-yl-phenyl)-(2,4-dichloro-benzoyl)-amino]-3-phenyl-propionic acid, compound #114

(2s)-2-[(2,4-Dichloro-benzoyl)-(3-methyl-but-2-enyl)-amino]-3-phenyl-propionic acid, compound #115

2-[(2-Bromo-allyl)-(2,4-dichloro-benzoyl)-amino]-3-phenyl-propionic acid, compound #116

3-{[(1-Carboxy-2-phenyl-ethyl)-(2,4-dichloro-benzoyl)-amino]-methyl}-benzoic acid methyl ester, compound #117

3-[[5-(3-Chloro-4-fluoro-phenyl)-thiophen-2-ylmethyl]-(2,4-dichloro-benzoyl)-amino]-5-phenyl-thiophene-2-carboxylic acid, compound #118

2-[[5-(3-Cyano-phenyl)-furan-2-ylmethyl]-(2,4-dichloro-benzoyl)-amino]-3-phenyl-propionic acid, compound #119

(2s)-2-{(2,4-Dichloro-benzoyl)-[5-(2-trifluoromethyl-phenyl)-furan-2-ylmethyl]-amino}-3-phenyl-propionic acid, compound #120

(2s)-2-(5-{[(1s-1-Carboxy-2-phenyl-ethyl)-(2,4-dichloro-benzoyl)-amino]-methyl}-thiophen-2-yl)-benzoic acid ethyl ester, compound #121

3-(5-{[(1s-1-Carboxy-2-phenyl-ethyl)-(2,4-dichloro-benzoyl)-amino]-methyl}-thiophen-2-yl)-benzoic acid ethyl ester, compound #122

(2s)-2-[[5-(3-Chloro-phenyl)-furan-2-ylmethyl]-(2,4-dichloro-benzoyl)-amino]-3-phenyl-propionic acid, compound #123

(2s)-2-[(4-Chloro-2-iodo-benzoyl)-(3,5-dibromo-thiophen-2-ylmethyl)-amino]-3-phenyl-propionic acid, compound #124

(2s)-3-(5-{[(1-Carboxy-2-phenyl-ethyl)-(2,4-dichloro-benzoyl)-amino]-methyl}-thiophen-2-yl)-benzoic acid, compound #125

(2s)-2-[[5-(5-Chloro-thiophen-2-yl)-furan-2-ylmethyl]-(2,4-dichloro-benzoyl)-amino]-3-phenyl-propionic acid, compound #126

(2s)-2-[[2,2']Bithiophenyl-5-ylmethyl-(2,4-dichloro-benzoyl)-amino]-3-phenyl-propionic acid, compound #127

(2s)-2-[(5'-Chloro-[2,2']bithiophenyl-5-ylmethyl)-(2,4-dichloro-benzoyl)-amino]-3-phenyl-propionic acid, compound #128

(2s)-2-{(2,4-Dichloro-benzoyl)-[4-(3,5-difluoro-phenyl)-thiophen-2-ylmethyl]-amino}-3-phenyl-propionic acid, compound #129

(2s)-2-{(2,4-Dichloro-benzoyl)-[4-(3-fluoro-phenyl)-thiophen-2-ylmethyl]-amino}-3-phenyl-propionic acid, compound #130

(2s)-2-{(4-Chloro-2-iodo-benzoyl)-[5-(3-trifluoromethyl-phenyl)-furan-2-ylmethyl]-amino}-3-phenyl-propionic acid, compound #131

(2s)-2-{(4-Chloro-2-methyl-benzoyl)-[5-(3-trifluoromethyl-phenyl)-furan-2-ylmethyl]-amino}-3-phenyl-propionic acid, compound #132

(2s)-2-[(5-Chloro-[2,3']bithiophenyl-5'-ylmethyl)-(2,4-dichloro-benzoyl)-amino]-3-phenyl-propionic acid, compound #133

(2s)-2-{(2,4-Dichloro-benzoyl)-[5-(4-methoxy-phenyl)-furan-2-ylmethyl]-amino}-3-phenyl-propionic acid, compound #134

(2s)-2-{(2,4-Dichloro-benzoyl)-[5-(4-methoxy-phenyl)-thiophen-2-ylmethyl]-amino}-3-phenyl-propionic acid, compound #135

(2s)-2-{(2,4-Dichloro-benzoyl)-[4-(4-methoxy-phenyl)-thiophen-2-ylmethyl]-amino}-3-phenyl-propionic acid, compound #136

(2s)-2-[(2,4-Dichloro-benzoyl)-(5-pyridin-4-yl-furan-2-ylmethyl)-amino]-3-phenyl-propionic acid, compound #137

(2s)-2-[(2,4-Dichloro-benzoyl)-(5-pyridin-4-yl-thiophen-2-ylmethyl)-amino]-3-phenyl-propionic acid, compound #138

(2s)-2-[(2,4-Dichloro-benzoyl)-(4-pyridin-4-yl-thiophen-2-ylmethyl)-amino]-3-phenyl-propionic acid, compound #139

(2s)-2-[(2-Chloro-thiazol-5-ylmethyl)-(2,4-dichloro-benzoyl)-amino]-3-phenyl-propionic acid, compound #140

(2s)-2-{(2,4-Dichloro-benzoyl)-[5-(4-fluoro-phenyl)-thiophen-2-ylmethyl]-amino}-3-phenyl-propionic acid, compound #141

(2s)-2-[(2,4-Dichloro-benzoyl)-(3,5-dichloro-benzyl)-amino]-3-phenyl-propionic acid, compound #142

(2s)-2-[(2,4-Dichloro-benzoyl)-thiophen-3-ylmethyl-amino]-3-phenyl-propionic acid, compound #143

(2s)-2-[(2,4-Dichloro-benzoyl)-(3-trifluoromethyl-benzyl)-amino]-3-phenyl-propionic acid, compound #144

(2s)-2-[[3-(3-Chloro-4-fluoro-phenyl)-thiophen-2-ylmethyl]-(2,4-dichloro-benzoyl)-amino]-3-phenyl-propionic acid, compound #145

(2s)-2-[(3-Bromo-thiophen-2-ylmethyl)-(2,4-dichloro-benzoyl)-amino]-3-phenyl-propionic acid, compound #146

(2s)-2-{(2,4-Dichloro-benzoyl)-[5-(3-trifluoromethyl-phenyl)-furan-2-ylmethyl]-amino}-2-methyl-propionic acid, compound #147

(2s)-2-{(2,4-Dichloro-benzoyl)-[2-(3-trifluoromethyl-phenyl)-thiazol-5-ylmethyl]-amino}-3-phenyl-propionic acid, compound #148

(2s)-2-[(2,4-Dichloro-benzoyl)-(5-nitro-thiophen-3-ylmethyl)-amino]-3-phenyl-propionic acid, compound #149

(2s)-2-[(2,4-Dichloro-benzoyl)-(4-methanesulfonyl-benzyl)-amino]-3-phenyl-propionic acid, compound #150

(2s)-2-[(2,4-Dichloro-benzoyl)-(3-methoxy-benzyl)-amino]-3-phenyl-propionic acid, compound #151

(2s)-2-[(2,4-Dichloro-benzoyl)-(3-methyl-benzyl)-amino]-3-phenyl-propionic acid, compound #152

(2s)-2-[[5-(3-Chloro-phenoxy)-1-methyl-3-trifluoromethyl-1h-pyrazol-4-ylmethyl]-(2,4-dichloro-benzoyl)-amino]-3-phenyl-propionic acid, compound #153

(2s)-2-{(2,4-Dichloro-benzoyl)-[3-(3,5-difluoro-phenyl)-thiophen-2-ylmethyl]-amino}-3-phenyl-propionic acid, compound #154

(2s)-2-{(2,4-Dichloro-benzoyl)-[3-(3,4-dichloro-phenyl)-thiophen-2-ylmethyl]-amino}-3-phenyl-propionic acid, compound #155

(2s)-2-[[3-(4-Chloro-3-fluoro-phenyl)-thiophen-2-ylmethyl]-(2,4-dichloro-benzoyl)-amino]-3-phenyl-propionic acid, compound #156

(2s)-2-{(2,4-Dichloro-benzoyl)-[3-(2,4-dichloro-phenyl)-thiophen-2-ylmethyl]-amino}-3-phenyl-propionic acid, compound #157

(2s)-2-[(2,4-Dichloro-benzoyl)-(3-m-tolyl-thiophen-2-ylmethyl)-amino]-3-phenyl-propionic acid, compound #158

(2s)-2-(2-{[(1s-1-Carboxy-2-phenyl-ethyl)-(2,4-dichloro-benzoyl)-amino]-methyl}-thiophen-3-yl)-benzoic acid ethyl ester, compound #159

(2s)-4-(2-{[(1s-1-Carboxy-2-phenyl-ethyl)-(2,4-dichloro-benzoyl)-amino]-methyl}-thiophen-3-yl)-benzoic acid ethyl ester, compound #160

(2s)-2-{(2,4-Dichloro-benzoyl)-[3-(3-fluoro-phenyl)-thiophen-2-ylmethyl]-amino}-3-phenyl-propionic acid, compound #161

(2s)-2-[[3-(3-Cyano-phenyl)-thiophen-2-ylmethyl]-(2,4-dichloro-benzoyl)-amino]-3-phenyl-propionic acid, compound #162

{(2,4-Dichloro-benzoyl)-[5-(3-trifluoromethyl-phenyl)-furan-2-ylmethyl]-amino}-thiophen-2-yl-acetic acid, compound #163

L-2-{[(1-Carboxy-2-phenyl-ethyl)-(2,4-dichloro-benzoyl)-amino]-methyl}-pyrrolidine-1-carboxylic acid #tert!-butyl ester, compound #164 d-2-{[(1-carboxy-2-phenyl-ethyl)-(2,4-dichloro-benzoyl)-amino]-methyl}-pyrrolidine-1-carboxylic acid #tert!-butyl ester, compound #165

4-[(1-Carboxy-2-phenyl-ethyl)-(2,4-dichloro-benzoyl)-amino]-piperidine-1-carboxylic acid benzyl ester, compound #166

1-2-[(2,4-Dichloro-benzoyl)-pyrrolidin-2-ylmethyl-amino]-3-phenyl-propionic acid, compound #167 d-2-[(2,4-Dichloro-benzoyl)-pyrrolidin-2-ylmethyl-amino]-3-phenyl-propionic acid, compound #168

3-(5-Bromo-thiophen-2-yl)-2-[(2,4-dichloro-benzoyl)-methyl-amino]-propionic acid, compound #169

2-[(2,4-Dichloro-benzoyl)-pyridin-3-ylmethyl-amino]-3-phenyl-propionic acid, compound #170

2-[(2,4-Dichloro-benzoyl)-(4-trifluoromethyl-benzyl)-amino]-3-phenyl-propionic acid, compound #171

2-{(2,4-Dichloro-benzoyl)-[4-(4-fluoro-benzyloxy)-benzyl]-amino}-3-phenyl-propionic acid, compound #172

2-[(2,4-Dichloro-benzoyl)-(4-fluoro-3-trifluoromethyl-benzyl)-amino]-3-phenyl-propionic acid, compound #173
2-[(1-Benzenesulfonyl-1h-pyrrol-2-ylmethyl)-(2,4-dichloro-benzoyl)-amino]-3-phenyl-propionic acid, compound #174
2-[[3-(4-Chloro-phenoxy)-benzyl]-(2,4-dichloro-benzoyl)-amino]-3-phenyl-propionic acid, compound #175
2-[(5-Chloro-2-chloromethyl-hepta-2,4,6-trienoyl)-quinolin-3-ylmethyl-amino]-3-phenyl-propionic acid, compound #176
2-[(2-Benzyloxy-benzyl)-(2,4-dichloro-benzoyl)-amino]-3-phenyl-propionic acid, compound #177
2-{(2,4-Dichloro-benzoyl)-[3-(5-isopropyl-2-methoxy-phenyl)-thiophen-2-ylmethyl]-amino}-3-phenyl-propionic acid, compound #178
2-{(2,4-Dichloro-benzoyl)-[3-(4-trifluoromethoxy-phenyl)-thiophen-2-ylmethyl]-amino}-3-phenyl-propionic acid, compound #179
2-{(2,4-Dichloro-benzoyl)-[3-(3-trifluoromethyl-phenyl)-thiophen-2-ylmethyl]-amino}-3-phenyl-propionic acid, compound #180
2-[[3-(3,5-Bis-trifluoromethyl-phenyl)-thiophen-2-ylmethyl]-(2,4-dichloro-benzoyl)-amino]-3-phenyl-propionic acid, compound #181
2-[(2,4-Dichloro-benzoyl)-(3-pyridin-4-yl-thiophen-2-ylmethyl)-amino]-3-phenyl-propionic acid, compound #182
2-{(2,4-Dichloro-benzoyl)-[3-(4-methylsulfanyl-phenyl)-thiophen-2-ylmethyl]-amino}-3-phenyl-propionic acid, compound #183
2-{(2,4-Dichloro-benzoyl)-[3-(4-fluoro-phenyl)-thiophen-2-ylmethyl]-amino}-3-phenyl-propionic acid, compound #184
2-[(2,4-Dichloro-benzoyl)-(3-pyridin-3-yl-thiophen-2-ylmethyl)-amino]-3-phenyl-propionic acid, compound #185
2-{(2,4-Dichloro-benzoyl)-[1-(toluene-2-sulfonyl)-pyrrolidin-2-ylmethyl]-amino}-3-phenyl-propionic acid, compound #186
2-[(2-Bromo-benzyl)-(2,4-dichloro-benzoyl)-amino]-3-phenyl-propionic acid, compound #187
3-(2-Bromo-phenyl)-2-[(2,4-dichloro-benzoyl)-methyl-amino]-propionic acid, compound #188
3-(4-Bromo-phenyl)-2-[(2,4-dichloro-benzoyl)-methyl-amino]-propionic acid, compound #189
2-[(3-Bromo-phenyl)-(2,4-dichloro-benzoyl)-amino]-3-phenyl-propionic acid, compound #190
2-[(4-Bromo-phenyl)-(2,4-dichloro-benzoyl)-amino]-3-phenyl-propionic acid, compound #191
2-[[4-(3-Chloro-4-fluoro-phenyl)-thiophen-2-ylmethyl]-(2,4-dimethyl-benzoyl)-amino]-3-phenyl-propionic acid, compound #192
3-{[(1-Carboxy-2-phenyl-ethyl)-(2,4-dichloro-benzoyl)-amino]-methyl}-benzoic acid, compound #193
2-[(3-Amino-benzyl)-(2,4-dichloro-benzoyl)-amino]-3-phenyl-propionic acid, compound #194
3-Phenyl-2-{(2-trifluoromethyl-benzoyl)-[5-(2-trifluoromethyl-phenyl)-furan-2-ylmethyl]-amino}-propionic acid, Compound #195
2-{(3-Cyano-benzoyl)-[5-(2-trifluoromethyl-phenyl)-furan-2-ylmethyl]-amino}-3-phenyl-propionic acid, Compound #196
2-{(4-Nitro-benzoyl)-[5-(2-trifluoromethyl-phenyl)-furan-2-ylmethyl]-amino}-3-phenyl-propionic acid, Compound #197
2-{(2-Fluoro-benzoyl)-[5-(2-trifluoromethyl-phenyl)-furan-2-ylmethyl]-amino}-3-phenyl-propionic acid, Compound #198
2-[Benzyl-(2,4-dichloro-benzoyl)-amino]-3-phenyl-propionic acid Compound #199
2-{(2,4-DICHLORO-BENZOYL)-[3-(2H-TETRAZOL-5-YL)-BENZYL]-AMINO}-3-PHENYL-PROPIONIC ACID Compound #200
2-[(2,4-DICHLORO-BENZOYL)-(2-NITRO-BENZYL)-AMINO]-3-PHENYL-PROPIONIC ACID Compound #201
2-[(2,4-DICHLORO-BENZOYL)-(4-NITRO-BENZYL)-AMINO]-3-PHENYL-PROPIONIC Compound #202
2-[(2-CYANO-BENZYL)-(2,4-DICHLORO-BENZOYL)-AMINO]-3-PHENYL-PROPIONIC ACID Compound #203
2-[(4-CYANO-BENZYL)-(2,4-DICHLORO-BENZOYL)-AMINO]-3-PHENYL-PROPIONIC ACID Compound #204
2-[[1-(3-CYANO-PHENYL)-ETHYL]-(2,4-DICHLORO-BENZOYL)-AMINO]-3PHENYL-PROPIONIC ACID Compound #205
3-{[(1-Carboxy-2-phenyl-ethyl)-(2,4-dichloro-benzoyl)-amino]-methyl}-benzoic acid methyl ester Compound #206
3-{[(1-Carboxy-2-phenyl-ethyl)-(2,4-dichloro-benzoyl)-amino]-methyl}-benzoic acid Compound #207
2-[(2,4-DICHLORO-BENZOYL)-(3-METHANESULFONYL-BENZYL)-AMINO]-3-PHENYL-PROPIONIC ACID Compound #208
2-[(3-ACETYL-BENZYL)-(2,4-DICHLORO-BENZOYL)-AMINO]-3-PHENYL-PROPIONIC ACID Compound #209
2-[(2,4-DICHLORO-BENZOYL)-(1-OXY-PYRIDIN-3-YLMETHYL)-AMINO]-3-PHENYL-PROPIONIC ACID Compound #210
2-{(2,4-Dichloro-benzoyl)-[5-(3-trifluoromethyl-phenyl)-thiophen-2-ylmethyl]-amino}-3-phenyl-propionic acid Compound #211.

Preferably, the compounds of the present invention are provided in the form of a single enantiomer at least 95%, more preferrably at least 97% and most preferably at least 99% free of the corresponding enantiomer.

More preferably the compound of the present invention is in the form of the (+) enantiomer at least 95% free of the corresponding (−) enantiomer.

More preferably the compound of the present invention is in the form of the (+) enantiomer at least 97% free of the corresponding (−) enantiomer.

More preferably the compound of the present invention is in the form of the (+) enantiomer at least 99% free of the corresponding (−) enantiomer.

In a more preferred embodiment, the compound of the present invention is in the form of the (−) enantiomer at least 95% free of the corresponding (+) enantiomer.

Most preferably the compound of the present invention is in the form of the (−) enantiomer at least 97% free of the corresponding (+) enantiomer.

More preferably the compound of the present invention is in the form of the (−) enantiomer at least 99% free of the corresponding (+) enantiomer.

There is also provided a pharmaceutically acceptable salts of the present invention. By the term pharmaceutically acceptable salts of compounds of general formula (I) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4+$ (where R is $C_{1-4}$ alkyl) salts.

Reference hereinafter to a compound according to the invention includes compounds of the general formula (I) and their pharmaceutically acceptable salts.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents an unsubstituted or substituted (by a halogen, nitro, $SO_3R_4$, $PO_3R_4R_4$, $CONH_2$, COOH, $SR_5$, O—$C_{1-6}$ alkyl, O—$C_{2-6}$ alkenyl, O—$C_{2-6}$ alkynyl, $C_{6-12}$ aryl, $C_{3-10}$ heterocycle, hydroxyl, amino, $NR_4R_4$, or COOQ, wherein Q is $C_{1-6}$ alkyl; $C_{2-6}$ alkenyl; $C_{2-6}$ alkynyl, $C_{6-12}$ aryl and $R_4$ is H, $C_{1-6}$ alkyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

The terms "alkenyl" and "alkynyl" represent an alkyl containing at least one unsaturated group (e.g. allyl, acetylene, ethylene).

The term "aryl" represents a carbocyclic moiety which may be substituted(by H, $C_{1-6}$ alkyl, $C_{2-6}$ alkenyl, $C_{2-6}$ alkynyl, $C_{3-8}$ heterocycle, halogen, nitro, aminoamidino, amidino, guanido, $CONH_2$, COOH, O—$C_{1-6}$ alkyl, O—$C_{2-6}$ alkenyl, O—$C_{2-6}$ alkynyl, $SCH_3$, $SO_2CH_3$, amino, $NR_4R_4$, hydroxyl or COOQ, wherein Q is $C_{1-6}$ alkyl, $C_{2-6}$ alkenyl, a $C_{2-6}$ alkynyl) and containing at least one benzenoid-type ring (e.g., phenyl, naphthyl and anthraquinonyl).

The term "aralkyl" represents an aryl group attached to the adjacent atom by a $C_{1-6}$alkyl, $C_{1-6}$alkenyl, or $C_{1-6}$alkynyl (e.g., benzyl).

The term "heterocycle" represents a mono or di-substituted (e.g. by a $C_{1-6}$ alkyl, O—$C_{1-6}$ alkyl, O—$C_{6-12}$ aryl, $C_{6-12}$ aryl, $C_{6-12}$ aralkyl, $C_{3-10}$ heterocycle, halogen, amino, COOH, $COOR_5$ or $NO_2$; wherein $R_5$ is a $C_{1-6}$ alkyl), or unsubstituted, saturated or unsaturated, cyclic moiety wherein said cyclic moiety is interrupted by at least one heteroatom, e.g. oxygen, sulfur or nitrogen. It is understood that the term heterocyclic ring represents a mono or polycyclic (e.g., bicyclic) ring. Examples of heterocyclic rings include but are not limited to epoxide; furan; benzofuran; isobenzofuran; oxathiolane; dithiolane; dioxolane; pyrrole; pyrrolidine; imidazole; pyridine; pyrimidine; indole; piperidine; morpholine; thiophene and thiomorpholine.

The term "heteroaralkyl" represents an heterocycle group attached to the adjacent atom by a $C_{1-6}$ alkyl, $C_{1-6}$ alkenyl, or $C_{1-6}$ alkynyl (e.g.,thiophenyl).

When there is a sulfur atom present, the sulfur atom can be at different oxidation levels, ie. S, SO, or $SO_2$. All such oxidation levels are within the scope of the present invention.

The term "independently" means that a substituent can be the same or different definition for each item.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The compounds of the invention may also be used in combination with other antiviral agents.

In one aspect of the invention, the compounds of the invention may be employed together with at least one other antiviral agent chosen from protease inhibitors, polymerase inhibitors, and helicase inhibitors.

In another aspect of the invention, the compounds of the invention may be employed together with at least one other antiviral agent chosen from Interferon-α and Ribavirin.

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The individual components of such combinations may be administered either sequentially or simultaneously in separate or combined pharmaceutical formulations.

When the compound (I) or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

The following general schemes and examples are provided to illustrate various embodiments of the present invention and shall not be considered as limiting in scope.

General scheme 1 for the preparation of biaryl carboxamide analogs with a five membered ring

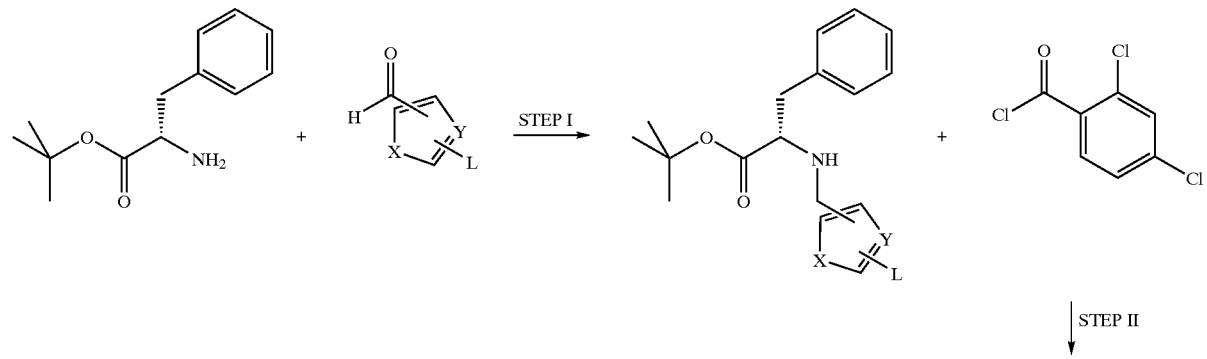

STEP II

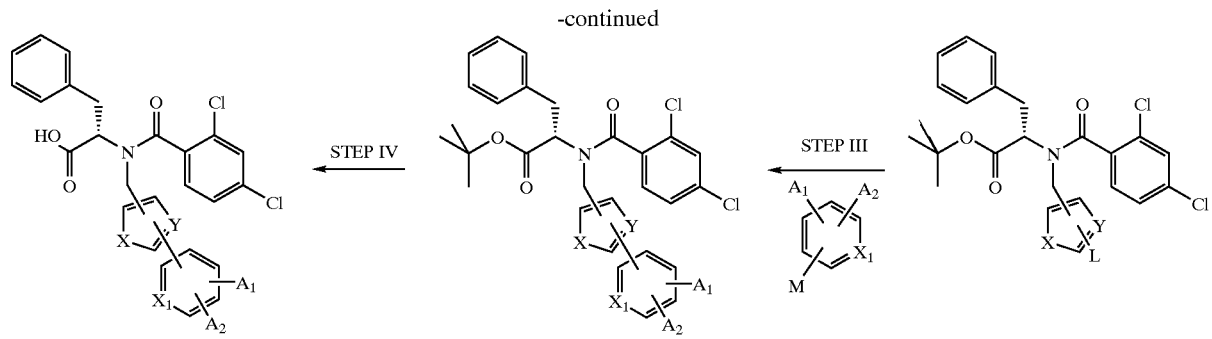

-continued

Legend:
X = O, S, N
Y = N
X1 = N, O or S for five-membered heterocycles
L = Cl, Br, I, NR1R2
A1, A2 = substituents, F, Cl, OMe, CH3, CN
M = Zn, B, Sn The following compounds were prepared in a similar manner as described in general scheme 1:
compound #38 compound #55 compound #56 Compound #57 Compound #58 Compound #59 compound #60 compound #61 compound #62 compound #63 compound #64 compound #65 compound #66 compound #67 compound #68 Compound #69 Compound #70 Compound #71 compound #72 compound #73 compound #74 Compound #75 Compound #76 compound #77 compound #78 compound #79 compound # compound #81 compound #82 compound #83 compound #84 compound #85 compound #87 compound #88 compound #compound #90 compound #91 compound #92 compound #93 compound #94 compound #95 compound #96 compound #compound #98 compound #99 compound #100 compound #101 compound #102 compound #103 compound #104 compound #105 compound #106 compound #107 compound #113 compound #120 compound #121 compound #122 compound #123 compound #124 compound #125 compound #126 compound #127 compound #128 compound #129 compound #130 compound #131 compound #132 compound #133 compound #134 compound #135 compound #136 compound #137 compound #138 compound #139 compound #140 compound #141 compound #142 Bcompound #143 compound #144 compound #145 compound #146 compound #147 compound #148 compound #149 compound #150 compound #151 compound #152 compound #153 compound #154 compound #155 compound #156 compound #157 compound #158 compound #159 compound #160 compound #161 compound #162 compound #163 compound #164 compound #165 compound #166 compound #167 compound #168 compound #169 compound #170 compound #171 compound #172 compound #173 compound #174 compound #175 compound #176 compound #177 compound #178 compound #179 compound #180 compound #181 compound #182 compound #183 compound #184 compound #185 compound #186 compound #187 compound #188 compound #189 compound #190 compound #191

EXAMPLE 1

2-{(2,4-Dichloro-benzoyl)-[3-(3,5-difluoro-phenyl)-thiophen-2-ylmethyl]-amino}-3-phenyl-propionic acid compound #154

Step I
2-[(3-Bromo-thiophen-2-ylmethyl)-amino]-3-phenyl-propionic acid tert-butyl ester

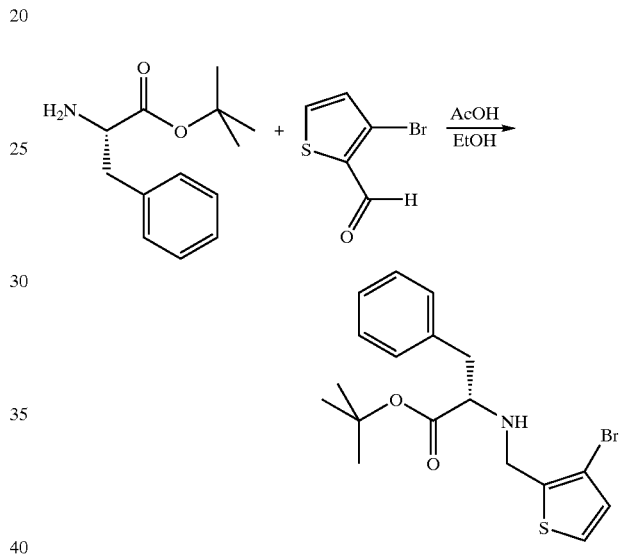

To a stirred solution of 2-Amino-3-phenyl-propionic acid tert-butyl ester (50.6 mg, 0.229 mmol) in ethanol (1 mL), were added 3-Bromo-thiophene-2-carbaldehyde (50 mg, 0.208 mmol.) and acetic acid (21 μL). The reaction mixture was stirred at room temperature under nitrogen for 2 hrs as the progress of imine formation was monitored by TLC. Then, sodium cyanoborohydride (20 mg, 0.312 mmol) was added. The mixture was acidified with sodium bicarbonate and then extracted with dichloromethane. After removal of the solvent, the crude product was purified by silica plate (hexane/ethylacetate 90%:10%) to give 2-[(3-Bromo-thiophen-2-ylmethyl)-amino]-3-phenyl-propionic acid tert-butyl ester in 80% yield: $^1$H NMR (Varian 400 MHz, $CDCl_3$) δ7.23 (m, 6H, ArH), 6.90 (d, 1H, J=5.3 Hz, thiophenH), 4.00 (d, 1H, J=14.6 Hz, $NCH_2$), 3.85 (d, 1H, J=14.6 Hz, $NCH_2$), 3.48 (m, 1H, $CHCH_2$), 3.00 (m, 2H, $CHCH_2$), 1.37 (s, 9H, tBu).

Step II

2-[(3-Bromo-thiophen-2-ylmethyl)-(2,4-dichloro-benzoyl)-amino]-3-phenyl-propionic acid tert-butyl ester

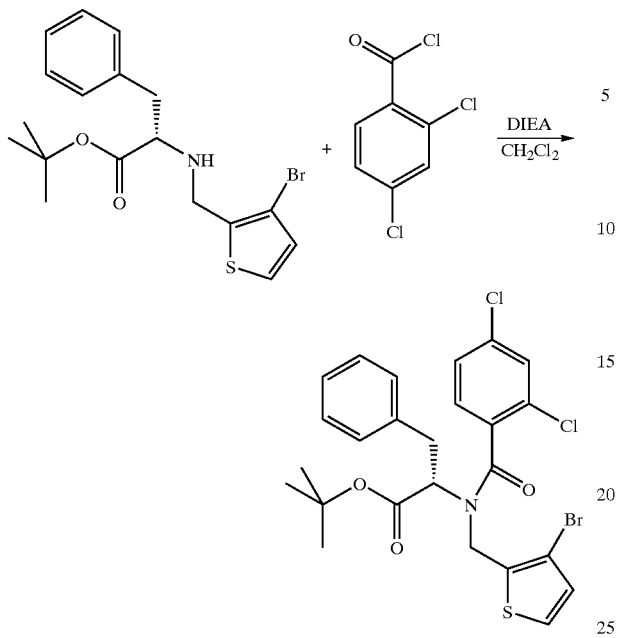

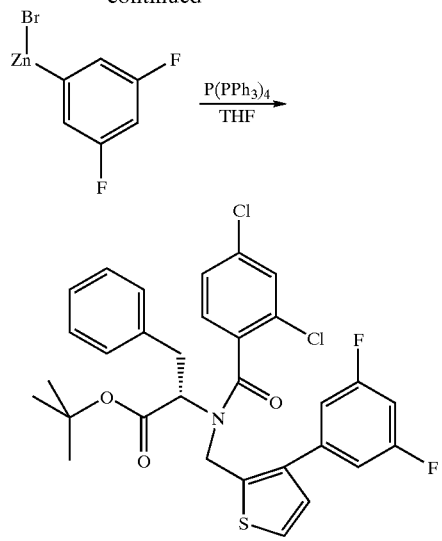

To a stirred solution of 2-[(3-Bromo-thiophen-2-ylmethyl)-amino]-3-phenyl-propionic acid tert-butyl ester (91.6 mg, 0.231 mmol) in dichloromethane (3.3 ml) and N,N-diisopropylethylamine (44 μl) was added a solution of 2,4-Dichloro-benzoyl chloride (34 μl, 0.243 mmol) in dichloromethane (1.3 ml). The reaction mixture was stirred at room temperature under nitrogen overnight. Then, the mixture was extracted with sodium bicarbonate/dichloromethane. The extract was dried (sodium sulfate) and evaporated under reduced pressure to yield 2-[(3-Bromo-thiophen-2-ylmethyl)-(2,4-dichloro-benzoyl)-amino]-3-phenyl-propionic acid tert-butyl ester with 92% yield. $^1$H NMR(Varian 400 MHz, CDCl$_3$) δ(ppm) presence of rotomers 8.08 (d, 0.5H, J=8.7 Hz, ArH), 7.56 (d, 0.5H, J=2.0 Hz, ArH), 7.40 (m, 2H, ArH), 7.23 (m, 2.5H, ArH), 6.99 (d, 0.5H, J=5.4 Hz, ArH), 6.92 (m, 2H, ArH), 6.83 (d, 0.5H, J=5.0 Hz, ArH), 6.54 (d, 1H, J=7.1 Hz, ArH), 5.78 (d, 0.5H, J=8.0 Hz, ArH), 5.20 (m, 1H, NCH$_2$), 4.85 (m, 1H, NCH$_2$), 4.16 (m, 1H, CHCH$_2$), 3.10 (m, 2H, CHCH$_2$), 1.47 (s, 9H, tBu).

Step III

2-{(2,4-Dichloro-benzoyl)-[3-(3,5-difluoro-phenyl)-thiophen-2-ylmethyl]-amino}-3-phenyl-propionic acid tert-butyl ester To 3 mL of THF solution of 2-[(3-Bromo-thiophen-2-ylmethyl)-( 2,4-dichloro-benzoyl)-amino]-3-phenyl-propionic acid tert-butyl ester (50 mg, 0.0879 mmol) was sequentially added tetrakis (triphenylphosphine)palladium (0) (10 mg, 0.00878 mmol). To the resulting brown solution was added a THF solution of 3,5-difluorozinc bromide (0.5M, 1.06 mL). The reaction was stirred and heated to reflux overnight. TLC showed complete conversion of the starting material to a less polar product. A few drop of acetic acid was added before complete removal of the solvent using a rotavap. The crude product was chromatographed to give 2-{(2,4-Dichloro-benzoyl)-[3-(3,5-difluoro-phenyl)-thiophen-2-ylmethyl]-amino}-3-phenyl-propionic acid tert-butyl ester, 37 mg, in 72% yield. $^1$H NMR(Varian 400 MHz, CDCl$_3$), δ(ppm), presence of rotomers, 7.45 (m, <1H), 7.36 (s, <1H), 7.20 (m, ~8H), 7.05 (m, <1H), 6.98 (m, 1H), 6.90 (m, 4H), 6.82 (m, <1H), 6.51 (m, <1H), 5.80 (m, <1H), 5.20 (m, <1H), 4.84 (m, <1H), 4.18 (m, 2H), 3.38 (m, 2H), 2.90 (m, 1H), 1.33, 1.42, 1.44 (s, 9H).

Step IV

2-{(2,4-Dichloro-benzoyl)-[3-(3,5-difluoro-phenyl)-thiophen-2-ylmethyl]-amino}-3-phenyl-propionic acid

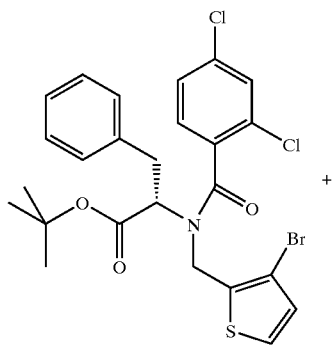

+

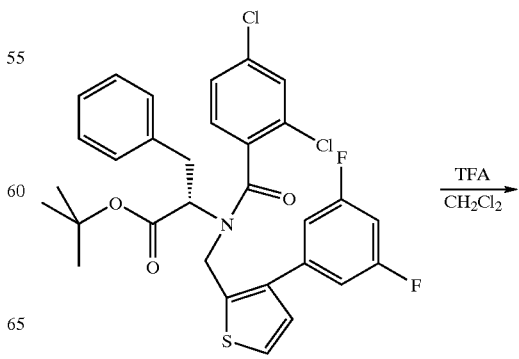

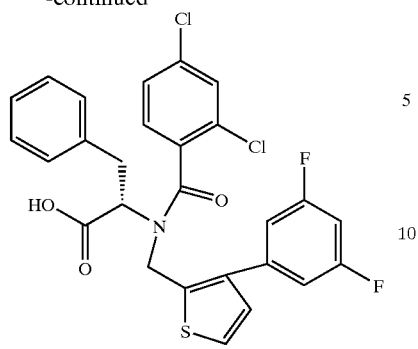

To a stirred solution of 2-{(2,4-Dichloro-benzoyl)-[3-(3,5-difluoro-phenyl)-thiophen-2-ylmethyl]-amino}-3-phenyl-propionic acid tert-butyl ester (37.63 mg, 0.0625 mmol.) in dichloromethane (1 ml.), was added trifluoroacetic acid (1 ml.). The reaction mixture was stirred at room temperature during 1 hr. TLC monitored the progress of the reaction. When the reaction was completed, the mixture was concentrated under reduced pressure on a rotary evaporator, followed by silica chromatography using 90% ethylacetate, 10% methanol and 1 drop of acetic acid, afforded 2-{(2,4-Dichloro-benzoyl)-[3-(3,5-difluoro-phenyl)-thiophen-2-ylmethyl]-amino}-3-phenyl-propionic acid in 85% yield. $^1$H NMR (Varian 400 MHz, CDCl$_3$) δ(ppm), 7.22 (m, 8H, ArH), 7.00 (m, 2H, ArH), 6.82 (m, 2H, ArH), 6.50 (m, 1H, ArH), 4.95 (m, 0.5H, NCH$_2$), 4.65 (m, 0.5H, NCH$_2$), 4.10 (m, 1H, NCH$_2$), 3.60 (m, 1H, CHCH$_2$), 3.20 (m, 1H, CHCH$_2$), 3.05 (m, 1H, CHCH$_2$). MS, 546.00 found.

The following compounds were prepared in a similar manner as described in general scheme 2:

compound #2, compound #, compound #4, compound #9, Compound #10, Compound #11, Compound #12 Compound #15, Compound #19, compound #21, compound #22, compound #25, compound #28, compound #31, Compound #, Compound #34, Compound #35, compound #36, compound #37, compound #39, compound #, compound #41, compound #42, compound #43, compound #44, compound #45, compound #46, compound #47 Compound #48, Compound #49, compound #50, General Scheme 3 for the Preparation of Biaryl Sulfonamide Analogs with Six Membered Aromatic Ring Spacer

EXAMPLE 2

2-[(4-Benzofuran-2-yl-benzyl)-(4-methoxy-2,3,6-trimethyl-benzenesulfonyl)-amino]-3-phenyl-propionic acid Compound #5

Step I 2-(4-Methoxy-2,3,6-trimethyl-benzenesulfonylamino)-3-phenyl-propionic acid methyl ester General scheme 2 for the preparation of biaryl carboxamide analogs with six membered aromatic ring

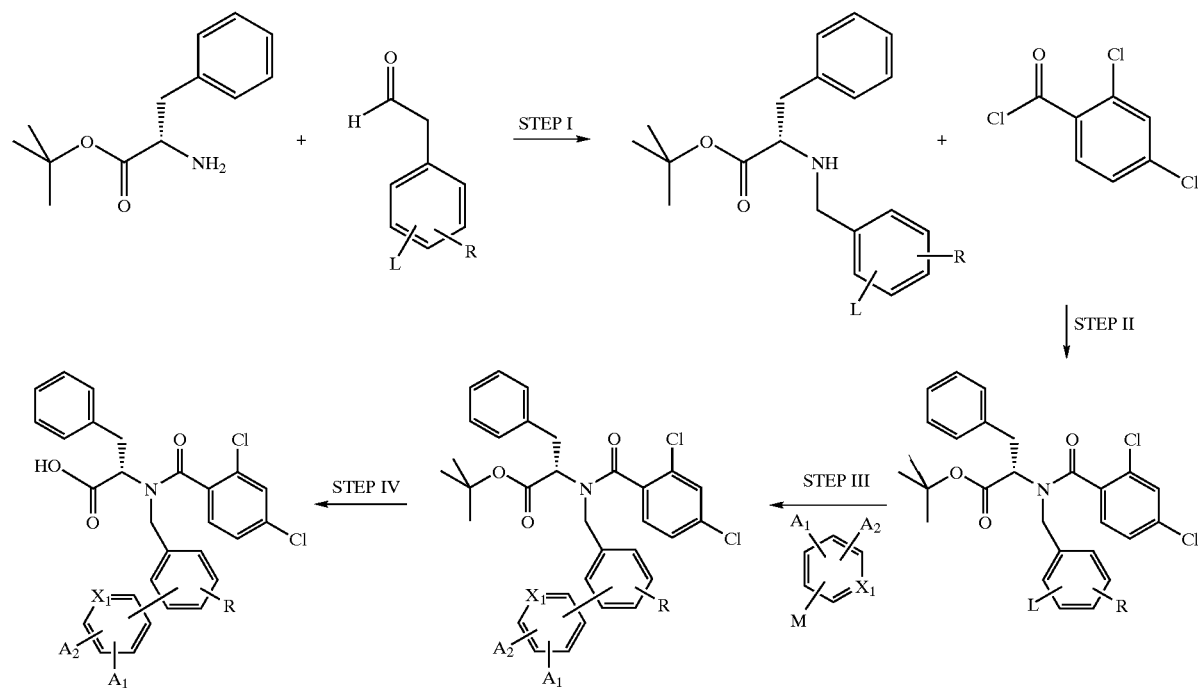

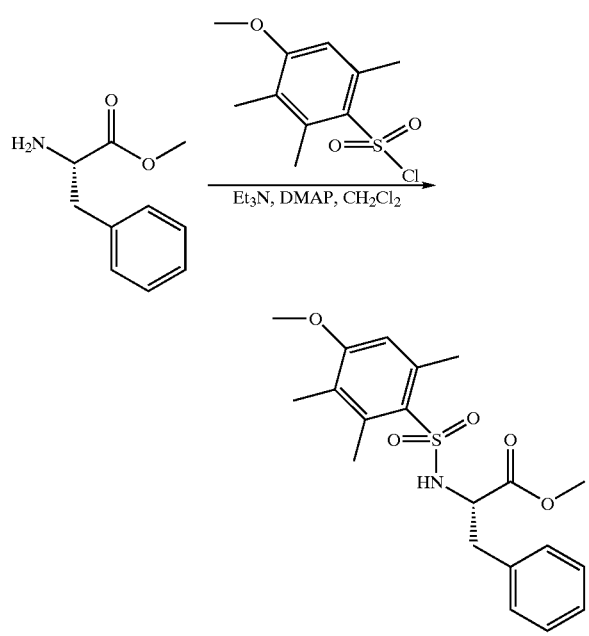

A solution of L-phenylalanine methyl ester (300 mg, 1.68 mmol) in anhydrous $CH_2Cl_2$ (10 mL) was cooled to 0° C. in an ice bath, then triethylamine (0.35 mL), 4-methoxy-2,3,6-trimethyl-benzenesulfonyl chloride (438 mg, 1.76 mmol) and catalytic amount of DMAP (25 mg) were added under a $N_2$ atmosphere. The reaction mixture was stirred at room temperature for 12 h. After that period of time, the mixture was partitioned between water and $CH_2Cl_2$, the organic layer was separated, dried ($Na_2SO_4$) and concentrated. The residue was purified by silica gel column chromatography using ethyl acetate and hexane (1:2) as eluent to obtain 2-(4-Methoxy-2,3,6-trimethyl-benzenesulfonylamino)-3-phenyl-propionic acid methyl ester as a white solid, 500 mg (77%). $^1$H NMR (CDCl$_3$, 400 MHz): δ7.26–7.18 (m, 3H), 7.02–6.99 (m, 2H), 6.53 (s, 1H), 5.12 (d, 1H), 4.09–4.04 (m, 1H), 3.84 (s, 3H), 3.55 (s, 3H), 3.05 (dd, 1H), 3.03 (dd, 1H), 2.64, 2.38, 2.08 (3s, 9H).

Step II

2-[(4-Iodo-benzyl)-(4-methoxy-2,3,6-trimethyl-benzenesulfonyl)-amino]-3-phenyl-propionic acid methyl ester

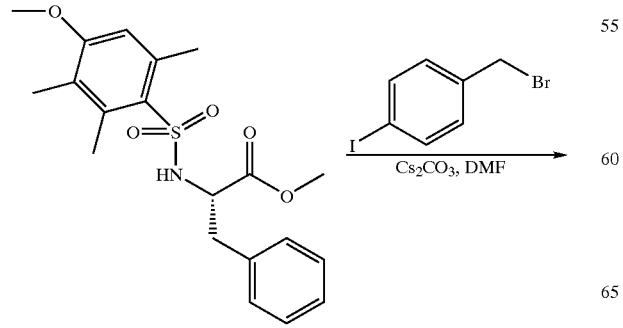

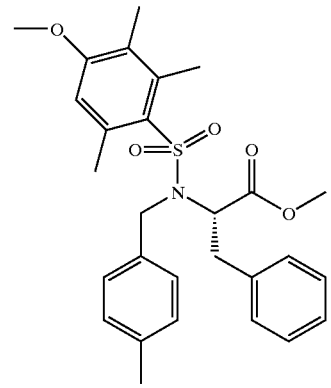

To a solution of 2-(4-Methoxy-2,3,6-trimethyl-benzenesulfonylamino)-3-phenyl-propionic acid methyl ester (50 mg, 0.129 mmol) in anhydrous DMF (1 mL), 4-iodobenzyl bromide (46 mg, 0.154 mmol) and cesium carbonate (50 mg, 0.154 mmol) were added and the reaction mixture was stirred at room temperature under a $N_2$ atmosphere for 12 h. The reaction mixture was partitioned between water and ether. The ether layer was separated, dried ($Na_2SO_4$), concentrated. The residue was purified by silica gel column chromatography using ethyl acetate and hexane (1:3) as eluent to obtain 2-[(4-Iodo-benzyl)-(4-methoxy-2,3,6-trimethyl-benzenesulfonyl)-amino]-3-phenyl-propionic acid methyl ester (68 mg, 90%) as a foam.
$^1$H NMR (CDCl$_3$, 400 MHz): δ7.48 (d, 2H), 7.21 (m, 3H), 7.09 (d, 2H), 6.91(d, 2H), 6.45 (s, 1H), 4.60 (m, 3H), 3.81 (s, 3H), 3.38 (s, 3H), 3.17 (dd, 1H), 2.81 (dd, 1H), 2.63, 2.44, 2.14 (3s, 9H).

Step III

2-[(4-Benzofuran-2-yl-benzyl)-(4-methoxy-2,3,6-trimethyl-benzenesulfonyl)-amino]-3-phenyl-propionic acid methyl ester

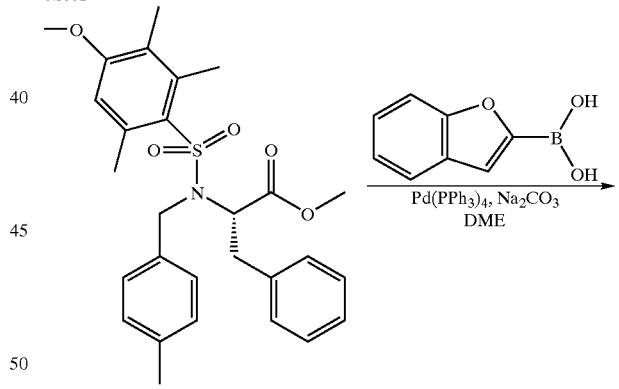

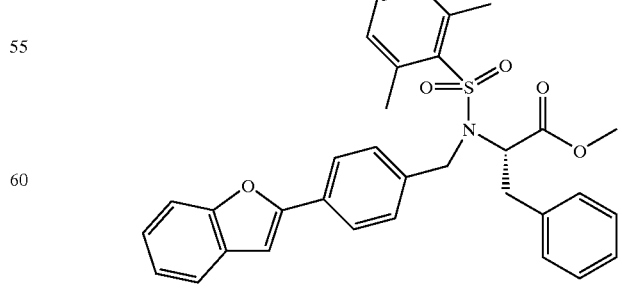

To a degassed solution of 2-[(4-Iodo-benzyl)-(4-methoxy-2,3,6-trimethyl-benzenesulfonyl)-amino]-3-phenylpropionic acid methyl ester (40 mg, 0.068 mmol) and benzofuran-2-boronic acid (20 mg, 0.124 mmol) in a mixture of DME (3 mL) and 2M aqueous Na$_2$CO$_3$ (1.5 mL), Pd(PPh$_3$)$_4$ (4 mg) was added and the reaction mixture was stirred at 65° C. for 2 h under a N$_2$ atmosphere. The reaction mixture was diluted with ethyl acetate and water. The organic layer was separated, dried (Na$_2$SO$_4$), concentrated. The residue was purified by column chromatography using ethyl acetate and hexane (1:9) to obtain 2-[(4-Benzofuran-2-yl-benzyl)-(4-methoxy-2,3,6-trimethyl-benzenesulfonyl)-amino]-3-phenyl-propionic acid methyl ester (39 mg, 100%) as a thick syrup. $^1$H NMR (af-2783) (CDCl$_3$, 400 MHz): δ7.2 (d, 2H), 7.62 (d, 1H), 7.55 (d, 1H), 7.30–7.15 (m, 7H), 7.12 (d, 2H), 6.96 (s, 1H), 6.51 (s, 1H), 4.72 (m, 3H), 3.80, 3.40 (2s, 6H), 3.28 (dd, 1H), 3.02 (dd, 1H), 2.71, 2.58, 2.12 (3s, 9H).

Step IV
2-[(4-Benzofuran-2-yl-benzyl)-(4-methoxy-2,3,6-trimethyl-benzenesulfonyl)-amino]-3-phenyl-propionic acid

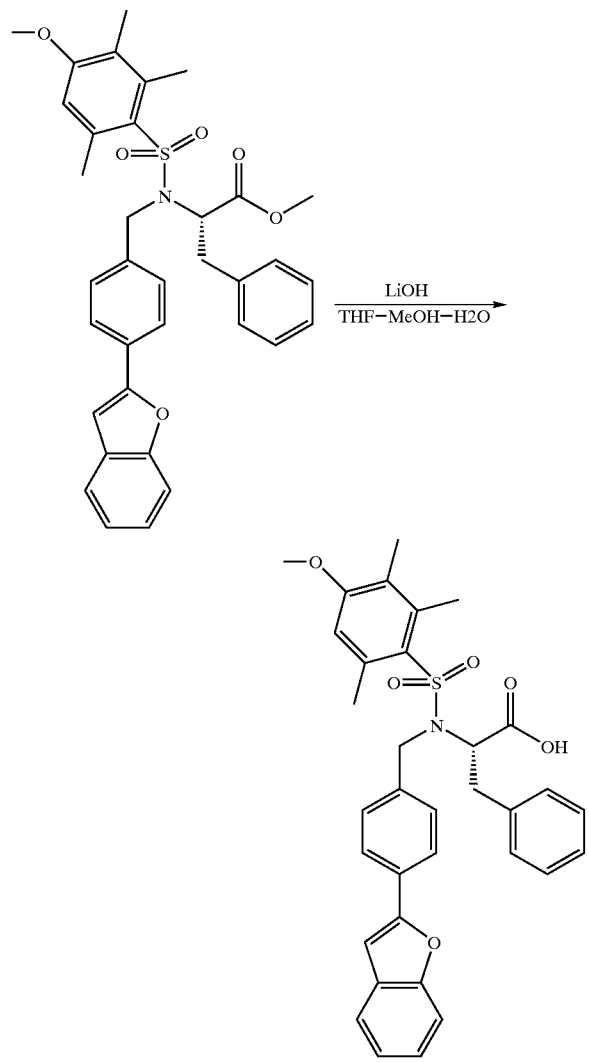

2-[(4-Benzofuran-2-yl-benzyl)-(4-methoxy-2,3,6-trimethyl-benzenesulfonyl)-amino]-3-phenyl-propionic acid methyl ester (40 mg, 0.067 mmol) was taken in a mixture of THF:MeOH:H$_2$O (3:2:1) and then added 1N aqueous solution of LiOH.H$_2$O (0.40 mL, 0.40 mmol). The reaction mixture was stirred at room temperature for 12 h. Solvents were removed and the residue was partitioned between water and ethyl acetate. The aqueous layer was acidified using 10% KHSO$_4$ solution. The organic layer was separated, dried (Na$_2$SO$_4$) and concentrated. The residue was purified by silica gel column chromatography using ethyl acetate and methanol (9:1) to obtain 2-[(4-Benzofuran-2-yl-benzyl)-(4-methoxy-2,3,6-trimethyl-benzenesulfonyl)-amino]-3-phenyl-propionic acid. (29 mg, 75%) as a white solid. 1H NMR (CDCl$_3$, 400 MHz): δ7.59 (d, 2H), 7.48 (d, 2H), 7.42 (d, 2H), 7.19 (m, 4H), 7.06, 6.88 (2m, 6H), 6.37 (s, 1H), 4.55 (m, 3H), 3.70 (s, 3H), 3.19, 2.85 (2m, 2H), 2.56, 2.00, 1.98 (3s, 9H). ESI– (M–H): 582.

Step V
2-[(4-Methoxy-2,3,6-trimethyl-benzenesulfonyl)-(4-tributylstannanyl-benzyl)-amino]-3-phenyl-propionic acid methyl ester

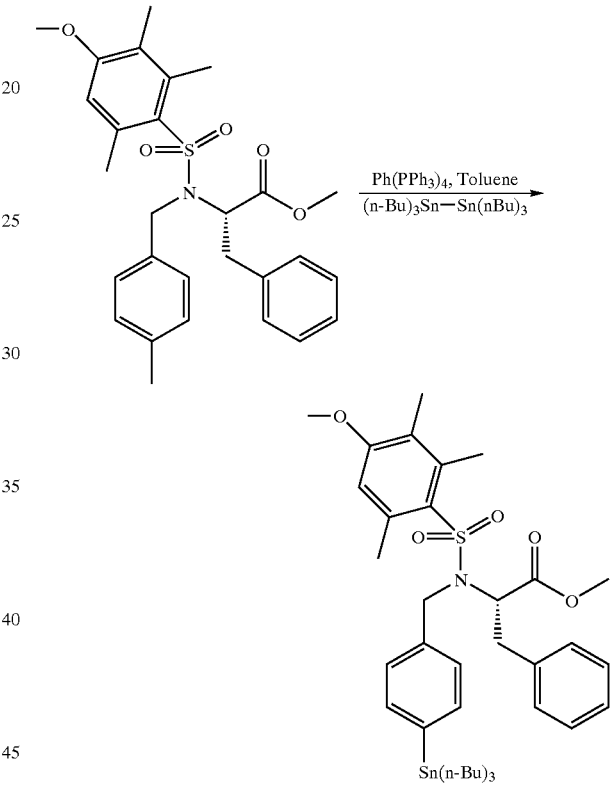

To a stirred solution of 2-[(4-Iodo-benzyl)-(4-methoxy-2,3,6-trimethyl-benzenesulfonyl)-amino]-3-phenyl-propionic acid methyl ester (1 g. 1.65 mmol.) in toluene (100 ml.) were added P(Ph$_3$)$_4$Pd (123 mg., 0.107 mmol.) and 1,1,1,2,2,2-Hexabutyl-distannane (1.7 ml. 3.3 mmol.) under nitrogen. The reaction mixture was stirred and heated to 115° C. during 8 hrs. The progress of the reaction was monitored by TLC. Filtration and removal of the solvent under reduced pressure on a rotary evaporator followed by flash column chromatographic purification using 5% of EtOAc in hexane, afforded 2-[(4-Methoxy-2,3,6-trimethyl-benzenesulfonyl)-(4-tributylstannanyl-benzyl)-amino]-3-phenyl-propionic acid methyl ester in 50% yield: $^1$HNMR (Varian 400 MHz, CDCl$_3$) δ7.30 (d, 2H, J=7.9 Hz, HPhSn), 7.26 (m, 3H, HPh), 7.18 (d, 2H, J=7.0 Hz, HPh), 7.14 (d, 2H, J=8.1 Hz, HPhI), 6.53 (s, 1H, MTRH), 4.59 (m, 2H, NCH$_2$Ph), 3.83 (s, 3H, OCH$_3$), 3.26 (s, 3H, COOCH$_3$), 3.18(dd, 1H, J=10.5 and 13.3 Hz, CHCH$_2$), 2.92 (dd, 1H, J=4.3 and 13.3 Hz, CHCH$_2$), 2.69 (s, 3H, ArCH$_3$), 2.51 (s, 3H, ArCH$_3$), 2.11 (s, 3H, ArCH$_3$), 1.00(m, 27H, SnBu$_3$) ppm.

Step VI
5-(4-{[(1-Methoxycarbonyl-2-phenyl-ethyl)-(4-methoxy-2,3,6-trimethyl-benzenesulfonyl)-amino]-methyl}-phenyl)-thiophene-2-carboxylic acid methyl ester

Step VII
5-(4-{[(1-Carboxy-2-phenyl-ethyl)-(4-methoxy-2,3,6-trimethyl-benzenesulfonyl)-amino]-methyl}-phenyl)-furan-2-carboxylic acid

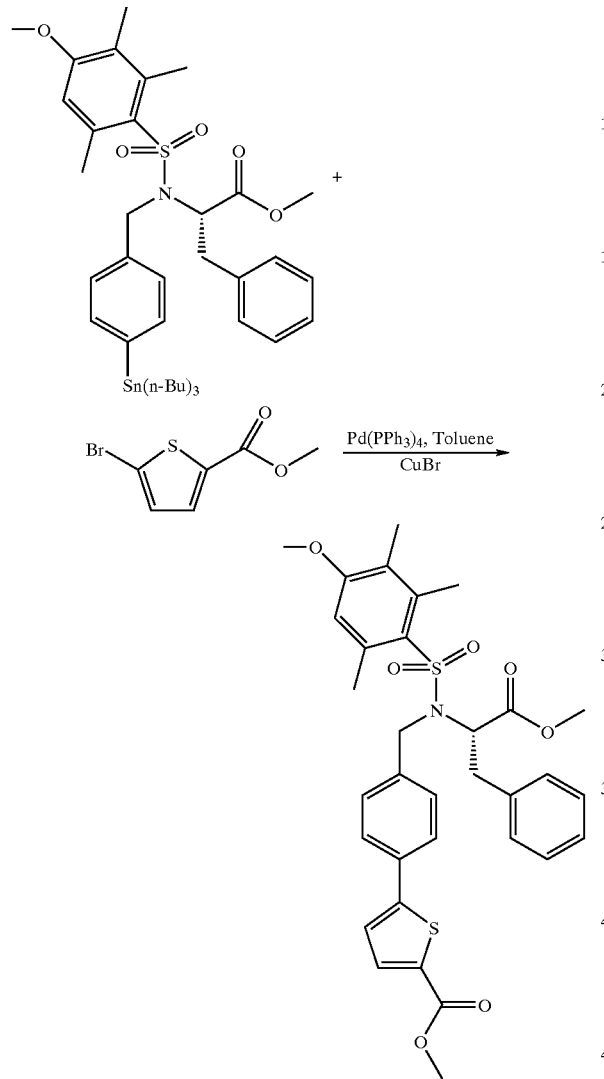

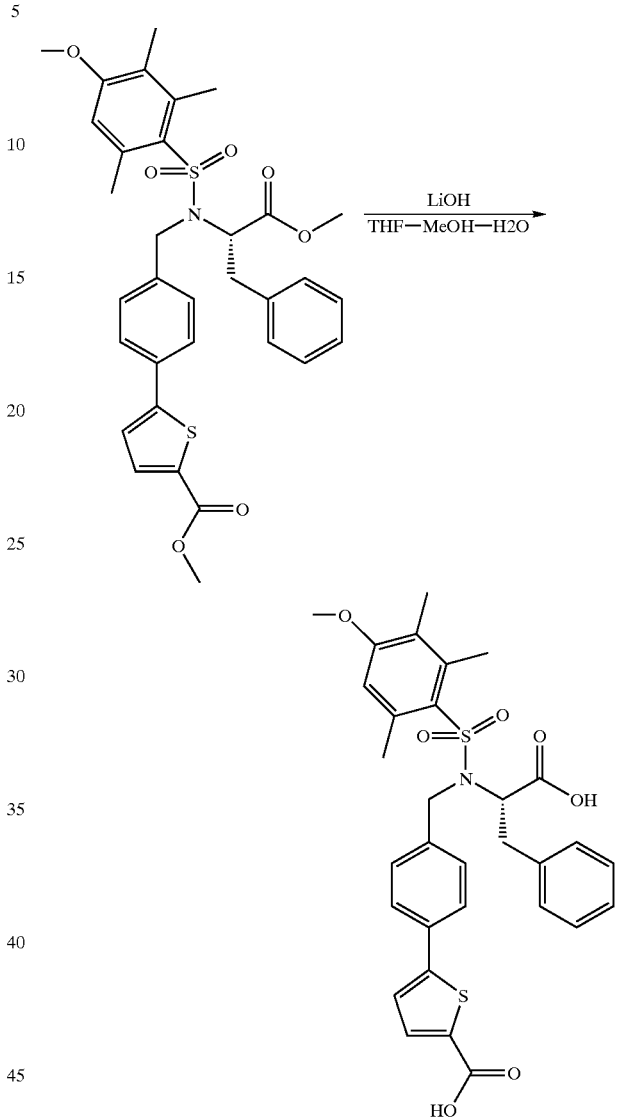

To a stirred solution of 2-[(4-Methoxy-2,3,6-trimethyl-benzenesulfonyl)-(4-tributylstannanyl-benzyl)-amino]-3-phenyl-propionic acid methyl ester (100 mg. 0.13 mmol.) in toluene (3 ml.) were added P(Ph$_3$)$_4$Pd (6 mg. 0.039eq.), CuBr (2 mg.) and 5-Bromo-thiophene-2-carboxylic acid methyl ester (26.5 mg, 0.12 mmol.) under nitrogen. The reaction mixture was stirred and heated to reflux during 5 hrs. The progress of the reaction was monitored by TLC. Filtration and removal of the solvent under reduced pressure on a rotary evaporator followed by silica plate for purification using 80% hexane 20% EtOAc afforded 5-(4-{[(1-Methoxycarbonyl-2-phenyl-ethyl)-(4-methoxy-2,3,6-trimethyl-benzenesulfonyl)-amino]-methyl}-phenyl)-thiophene-2-carboxylic acid methyl ester in 41% yield: $^1$HNMR (Varian 400 MHz, CDCl$_3$) δ8.67(d, 1H, HPh), 8.35 (d, 2H, thiopheneH), 8.10(m, 6H, HPh), 8.00(d, 2H, thiopheneH), 7.38(s, 1H, MTRH), 5.72(m, 3H, NCH$_2$Ph, CHCH$_2$), 4.82(s, 3H, OCH$_3$), 4.68(s, 3H, COOCH$_3$), 4.29(s, 3H, COOCH$_3$), 4.10 (m, 1H, CHCH$_2$), 3.85 (m, 1H, CHCH$_2$), 3.57(s, 3H, ArCH$_3$), 3.40(s, 3H, ArCH$_3$), 3.0(s, 3H, ArCH$_3$) ppm. MS 622.6 (M$^+$).

To a stirred solution of 5-(4-{[(1-Methoxycarbonyl-2-phenyl-ethyl)-(4-methoxy-2,3,6-trimethyl-benzenesulfonyl)-amino]-methyl}-phenyl)-furan-2-carboxylic acid methyl ester (16 mg, 0.026 mmol.) in THF:H$_2$O:MeOH (3:1:2) (1 ml.), was added LiOH in water (1N) (0.2 ml. 0.26 mmol.). The reaction mixture was stirred at room temperature during 1 hr. TLC monitored the progress of the reaction. When the reaction was completed, the mixture was concentrated under reduced pressure on a rotary evaporator. The residue was treated with a solution 20% of KHSO$_4$ and extracted in EtOAc. The EtOAc layer was dried over Na$_2$SO$_4$. Filtration and removal of the solvent under reduced pressure on a rotary evaporator followed by silica chromatography using 90% EtOAc, 10% MeOH and 1 drop of AcOH, afforded 5-(4-{[(1-Carboxy-2-phenyl-ethyl)-(4-methoxy-2,3,6-trimethyl-benzenesulfonyl)-amino]-methyl}-phenyl)-furan-2-carboxylic acid. $^1$HNMR (Varian 400 MHz, DMSO) δ7.37 (d, 2H, J=8.5 Hz, HPh), 7.27 (d, 2H, J=8.3 Hz, HPh), 7.13 (m, 6H, HPh), 6.69 (d, 1H, J=3.2 Hz, furanH), 6.58 (d, 1H, J=3.2 Hz, furanH), 6.50 (s, 1H, MTRH), 4.81 (d, 1H, J=15.5 Hz, NCH₂Ph), 4.41 (d, 1H, J=15.9 Hz, NCH₂Ph), 4.06 (dd, 1H, J=3.5 and 9.5 Hz, CHCH₂), 3.64 (s, 3H, OCH₃), 3.10 (dd, 1H, J=9.5 and 12.6 Hz, CHCH₂), 2.65 (dd, 1H, J=3.8 and 12.6 Hz, CHCH₂), 2.49 (s, 3H, ArCH₃), 2.38 (s, 3H, ArCH₃), 1.92 (s, 3H, ArCH₃) ppm. MS 576.5 (M⁻).

The following compounds were prepared in a similar manner as described in example 2:

compound #5 compound #6 Compound #7 compound #8 Compound #13 Compound #14 Compound #16 Compound #17 BCH-19067 Compound #18 Compound #20 compound #23 compound #24 compound #26 compound #27 compound #29 compound #32 compound #192 compound #193 compound #194

EXAMPLE 3

2-[(2,4-dichloro-benzoyl)-prop-2-ynyl-amino]-3-phenyl-propionic acid compound #111

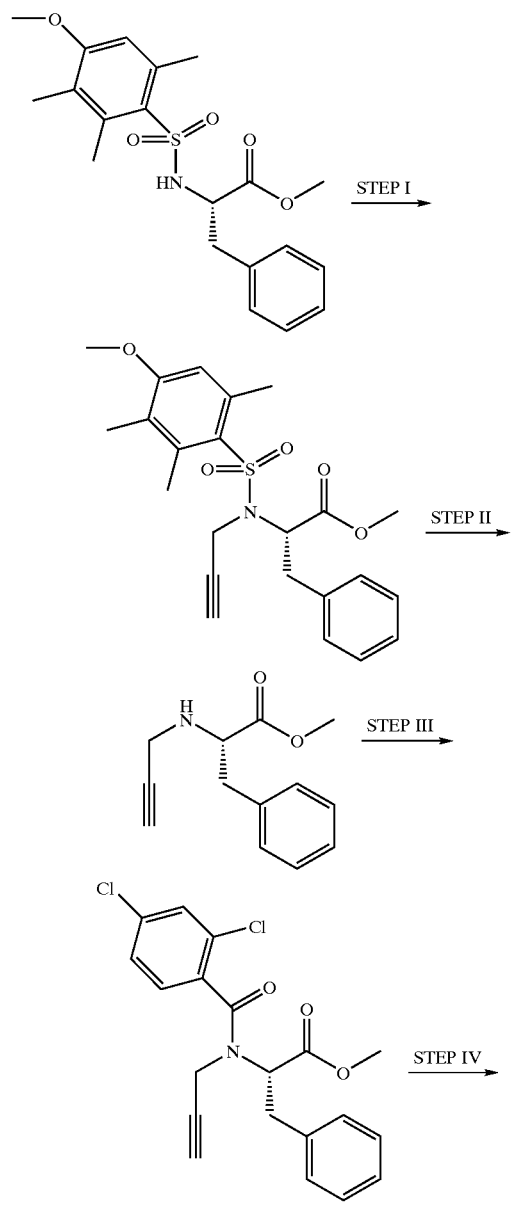

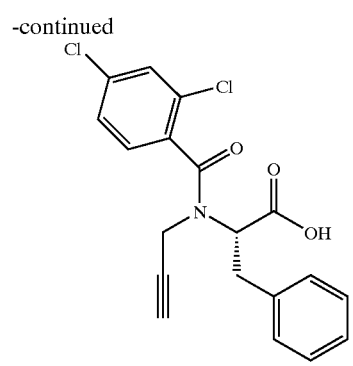

Step I

2-[(4-Methoxy-2,3,6-trimethyl-benzenesulfonyl)-prop-2-ynyl-amino]-3-phenyl-propionic acid methyl ester

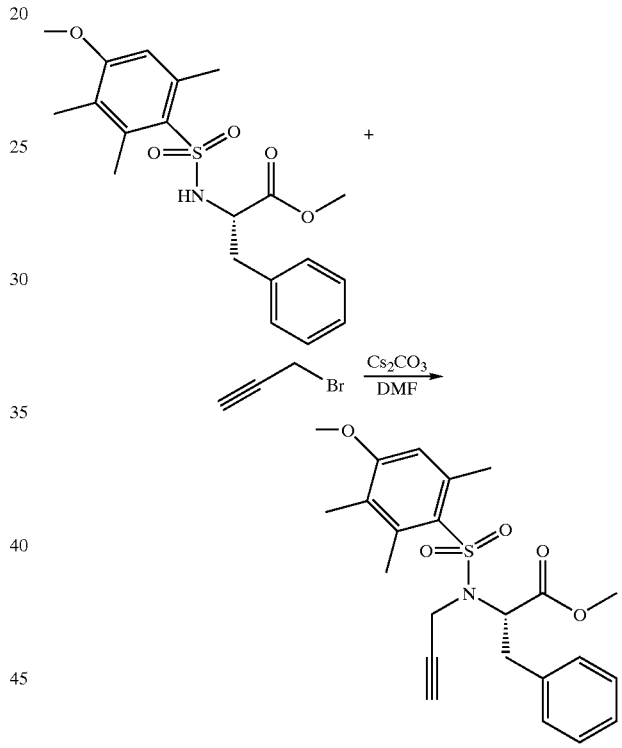

A DMF (8 mL) solution of 2-(4-Methoxy-2,3,6-trimethyl-benzenesulfonylamino)-3-phenyl-propionic acid methyl ester (prepared according to example 2, step I) (200 mg) was cooled to 0° C. and then propargyl bromide (80%, 0.07 mL, 0.61 mmol) and Cs₂CO₃ (200 mg, 0.61 mmol) were added under an atmosphere of N₂. The ice bath was removed and the reaction mixture was stirred at room temperature for 12 h. The mixture was partitioned between ether and water, the ether layer was separated, dried (Na₂SO₄) and concentrated. The residue was purified by silica gel column chromatography using ethyl acetate and hexane (1:3) as eluent to obtain 2-[(4-Methoxy-2,3,6-trimethyl-benzenesulfonyl)-prop-2-ynyl-amino]-3-phenyl-propionic acid methyl ester (185 mg, 85%) as a solid. ¹H NMR (CDCl₃, 400 MHz): δ7.20–7.17 (m, 3H), 7.10–7.08 (m, 2H), 6.56 (s, 1H), 4.42–4.29 (m, 3H), 3.86 (s, 3H), 3.56 (s, 3H), 3.32 (dd, 1H), 3.26 (dd, 1H), 2.66, 2.35 (2s, 6H), 2.21 (t, 1H), 2.08(s, 3H).

Step II
3-Phenyl-2-prop-2-ynylamino-propionic acid methyl ester

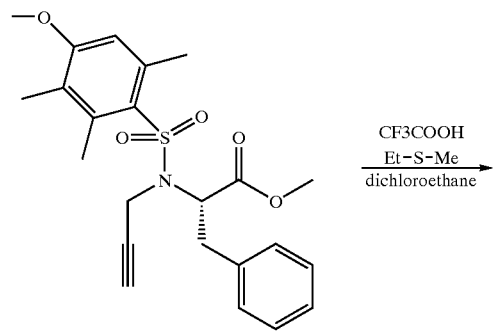

To a solution of 2-[(4-Methoxy-2,3,6-trimethyl-benzenesulfonyl)-prop-2-ynyl-amino]-3-phenyl-propionic acid methyl ester (150 mg, 0.349 mmol) in anhydrous dichloroethane (1.5 mL), trifluoroacetic acid (3.5 mL) and ethyl methyl sulfide (0.16 mL, 1.75 mmol) were added. The reaction mixture was stirred at room temperature under a $N_2$ atmosphere for 12 h. Excess of solvents were removed under reduced pressure and the residue was extracted between saturated $NaHCO_3$ solution and ethyl acetate. The organic layer was separated, dried ($Na_2SO_4$), concentrated. The crude product was purified by silica gel column chromatography using ethyl acetate and hexane (1:3) as eluent to obtain 3-Phenyl-2-prop-2-ynylamino-propionic acid methyl ester as a thick syrup, 70 mg (92%). $^1$H NMR ($CDCl_3$, 400 MHz): δ7.32–7.19 (m, 5H), 3.78 (t, 1H), 3.68 (s, 3H), 3.40 (ABq, 2H), 3.03 (dd, 1H), 2.98 (dd, 1H), 1.99 (t, 1H).

Step III
2-[(2,4-Dichloro-benzoyl)-prop-2-ynyl-amino]-3-phenyl-propionic acid methyl ester

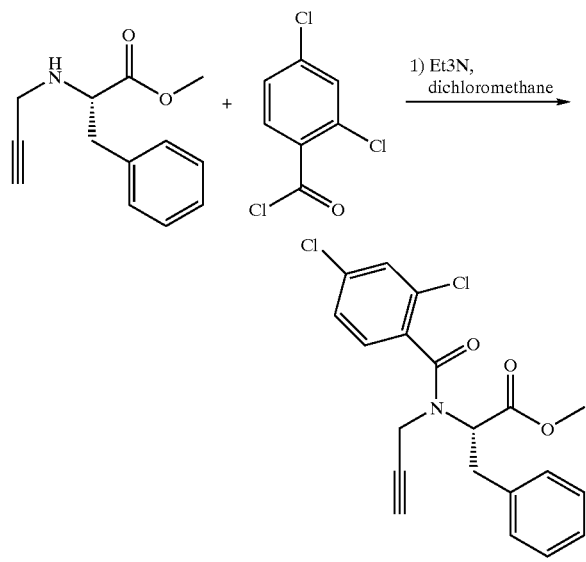

A solution of 3-Phenyl-2-prop-2-ynylamino-propionic acid methyl ester (75 mg, 0.346 mmol) in anhydrous $CH_2Cl_2$ (2 mL) was cooled to 0° C. in an ice bath, then triethylamine (0.1 mL) and 2,4-dichlorobenzoyl chloride (0.06 mL, 0.45 mmol) were added. The mixture was stirred at room temperature for 3 h. Excess of benzoyl chloride was quenched by adding ice-cold water and then the reaction mixture was partitioned between water and $CH_2Cl_2$. The organic layer was separated, dried ($Na_2SO_4$), and concentrated. The residue was purified by silica gel column chromatography using ethyl acetate and hexane (1:3) as eluent to obtain 2-[(2,4-Dichloro-benzoyl)-prop-2-ynyl-amino]-3-phenyl-propionic acid methyl ester as a syrup, 125 mg (93%).

Step IV
2-[(2,4-Dichloro-benzoyl)-prop-2-ynyl-amino]-3-phenyl-propionic acid

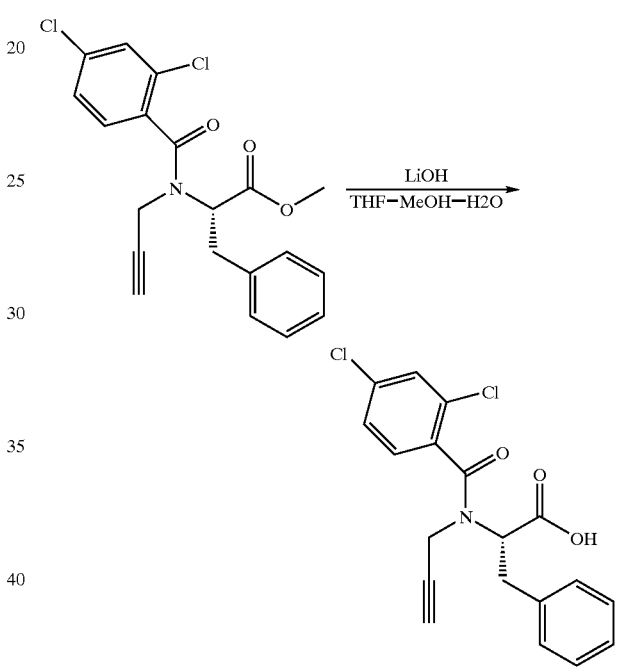

To a THF:MeOH:$H_2O$ (3:2:1) (3 mL) solution of 2-[(2,4-Dichloro-benzoyl)-prop-2-ynyl-amino]-3-phenyl-propionic acid methyl ester (30 mg, 0.076 mmol), 1N aqueous solution of lithium hydroxide (0.46 mL, 0.46 mmol) was added and the reaction mixture was stirred at room temperature for 6 h. Solvents were removed under reduced pressure and the residue was partitioned between ethyl acetate and water. The water layer was acidified using 10% $KHSO_4$ solution and then the organic layer was separated, dried ($Na_2SO_4$), concentrated. The residue was purified by column chromatography (ethyl acetate:hexane 1:1 to ethyl acetate) to obtain 2-[(2,4-dichloro-benzoyl)-prop-2-ynyl-amino]-3-phenyl-propionic acid, 23 mg (81%) as a white solid. The compound contains two other minor rotamers. $^1$H NMR ($CDCl_3$, 400 MHz): δ7.45–7.05 (m, 8H), 6.77 (dd, minor rotamer), 5.70 (d, minor rotamer), 4.99 (bs, minor rotamer), 4.64–4.59 (m, minor rotamer), 4.28 (d, minor rotamer), 4.29–4.18 (m, minor rotamer), 3.79–3.09 (m, 5H), 2.37 (t, minor rotamer), 2.31 (t, minor rotamer), 2.17 (t, 1H). ESI$^-$ (M–H): 375.

The following compounds were prepared in a similar manner as described in example 3:

| compound | #109 |
| compound | #110 |
| compound | #111 |
| compound | #112 |
| compound | #115 |
| compound | #116 |

EXAMPLE 4

2-[(3-Benzofuran-2-yl-prop-2-ynyl)-(2,4-dichloro-benzoyl)-amino]-3-phenyl-propionic acid compound #113

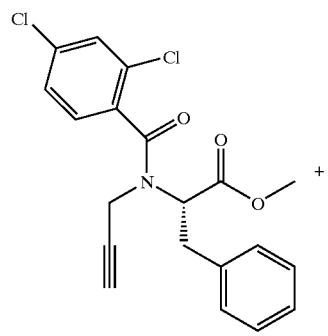

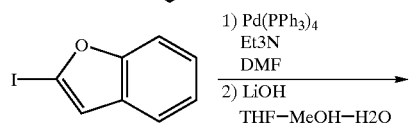

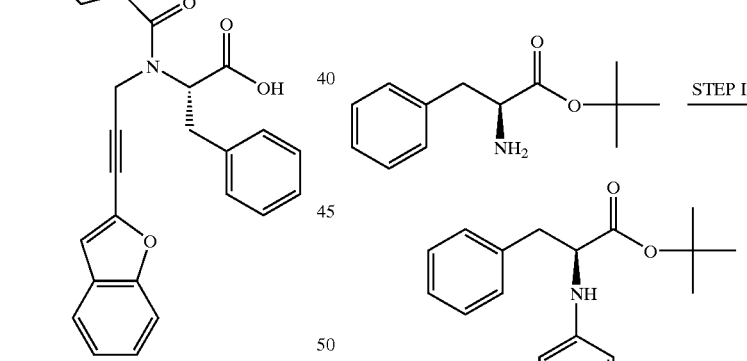

To a solution of 2-[(2,4-Dichloro-benzoyl)-prop-2-ynyl-amino]-3-phenyl-propionic acid methyl ester (prepared according to example 9) (50 mg, 0.128 mmol) and 2-iodobenzofuran (41 mg, 0.166 mmol) in DMF (2 mL), triethylamine (2 mL) and tetrakis(triphenylphosphine)palladium(0) (15 mg, 0.01 mmol) were added and the reaction mixture was stirred under reflux conditions for 4 h under a $N_2$ atmosphere. DMF and triethylamine were removed under reduced pressure and the residue was partitioned between water and ethyl acetate. The organic layer was separated, dried ($Na_2SO_4$), concentrated and the residue was purified by column chromatography using ethyl acetate and hexane (1:4) as eluent to obtain 2-[(3-Benzofuran-2-yl-prop-2-ynyl)-(2,4-dichloro-benzoyl)-amino]-3-phenyl-propionic acid methyl ester as a thick syrup, 50 mg (76%). The compound contains two other rotamers. $^1$H-NMR (CDCl$_3$, 300 MHz): δ7.58–7.09 (m, 12H), 6.98 (s, minor rotamer), 6.97 (d, minor rotamer), 6.85 (dd, minor rotamer), 6.83 (s, 1H), 5.82 (d, minor rotamer), 5.25 (bs, minor rotamer), 5.10 (bs, minor rotamer), 4.88–4.52 (m, minor rotamer), 4.35–3.21 (m, 5H), 3.78 (s, 3H), 3.76, 3.65 (2s, minor rotamer).

A procedure similar to step IV (example 9) was used for the hydrolysis of 2-[(3-Benzofuran-2-yl-prop-2-ynyl)-(2,4-dichloro-benzoyl)-amino]-3-phenyl-propionic acid methyl ester. 2-[(3-Benzofuran-2-yl-prop-2-ynyl)-(2,4-dichloro-benzoyl)-amino]-3-phenyl-propionic acid was isolated after silica gel column chromatography using ethyl acetate:hexane (1:1) to ethyl acetate as eluent as a solid, 20 mg (69%). The compound contains two other rotamers. $^1$H-NMR (CDCl$_3$, 400 MHz): 7.82 (d, minor rotamer), 7.53–7.05 (m, 12H), 6.93 (s, minor rotamer), 6.89 (d, minor rotamer), 6.81 (s, 1H), 6.80 (dd, minor rotamer), 6.49 (m, minor rotamer), 6.26 (d, minor rotamer), 5.73 (d, minor rotamer), 5.22 (bs, minor rotamer), 5.09–4.45 (m, minor rotamers), 4.36–3.11 (m, 5H). ESI$^-$ (M–H): 491.

EXAMPLE 5

2-[(4-Benzofuran-2-yl-phenyl)-(2,4-dichloro-benzoyl)-amino]-3-phenyl-propionic acid compound #114

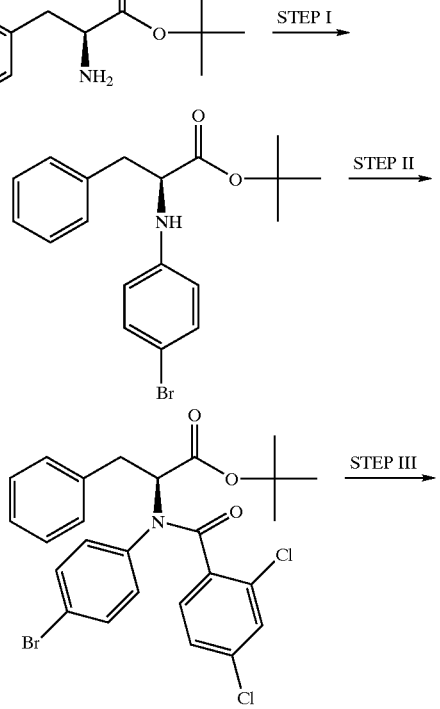

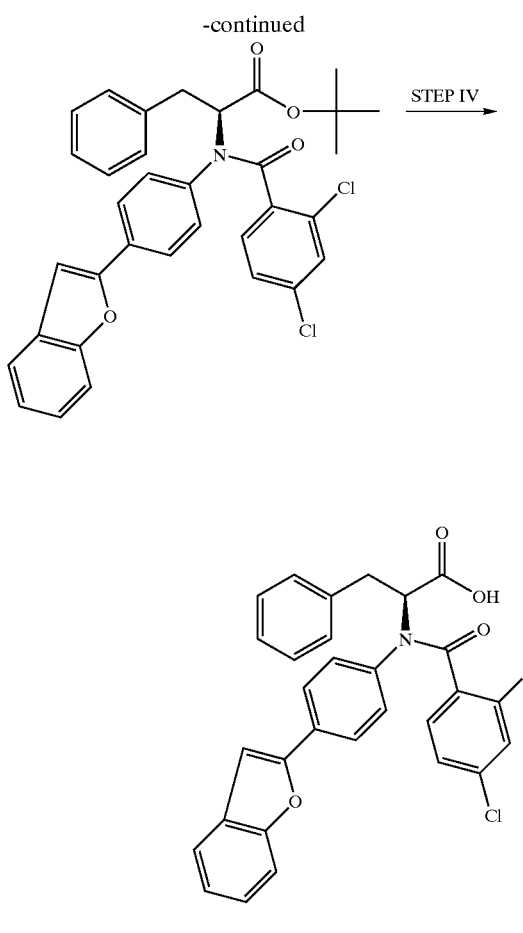

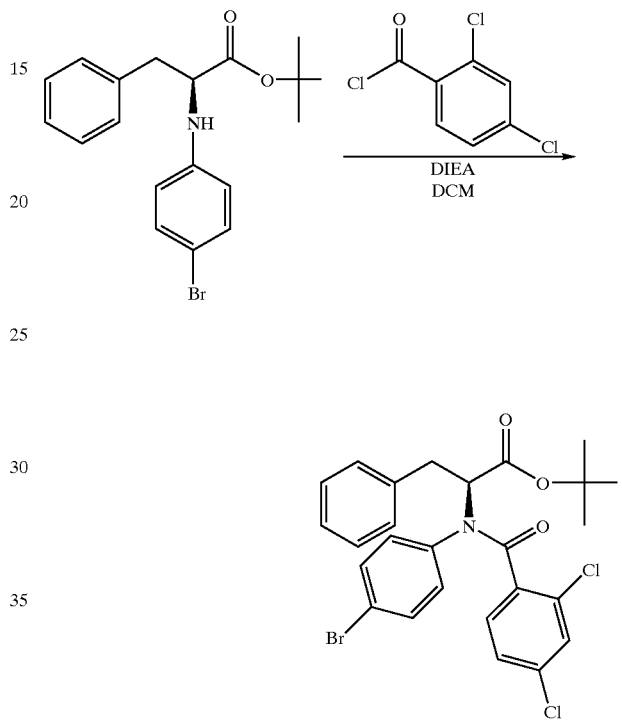

Step I
2-(4-Bromo-phenylamino)-3-phenyl-propionic acid tert-butyl ester

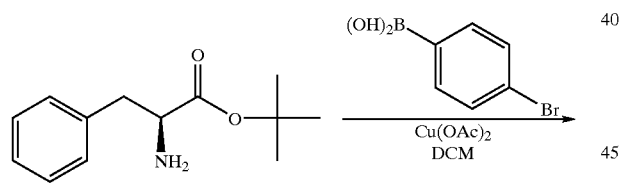

A mixture of L-phenylalanine tert-butyl ester (1.47 g, 6.64 mmol), 4-bromophenylboronic acid (2.67 g, 13.28 mmol), triethylamine (1.9 mL, 13.28 mmol) and copper (II) acetate (1.21 g, 6.64 mmol) in dichloromethane (50 mL) was stirred at room temperature for 24 h. The solids were removed by filtration through a pad of silica gel and the desired product was obtained by chromatography eluting with 5% ethyl acetate in hexanes. $^1$H NMR (CDCl$_3$)7.2 (m, 8 H), 6.48 (d, 2 H), 4.18 (t, 2 H, H-2 and NH), 3.08 (d, 2 H), 1.35 (s, 9 H)

Step II

2-[(4-Bromo-phenyl)-(2,4-dichloro-benzoyl)-amino]-3-phenyl-propionic acid tert-butyl ester This compound was prepared in a similar manner as for step I in example 1. $^1$H NMR (CDCl3) 7.2 (m, )7.2 (d), 7.0 (d, 6.93 (d), 6.4 br s), 4.62 (t, 1 H), 3.4 9 m, 2 H), 1.3 (s, 9 H)

Step III

2-[(4-Benzofuran-2-yl-phenyl)-(2,4-dichloro-benzoyl)-amino]-3-phenyl-propionic acid tert-butyl ester

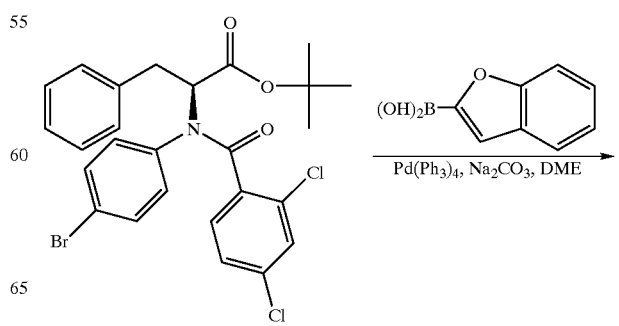

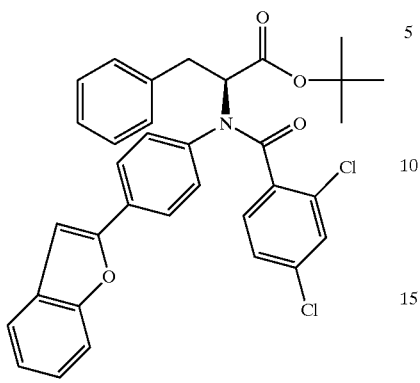

This compound was prepared in a similar manner as for step III in example 2. $^1$H NMR (CDCl$_3$) 7.6 (m), 7.3 (m), 6.9 (m), 6.7 (m), 4.8 (m), 4.2 (m), 3.5 (m)

Step IV

2-[(4-Benzofuran-2-yl-phenyl)-(2,4-dichloro-benzoyl)-amino]-3-phenyl-propionic acid

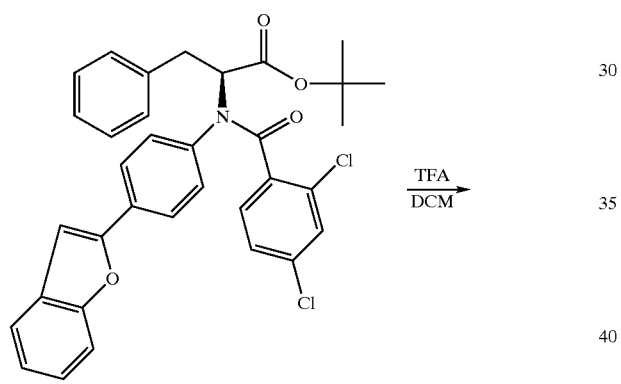

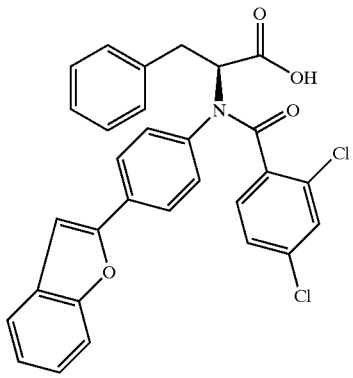

This compound was prepared in a similar manner as for step IV in example 1. $^1$H NMR (DMSO) 13.1 (br s, 1 H), 7.6 (m, 5 H), 7.3 (m, 9 H), 7.01 (d, 2 H), 6.72 (d, 2 H), 4.95 (dd, 1 H), 3.39 (2 H)

The following compounds were prepared in a similar manner as described in example 5:

Compound 190 Compound 191

EXAMPLE 5

The following compound was obtained from Oxford Diversity:

Compound #1,

The following compounds were prepared as listed in Table 1 and Table 2.

TABLE 1

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #1 | 3-[3-(2,6-Dichloro-py-ridin-4-yl)-1-(4-thio-phen-2-yl-ben-zyl)-ureido]-3-thio-phen-2-yl-propionic acid | 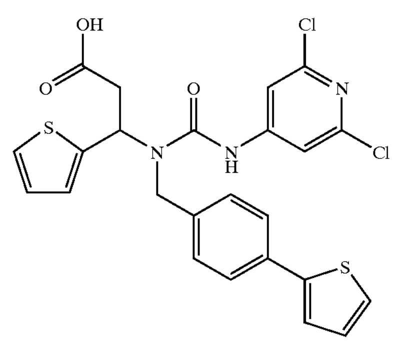 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #2 | (2s)-2-[(2,4-Dichloro-benzoyl)-4-thiazol-2-yl-benzyl)-amino]-3-phenyl-propionic acid, | 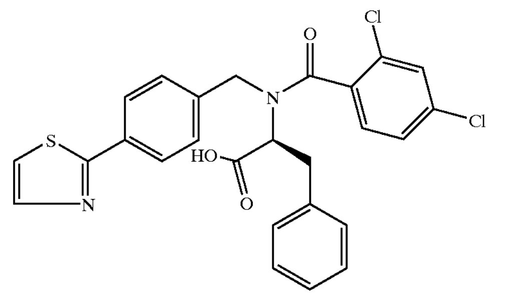 | +++ | |
| compound #3 | (2s)-3-[(4-Bromo-benzyl)-(2,4-dichloro-benzoyl)-amino]-3-phenyl-propionic acid, | 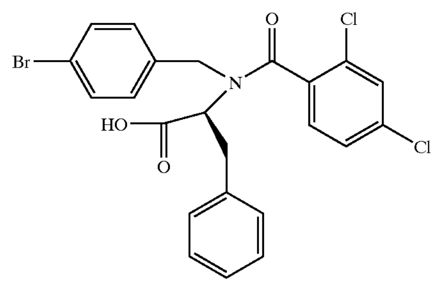 | +++ | |
| compound #4 | (2s)-2-[(4-Benzofuran-2-yl-benzyl)-(2,4-dichloro-benzoyl)-amino]-3-phenyl-propionic acid, | 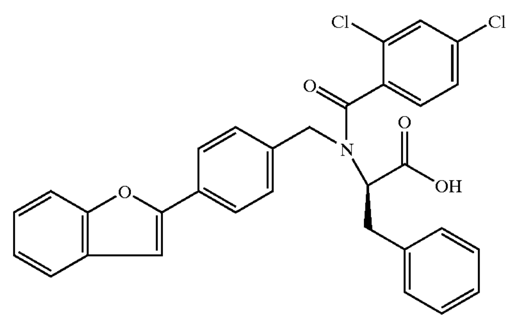 | +++ | |
| compound #5 | (2s)-2-[(4-Benzofuran-2-yl-benzyl)-(4-methoxy-2,3,6-trimethyl-benzenesulfonyl)-amino]-3-phenyl-propionic acid, | 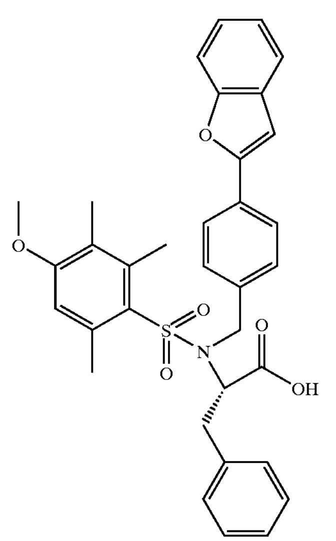 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #6 | (2s)-2-[(4-Benzo-furan-2-yl-ben-zyl)-(4-methoxy-2,3,6-tri-methyl-benzene-sulfonyl)-a-mino]-3-phenyl-propionic acid, | 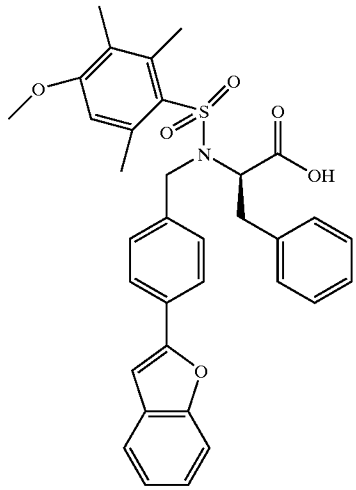 | +++ | |
| compound #7 | (2s)-2-[(3-Benzo-furan-2-yl-ben-zyl)-(4-methoxy-2,3,6-tri-methyl-benzene-sulfonyl)-a-mino]-3-phenyl-propionic acid, compound #7 | 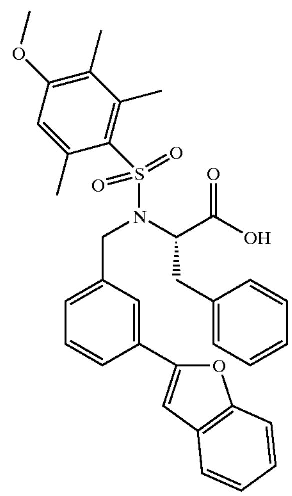 | +++ | |
| compound #8 | 3-[(4-Iodo-benzyl)-(4-meth-oxy-2,3,6-tri-methyl-benzene-sulfonyl)-a-mino]-3-thiophen-2-yl-priopionic acid ethyl ester, | 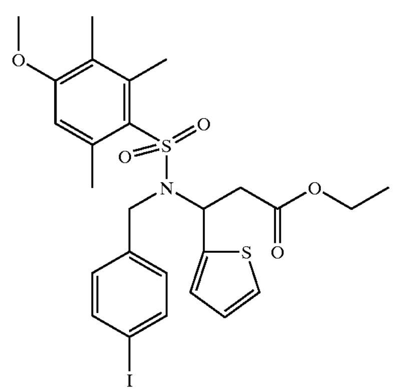 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #9 | (2s)-2-[(3-Bromo-benzyl)-(2,4-dichloro-benzoyl)-amino]-3-phenyl-propionic acid, | 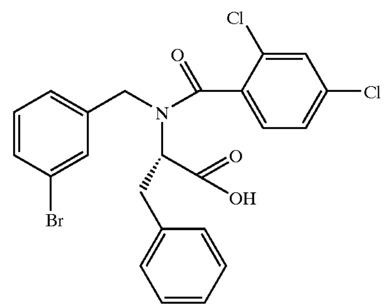 | +++ | |
| compound #10 | (2s)-2-[(3-Bromo-benzyl)-(2-chloro-benzoyl)-amino]-3-phenyl-propionic acid, | 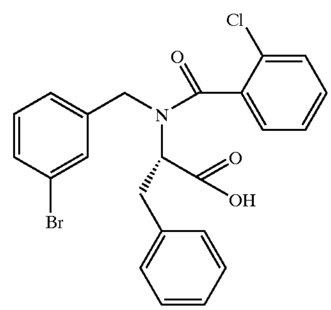 | + | |
| compound #11 | (2s)-2-[(3-Benzofuran-2-yl-benzyl)-(2,4-dichloro-benzoyl)-amino]-3-phenyl-propionic acid, | 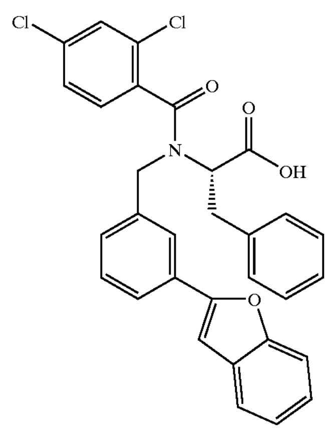 | ++ | |
| compound #12 | (2s)-2-[(2,4-Dichloro-benzoyl)-(4-iodo-benzyl)-amino]-3-phenyl-propionic acid, | 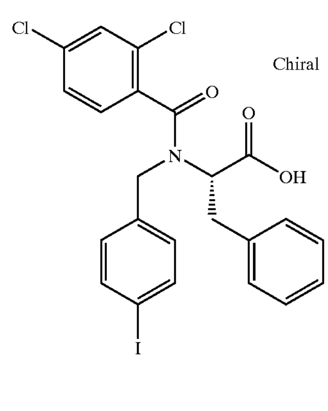 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #13 | (2s)-2-[(3-Iodo-benzyl)-(4-methoxy-2,3,6-trimethyl-benzene-sulfonyl)-amino]-3-phenyl-propionic acid, | 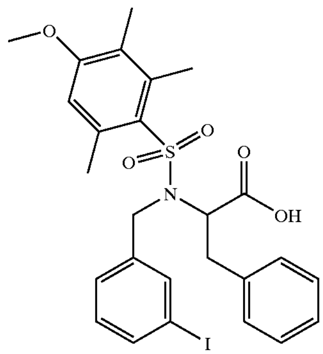 | ++ | |
| compound #14 | (2s)-2-[(4-Bromo-benzyl)-(4-methoxy-2,3,6-trimethyl-benzene-sulfonyl)-amino]-3-phenyl-propionic acid, | 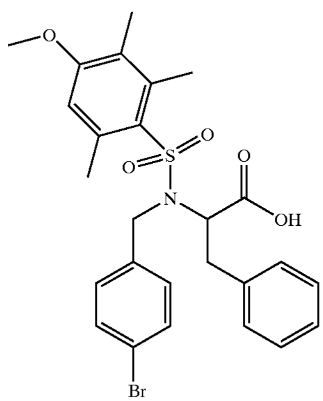 | ++ | |
| compound #15 | (2s)-2-[(3-Bromo-benzyl)-(4-chloro-benzoyl)-amino]-3-phenyl-propionic acid, | 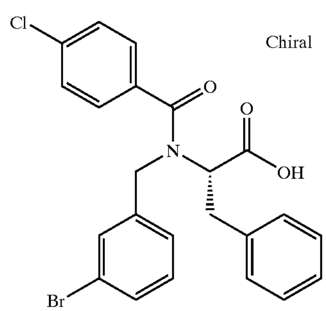 | ++ | |
| compound #16 | (2s)-2-[(4-Iodo-benzyl)-(4-methoxy-2,3,6-trimethyl-benzene-sulfonyl)-amino]-3-phenyl-propionic acid | 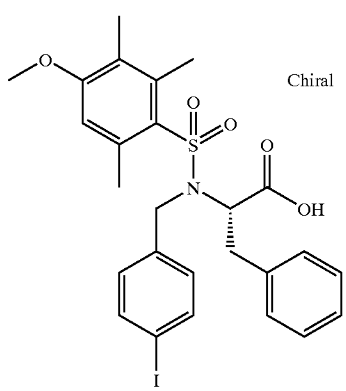 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #17 | (2s)-2-[(3-Bromo-benzyl)-(4-methoxy-2,3,6-trimethyl-benzenesulfonyl)-amino]-3-phenyl-propionic acid | 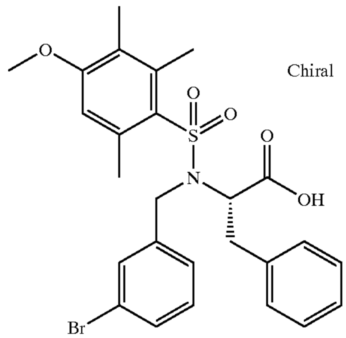 | ++ | |
| compound #18 | (2s)-5-(4-{[(1s-1-Carboxy-2-phenyl-ethyl)-(4-methoxy-2,3,6-trimethyl-benzenesulfonyl)-amino]-methyl}-phenyl)-furan-2-carboxylic acid methyl ester | 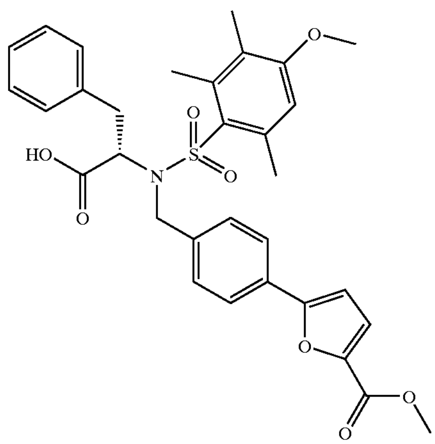 | + | |
| compound #19 | (2s)-2-[(3-Bromo-benzyl)-(3,4-dichloro-benzoyl)-amino]-3-phenyl-propionic acid | 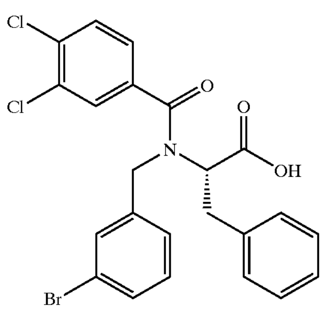 | + | |
| compound #20 | (2s)-2-[(3-Bromo-benzyl)-(2,4-dichloro-benzenesulfonyl)-amino]-3-phenyl-propionic acid | 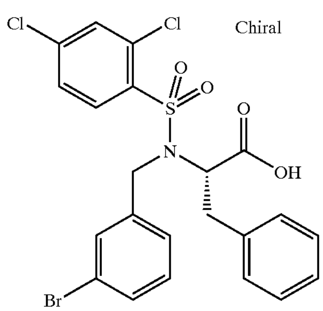 | + | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #21 | (2s)-3-(1-Benzyl-1h-imidazol-4-yl)-2-[(3-bromo-benzyl)-(2,4-dichloro-benzoyl)-amino]-propionic acid | 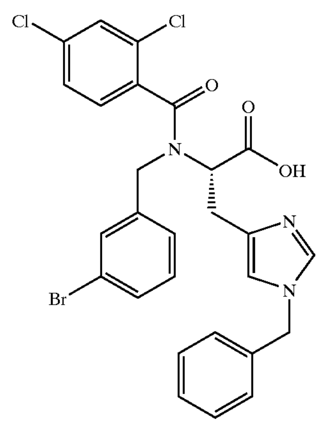 | ++ | |
| compound #22 | (2s)-2-{(3-Bromo-benzyl)-[(2,4-dichloro-phenyl)-acetyl]-amino}-3-phenyl-propionic acid | 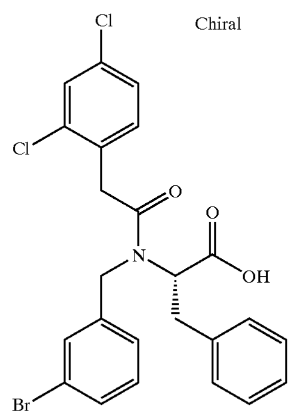 | ++ | |
| compound #23 | (2s)-5-(4-{[(1s-1-Carboxy-2-phenyl-ethyl)-(4-methoxy-2,3,6-trimethyl-benzene-sulfonyl)-amino]-methyl}-phenyl)-thiophene-2-carboxylic acid methyl ester | 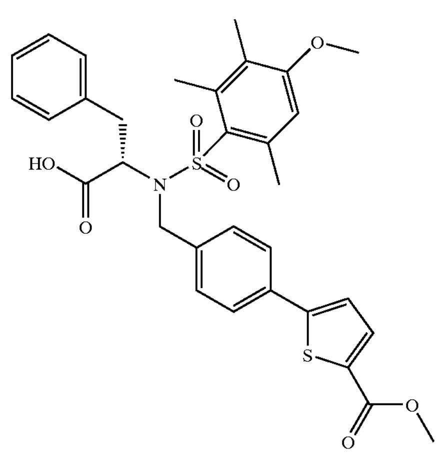 | + | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #24 | (2s)-2-[(2-Bromo-benzyl)-(4-methoxy-2,3,6-trimethyl-benzenesulfonyl)-amino]-3-phenyl-propionic acid | 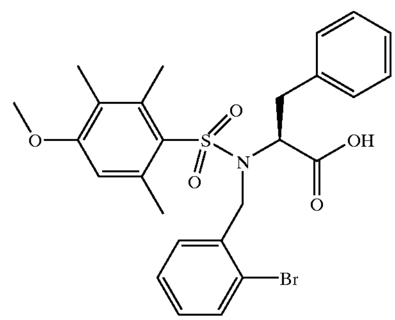 | ++ | |
| compound #25 | (2s)-2-[(3-Bromo-benzyl)-(4-chloro-phenoxy-carbonyl)-amino]-3-phenyl-propionic acid | 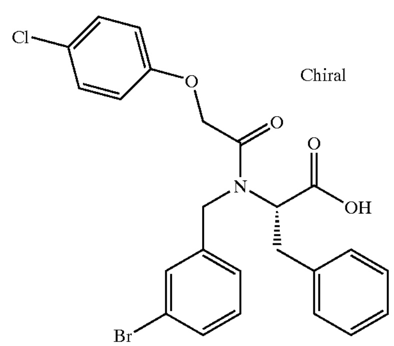 | + | |
| compound #26 | (2s)-Triethyl-ammonium; 2-[(3-benzofuran-2-yl-benzyl)-(4-methoxy-2,3,6-trimethyl-benzenesulfonyl)-amino]-3-phenyl-propionate | 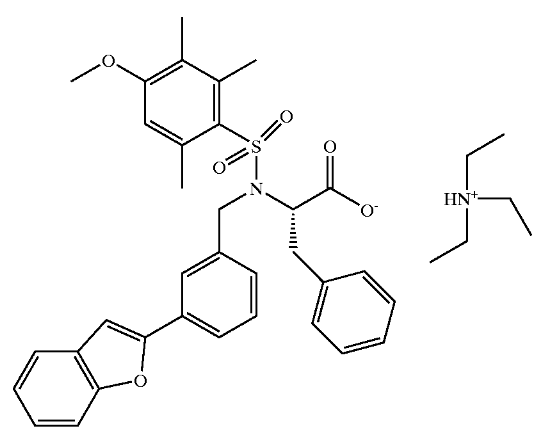 | +++ | |
| Compound #27 | 2-[Allyl-(4-chloro-2-iodo-benzoyl)-amino]-3-phenyl-propionic acid | 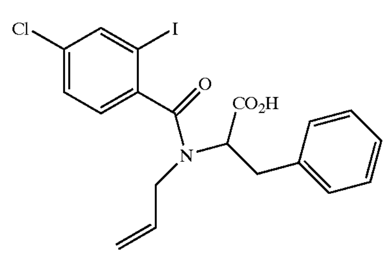 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #28 | (2s)-2-[(3-Bromo-benzyl)-(2,4-dimethyl-benzoyl)-amino]-3-phenyl-propionic acid | 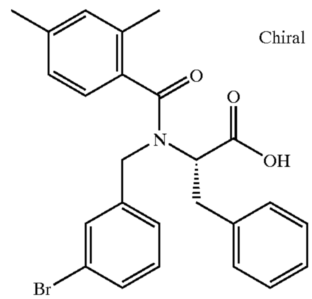 | +++ | |
| Compound #29 | 3-(4-Benzofuran-2-yl-phenyl)-2-[(2,4-dichloro-benzoyl)-methyl-amino]-propionic acid | 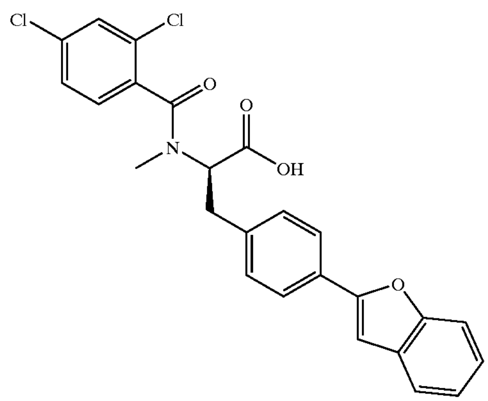 | ++ | |
| compound #30 | (2s)-2-[(3-Bromo-benzyl)-(2,4-dichloro-benzoyl)-amino]-3-phenyl-propionic acid | 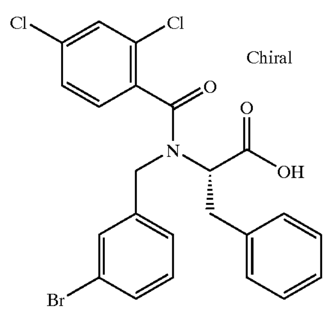 | +++ | |
| compound #31 | (2s)-2-[(3-Benzofuran-2-yl-benzyl)-(2,4-dimethyl-benzoyl)-amino]-3-phenyl-propionic acid | 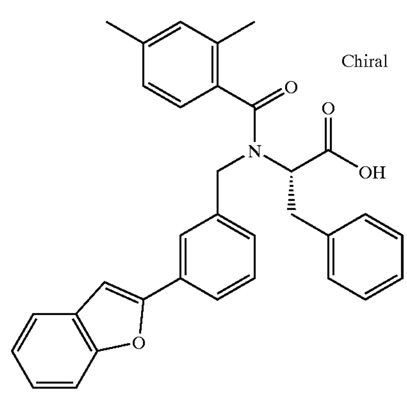 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #32 | (2s)-2-[(4-Benzo-furan-2-yl-ben-zyl)-(4-methoxy-2,3,6-tri-methyl-benzene-sulfonyl)-a-mino]-3-(4-hy-droxy-phenyl)-propionic acid | 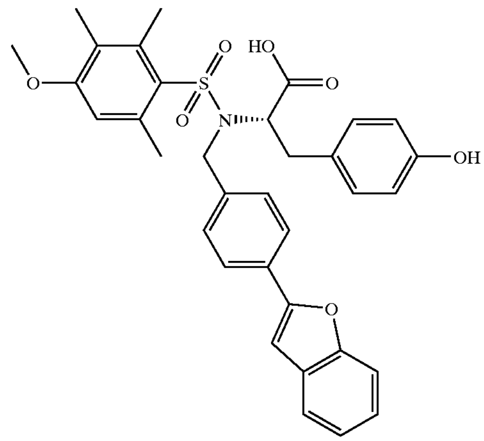 | +++ | |
| compound #33 | (2s)-2-[(4-Benzo-furan-2-yl-ben-zyl)-(2,4-di-chloro-benzoyl)-a-mino]-3-(4-hy-droxy-phenyl)-propionic acid | 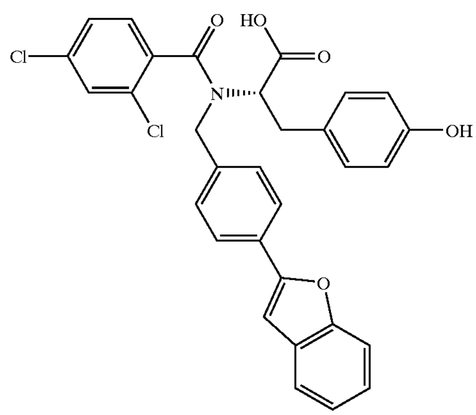 | +++ | |
| compound #34 | (2s)-2-[(3-Bromo-ben-zyl)-(4-chloro-2-meth-yl-benzoyl)-a-mino]-3-phenyl-propionic acid | 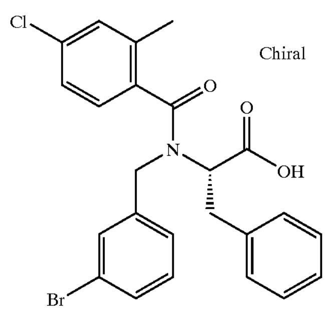 | +++ | |
| compound #35 | (2s)-3-[(3-Bromo-ben-zyl)-(4-chloro-2-i-odo-benzoyl)-a-mino]-3-phenyl-propionic acid | 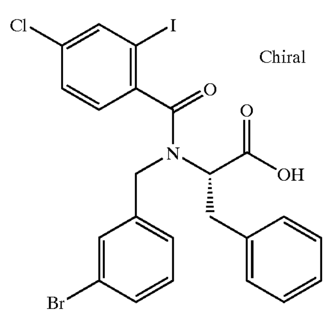 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #36 | (2s)-2-[(3-Bromo-benzyl)-(2-bromo-4-chloro-benzoyl)-amino]-3-phenyl-propionic acid | 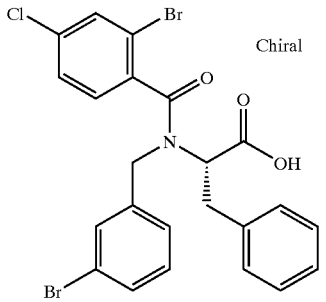 | +++ | |
| compound #37 | (2s)-2-{(3-Benzofuran-2-yl-benzyl)-[(2,4-dichloro-phenyl)-acetyl]-amino}-3-phenyl-propionic acid | 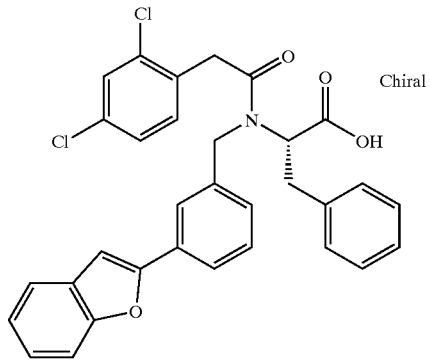 | +++ | |
| compound #38 | (2s)-2-[(4-Benzofuran-2-yl-benzyl)-(2,4-dichloro-phenyl)-amino]-3-phenyl-propionic acid | 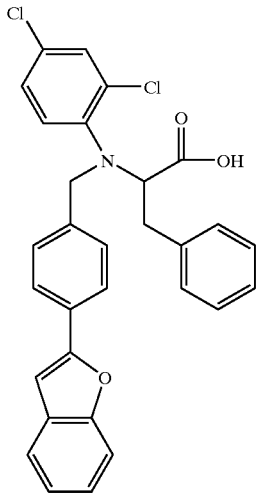 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #39 | (2s)-2-[(2,4-Dichloro-benzoyl)-naphthalen-2-ylmethyl-amino]-3-phenyl-propionic acid | 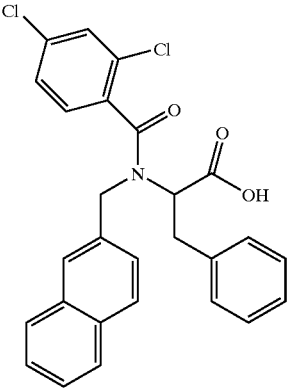 | +++ | |
| compound #40 | (2s)-2-[(2,4-Dichloro-benzoyl)-(9,10-dioxo-9,10-dihydro-anthracen-2-ylmethyl)-amino]-3-phenyl-propionic acid | 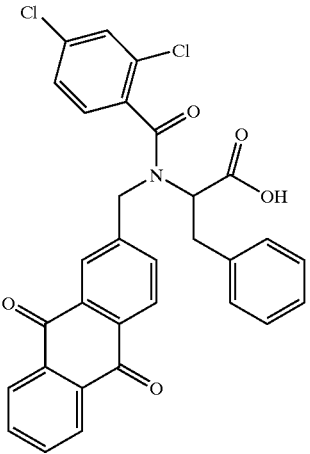 | +++ | |
| compound #41 | (2s)-2-[[3-(3-Chloro-benzoyl)-benzyl]-(2,4-dichloro-benzoyl)-amino]-3-phenyl-propionic acid | 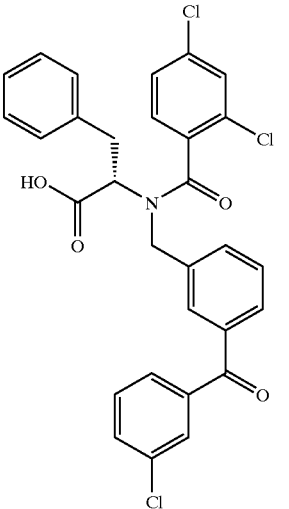 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #42 | (2s)-2-{(2,4-Di-chloro-benzoyl)-[3-(2,4-di-fluoro-ben-zoyl)-benzyl]-a-mino}-3-phenyl-propionic acid | 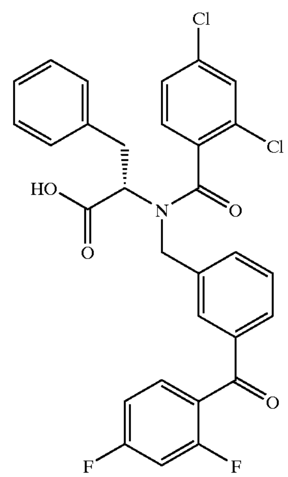 | +++ | |
| compound #43 | (2s)-2-[{3-[3-(2-Chlor-o-phenyl)-5-meth-yl-isoxazole-4-carbo-nyl]-benzyl}-(2,4-di-chloro-ben-zoyl)-amino]-3-phe-nyl-propionic acid | 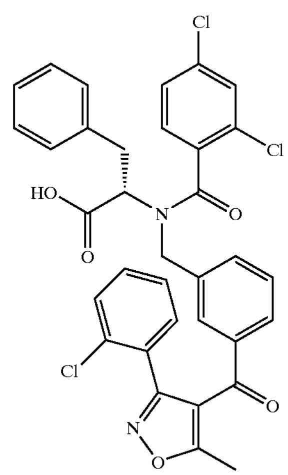 | +++ | |
| compound #44 | (2s)-2-{(2,4-Di-chloro-benzoyl)-[3-(2,4-di-chloro-ben-zoyl)-benzyl]-a-mino}-3-phenyl-propionic acid | 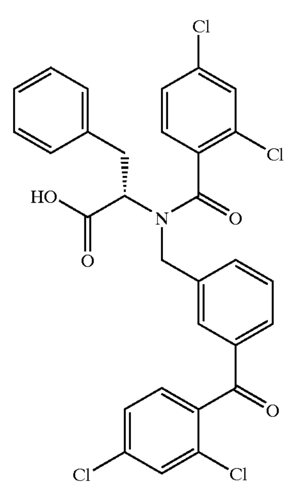 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #45 | (2s)-2-[(3-Benzo-oxazol-2-yl-ben-zyl)-(2,4-di-chloro-benzoyl)-a-mino]-3-phenyl-propionic acid | 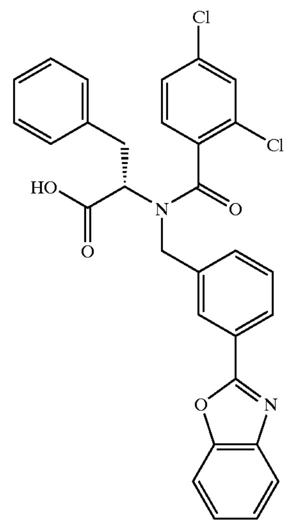 | +++ | |
| compound #46 | (2s)-2-[(3-Bromo-ben-zyl)-(4-chloro-2-eth-yl-benzoyl)-a-mino]-3-phenyl-propionic acid | 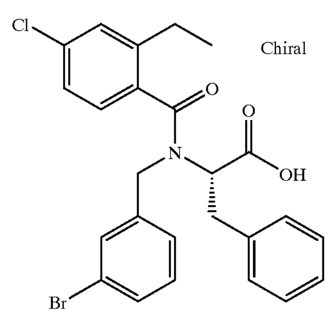 | +++ | |
| compound #47 | (2s)-2-[(4-Benzo-furan-2-yl-ben-zyl)-(2,4-di-chloro-benzoyl)-a-mino]-3-cyclo-hexyl-propionic acid | 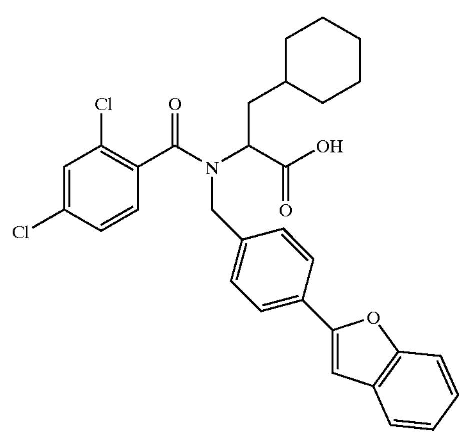 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #48 | (2s)-2-[(3-Benzo-furan-2-yl-benzyl)-(4-chloro-2-methyl-benzoyl)-amino]-3-phenyl-propionic acid | 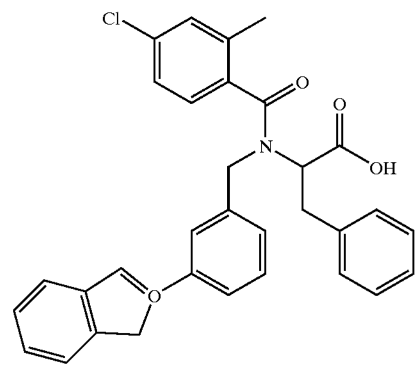 | +++ | |
| compound #49 | (2s)-2-[(3-Benzo-furan-2-yl-benzyl)-(2-bromo-4-chloro-benzoyl)-amino]-3-phenyl-propionic acid | 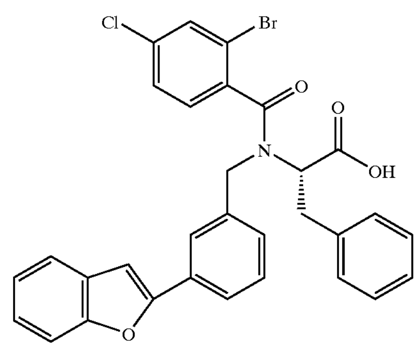 | +++ | |
| compound #50 | (2s)-2-[(3-Bromo-benzyl)-(4-chloro-2-vinyl-benzoyl)-amino]-3-phenyl-propionic acid | 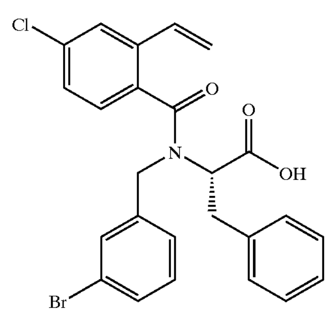 | +++ | |
| compound #51 | (2s)-2-[(2,4-Dichloro-benzoyl)-(3-fluoro-benzyl)-amino]-3-phenyl-propionic acid | 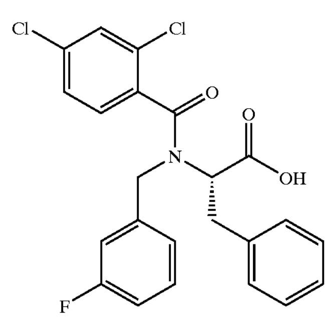 | +++ | |

TABLE 1-continued

LIST OF COMPOUNDS HAVING POLYMERASE ACTIVITY

| Compound # | Compound Name | Structure | RNA pol Assay 1 IC$_{50}$ (μm) | RNA pol Assay 2 IC$_{50}$ (μm) |
|---|---|---|---|---|
| compound #52 | (2s)-2-[(3-Chloro-benzyl)-(2,4-dichloro-benzoyl)-amino]-3-phenyl-propionic acid | 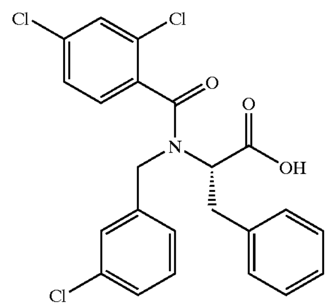 | +++ | |
| Compound #53 | (2S)-2-[(2,4-Dichloro-benzoyl)-(3-nitro-benzyl)-amino]-3-phenyl-propionic acid, | 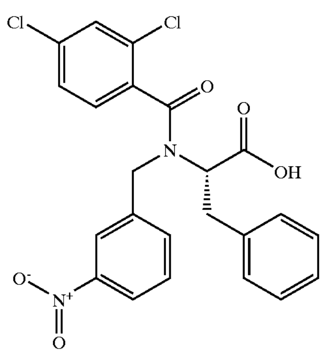 | +++ | |
| compound #54 | (2S)-2-[(3-Cyano-benzyl)-(2,4-dichloro-benzoyl)-amino]-3-phenyl-propionic acid | 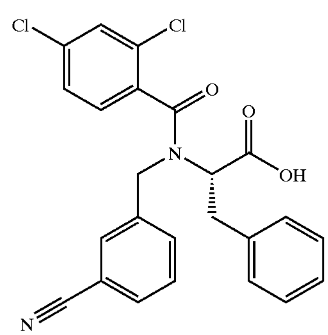 | +++ | |
| compound #55 | (2s)-2-{(2-Chloro-benzoyl)-[5-(3-chloro-phenyl)-furan-2-ylmethyl]-amino}-3-phenyl-propionic acid | 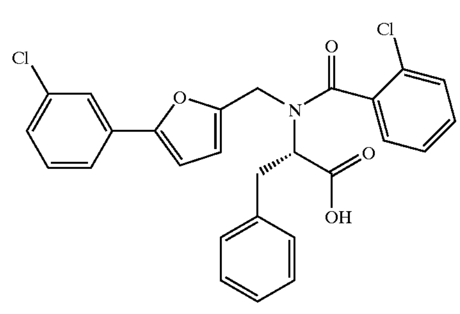 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #56 | (2s)-2-{(2,4-Dichloro-benzoyl)-[5-(3-trifluoromethyl-phenyl)-furan-2-ylmethyl]-amino}-3-phenyl-propionic acid | 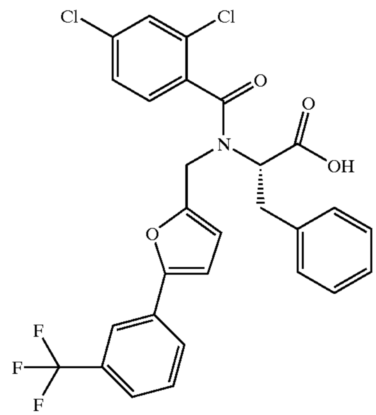 | +++ | |
| compound #57 | (2s)-2-[(5-Bromo-furan-2-ylmethyl)-(2,4-dichloro-benzoyl)-amino]-3-phenyl-propionic acid | 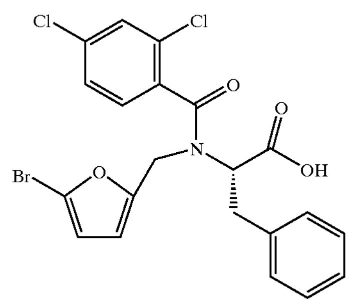 | ++ | |
| compound #58 | (2s)-2-[(5-Benzofuran-2-yl-furan-2-ylmethyl)-(2,4-dichloro-benzoyl)-amino]-3-phenyl-propionic acid | 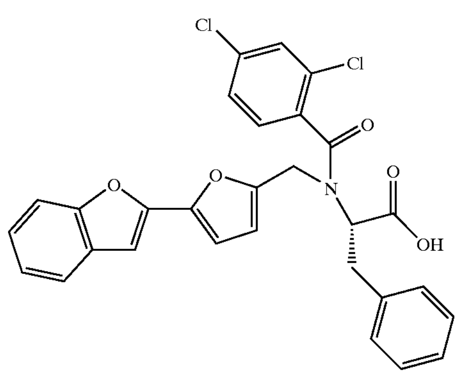 | +++ | |
| compound #59 | (2s)-2-[[5-(4-Bromo-phenyl)-furan-2-ylmethyl]-(2,4-dichloro-benzoyl)-amino]-3-phenyl-propionic acid | 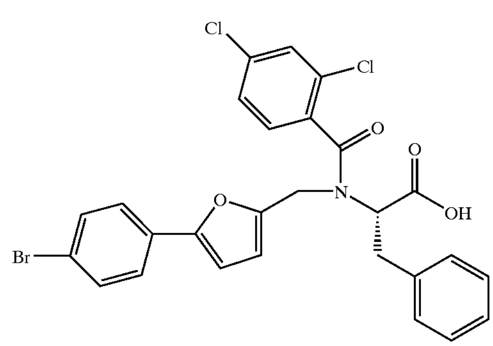 | +++ | |

TABLE 1-continued

LIST OF COMPOUNDS HAVING POLYMERASE ACTIVITY

| Compound # | Compound Name | Structure | RNA pol Assay 1 IC$_{50}$ (μm) | RNA pol Assay 2 IC$_{50}$ (μm) |
|---|---|---|---|---|
| compound #60 | (2s)-2-[[5-(2-Chloro-phenyl)-furan-2-ylmethyl]-(2,4-dichloro-benzoyl)-amino]-3-phenyl-propionic acid | 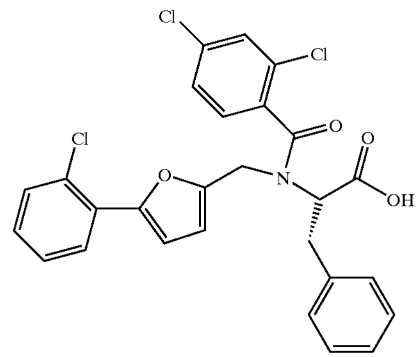 | +++ | |
| compound #61 | (2s)-2-[[5-(2-Chloro-5-trifluoromethyl-phenyl)-furan-2-ylmethyl]-(2,4-dichloro-benzoyl)-amino]-3-phenyl-propionic acid | 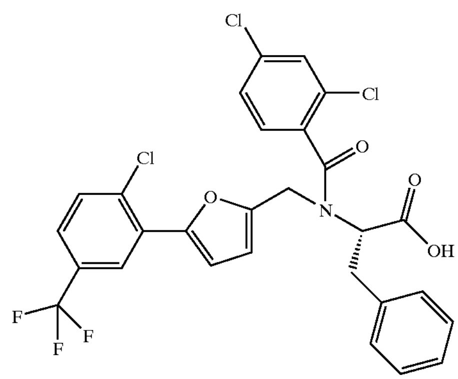 | +++ | |
| compound #62 | (2s)-2-{(2,4-Dichloro-benzoyl)-[5-(2-nitro-phenyl)-furan-2-ylmethyl]-amino}-3-phenyl-propionic acid | 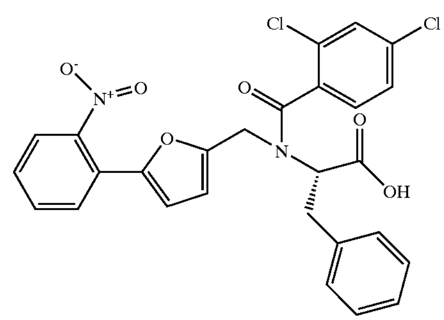 | +++ | |
| compound #63 | (3s)-3-{(2,4-Dichloro-benzoyl)-[5-(3-trifluoromethyl-phenyl)-furan-2-ylmethyl]-amino}-4-phenyl-butyric acid | 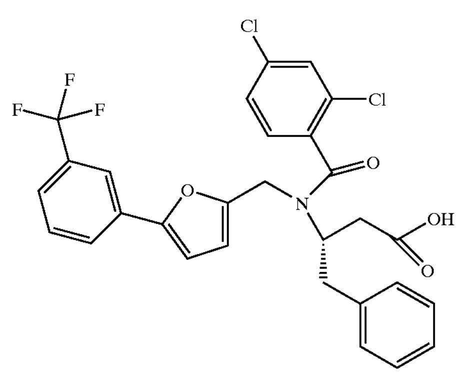 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #64 | 2-{(2,4-Dichloro-benzoyl)-[2-(3-nitro-phenyl)-thiazol-5-ylmethyl]-amino}-3-phenyl-propionic acid | 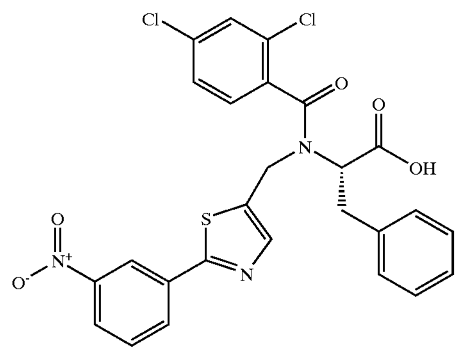 | | +++ |
| compound #65 | (2s)-2-{(2,4-Dichloro-benzoyl)-[5-(3,4-dichloro-phenyl)-furan-2-ylmethyl]-amino}-3-phenyl-propionic acid | 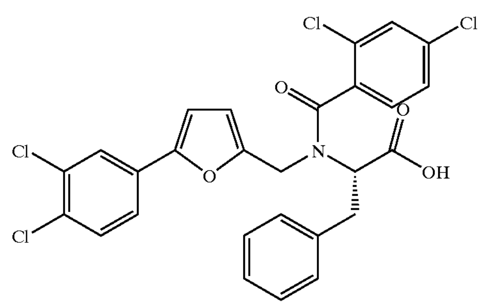 | | +++ |
| compound #66 | (2s)-2-[Benzofuran-2-ylmethyl-(2,4-dichloro-benzyl)-amino]-3-phenyl-propionic acid | 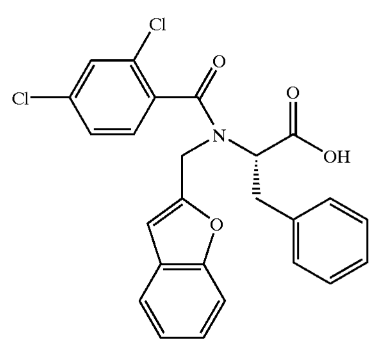 | | +++ |
| compound #67 | (2s)-2-{(2,4-Dichloro-benzoyl)-[5-(2,4-dichloro-phenyl)-furan-2-ylmethyl]-amino}-3-phenyl-propionic acid | 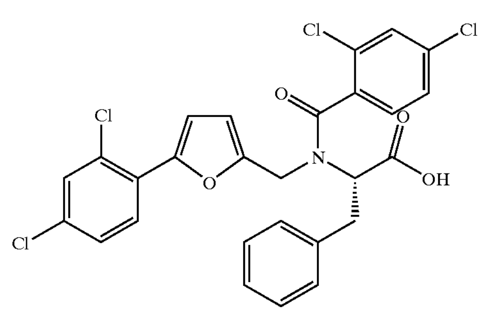 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #68 | (2s)-2-[(2-Bromo-4-chloro-benzoyl)-(5-bromo-furan-2-ylmethyl)-amino]-3-phenyl-propionic acid | 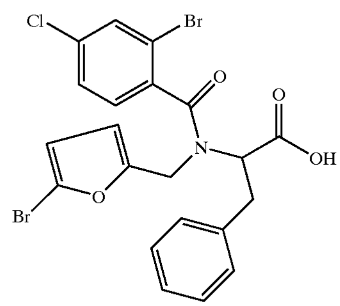 | +++ | |
| compound #69 | (2s)-2-[[5-(3-Chloro-4-fluoro-phenyl)-furan-2-ylmethyl]-(2,4-dichloro-benzoyl)-amino]-3-phenyl-propionic acid | 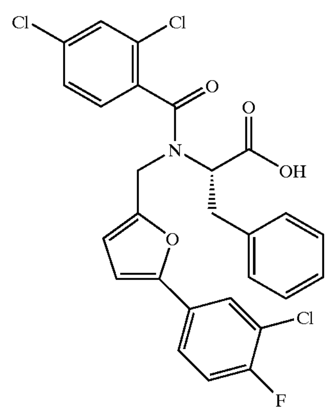 | +++ | |
| compound #70 | (2s)-2-[[5-(4-Chloro-3-fluoro-phenyl)-furan-2-ylmethyl]-(2,4-dichloro-benzoyl)-amino]-3-phenyl-propionic acid | 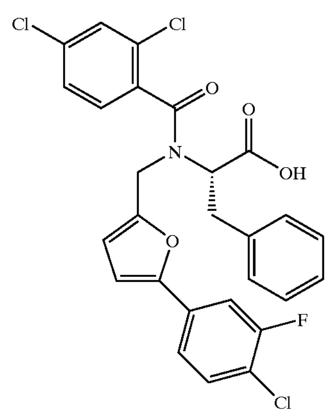 | +++ | |
| compound #71 | (2s)-2-[(5-Bromo-furan-2-ylmethyl)-(4-chloro-2-iodo-benzoyl)-amino]-3-phenyl-propionic acid | 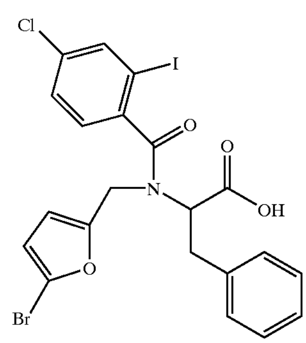 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #72 | (2s)-2-(5-{[(1s-1-Carboxy-2-phenyl-ethyl)-(2,4-dichloro-benzoyl)-amino]-methyl}-furan-2-yl)-benzoic acid ethyl ester | 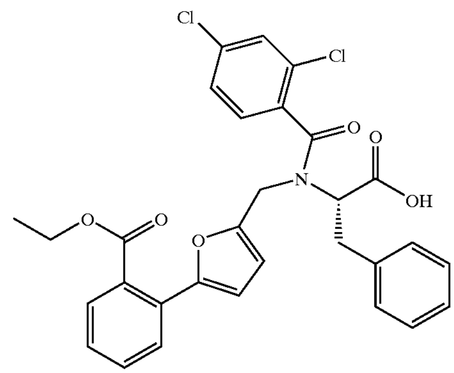 | +++ | |
| compound #73 | (2s)-2-(5-{[(1-Carboxy-2-phenyl-ethyl-(2,4-dichloro-benzoyl)-amino]-methyl}-furan-2-yl)-benzoic acid | 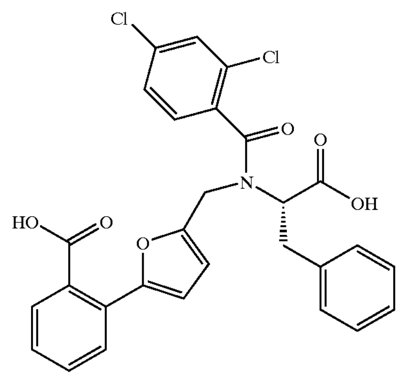 | +++ | |
| compound #74 | (2s)-2-{(2,4-Dichloro-benzoyl)-(5-thiazol-2-yl-furan-2-ylmethyl)-amino]-3-phenyl-propionic acid | 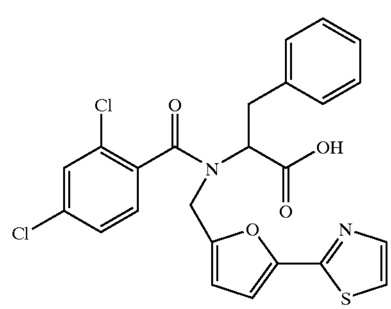 | +++ | |
| compound #75 | (2s)-2-[(2,4-Dichloro-benzoyl)-furan-2-ylmethyl-amino]-3-phenyl-propionic acid | 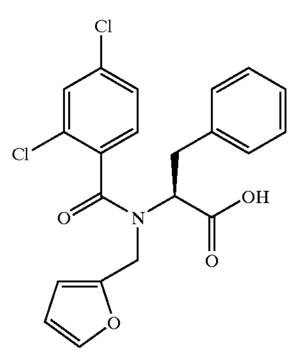 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #76 | (2s)-3-(5-{[(1s-1-Carboxy-2-phenyl-ethyl)-(2,4-dichloro-benzoyl)-amino]-methyl}-furan-2-yl)-benzoic acid | 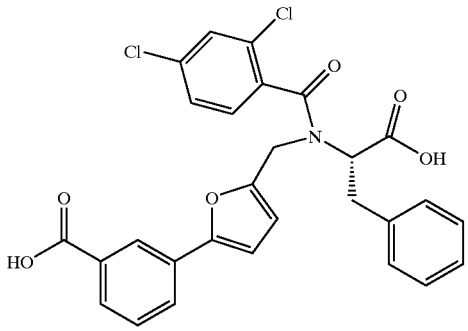 | +++ | |
| compound #77 | (2s)-4-(5-{[(1s-1-Carboxy-2-phenyl-ethyl)-(2,4-dichloro-benzoyl)-amino]-methyl}-furan-2-yl)-benzoic acid | 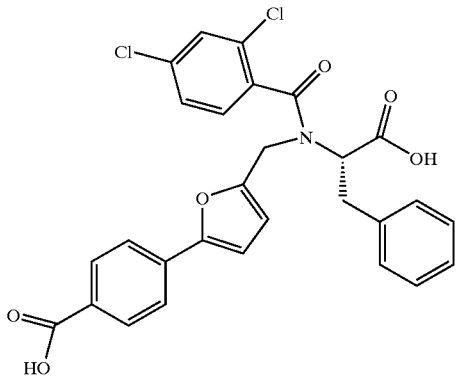 | +++ | |
| compound #78 | (2s)-2-{(2-Bromo-4-chloro-benzoyl)-[5-(3-trifluoromethyl-phenyl)-furan-2-ylmethyl]-amino}-3-phenyl-propionic acid | 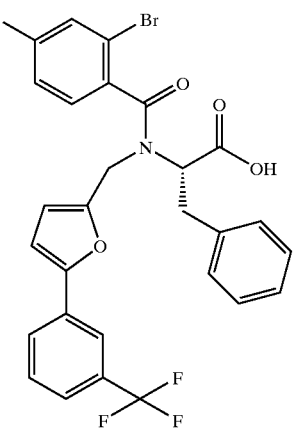 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #79 | (2s)-2-{(2,4-Di-chloro-benzoyl)-[5-(3,5-di-fluoro-phenyl)-furan-2-ylmethyl]-amino}-3-phenyl-propionic acid | 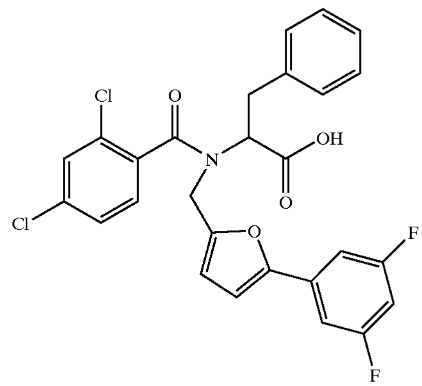 | +++ | |
| compound #80 | (2s)-2-[(2,4-Di-chloro-benzoyl)-(5-m-tolyl-furan-2-ylmethyl)-amino]-3-phenyl-propionic acid | 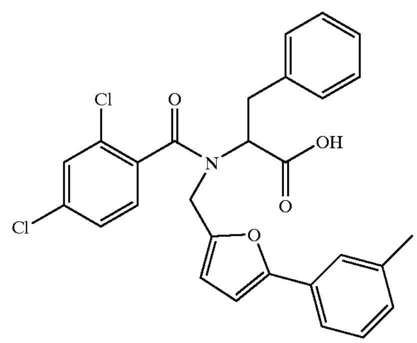 | +++ | |
| compound #81 | (2s)-2-{(2,4-Di-chloro-benzoyl)-[5-(3-fluoro-phenyl)-furan-2-ylmethyl]-amino}-3-phenyl-propionic acid | 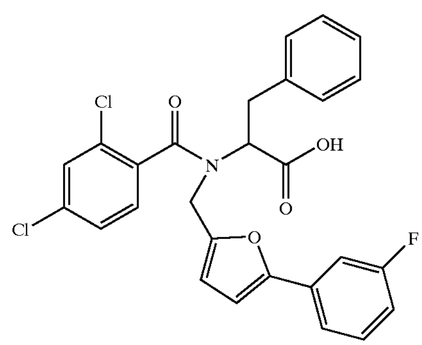 | +++ | |
| compound #82 | (2s)-2-[(5-Bromo-thiophen-2-ylmethyl)-(2,4-di-chloro-benzoyl)-amino]-3-phenyl-propionic acid | 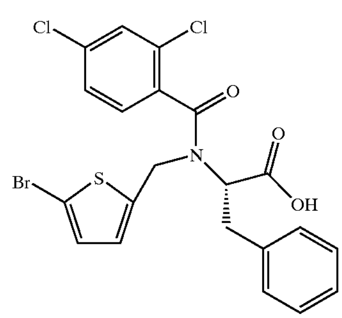 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #83 | (2s)-4-(5-{[(1s-1-Carboxy-2-phenyl-ethyl)-(2,4-dichloro-benzoyl)-amino]-methyl}-thiophen-2-yl)-benzoic acid | 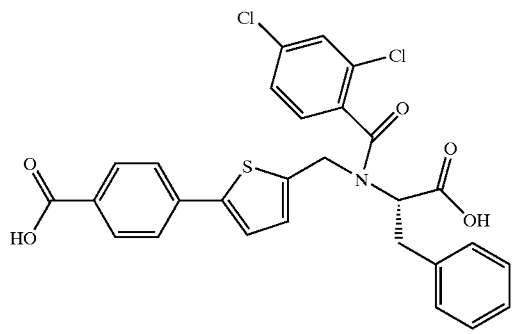 | +++ | |
| compound #84 | (2s)-4-(5-{[(1-Carboxy-2-phenyl-ethyl)-(2,4-dichloro-benzoyl)-amino]-methyl}-thiophen-2-yl)-benzoic acid methyl ester | 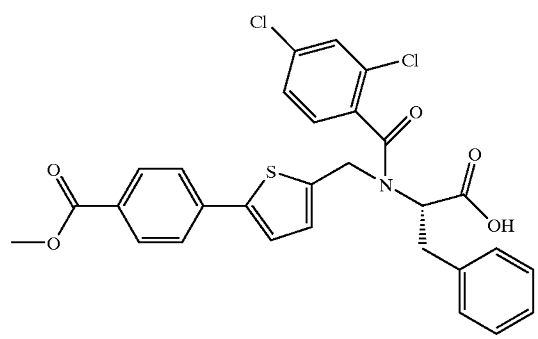 | +++ | |
| compound #85 | (2s)-2-[(5-Benzofuran-2-yl-thiophen-2-ylmethyl)-(2,4-dichloro-benzoyl)-amino]-3-phenyl-propionic acid | 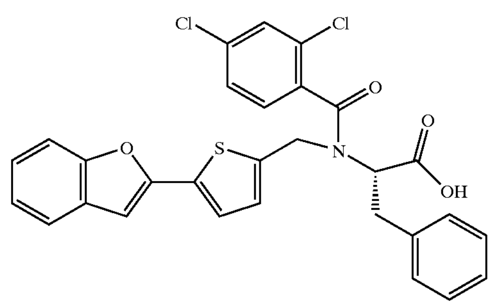 | +++ | |
| compound #86 | 2-[(2-Benzofuran-2-yl-thiazol-5-ylmethyl)-(2,4-dichloro-benzoyl)-amino]-3-phenyl-propionic acid | 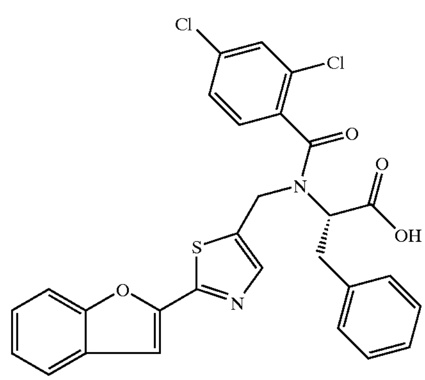 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #87 | (2s)-2-{(2,4-Di-chloro-benzoyl)-[4-(3,4-di-chloro-phe-nyl)-thiophen-2-ylmeth-yl]-amino}-3-phe-nyl-propionic acid | 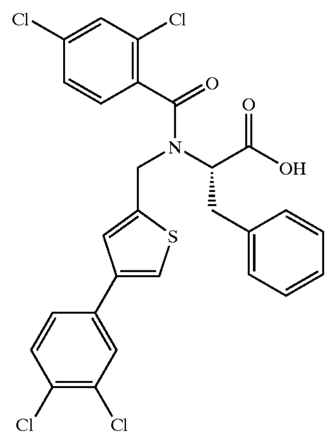 | +++ | |
| compound #88 | (2s)-2-[[4-(4-Chlor-o-3-fluoro-phe-nyl)-thiophen-2-ylmeth-yl]-(2,4-di-chloro-benzoyl)-a-mino]-3-phenyl-propionic acid | 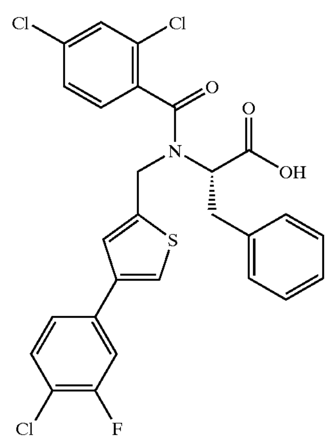 | +++ | |
| compound #89 | (2s)-2-[[4-(3-Chlor-o-4-fluoro-phe-nyl)-thiophen-2-ylmeth-yl]-(2,4-di-chloro-benzoyl)-a-mino]-3-phenyl-propionic acid, | 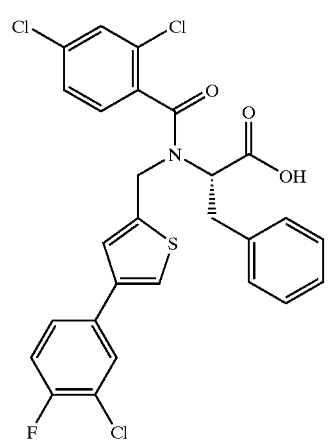 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #90 | (2s)-2-{(2,4-Di-chloro-benzoyl)-[4-(2,4-di-chloro-phe-nyl)-thiophen-2-ylmeth-yl]-amino}-3-phe-nyl-propionic acid | 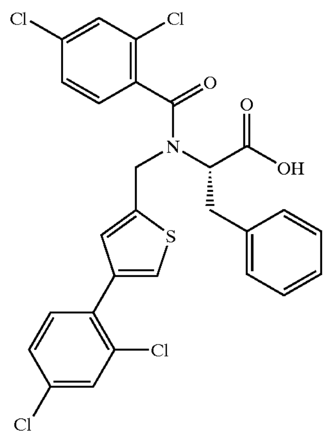 | +++ | |
| compound #91 | (2s)-2-[[5-(3-Chlor-o-4-fluoro-phe-nyl)-thiophen-2-ylmeth-yl]-(2,4-di-chloro-benzoyl)-a-mino]-3-phenyl-propionic acid | 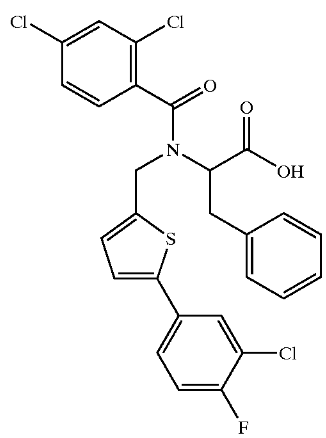 | +++ | |
| compound #92 | (2s)-2-[[5-(4-chlor-o-3-fluoro-phe-nyl)-thiophen-2-ylmeth-yl]-(2,4-di-chloro-benzoyl)-a-mino]-3-phenyl-propionic acid | 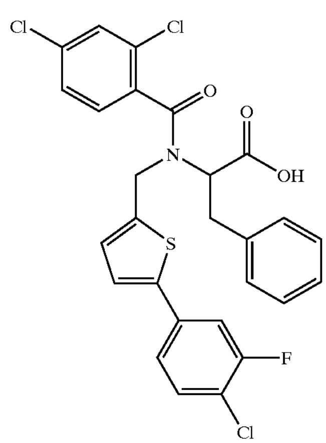 | +++ | |

TABLE 1-continued

LIST OF COMPOUNDS HAVING POLYMERASE ACTIVITY

| Compound # | Compound Name | Structure | RNA pol Assay 1 IC$_{50}$ (μm) | RNA pol Assay 2 IC$_{50}$ (μm) |
|---|---|---|---|---|
| compound #93 | (2s)-2-{(2,4-Di-chloro-benzoyl)-[5-(2,4-di-chloro-phe-nyl)-thiophen-2-ylmeth-yl]-amino}-3-phenyl-pro-pionic acid | 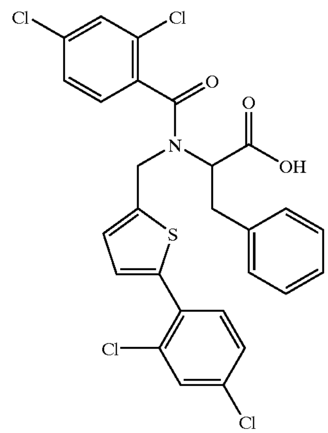 | +++ | |
| compound #94 | (2s)-2-[(2,4-Di-chloro-benzoyl)-(5-thia-zol-2-yl-thio-phen-2-ylmeth-yl)-amino]-3-phe-nyl-propionic acid | 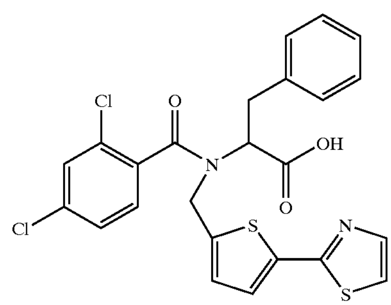 | +++ | |
| compound #95 | (2s)-2-{(2,4-Di-chloro-benzoyl)-[5-(3,5-di-fluoro-phe-nyl)-thiophen-2-ylmeth-yl]-amino}-3-phe-nyl-propionic acid | 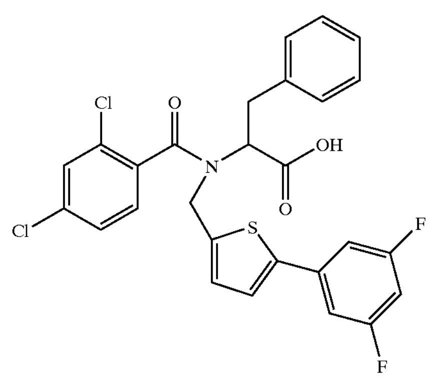 | +++ | |
| compound #96 | (2s)-2-{(2,4-Di-chloro-benzoyl)-[5-(3-meth-oxy-phe-nyl)-thiophen-2-ylmeth-yl]-amino}-3-phe-nyl-propionic acid | 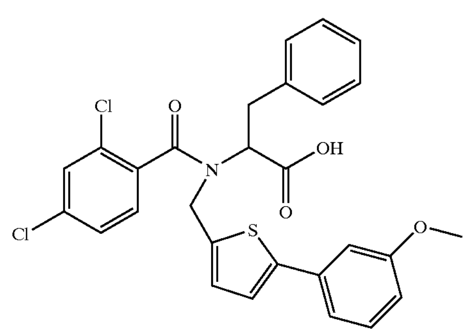 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #97 | (2s)-2-{(2,4-Di-chloro-benzoyl)-[5-(3-fluor-o-phenyl)-thio-phen-2-ylmeth-yl]-amino}-3-phe-nyl-propionic acid | 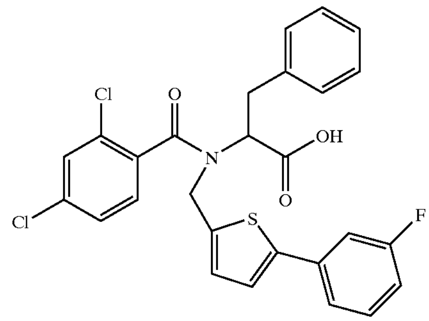 | +++ | |
| compound #98 | (2s)-2-[(2,4-Di-chloro-benzoyl)-thio-phen-2-ylmeth-yl-amino]-3-phe-nyl-propionic acid | 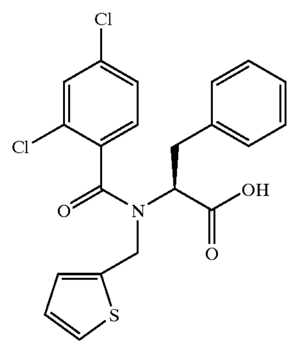 | +++ | |
| compound #99 | (2s)-2-[(4-Bromo-thio-phen-2-ylmeth-yl)-(2,4-di-chloro-benzoyl)-a-mino]-3-phenyl-propionic acid | 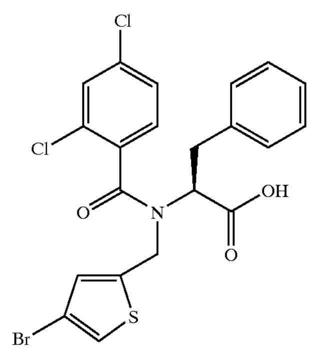 | +++ | |
| compound #100 | (2s)-2-{(2,4-Di-chloro-benzoyl)-[2-(4-phe-nyl-pipera-zin-1-yl)-thia-zol-5-ylmeth-yl]-amino}-3-phe-nyl-propionic acid | 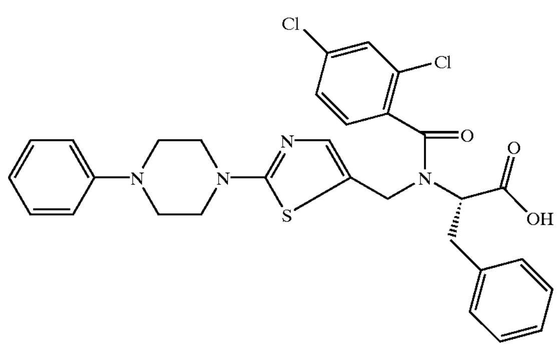 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #101 | (2s)-1-(5-{[(1s-1-Carboxy-2-phenyl-ethyl)-(2,4-dichloro-benzoyl)-amino]-methyl}-thiazol-2-yl)-piperidine-4-carboxylic acid | 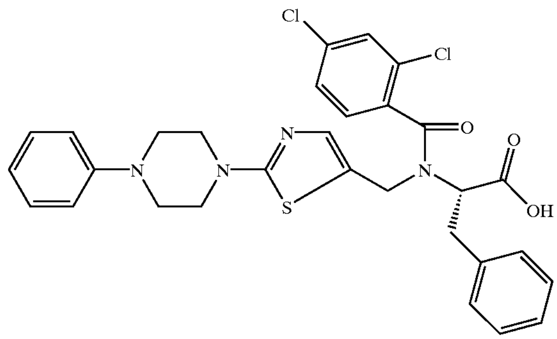 | ++ | |
| compound #102 | (2s)-2-[[2-(4-Benzyl-piperazin-1-yl)-thiazol-5-ylmethyl]-(2,4-dichloro-benzoyl)-amino]-3-phenyl-propionic acid | 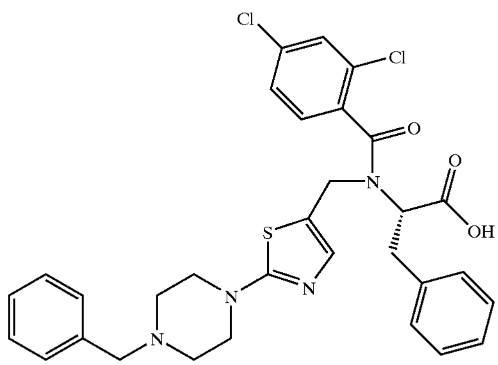 | +++ | |
| compound #103 | (2s)-2-[(2,4-Dichloro-benzoyl)-(2-piperidin-1-yl-thiazol-5-ylmethyl)-amino]-3-phenyl-propionic acid | 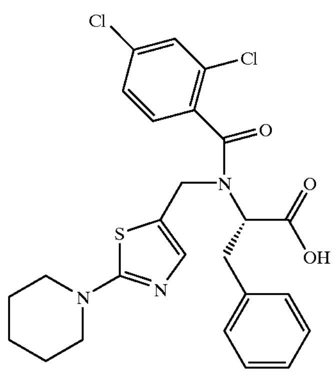 | +++ | |
| compound #104 | (2s)-2-[(2,4-Dichloro-benzoyl)-(2-diethylamino-thiazol-5-ylmethyl)-amino]-3-phenyl-propionic acid | 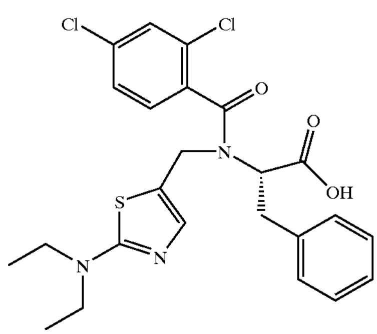 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #105 | (2s)-2-[[2-(4-Chloro-benzoyl)-benzofuran-3-ylmethyl]-(4-methoxy-2,3,6-trimethyl-benzenesulfonyl)-amino]-3-phenyl-propionic acid | 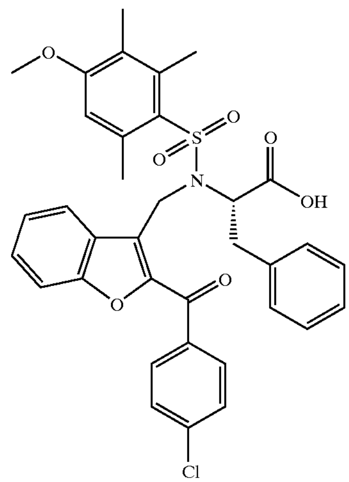 | ++ | |
| compound #106 | (2s)-2-[[5-(2,4-Dichloro-phenoxy)-1-methyl-3-trifluoromethyl-1h-pyrazol-4-ylmethyl]-(4-methoxy-2,3,6-trimethyl-benzenesulfonyl)-amino]-3-phenyl-propionic acid | 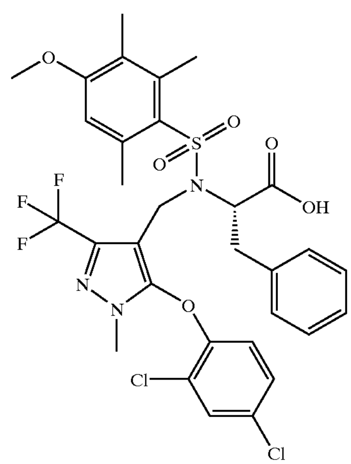 | ++ | |
| compound #107 | (2s)-2-((2,4-Dichloro-benzoyl)-{2-[5-(2,4-dichloro-phenyl)-furan-2-yl]-2-oxo-ethyl}-amino)-3-phenyl-propionic acid | 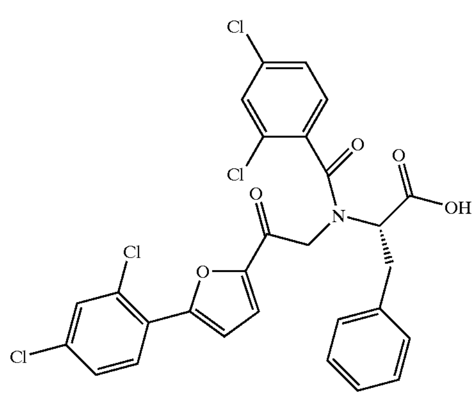 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #108 | (2s)-2-Benzyl-4-(2,4-di-chloro-phenyl)-3-[3-(2,6-di-chloro-phenyl)-5-methyl-isoxazol-4-ylmethyl]-4-oxo-butyric acid | 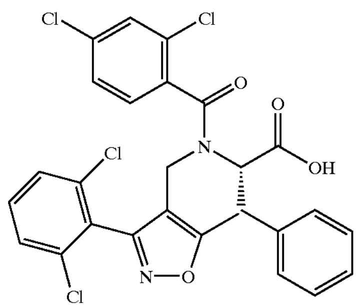 | +++ | |
| compound #109 | (2s)-2-[Allyl-(2,4-di-chloro-benzoyl)-amino]-3-phenyl-propionic acid | 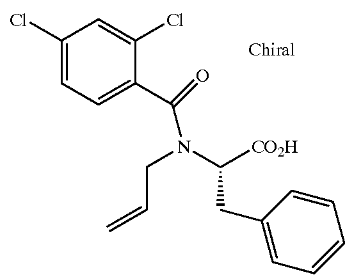 | ++ | |
| compound #110 | (2s)-2-[(2,4-Di-chloro-benzoyl)-methyl-amino]-3-phenyl-propionic acid | 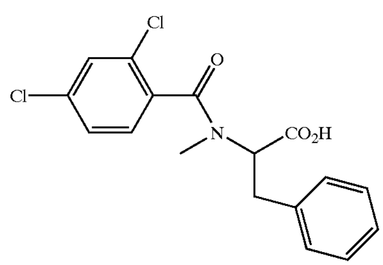 | ++ | |
| compound #111 | (2s)-2-[(2,4-Di-chloro-benzoyl)-prop-2-ynyl-amino]-3-phenyl-propionic acid | 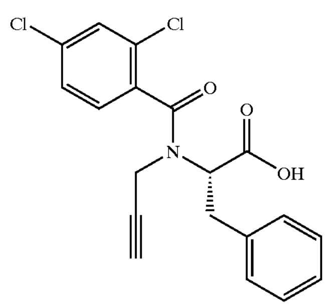 | ++ | |
| compound #112 | (2s)-2-[(2,4-Di-chloro-benzoyl)-propyl-amino]-3-phenyl-propionic acid | 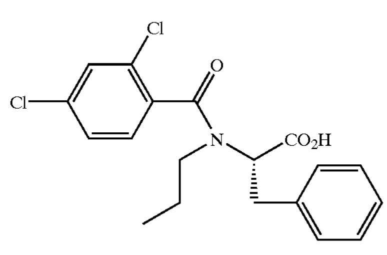 | + | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #113 | (2s)-2-[(3-Benzo-furan-2-yl-prop-2-ynyl)-(2,4-di-chloro-benzoyl)-a-mino]-3-phenyl-propionic acid | 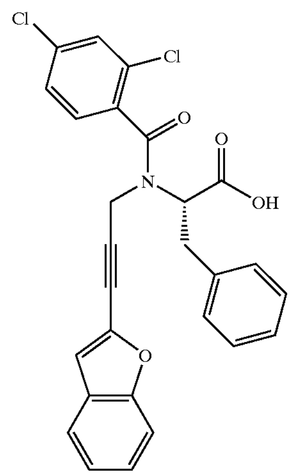 | +++ | |
| compound #114 | (2s)-2-[(4-Benzo-furan-2-yl-phe-nyl)-(2,4-di-chloro-benzoyl)-a-mino]-3-phenyl-propionic acid | 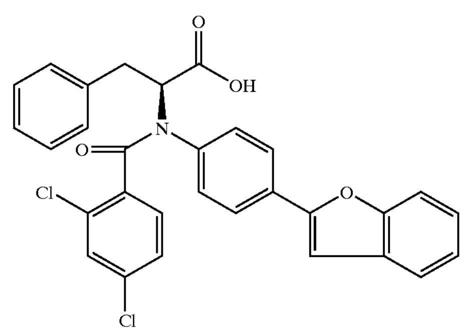 | +++ | |
| compound #115 | (2s)-2-[(2,4-Di-chloro-benzoyl)-(3-meth-yl-but-2-enyl)-a-mino]-3-phenyl-pro-pionic acid | 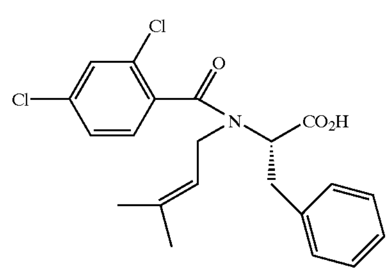 | ++ | |
| compound #116 | 2-[(2-Bromo-allyl)-(2,4-di-chloro-ben-zoyl)-amino]-3-phe-nyl-propionic acid | 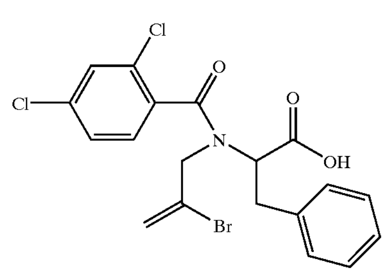 | ++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| Compound #117 | 3-{[(1-Carboxy-2-phenyl-ethyl)-(2,4-dichloro-benzoyl)-amino]-methyl}-benzoic acid methyl ester | 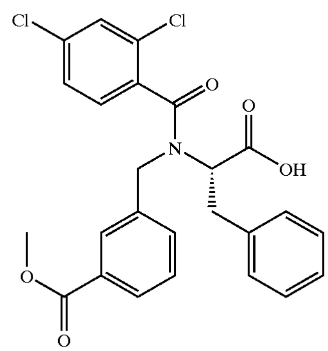 | | +++ |
| Compound #118 | 3-[[5-(3-Chloro-4-fluoro-phenyl)-thiophen-2-ylmethyl]-(2,4-dichloro-benzoyl)-amino]-5-phenyl-thiophene-2-carboxylic acid | 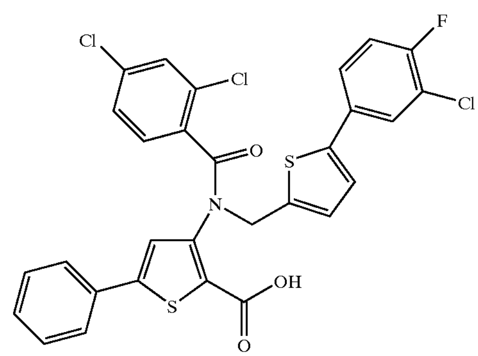 | | +++ |
| Compound #119 | 2-[[5-(3-Cyano-phenyl)-furan-2-ylmethyl]-(2,4-dichloro-benzoyl)-amino]-3-phenyl-propionic acid | 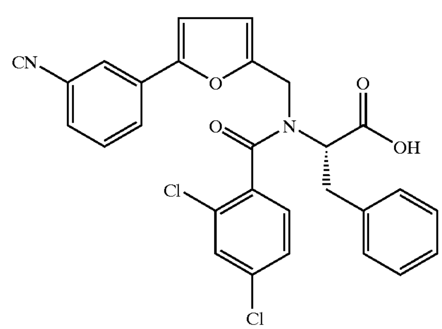 | | +++ |
| compound #120 | (2s)-2-{(2,4-Dichloro-benzoyl)-[5-(2-trifluoromethyl-phenyl)-furan-2-ylmethyl]-amino}-3-phenyl-propionic acid, | 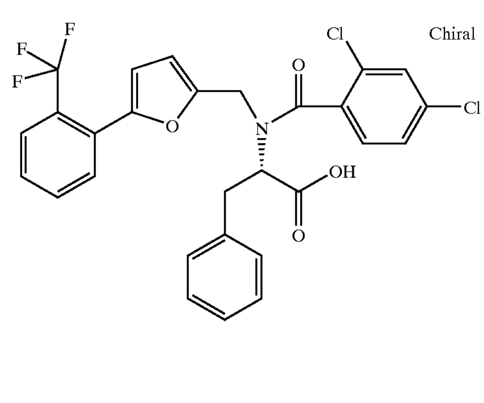 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #121 | (2s)-2-(5-{[(1s-1-Car-boxy-2-phenyl-eth-yl)-(2,4-di-chloro-benzoyl)-a-mino]-methyl}-thio-phen-2-yl)-benzoic acid ethyl ester | 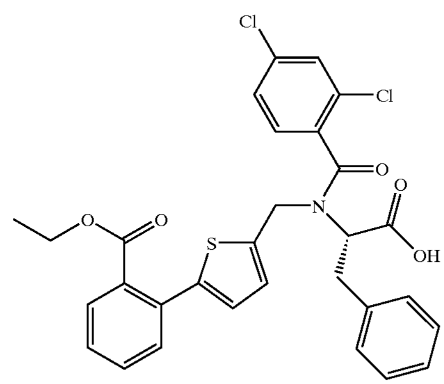 | +++ | |
| compound #122 | 3-(4-{[(1s-1-Car-boxy-2-phenyl-eth-yl)-(2,4-di-chloro-benzoyl)-a-mino]-methyl}-thio-phen-2-yl)-benzoic acid ethyl ester | 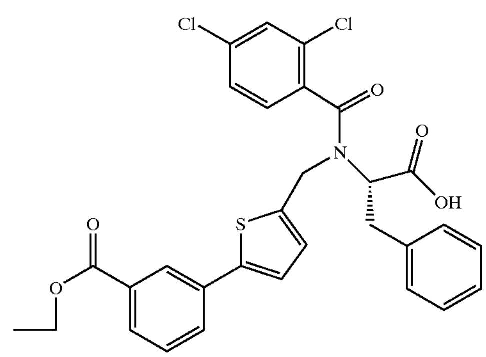 | +++ | |
| compound #123 | (2s)-2-[[5-(3-Chlor-o-phenyl)-fur-an-2-ylmethyl]-(2,4-di-chloro-benzoyl)-a-mino]-3-phe-nyl-propionic acid | 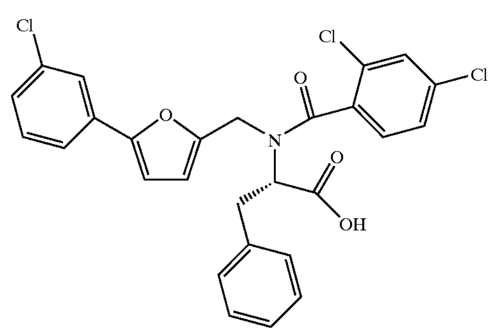 | +++ | |
| compound #124 | (2s)-2-[(4-Chloro-2-iodo-ben-zoyl)-(3,5-di-bromo-thio-phen-2-ylmeth-yl)-amino]-3-phe-yl-propionic acid | 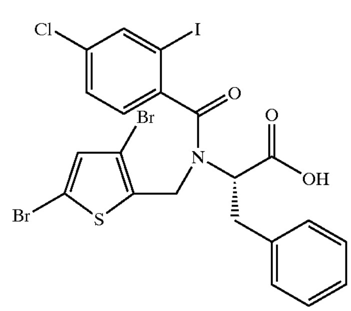 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #125 | (2s)-3-(5-{[(1-Carboxy-2-phenyl-ethyl)-(2,4-dichloro-benzoyl)-amino]-methyl}-thiophen-2-yl)-benzoic acid | 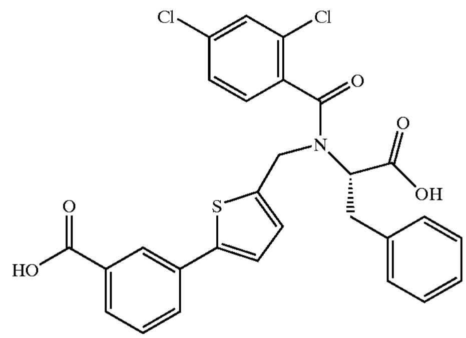 | +++ | |
| compound #126 | (2s)-2-[[5-(5-Chloro-thiophen-2-yl)-furan-2-ylmethyl]-(2,4-dichloro-benzoyl)-amino]-3-pheny-propionic acid | 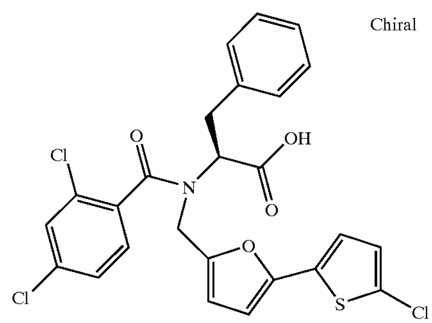 | +++ | |
| compound #127 | (2s)-2-[[2,2']Bithiophenyl-5-ylmethyl-(2,4-dichloro-benzoyl)-amino]-3-phenyl-propionic acid | 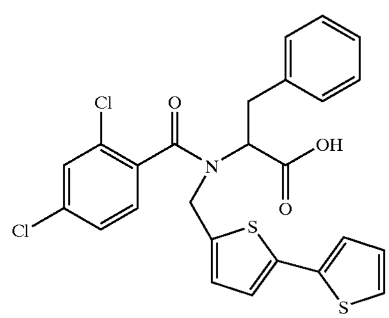 | +++ | |
| compound #128 | (2s)-2-[(5'-Chloro-[2,2']bithiophenyl-5-ylmethyl)-(2,4-dichloro-benzoyl)-amino]-3-phenyl-propionic acid | 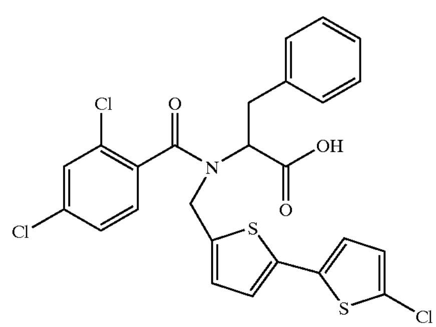 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #129 | (2s)-2-{(2,4-Di-chloro-benzoyl)-[4-(3,5-di-fluoro-phenyl)-thio-phen-2-ylmeth-yl]-amino}-3-phe-nyl-propionic acid | 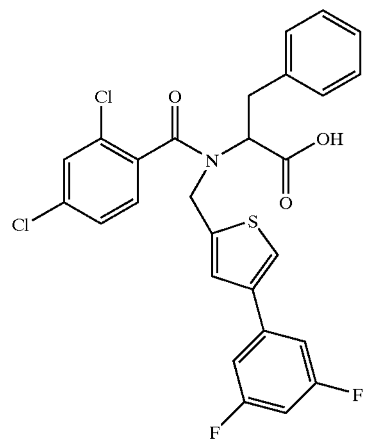 | +++ | |
| compound #130 | (2s)-2-{(2,4-Di-chloro-benzoyl)-[4-(3-fluoro-phe-nyl)-thiophen-2-ylmeth-yl]-amino}-3-phe-nyl-propionic acid | 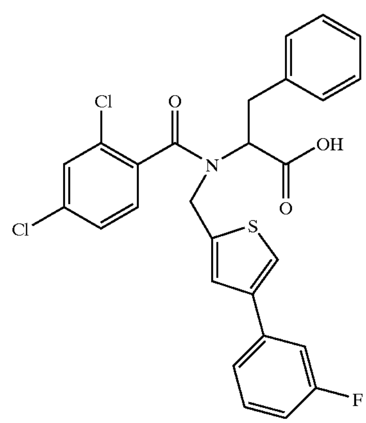 | +++ | |
| compound #131 | (2s)-2-{(4-Chloro-2-iodo-ben-zoyl)-[5-(3-tri-fluoromethyl-phe-nyl)-furan-2-ylmeth-yl]-amino}-3-phe-nyl-propionic acid | 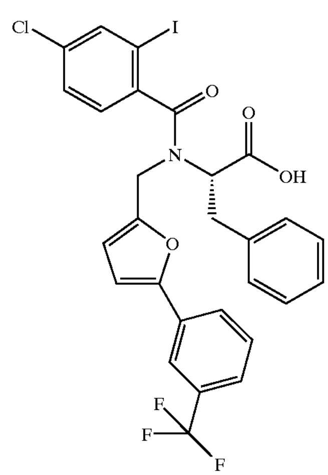 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #132 | (2s)-2-{(4-Chloro-2-methyl-benzoyl)-[5-(3-trifluoromethyl-phenyl)-furan-2-ylmethyl]-amino}-3-phenyl-propionic acid | 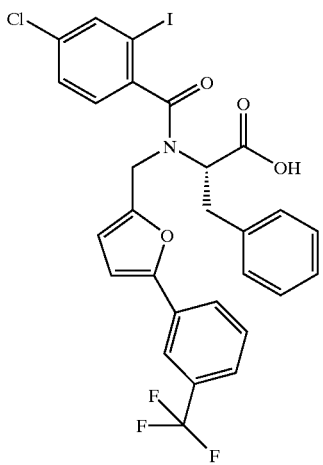 | +++ | |
| compound #133 | (2s)-2-[(5-Chloro-[2,3']bithiophenyl-5'-ylmethyl)-(2,4-dichloro-benzoyl)-amino]-3-phenyl-propionic acid | 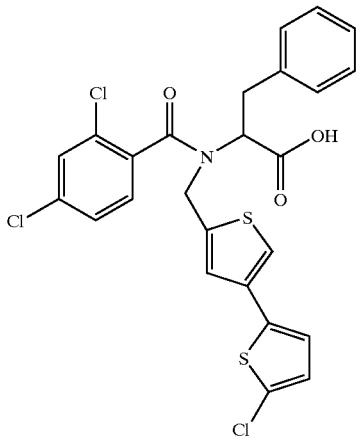 | +++ | |
| compound #134 | (2s)-2-{(2,4-Dichloro-benzoyl)-[5-(4-methoxy-phenyl)-furan-2-ylmethyl]-amino}-3-phenyl-propionic acid | 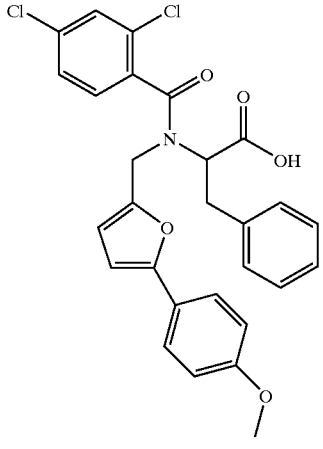 | +++ | |

TABLE 1-continued

LIST OF COMPOUNDS HAVING POLYMERASE ACTIVITY

| Compound # | Compound Name | Structure | RNA pol Assay 1 IC$_{50}$ (μm) | RNA pol Assay 2 IC$_{50}$ (μm) |
|---|---|---|---|---|
| compound #135 | (2s)-2-{(2,4-Dichloro-benzoyl)-[5-(4-methoxy-phenyl)-thiophen-2-ylmethyl]-amino}-3-phenyl-propionic acid | 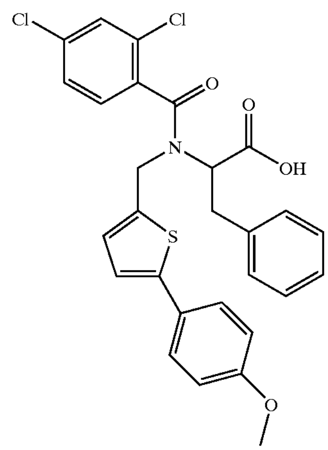 | +++ | |
| compound #136 | (2s)-2-{(2,4-Dichloro-benzoyl)-[4-(4-methoxy-phenyl)-thiophen-2-ylmethyl]-amino}-3-phenyl-propionic acid | 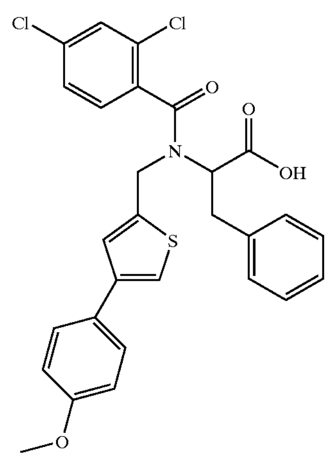 | +++ | |
| compound #137 | (2s)-2-[(2,4-Dichloro-benzoyl)-(5-pyridin-4-yl-furan-2-ylmethyl)-amino]-3-phenyl-propionic acid | 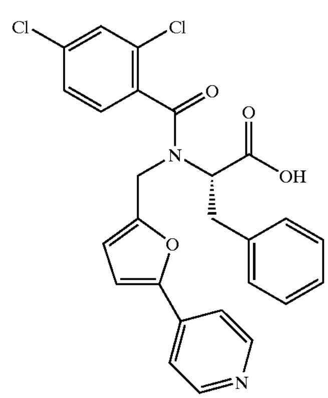 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
| --- | --- | --- | --- | --- |
| compound #138 | (2s)-2-[(2,4-Di-chloro-benzoyl)-(5-pyridin-4-yl-thiophen-2-ylmethyl)-amino]-3-phenyl-propionic acid | 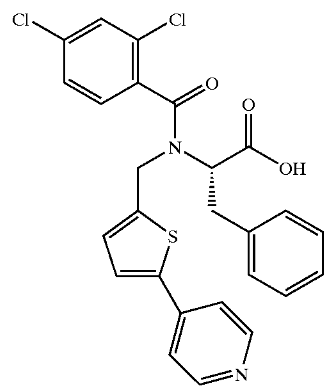 | +++ | |
| compound #139 | (2s)-2-[(2,4-Di-chloro-benzoyl)-(4-pyridin-4-yl-thiophen-2-ylmethyl)-amino]-3-phenyl-propionic acid | 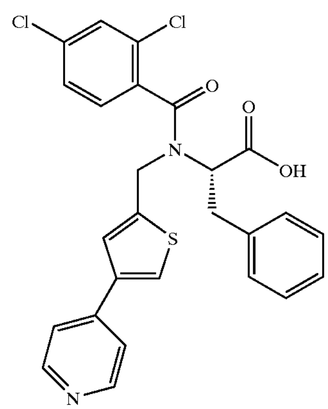 | +++ | |
| compound #140 | (2s)-2-[(2-Chloro-thiazol-5-ylmethyl)-(2,4-di-chloro-benzoyl)-amino]-3-phenyl-propionic acid | 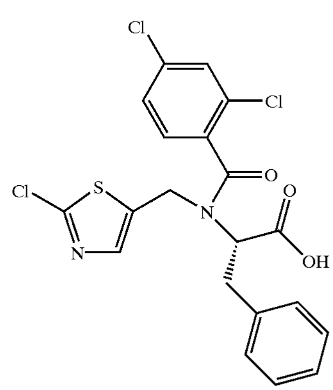 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #141 | (2s)-2-{(2,4-Di-chloro-benzoyl)-[5-(4-fluoro-phe-nyl)-thiophen-2-ylmeth-yl]-amino}-3-phe-nyl-propionic acid | 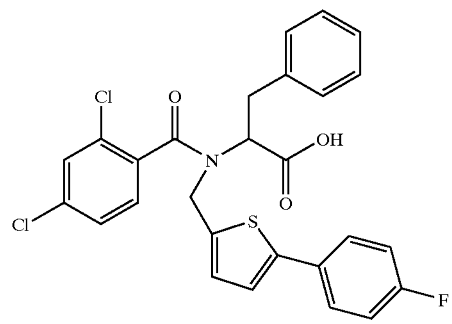 | +++ | |
| compound #142 | (2s)-2-[(2,4-Di-chloro-benzoyl)-(3,5-di-chloro-ben-zyl)-amino]-3-phe-nyl-propionic acid | 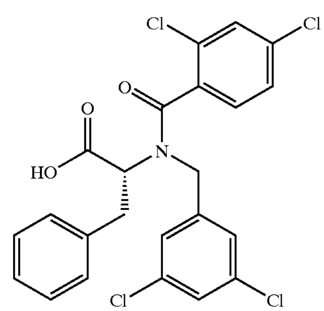 | +++ | |
| compound #143 | (2s)-2-[(2,4-Di-chloro-benzoyl)-thio-phen-3-ylmeth-yl-amino]-3-phe-nyl-propionic acid | 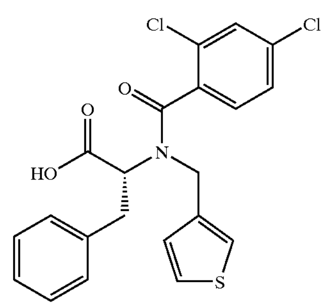 | +++ | |
| compound #144 | (2s)-2-[(2,4-Di-chloro-benzoyl)-(3-tri-fluoromethyl-ben-zyl)-amino]-3-phe-nyl-propionic acid | 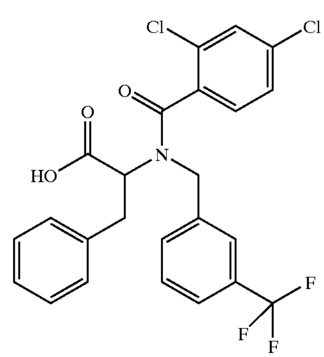 | +++ | |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #145 | (2s)-2-[[3-(3-Chloro-4-fluoro-phenyl)-thiophen-2-ylmethyl]-(2,4-dichloro-benzoyl)-amino]-3-phenyl-propionic acid | 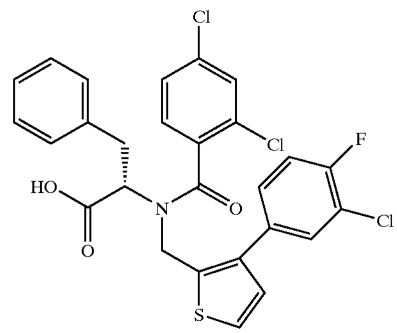 | | ++ |
| compound #146 | (2s)-2-[(3-Bromo-thiophen-2-ylmethyl)-(2,4-dichloro-benzoyl)-amino]-3-phenyl-propionic acid | 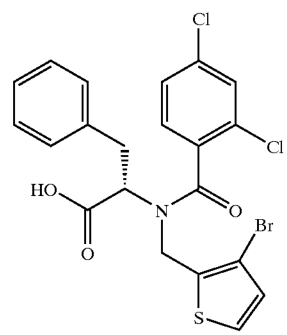 | | +++ |
| compound #147 | (2s)-2-{(2,4-Dichloro-benzoyl)-[5-(3-trifluoromethyl-phenyl)-furan-2-ylmethyl]-amino}-2-methyl-propionic acid | 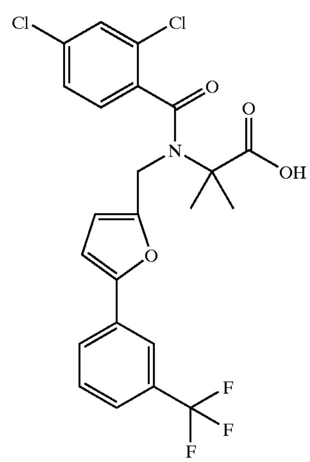 | | ++ |
| compound #148 | (2s)-2-{(2,4-Dichloro-benzoyl)-[2-(3-trifluoromethyl-phenyl)-thiazol-5-ylmethyl]-amino}-3-phenyl-propionic acid | 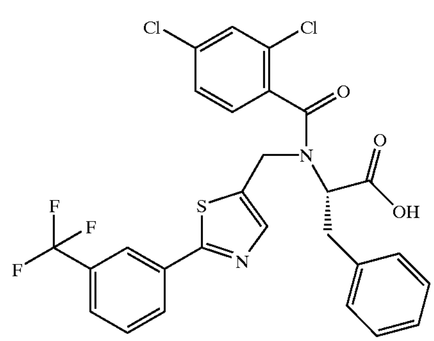 | | +++ |

TABLE 1-continued

LIST OF COMPOUNDS HAVING POLYMERASE ACTIVITY

| Compound # | Compound Name | Structure | RNA pol Assay 1 IC$_{50}$ (μm) | RNA pol Assay 2 IC$_{50}$ (μm) |
|---|---|---|---|---|
| compound #149 | (2s)-2-[(2,4-Dichloro-benzoyl)-(5-nitro-thiophen-3-ylmethyl)-amino]-3-phenyl-propionic acid | 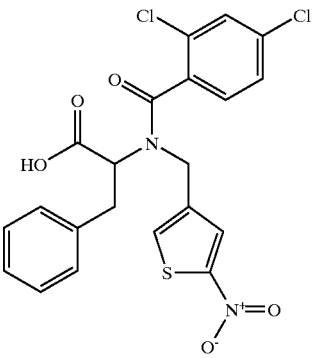 | | +++ |
| compound #150 | (2s)-2-[(2,4-Dichloro-benzoyl)-(4-methanesulfonyl-benzyl)-amino]-3-phenyl-propionic acid | 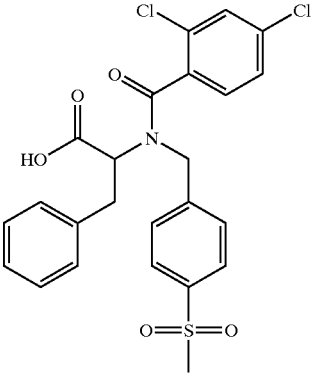 | | +++ |
| compound #151 | (2s)-2-[(2,4-Dichloro-benzoyl)-(3-methoxy-benzyl)-amino]-3-phenyl-propionic acid | 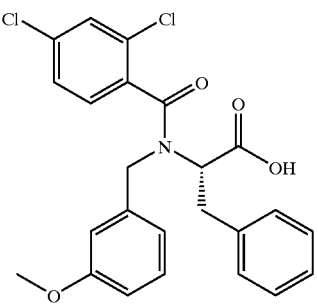 | | +++ |
| compound #152 | (2s)-2-[(2,4-Dichloro-benzoyl)-(3-methyl-benzyl)-amino]-3-phenyl-propionic acid | 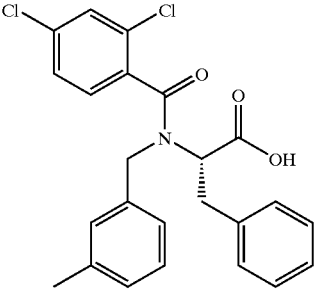 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #153 | (2s)-2-[[5-(3-Chloro-phenoxy)-1-methyl-3-trifluoromethyl-1h-pyrazol-4-ylmethyl]-(2,4-dichloro-benzoyl)-amino]-3-phenyl-propionic acid | 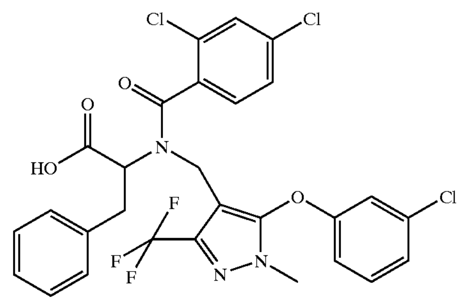 | | ++ |
| compound #154 | (2s)-2-{(2,4-Dichloro-benzoyl)-[3-(3,5-difluoro-phenyl)-thiophen-2-ylmethyl]-amino}-3-phenyl-propionic acid | 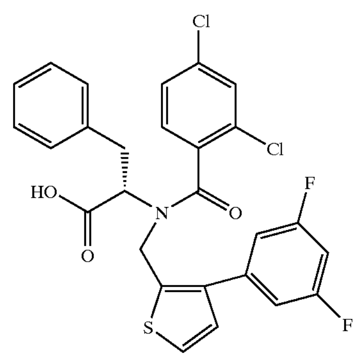 | | +++ |
| compound #155 | (2s)-2-{(2,4-Dichloro-benzoyl)-[3-(3,4-dichloro-phenyl)-thiophen-2-ylmethyl]-amino}-3-phenyl-propionic acid | 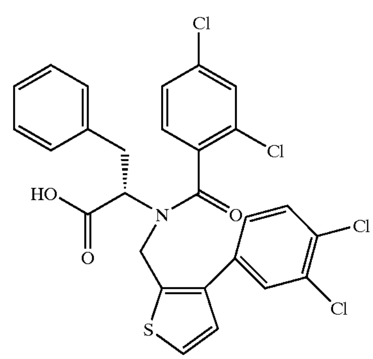 | | +++ |
| compound #156 | (2s)-2-[[3-(4-Chloro-3-fluoro-phenyl)-thiophen-2-ylmethyl]-(2,4-dichloro-benzoyl)-amino]-3-phenyl-propionic acid | 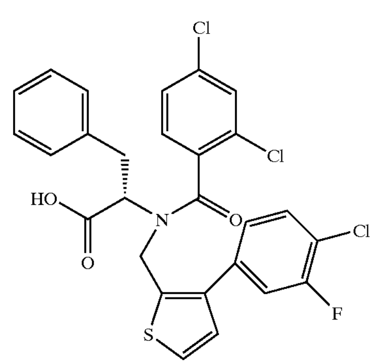 | | ++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #157 | (2s)-2-{(2,4-Di-chloro-benzoyl)-[3-(2,4-di-chloro-phe-nyl)-thiophen-2-ylmeth-yl]-amino}-3-phe-nyl-propionic acid | 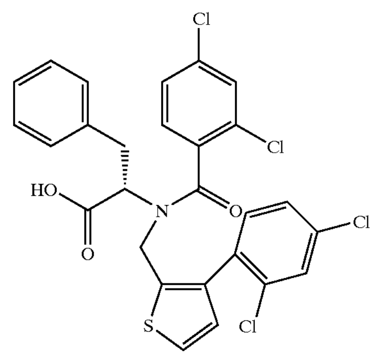 | | ++ |
| compound #158 | (2s)-2-[(2,4-Di-chloro-benzoyl)-(3-m-to-lyl-thiophen-2-ylmeth-yl)-amino]-3-phe-nyl-propionic acid | 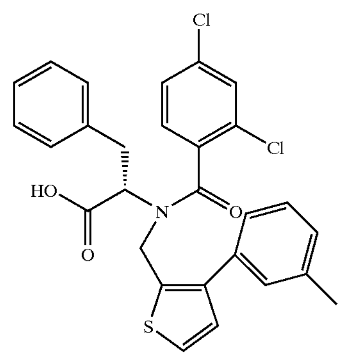 | | +++ |
| compound #159 | (2s)-2-(2-{[(1s-1-Car-boxy-2-phenyl-eth-yl)-(2,4-di-chloro-benzoyl)-a-mino]-methyl}-thio-phen-3-yl)-benzoic acid ethyl ester | 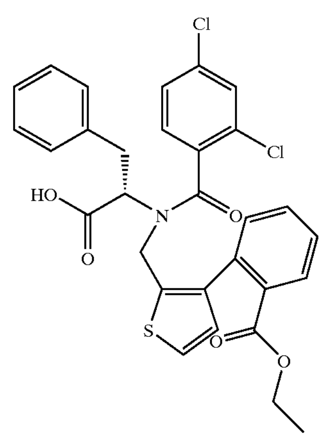 | | ++ |
| compound #160 | (2s)-4-(2-{[(1s-1-Car-boxy-2-phenyl-eth-yl)-(2,4-di-chloro-benzoyl)-a-mino]-methyl}-thio-phen-3-yl)-benzoic acid ethyl ester | 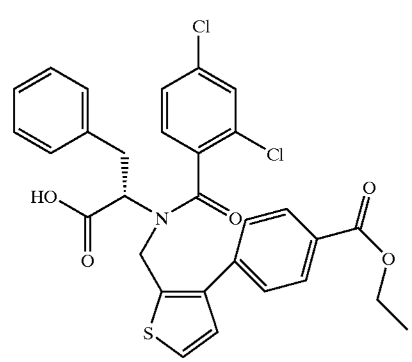 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #161 | (2s)-2-{(2,4-Dichloro-benzoyl)-[3-(3-fluoro-phenyl)-thiophen-2-ylmethyl]-amino}-3-phenyl-propionic acid | 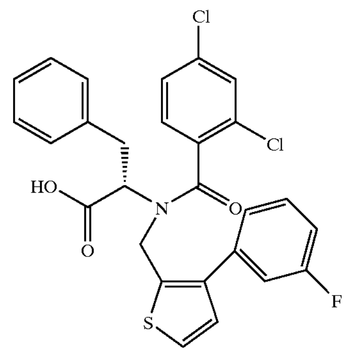 | | ++ |
| compound #162 | (2s)-2-[[3-(3-Cyano-phenyl)-thiophen-2-ylmethyl]-(2,4-dichloro-benzoyl)-amino]-3-phenyl-propionic acid | 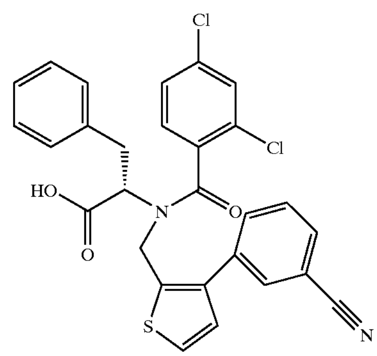 | | +++ |
| compound #163 | {(2,4-Dichloro-benzoyl)-[5-(3-trifluoromethyl-phenyl)-furan-2-ylmethyl]-amino}-thiophen-2-yl-acetic acid | 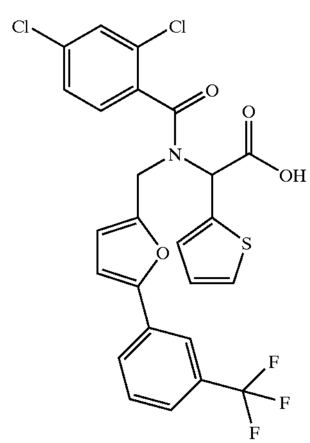 | | ++ |
| compound #164 | L-2-{[(1-Carboxy-2-phenyl-ethyl)-(2,4-dichloro-benzoyl)-amino]-methyl}-pyrrolidine-1-carboxylic acid #tert!-butyl ester | 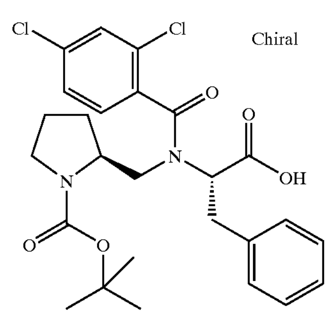 | | ++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #165 | d-2-{[(1-carboxy-2-phenyl-ethyl)-(2,4-dichloro-benzoyl)-amino]-methyl}-pyrrolidine-1-carboxylic acid #tert!-butyl ester | 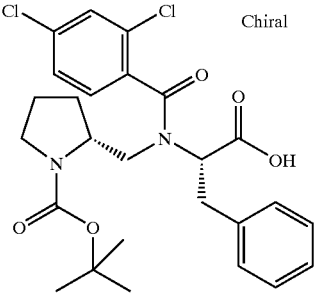 |  | ++ |
| compound #166 | 4-[(1-Carboxy-2-phenyl-ethyl)-(2,4-dichloro-benzoyl)-amino]-piperidine-1-carboxylic acid benzyl ester | 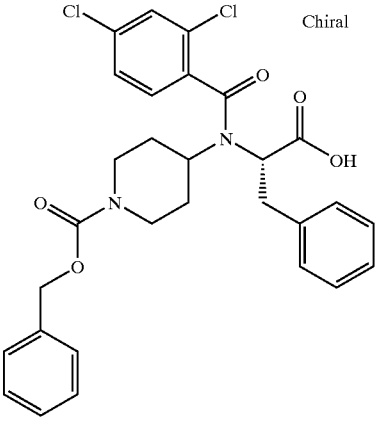 |  | ++ |
| compound #167 | 1-2-[(2,4-Dichloro-benzoyl)-pyrrolidin-2-ylmethyl-amino]-3-phenyl-propionic acid | 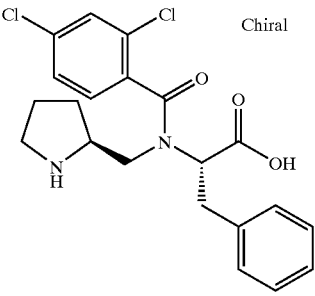 |  | ++ |
| compound #168 | d-2-[(2,4-Dichloro-benzoyl)-pyrrolidin-2-ylmethyl-amino]-3-phenyl-propionic acid | 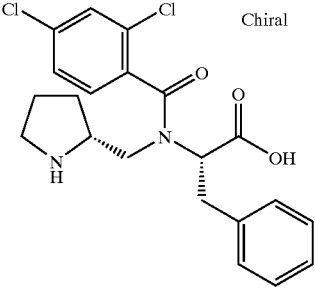 |  | ++ |

TABLE 1-continued

LIST OF COMPOUNDS HAVING POLYMERASE ACTIVITY

| Compound # | Compound Name | Structure | RNA pol Assay 1 IC$_{50}$ (μm) | RNA pol Assay 2 IC$_{50}$ (μm) |
|---|---|---|---|---|
| compound #169 | 3-(5-Bromo-thiophen-2-yl)-2-[(2,4-dichloro-benzoyl)-methyl-amino]-propionic acid | 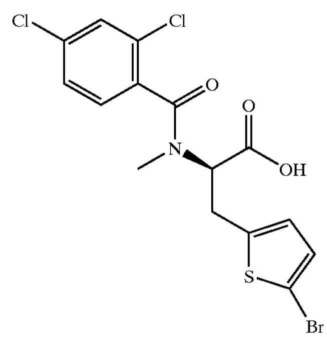 | | +++ |
| compound #170 | 2-[(2,4-Dichloro-benzoyl)-pyridin-3-ylmethyl-amino]-3-phenyl-propionic acid | 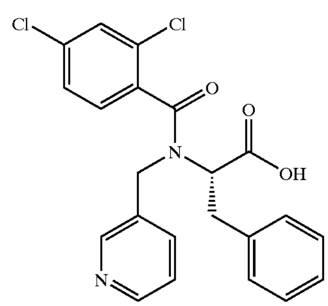 | | ++ |
| compound #171 | 2-[(2,4-Dichloro-benzoyl)-(4-trifluoromethyl-benzyl)-amino]-3-phenyl-propionic acid | 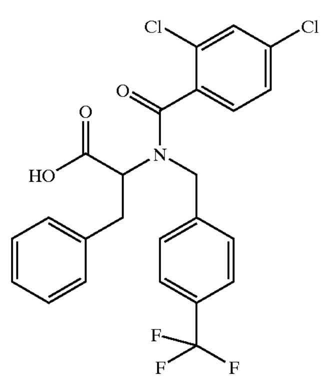 | | ++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #172 | 2-{(2,4-Dichloro-benzoyl)-[4-(4-fluoro-benzyloxy)-benzyl]-amino}-3-phenyl-propionic acid | 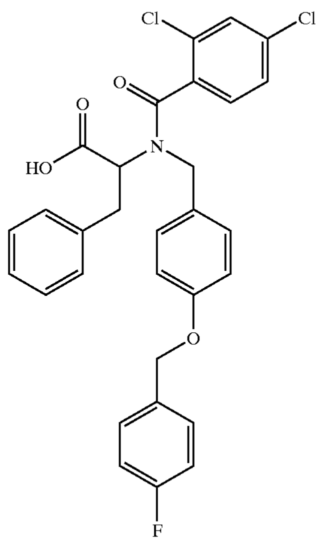 | | ++ |
| compound #173 | 2-[(2,4-Dichloro-benzoyl)-(4-fluoro-3-trifluoromethyl-benzyl)-amino]-3-phenyl-propionic acid | 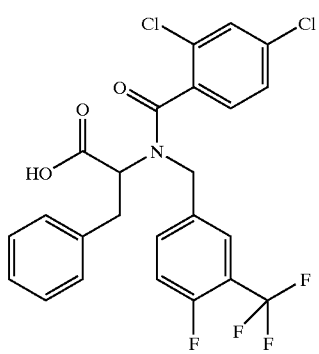 | | ++ |
| compound #174 | 2-[(1-Benzenesulfonyl-1h-pyrrol-2-ylmethyl)-2,4-dichloro-benzoyl)-amino]-3-phenyl-propionic acid | 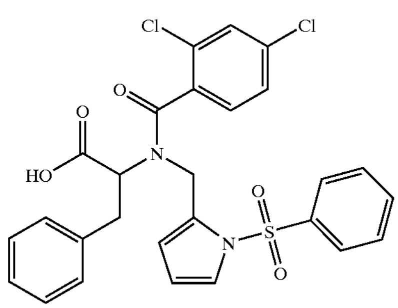 | | ++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #175 | 2-[[3-(4-Chloro-phenoxy)-benzyl]-(2,4-dichloro-benzoyl)-amino]-3-phenyl-propionic acid | 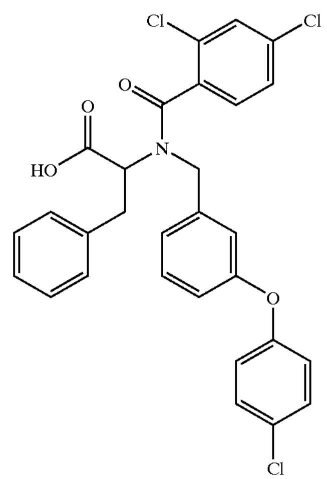 | | ++ |
| compound #176 | 2-[(5-Chloro-2-chloromethyl-hepta-2,4,6-trienoyl)-quinolin-3-ylmethyl-amino]-3-phenyl-propionic acid | 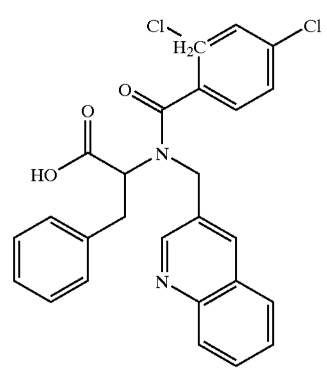 | | ++ |
| compound #177 | 2-[(2-Benzyloxy-benzyl)-(2,4-dichloro-benzoyl)-amino]-3-phenyl-propionic acid | 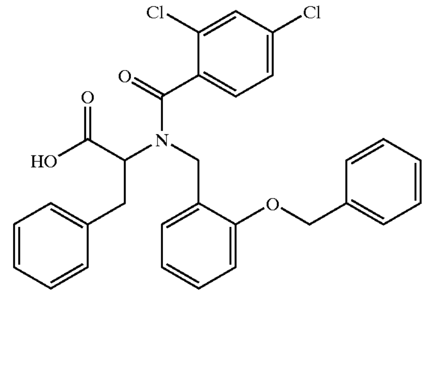 | | ++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #178 | 2-{(2,4-Dichloro-benzoyl)-[3-(5-isopropyl-2-methoxy-phenyl)-thiophen-2-ylmethyl]-amino}-3-phenyl-propionic acid | 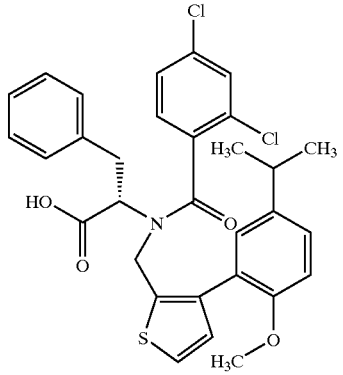 | | ++ |
| compound #179 | 2-{(2,4-Dichloro-benzoyl)-[3-(4-trifluoromethoxy-phenyl)-thiophen-2-ylmethyl]-amino}-3-phenyl-propionic acid | 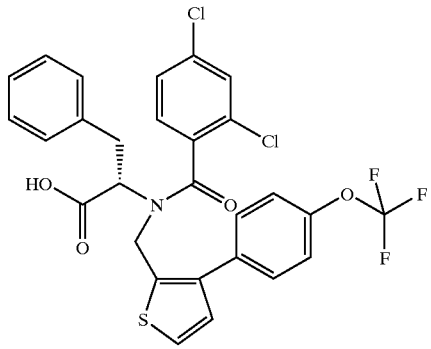 | | ++ |
| compound #180 | 2-{(2,4-Dichloro-benzoyl)-[3-(3-trifluoromethyl-phenyl)-thiophen-2-ylmethyl]-amino}-3-phenyl-propionic acid | 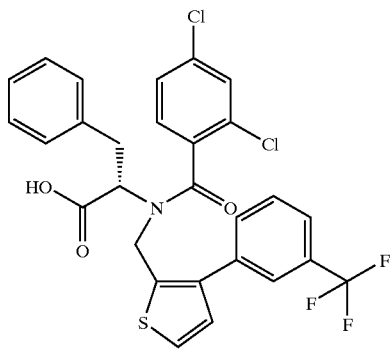 | | ++ |
| compound #181 | 2-[[3-(3,5-Bis-trifluoromethyl-phenyl)-thiophen-2-ylmethyl]-(2,4-dichloro-benzoyl)-amino]-3-phenyl-propionic acid | 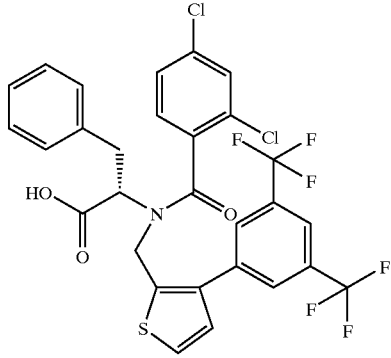 | | ++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #182 | 2-[(2,4-Dichloro-benzoyl)-(3-pyridin-4-yl-thiophen-2-ylmethyl)-amino]-3-phenyl-propionic acid | 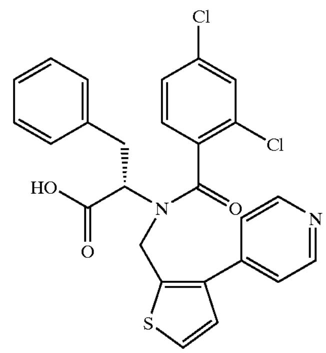 | | ++ |
| compound #183 | 2-{(2,4-Dichloro-benzoyl)-[3-(4-methylsulfanyl-phenyl)-thiophen-2-ylmethyl]-amino}-3-phenyl-propionic acid | 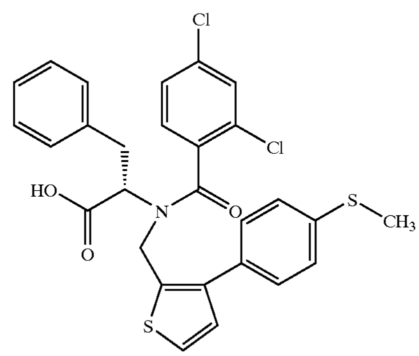 | | ++ |
| compound #184 | 2-{(2,4-Dichloro-benzoyl)-[3-(4-fluoro-phenyl)-thiophen-2-ylmethyl]-amino}-3-phenyl-propionic acid | 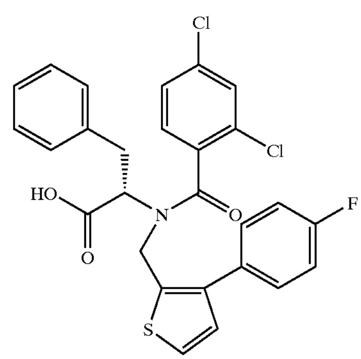 | | +++ |
| compound #185 | 2-[(2,4-Dichloro-benzoyl)-(3-pyridin-3-yl-thiophen-2-ylmethyl)-amino]-3-phenyl-propionic acid | 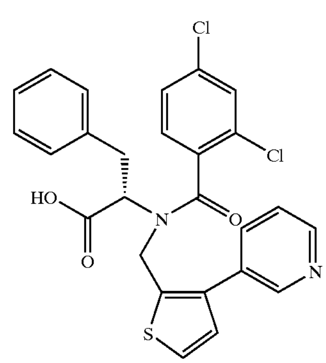 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #186 | 2-{(2,4-Dichloro-benzoyl)-[1-(toluene-2-sulfonyl)-pyrrolidin-2-ylmethyl]-amino}-3-phenyl-propionic acid | 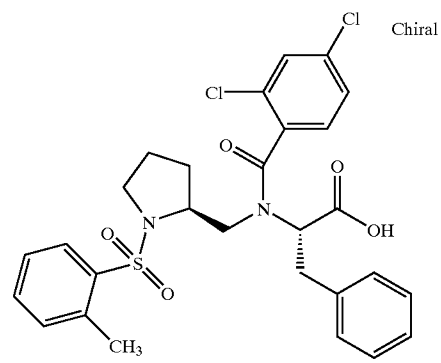 | | |
| compound #187 | 2-[(2-Bromo-benzyl)-(2,4-dichloro-benzoyl)-amino]-3-phenyl-propionic acid | 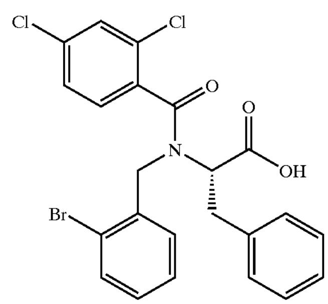 | | ++ |
| compound #188 | 3-(2-Bromo-phenyl)-2-[(2,4-dichloro-benzoyl)-methyl-amino]-propionic acid | 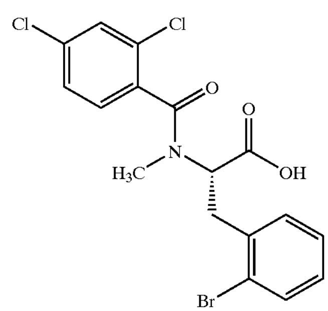 | | ++ |
| compound #189 | 3-(4-Bromo-phenyl)-2-[(2,4-dichloro-benzoyl)-methyl-amino]-propionic acid | 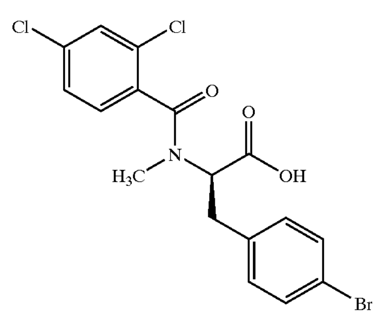 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| compound #190 | 2-[(3-Bromo-phenyl)-(2,4-dichloro-benzoyl)-amino]-3-phenyl-propionic acid | 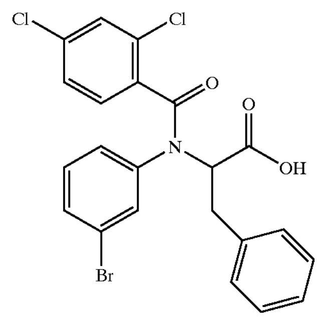 | | ++ flash-plate |
| compound #191 | 2-[(4-Bromo-phenyl)-(2,4-dichloro-benzoyl)-amino]-3-phenyl-propionic acid | 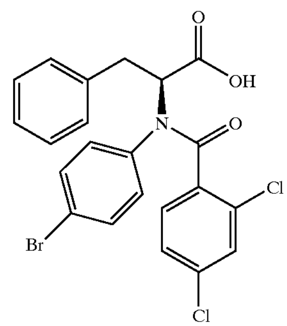 | | + |
| Compound #192 | 2-[[4-(3-Chloro-4-fluoro-phenyl)-thiophen-2-ylmethyl]-(2,4-dimethyl-benzoyl)-amino]-3-phenyl-propionic acid | 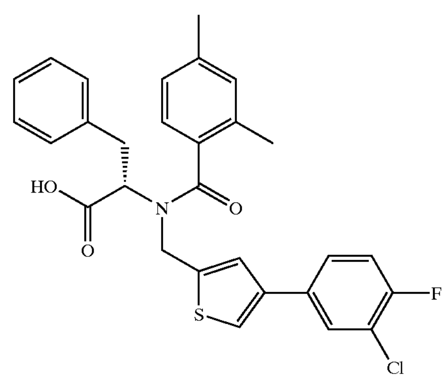 | | +++ |
| Compound #193 | 3-{[(1-Carboxy-2-phenyl-ethyl)-(2,4-dichloro-benzoyl)-amino]-methyl}-benzoic acid | 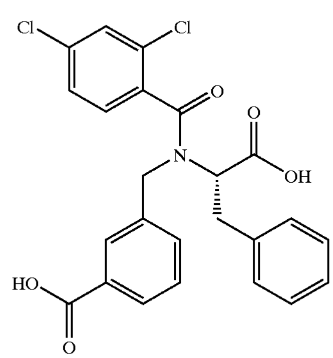 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| Compound #194 | 2-[(3-Amino-benzyl)-(2,4-dichloro-benzoyl)-amino]-3-phenyl-propionic acid | 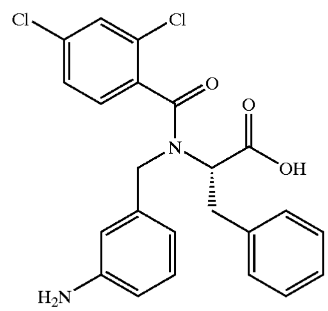 | | ++ |
| Compound #199 | 2-[Benzyl-(2,4-dichloro-benzoyl)-amino]-3-phenyl-propionic acid | 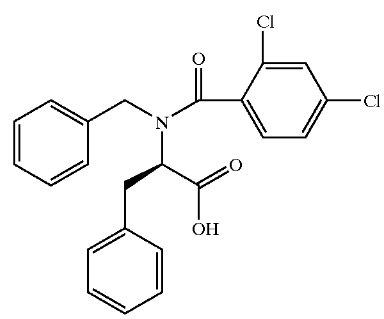 | | ++ |
| Compound #200 | 2-{(2,4-DICHLORO-BENZOYL)-[3-(2H-TETRAZOL-5-YL)-BENZYL]-AMINO}-3-PHENYL-PROPIONIC ACID | 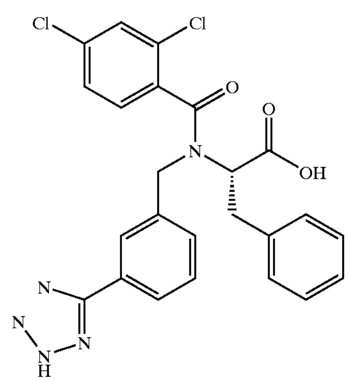 | | +++ |
| Compound #201 | 2-[(2,4-DICHLORO-BENZOYL)-(2-NITRO-BENZYL)-AMINO]-3-PHENYL-PROPIONIC ACID | 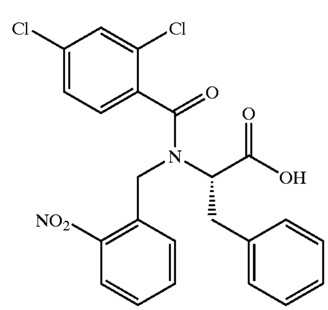 | | ++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| Compound #202 | 2-[(2,4-DICHLORO-BENZOYL)-(4-NITRO-BENZYL)-AMINO]-3-PHENYL-PROPIONIC ACID | 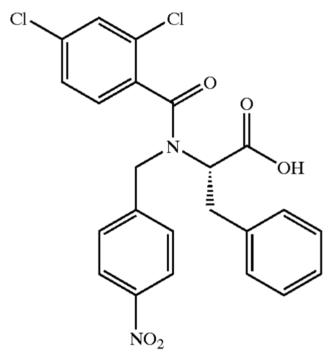 | | ++ |
| Compound #203 | 2-[(2-CYANO-BENZYL)-(2,4-DICHLORO-BENZOYL)-AMINO]-3-PHENYL-PROPIONIC ACID | 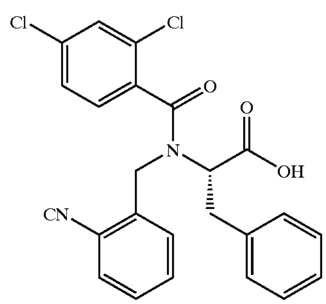 | | ++ |
| Compound #204 | 2-[(4-CYANO-BENZYL)-(2,4-DICHLORO-BENZOYL)-AMINO]-3-PHENYL-PROPIONIC ACID | 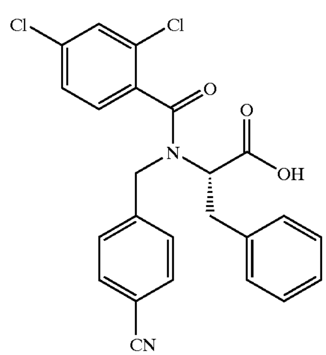 | | ++ |
| Compound #205 | 2-[[1-(3-CYANO-PHENYL)-ETHYL]-(2,4-DICHLORO-BENZOYL)-AMINO]-3-PHENYL-PROPIONIC ACID | 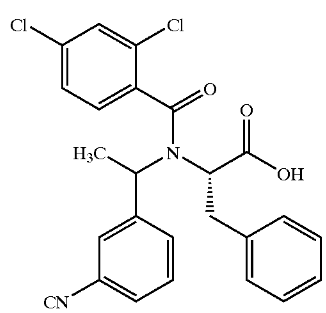 | | ++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| Compound #206 | 3-{[(1-Carboxy-2-phenyl-ethyl)-(2,4-dichloro-benzoyl)-amino]-methyl}-benzoic acid methyl ester | 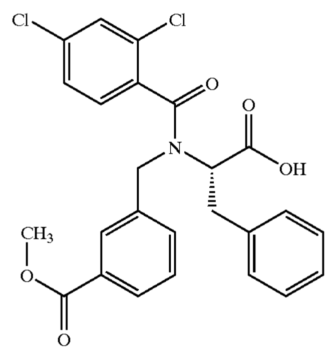 | | +++ |
| Compound #207 | 3-{[(1-Carboxy-2-phenyl-ethyl)-(2,4-dichloro-benzoyl)-amino]-methyl}-benzoic acid | 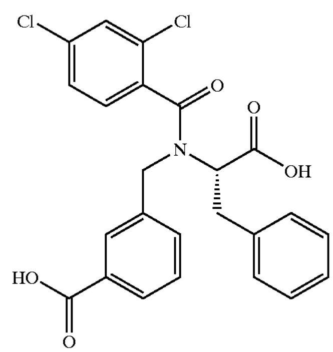 | | +++ |
| Compound #208 | 2-[(2,4-DICHLORO-BENZOYL)-(3-METHANESULFONYL-BENZYL)-AMINO]-3-PHENYL-PROPIONIC ACID | 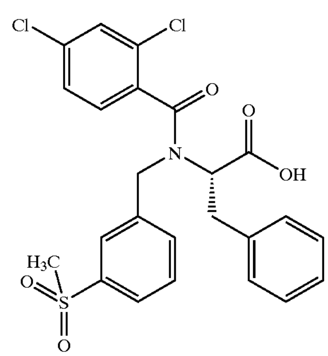 | | ++ |
| Compound #209 | 2-[(3-ACETYL-BENZYL)-(2,4-DICHLORO-BENZOYL)-AMINO]-3-PHENYL-PROPIONIC ACID | 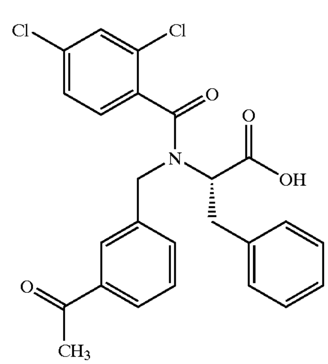 | | +++ |

TABLE 1-continued

LIST OF COMPOUNDS HAVING POLYMERASE ACTIVITY

| Compound # | Compound Name | Structure | RNA pol Assay 1 IC$_{50}$ ($\mu$m) | RNA pol Assay 2 IC$_{50}$ ($\mu$m) |
|---|---|---|---|---|
| Compound #210 | 2-[(2,4-DICHLORO-BENZOYL)-(1-OXY-PYRIDIN-3-YLMETHYL)-AMINO]-3-PHENYL-PROPIONIC ACID | 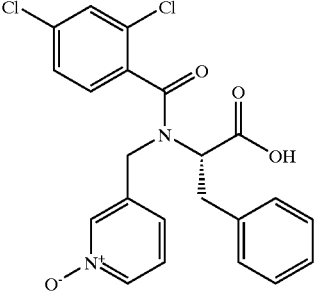 | | +++ |
| Compound #211 | 2-{(2,4-Dichloro-benzoyl)-[5-(3-trifluoromethyl-phenyl)-thiophen-2-ylmethyl]-amino}-3-phenyl-propionic acid | 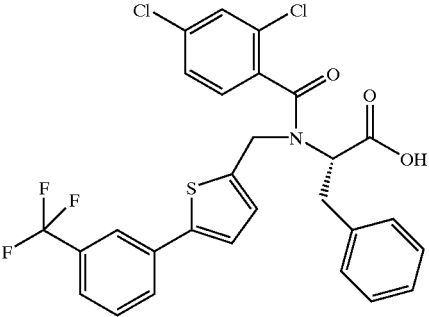 | | ++ |

*+++ IC$_{50}$ <5 $\mu$M
++ IC$_{50}$ 5 $\mu$M–20 $\mu$M
+ IC$_{50}$ >20 $\mu$M

TABLE 2

LIST OF COMPOUNDS HAVING ANTI-HELICASE ACTIVITY

| Compound # | Compound name | Structure | Anti-ATPase activity (Malachite Green assay) EC$_{50}$ ($\mu$m) | Anti-ATPase activity (HPLC method) EC$_{50}$ ($\mu$m) |
|---|---|---|---|---|
| Compound #4 | (2s)-2-[(4-Benzofuran-2-yl-benzyl)-(2,4-dichloro-benzoyl)-amino]-3-phenyl-propionic acid, | 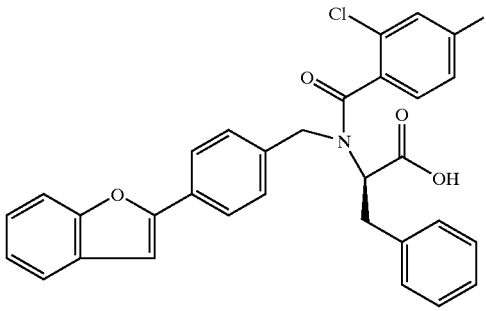 | ++ | ++ |

TABLE 2-continued

LIST OF COMPOUNDS HAVING ANTI-HELICASE ACTIVITY

| Compound # | Compound name | Structure | Anti-ATPase activity (Malachite Green assay) EC$_{50}$ (μm) | Anti-ATPase activity (HPLC method) EC$_{50}$ (μm) |
|---|---|---|---|---|
| Compound #11 | (2s)-2-[(3-Benzofuran-2-yl-benzyl)-(2,4-dichloro-benzoyl)-amino]-3-phenyl-propionic acid, | 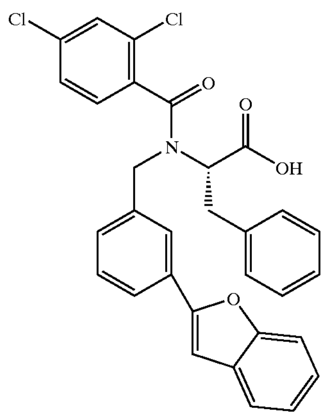 | +++ | ++ |
| Compound #85 | 2-[(5-Benzofuran-2-yl-thiophen-2-ylmethyl)-(2,4-dichloro-benzoyl)-amino]-3-phenyl-propionic acid | 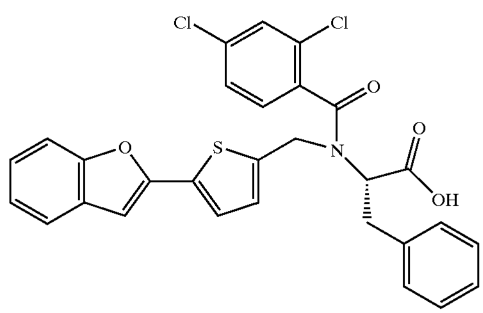 | ++ | ++ |
| Compound #5 | (2s)-2-[(4-Benzofuran-2-yl-benzyl)-(4-methoxy-2,3,6-trimethyl-benzenesulfonyl)-amino]-3-phenyl-propionic acid, | 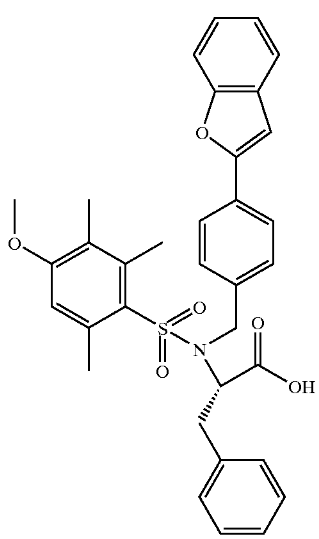 | ++ | ++ |

TABLE 2-continued

LIST OF COMPOUNDS HAVING ANTI-HELICASE ACTIVITY

| Compound # | Compound name | Structure | Anti-ATPase activity (Malachite Green assay) EC$_{50}$ ($\mu$m) | Anti-ATPase activity (HPLC method) EC$_{50}$ ($\mu$m) |
|---|---|---|---|---|
| Compound #7 | (2s)-2-[(3-Benzofuran-2-yl-benzyl)-(4-methoxy-2,3,6-trimethyl-benzenesulfonyl)-amino]-3-phenyl-propionic acid, compound #7 | 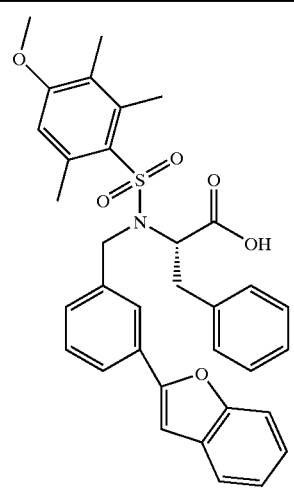 | ++ | + |
| Compound #195 | 3-Phenyl-2-{(2-trifluoromethyl-benzoyl)-[5-(2-trifluoromethyl-phenyl)-furan-2-ylmethyl]-amino}-propionic acid | 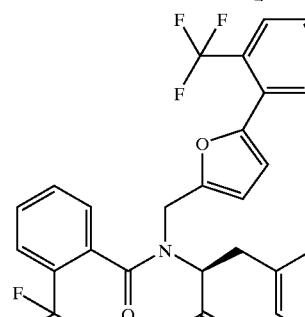 | ++ | ++ |
| Compound #196 | 2-{(3-Cyano-benzoyl)-[5-(2-trifluoromethyl-phenyl)-furan-2-ylmethyl]-amino}-3-phenyl-propionic acid | 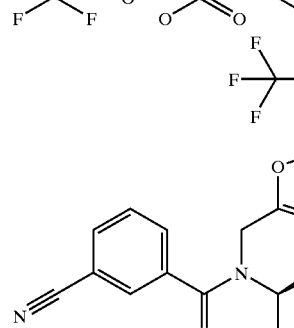 | +++ | +++ |
| Compound #197 | 2-{(4-Nitro-benzoyl)-[5-(2-trifluoromethyl-phenyl)-furan-2-ylmethyl]-amino}-3-phenyl-propionic acid | 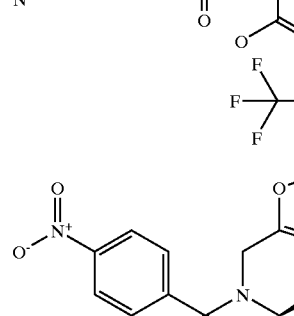 | +++ | +++ |

TABLE 2-continued

LIST OF COMPOUNDS HAVING ANTI-HELICASE ACTIVITY

| Compound # | Compound name | Structure | Anti-ATPase activity (Malachite Green assay) $EC_{50}$ (μm) | Anti-ATPase activity (HPLC method) $EC_{50}$ (μm) |
|---|---|---|---|---|
| Compound #198 | 2-{(2-Fluoro-benzoyl)-[5-(2-trifluoromethyl-phenyl)-furan-2-ylmethyl]-amino}-3-phenyl-propionic acid | 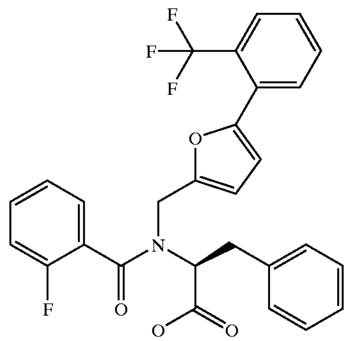 | +++ | ++ |

*+++ $IC_{50}$ <5 μM
++ $IC_{50}$ 5 μM–20 μM
+ $IC_{50}$ >20 μM

EXAMPLE 6

Evaluation of Biaryl Analogues in the HCV RNA-Dependent RNA Polymerase Assay The following references are all incorporated by reference:
1. Behrens, S., Tomei, L., De Francesco, R. (1996) *EMBO* 15, 12–22
2. Harlow, E, and Lane, D. (1988) *Antibodies: A Laboratory Manual*. Cold Spring Harbord Laboratory. Cold Spring Harbord. N.Y.
3. Lohmann, V., Körner, F., Herian, U., and Bartenschlager, R. (1997) *J. Virol.* 71, 8416–8428
4. Tomei, L., Failla, C., Santolini, E., De Francesco, R., and La Monica, N. (1993) *J Virol* 67, 4017–4026

Compounds were evaluated using an in vitro polymerase assay containing purified recombinant HCV RNA-dependent RNA polymerase (NS5B protein). HCV NS5B was expressed in sf9 insect cells using a recombinant baculovirus as vector. The experimental procedures used for the cloning, expression and purification of the HCV NS5B protein are described below. Follows, are details of the RNA-dependent RNA polymerase assays used to test the compounds.

The cDNA encoding the entire NS5B protein of HCV-Bk strain, genotype 1b, was amplified by PCR using the primers NS5Nhe5' (5'-GCTAGCGCTAGCTCAATGTCCTACACATGG-3') and XhoNS53' (5'-CTCGAGCTCGAGCGTCCATCGGTTGGGGAG-3') and the plasmid pCD 3.8–9.4 as template (Tomei et al, 1993). NS5Nhe5' and XhoNS53' contain two NheI and XhoI sites (underlined sequences), respectively, at their 5' end. The amplified DNA fragment was cloned in the bacterial expression plasmid pET-21b (Novagen) between the restriction sites NheI and XhoI, to generate the plasmid pET/NS5B. This plasmid was later used as template to PCR-amplify the NS5B coding region, using the primers NS5B-H9 (5'-ATACATATGGCTAGCATGTCAATGTCCTACACATGG-3') and NS5B-R4 (5'-GGATCCGGATCCCGTTCATCGGTTGGGGAG-3').

NS5B-H9 spans a region of 15 nucleotides in the plasmid pET-21b followed by the translation initiation codon (ATG) and 8 nucleotides corresponding to the 5' end of the NS5B coding region (nt. 7590–7607 in the HCV sequence with the accession number M58335). NS5B-R4 contains two BamHI sites (underlined) followed by 18 nucleotides corresponding to the region around the stop codon in the HCV genome (nt. 9365–9347). The amplified sequence, of 1.8 kb, was digested with NheI and BamHI and ligated to a predigested pBlueBacII plasmid (Invitrogen). The resulting recombinant plasmid was designated pBac/NS5B. Sf9 cells were co-transfected with 3 μg of pBac/NS5B, together with 1 μg of linearized baculovirus DNA (Invitrogen), as described in the manufacturer's protocol. Following two rounds of plaque purification, an NS5B-recombinant baculovirus, BacNS5B, was isolated. The presence of the recombinant NS5B protein was determined by western blot analysis (Harlow and Lane, 1988) of BacNS5B-infected Sf9 cells, using a rabbit polyclonal antiserum (anti-NS5B) raised against a His-tagged version of the NS5B protein expressed in *E. coli*. Infections of Sf9 cells with this plaque purified virus were performed in one-liter spinner flasks at a cell density of 1.2×10⁶ cells/ml and a multiplicity of infection of 5.

Sf9 cells were infected as described above. Sixty hours post-infection, cells were harvested then washed twice with phosphate buffer saline (PBS). Total proteins were solubilized as described in Lohmann et al. (1997) with some modifications. In brief, proteins were extracted in three steps, S1, S2, S3, using lysis buffers (LB) I, LB II and LB III (Lohmann et al, 1997). The composition of LBII was modified to contain 0.1% triton X-100 and 150 mM NaCl to reduce the amount of solubilized NS5B protein at this step. In addition, sonication of cell extracts was avoided throughout the protocol to preserve the integrity of the protein structure.

Purification of Recombinant NS5B Using Fast Protein Liquid Chromatography (FPLC)

Soluble NS5B protein in the S3 fraction was diluted to lower the NaCl concentration to 300 mM, then it incubated batchwise with DEAE sepharose beads (Amersham-Pharmacia) for 2 hrs at 4° C., as described by Behrens et al. (1996). Unbound material was cleared by centrifugation for 15 min at 4° C., at 25,000 rpm using a SW41 rotor (Beckman). The supernatant was further diluted to lower the NaCl concentration to 200 mM and subsequently loaded, with a flow rate of 1 ml/min, on a 5 ml HiTrap® heparin column (Amersham-Pharmacia) connected to an FPLC® system (Amersham-Pharmacia). Bound proteins were eluted in 1 ml fractions, using a continuous NaCl gradient of 0.2 to 1 M, over a 25 ml volume. NS5B-containing fractions were identified by sodium dodecyl sulfate polyacrylamide gel electrophoresis (SDS-PAGE), followed by western blotting using the anti-NS5B antiserum at a dilution of 1:2000. Positive fractions were pooled and the elution buffer was exchanged against a 50 mM $NaPO_4$ pH 7.0, 20% glycerol, 0.5% triton X-100 and 10 mM DTT, using a PD-10 column (Amersham-Pharmacia). The sample was then loaded onto a 1 ml HiTrap® SP column (Amersham-Pharmacia), with a flow rate of 0.1 ml/min. Bound proteins were eluted using a continuous 0 to 1 M NaCl gradient over a 15 ml volume. Eluted fractions were analyzed by SDS-PAGE and western blotting. Alternatively, proteins were visualized, following SDS-PAGE, by silver staining using the Silver Stain Plus kit (BioRad) as described by the manufacturer. Positive fractions were tested for RdRp activity (see below) and the most active ones were pooled, and stored as a 40% glycerol solution at −70° C.

In vitro RNA-dependent RNA Polymerase Assays Used to Evaluate Biaryl Analogues (Assay 1)

RdRp assays were conducted using the homopolymeric template/primer polyA/oligo dT. All RdRp reactions were performed in a total volume of 50 µl, and in a basic buffer consisting of 20 mM Tris-HCl pH 7.5, 1 mM DTT, 50 mM NaCl, 5 mM $MgCl_2$, 0.5 µCi [$\gamma^{32}P$]-UTP (3000 Ci/mmol), 15 µM cold UTP and 20 U RNasin (Promega). Standard HCV RdRp reactions contained 200 ng of purified NS5B protein. PolyA RNAs (Amersham-Pharmacia) was resuspended at 400 ng/µl. The primer oligodT$_{15}$ (Canadian life technologies) was diluted to a concentration of 20 pmol/ml (7.6 ng/µl). Templates and primers were mixed volume to volume, denatured at 95° C. for 5 min and annealed at 37° C. for 10 min. Following a two hour incubation at 22° C., reactions were stopped by the addition of 100 µg of sonicated salmon sperm DNA (Life Technologies) and 1 ml of 10% trichloroacetic acid-0.5% tetrasodium pyrophosphate (TCA-PPi). Nucleic acids were precipitated at 4° C. for 30 min after which samples were filtered on GF/C glass microfiber filters (Millipore). Membranes were subsequently washed with 25 ml of a 1% TCA-0.1% PPi solution, then air dried. Incorporated radioactivity was quantified using a liquid scintillation counter (1450-Microbeta, Wallac). Results are shown in Table 1, in the column indicated as Assay 1.

In vitro HCV RdRp Flashplate Scintillation Proximity Assay (Strep-Flash Assay) Used to Evaluate Analogues This assay consists on measuring the incorporation of [$^3$H] radiolabelled UTP in a polyrA/biotinylated-oligo dT template-primer, captured on the surface of streptavidin-coated microtiter flashplates (NEN SMP 103A). In brief, a 400 ng/µl polyrA solution (Amersham Pharmacia Biotech) was mixed volume-to-volume with 5' biotin-oligo dT$_{12}$ at 20 pmol/µl. The template and primers were denatured at 95 C for 5 minutes then incubated at 37 C for 10 minutes. Annealed template-primers were subsequently diluted in a Tris-HCl containing buffer and allowed to bind to streptavidin-coated flashplates overnight. Unbound material was discarded, compounds were added in a 10 µl solution followed by a 10 µl of a solution containing 100 mM $MgCl_2$, 200 mM Tris-HCl pH 7.5, 500 mM NaCl and 10 mM DTT. The enzymatic reaction was initiated upon addition of a 30 µl solution containing the enzyme and substrate to obtain the following concentrations: 25 µM UTP, 1 µCi [$^3$H] γ-UTP and 100 nM recombinant HCV NS5B. RdRp reactions were allowed to proceed for 2 hrs at room temperature after which wells were washed three times with a 0.15 M NaCl solution, air dried at 37 C, and counted in a Microbeta 1450 counter (Wallac). Results are shown in Table 1, in the column indicated as Assay 2.

EXAMPLE 7

Evaluation of Biaryl Analogues for Measurement of ATPase Activity of HCV NS3 Helicase Measurement of ATPase Activity for HCV NS3 Helicase Using the Malachite Green Method The measurement of ATPase activity was performed by measuring the amount of free inorganic phosphate released during the conversion of ATP to ADP by the HCV NS3 ATPase activity. The assay is as follows: In a 96-well microtiter-plate, compounds were dissolved at various concentrations in a final volume of 25 µL of ATPase buffer containing 400 µM ATP. The enzymatic reaction was initiated by the addition of 25 µl of ATPase buffer containing 6 nM of HCV NS3 enzyme without ATP to the wells followed by an incubation of 30 min. at 37 C. Essentially, the final concentration of the ATPase buffer components are as follows: 44 mM MOPS pH 7.0, 8.8 mM NaCl, 2.2 mM $MgCl_2$, 125 µg/ml poly A, 1% DMSO, 200 µM ATP, and 3 nM HCV NS3 enzyme. The reaction was stopped by the addition of 100 µl of Biomol Green™ reagent (BIOMOL® Research Laboratories Inc., Plymouth Meeting, Pa.). In order to allow the development of the green color, the plate was incubated for 15 min. at room temperature. Then the plate was read on a micro-plate reader at 620 nm. The 50% inhibitory concentration ($IC_{50}$) for anti-ATPase activity was defined as the concentration of compound that resulted in a 50% reduction of the signal compared to the signal observed in control sample without compound. The signal recorded was also corrected from the background signal obtained with control samples with compound only. The $IC_{50}$ was determined from dose-response curves using six to eight concentrations per compound. Curves were fitted to data points using a non-linear regression analysis, and $IC_{50}$s were interpolated from the resulting curves using GraphPad Prism software, version 2.0 (GraphPad Software Inc, San Diego, Calif.).

Measurement of ATPase Activity of HCV NS3 Helicase Using the HPLC method

The measurement of HCV NS3 ATPase activity was performed by measuring the amount of ADP produced during the conversion of ATP to ADP by the HCV NS3 enzyme using paired-ion HPLC on a reverse phase column. The assay is as follows: The same protocol as mentioned above was used except that the final concentration of HCV NS3 enzyme was reduced to 1 nM in a 50 µl reaction mixture and that the ATPase reaction was stopped by the addition of 12.5 µl of 0.5 M EDTA. A modular liquid chromatography system (TSP Spectrasystem®, ThermoQuest Corporation, San Diego, USA) using a ChromQuest™ software (ThermoQuest Corporation, San Diego, USA) controlled the autosampling of 25 µl from each reaction. The mobile phase was an isocratic solution of 0.15 M triethylamine, 6% methanol, and phosphoric acid to pH 5.5. ADP and ATP peaks were resolved using the Aqua 5µ, C18, 125 Å, (150×4.6 mm) reverse phase column. The extent of ATP conversion to ADP was evaluated by measuring the area under the ADP peak produced which was detected at 259 nm. The amount of ADP was corrected for the presence of ADP contaminant in the original ATP solution. The 50% inhibitory concentration ($IC_{50}$) for anti-ATPase activity was defined as the concentration of compound that resulted in a 50% reduction of the ADP peak area compared to the ADP peak area observed in control sample without compound. The $IC_{50}$ was determined from dose-response curves using six to eight concentrations per compound. Curves were fitted to data points using a non-linear regression analysis, and $IC_{50}$s were interpolated from the resulting curves using GraphPad Prism software, version 2.0 (GraphPad Software Inc, San Diego, Calif.).

Results of the ATPase activity for HCV NS3 helicase are shown in Table 2.

We claim:

1. A compound of formula I:

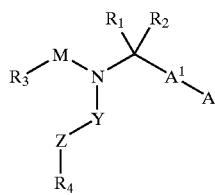

(I)

or a pharmaceutically acceptable salt thereof,
wherein,
M is

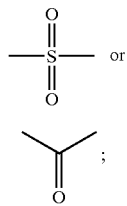

$A^1$ is a bond;
A is COOH;
$R_1$ is benzyl, thiophene, $CH_2$-thiophene, $CH_2$-imidazole, or $CH_2$-cyclohexyl which in each case is unsubstituted or substituted by at least one substituent chosen from halogen, OH or benzyl;
$R_2$ is H or methyl;
$R_3$ is 2,4-dichlorophenyl, 4-methoxy-2,3,6-trimethylphenyl, 2-chlorophenyl, 4-chlorophenyl, 3,4-dichlorophenyl, 4-chloro-2-iodo-phenyl, 2,4-dimethylphenyl, 4-chloro-2-methylphenyl, 4-chloro-2-bromo-phenyl, 4-chloro-2-ethylphenyl or 4-chloro-2-vinyl-phenyl;
Y is —$CH_2$—;
Z is $C_{1-6}$ alkyl, $C_{2-6}$ alkenyl, $C_{2-6}$ alkynyl, $C_{6-14}$ aryl, or $C_{3-10}$ heterocycle;
$R_4$ is H, halogen, CN, $NO_2$, $C_{1-6}$ alkyl, $C_{6-12}$ aryl, $C_{3-10}$ heterocycle, $C_{6-12}$ aralkyl $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$;
$R_5$ is in each case independently H or $C_{1-6}$ alkyl, and
$R_7$ is $C_{6-12}$ aryl or $C_{3-10}$ heterocycle.

2. A compound as defined in claim 1, wherein $R_1$ is benzyl substituted with OH.

3. A compound as defined in claim 1, wherein $R_1$ is benzyl substituted with Br.

4. A compound as defined in claim 1, wherein $R_1$ is $CH_2$-thiophene substituted with Br.

5. A compound as defined in claim 1, wherein $R_1$ is $CH_2$-cyclohexyl substituted with benzyl.

6. A compound as defined in claim 1, wherein M is:

(II)

7. A compound as defined in claim 1, wherein M is:

(III)

8. A compound according to claim 1, wherein $R_2$ is H.
9. A compound chosen from:
3-[3-(2,6-Dichloro-pyridin-4-yl)-1-(4-thiophen-2-yl-benzyl)-ureido]-3-thiophen-2-yl-propionic acid,
(2s)-2-[(2,4-Dichloro-benzoyl)-(4-thiazol-2-yl-benzyl)-amino]-3-phenyl-propionic acid,
(2s)-2-[(4-Bromo-benzyl)-(2,4-dichloro-benzoyl)-amino]-3-phenyl-propionic acid,
(2s)-2-[(4-Benzofuran-2-yl-benzyl)-(2,4-dichloro-benzoyl)-amino]-3-phenyl-propionic acid,
(2s)-2-[(4-Benzofuran-2-yl-benzyl)-(4-methoxy-2,3,6-trimethyl-benzenesulfonyl)-amino]-3-phenyl-propionic acid,
(2s)-2-[(4-Benzofuran-2-yl-benzyl)-(4-methoxy-2,3,6-trimethyl-benzenesulfonyl)-amino]-3-phenyl-propionic acid,
(2s)-2-[(3-Benzofuran-2-yl-benzyl)-(4-methoxy-2,3,6-trimethyl-benzenesulfonyl)-amino]-3-phenyl-propionic acid,
3-[(4-Iodo-benzyl)-(4-methoxy-2,3,6-trimethyl-benzenesulfonyl)-amino]-3-thiophen-2-yl-propionic acid ethyl ester,
(2s)-2-[(3-Bromo-benzyl)-(2,4-dichloro-benzoyl)-amino]-3-phenyl-propionic acid,
(2s)-2-[(3-Bromo-benzyl)-(2-chloro-benzoyl)-amino]-3-phenyl-propionic acid,
(2s)-2-[(3-Benzofuran-2-yl-benzyl)-(2,4-dichloro-benzoyl)-amino]-3-phenyl-propionic acid,
(2s)-2-[(2,4-Dichloro-benzoyl)-(4-iodo-benzyl)-amino]-3-phenyl-propionic acid,
(2s)-2-[(3-Iodo-benzyl)-(4-methoxy-2,3,6-trimethyl-benzenesulfonyl)-amino]-3-phenyl-propionic acid,
(2s)-2-[(4-Bromo-benzyl)-(4-methoxy-2,3,6-trimethyl-benzenesulfonyl)-amino]-3-phenyl-propionic acid,
(2s)-2-[(3-Bromo-benzyl)-(4-chloro-benzoyl)-amino]-3-phenyl-propionic acid,
(2s)-2-[(4-Iodo-benzyl)-(4-methoxy-2,3,6-trimethyl-benzenesulfonyl)-amino]-3-phenyl-propionic acid,
(2s)-2-[(3-Bromo-benzyl)-(4-methoxy-2,3,6-trimethyl-benzenesulfonyl)-amino]-3-phenyl-propionic acid,
(2s)-5-(4-{[(1s-1-Carboxy-2-phenyl-ethyl)-(4-methoxy-2,3,6-trimethyl-benzenesulfonyl)-amino]-methyl}-phenyl)-furan-2-carboxylic acid methyl ester,
(2s)-2-[(3-Bromo-benzyl)-(3,4-dichloro-benzoyl)-amino]-3-phenyl-propionic acid,
(2s)-2-[(3-Bromo-benzyl)-(2,4-dichloro-benzenesulfonyl)-amino]-3-phenyl-propionic acid, (2s)-3-(1-Benzyl-1h-imidazol-4-yl)-2-[(3-bromo-benzyl)-(2,4-dichloro-benzyl)-amino]-propionic acid,
(2s)-2-{(3-Bromo-benzyl)-[(2,4-dichloro-phenyl)-acetyl]-amino}-3-phenyl-propionic acid,
(2s)-5-(4-{[(1s-1-Carboxy-2-phenyl-ethyl)-(4-methoxy-2,3,6-trimethyl-benzenesulfonyl)-amino]-methyl}-phenyl)-thiophene-2-carboxylic acid methyl ester,
(2s)-2-[(2-Bromo-benzyl)-(4-methoxy-2,3,6-trimethyl-benzenesulfonyl)-amino]-3-phenyl-propionic acid,
(2s)-2-[(3-Bromo-benzyl)-(4-chloro-phenoxycarbonyl)-amino]-3-phenyl-propionic acid,
(2s)-2-[(4-Benzoyl-benzyl)-(4-methoxy-2,3,6-trimethyl-benzenesulfonyl)-amino]-3-phenyl-propionic acid,
(2s)-Trimethyl-ammonium; 2-[(3-benzofuran-2-yl-benzyl)-(4-methoxy-2,3,6-trimethyl-benzenesulfonyl)-amino]-3-phenyl-propionate,
2-[Allyl-(4-chloro-2-iodo-benzoyl)-amino]-3-phenyl-propionic acid,
(2s)-2-[(3-Bromo-benzyl)-(2,4-dimethyl-benzoyl)-amino]-3-phenyl-propionic acid,
3-(4-Benzofuran-2-yl-phenyl)-2-[(2,4-dichloro-benzoyl)-methyl-amino]-propionic acid,
(2s)-2-[(3-Bromo-benzyl)-(2,4-dichloro-benzoyl)-amino]-3-phenyl-propionic acid,
(2s)-2-[(3-Benzofuran-2-yl-benzyl)-(2,4-dimethyl-benzoyl)-amino]-3-phenyl-propionic acid,
(2s)-2-[(4-Benzofuran-2-yl-benzyl)-(4-methoxy-2,3,6-trimethyl-benzenesulfonyl)-amino]-3-(4-hydroxy-phenyl)-propionic acid,
(2s)-2-[(4-Benzofuran-2-yl-benzyl)-(2,4-dichloro-benzoyl)-amino]-3-(4-hydroxy-phenyl)-propionic acid,
(2s)-2-[(3-Bromo-benzyl)-(4-chloro-2-methyl-benzoyl)-amino]-3-phenyl-propionic acid,
(2s)-2-[(3-Bromo-benzyl)-(4-chloro-2-iodo-benzoyl)-amino]-3-phenyl-propionic acid,
(2s)-2-[(3-Bromo-benzyl)-(2-bromo-4-chloro-benzoyl)-amino]-3-phenyl-propionic acid,
(2s)-2-{(3-Benzofuran-2-yl-benzyl)-[(2,4-dichloro-phenyl)-acetyl]-amino}-3-phenyl-propionic acid,
(2s)-2-[(4-Benzofuran-2-yl-benzyl)-(2,4-dichloro-phenyl)-amino]-3-phenyl-propionic acid,
(2s)-2-[(2,4-Dichloro-benzoyl)-naphthalen-2-ylmethyl-amino]-3-phenyl-propionic acid,
(2s)-2-[(2,4-Dichloro-benzoyl)-(9,10-dioxo-9,10-dihydro-anthracen-2-ylmethyl)-amino]-3-phenyl-propionic acid,
(2s)-2-[[3-(3-Chloro-benzoyl)-benzyl]-(2,4-dichloro-benzoyl)-amino]-3-phenyl-propionic acid,
(2s)-2-{(2,4-Dichloro-benzoyl)-[3-(2,4-difluoro-benzoyl)-benzyl]-amino}-3-phenyl-propionic acid,
(2s)-2-[{3-[3-(2-Chloro-phenyl)-5-methyl-isoxazole-4-carbonyl]-benzyl}-(2,4-dichloro-benzoyl)-amino]-3-phenyl-propionic acid,
(2s)-2-{(2,4-Dichloro-benzoyl)-[3-(2,4-dichloro-benzoyl)-benzyl]-amino}-3-phenyl-propionic acid,
(2s)-2-[(3-Benzooxazol-2-yl-benzyl)-(2,4-dichloro-benzoyl)-amino]-3-phenyl-propionic acid,
(2s)-2-[(3-Bromo-benzyl)-(4-chloro-2-ethyl-benzoyl)-amino]-3-phenyl-propionic acid,
(2s)-2-[(4-Benzofuran-2-yl-benzyl)-(2,4-dichloro-benzoyl)-amino]-3-cyclohexyl-propionic acid,
(2s)-2-[(3-Benzofuran-2-yl-benzyl)-(4-chloro-2-methyl-benzoyl)-amino]-3-phenyl-propionic acid,
(2s)-2-[(3-Benzofuran-2-yl-benzyl)-(2-bromo-4-chloro-benzoyl)-amino]-3-phenyl-propionic acid,
(2s)-2-[(3-Bromo-benzyl)-(4-chloro-2-vinyl-benzoyl)-amino]-3-phenyl-propionic acid,
(2s)-2-[(2,4-Dichloro-benzoyl)-(3-fluoro-benzyl)-amino]-3-phenyl-propionic acid,
(2s)-2-[(3-Chloro-benzyl)-(2,4-dichloro-benzoyl)-amino]-3-phenyl-propionic acid,
(2S)-2-[(2,4-Dichloro-benzoyl)-(3-nitro-benzyl)-amino]-3-phenyl-propionic acid,
(2S)-2-[(3-Cyano-benzyl)-(2,4-dichloro-benzoyl)-amino]-3-phenyl-propionic acid,
(2s)-2-{(2-Chloro-benzoyl)-[5-(3-chloro-phenyl)-furan-2-ylmethyl]-amino}-phenyl-propionic acid,
(2s)-2-{(2,4-Dichloro-benzoyl)-[5-(3-trifluoromethyl-phenyl)-furan-2-ylmethyl]-amino}-3-phenyl-propionic acid,
(2s)-2-[(5-Bromo-furan-2-ylmethyl)-(2,4-dichloro-benzoyl)-amino]-3-phenyl-propionic acid,
(2s)-2-[(5-Benzofuran-2-yl-furan-2-ylmethyl)-(2,4-dichloro-benzoyl)-amino]-3-phenyl-propionic acid,
(2s)-2-[[5-(4-Bromo-phenyl)-furan-2-ylmethyl]-(2,4-dichloro-benzoyl)-amino]-3-phenyl-propionic acid,
(2s)-2-[[5-(2-Chloro-phenyl)-furan-2-ylmethyl]-(2,4-dichloro-benzoyl)-amino]-3-phenyl-propionic acid,
(2s)-2-[[5-(2-Chloro-5-trifluoromethyl-phenyl)-furan-2ylmethyl]-(2,4-dichloro-benzoyl)-amino]-3-phenyl-propionic acid,
(2s)-2-{(2,4-Dichloro-benzoyl)-[5-(2-nitro-phenyl)-furan-2-ylmethyl]-amino}-3-phenyl-propionic acid,
(3s)-3-{(2,4-Dichloro-benzoyl)-[5-(3-trifluoromethyl-phenyl)-furan-2-ylmethyl]-amino}-4-phenyl-butyric acid,
2-{(2,4-Dichloro-benzoyl)-[2-(3-nitro-phenyl)-thiazol-5-ylmethyl]-amino}-3-phenyl-propionic acid,
(2s)-2-{(2,4-Dichloro-benzoyl)-[5-(3,4-dichloro-phenyl)-furan-2-ylmethyl]-amino}-3-phenyl-propionic acid,
(2s)-2-[Benzofuran-2-ylmethyl-(2,4-dichloro-benzyl)-amino]-3-phenyl-propionic acid,
(2s)-2-{(2,4-Dichloro-benzoyl)-[5-(2,4-dichloro-phenyl)-furan-2-ylmethyl]-amino}-3-phenyl-propionic acid,
(2s)-2-[(2-Bromo-4-chloro-benzoyl)-(5-bromo-furan-2-ylmethyl)-amino]-3-phenyl-propionic acid,
(2s)-2-[[5-(3-Chloro-4-fluoro-phenyl)-furan-2-ylmethyl]-(2,4-dichloro-benzoyl)-amino]-3-phenyl-propionic acid,
(2s)-2-[[5-(4-Chloro-3-fluoro-phenyl)-furan-2-ylmethyl]-(2,4-dichloro-benzoyl)-amino]-3-phenyl-propionic acid,
(2s)-2-[(5-Bromo-furan-2-ylmethyl)-(4-chloro-2-iodo-benzoyl)-amino]-3-phenyl-propionic acid,
(2s)-2-(5-{[(1s-1-Carboxy-2-phenyl-ethyl)-(2,4-dichloro-benzoyl)-amino]-methyl}-furan-2-yl)-benzoic acid ethyl ester,
(2s)-2-(5-{[(1-Carboxy-2-phenyl-ethyl)-(2,4-dichloro-benzoyl)-amino]-methyl}-furan-2-yl)-benzoic acid,
(2s)-2-[(2,4-Dichloro-benzoyl)-(5-thiazol-2-yl-furan-2-ylmethyl)-amino]-3-phenyl-propionic acid,
(2s)-2-[(2,4-Dichloro-benzoyl)-furan-2-ylmethyl-amino]-3-phenyl-propionic acid,
(2s)-3-(5-{[(1s-1-Carboxy-2-phenyl-ethyl)-(2,4-dichloro-benzoyl)-amino]-methyl}-furan-2-yl)-benzoic acid,
(2s)-4-(5-{[(1s-1-Carboxy-2-phenyl-ethyl)-(2,4-dichloro-benzoyl)-amino]-methyl}-furan-2-yl)-benzoic acid,
(2s)-2-{(2-Bromo-4-chloro-benzoyl)-5-(3-trifluoromethyl-phenyl)-furan-2-ylmethyl]-amino}-3-phenyl-propionic acid,
(2s)-2-{(2,4-Dichloro-benzoyl)-[5-(3,5-difluoro-phenyl)-furan-2-ylmethyl]-amino}-3-phenyl-propionic acid,
(2s)-2-[(2,4-Dichloro-benzoyl)-(5-m-tolyl-furan-2-ylmethyl)-amino]-3-phenyl-propionic acid,
(2s)-2-{(2,4-Dichloro-benzoyl)-[5-(3-fluoro-phenyl)-furan-2-ylmethyl]-amino}-3-phenyl-propionic acid,
(2s)-2-[(5-Bromo-thiophen-2-ylmethyl)-(2,4-dichloro-benzoyl)-amino]-3-phenyl-propionic acid, (2s)-4-(5-{[(1s-1-Carboxy-2-phenyl-ethyl)-(2,4-dichloro-benzoyl)-amino]-methyl}-thiophen-2-yl)-benzoic acid,
(2s)-4-(5-{[(1-Carboxy-2-phenyl-ethyl)-(2,4-dichloro-benzoyl)-amino]-methyl}-thiophen-2-yl-benzoic acid methyl ester,
(2s)-2-[(5-Benzofuran-2-yl-thiophen-2-ylmethyl)-(2,4-dichloro-benzoyl)-amino]-3-phenyl-propionic acid,
2-[(2-Benzofuran-2-yl-thiazol-5-ylmethyl)-(2,4-dichloro-benzoyl)-amino]-3-phenyl-propionic acid,
(2s)-2-{(2,4-Dichloro-benzoyl)-[4-(3,4-dichloro-phenyl)-thiophen-2-ylmethyl]-amino}-3-phenyl-propionic acid,
(2s)-2-[[4-(4-Chloro-3-fluoro-phenyl)-thiophen-2-ylmethyl]-(2,4-dichloro-benzoyl)-amino]-3-phenyl-propionic acid,
(2s)-2-[[4-(3-Chloro-4-fluoro-phenyl)-thiophen-2-ylmethyl]-(2,4-dichloro-benzoyl)-amino]-3-phenyl-propionic acid,
(2s)-2-{(2,4-Dichloro-benzoyl)-[4-(2,4-dichloro-phenyl)-thiophen-2-ylmethyl]-amino}-3-phenyl-propionic acid,
(2s)-2-[[5-(3-Chloro-4-fluoro-phenyl)-thiophen-2-ylmethyl]-(2,4-dichloro-benzoyl)-amino]-3-phenyl-propionic acid,
(2s)-2-[[5-(4-chloro-3-fluoro-phenyl)-thiophen-2-ylmethyl]-(2,4-dichloro-benzoyl)-amino]-3-phenyl-propionic acid,
(2s)-2-{(2,4-Dichloro-benzoyl)-[5-(2,4-dichloro-phenyl)-thiophen-2-ylmethyl]-amino}-3-phenyl-propionic acid,
(2s)-2-[(2,4-Dichloro-benzoyl)-(5-thiazol-2-yl-thiophen-2-ylmethyl)-amino]-3-phenyl-propionic acid,
(2s)-2-{(2,4-Dichloro-benzoyl)-[5-(3,5-difluoro-phenyl)-thiophen-2-ylmethyl]-amino}-3-phenyl-propionic acid,
(2s)-2-{(2,4-Dichloro-benzoyl)-[5-(3-methoxy-phenyl)-thiophen-2-ylmethyl]-amino}-3-phenyl-propionic acid,
(2s)-2-{(2,4-Dichloro-benzoyl)-[5-(3-fluoro-phenyl)-thiophen-2-ylmethyl]-amino}-3-phenyl-propionic acid,
(2s)-2-[(2,4-Dichloro-benzoyl)-thiophen-2-ylmethyl-amino]-3-phenyl-propionic acid,
(2s)-2-[(4-Bromo-thiophen-2-ylmethyl)-(2,4-dichloro-benzoyl)-amino]-3-phenyl-propionic acid,
(2s)-2-{(2,4-Dichloro-benzoyl)-[2-(4-phenyl-piperazin-1-yl)-thiazol-5-ylmethyl]-amino}-3-phenyl-propionic acid,
(2s)-1-(5-{[(1s-1-Carboxy-2-phenyl-ethyl)-(2,4-dichloro-benzoyl)-amino]-methyl}-thiazol-2-yl)-piperidine-4-carboxylic acid,
(2s)-2-[[2-(4-Benzyl-piperazin-1-yl)-thiazol-5-ylmethyl]-(2,4-dichloro-benzoyl)-amino]-3-phenyl-propionic acid,
(2s)-2-[(2,4-Dichloro-benzoyl)-(2-piperidin-1-yl-thiazol-5-ylmethyl)-amino]-3-phenyl-propionic acid,
(2s)-2-[(2,4-Dichloro-benzoyl)-(2-diethylamino-thiazol-5-ylmethyl)-amino]-3-phenyl-propionic acid,
(2s)-2-[[2-(4-Chloro-benzoyl)-benzofuran-3-ylmethyl]-(4-methoxy-2,3,6-trimethyl-benzenesulfonyl)-amino]-3-phenyl-propionic acid,
(2s)-2-[[5-(2,4-Dichloro-phenoxy)-1-methyl-3-trifluoromethyl-1h-pyrazol-4-ylmethyl]-(4-methoxy-2,3,6-trimethyl-benzenesulfonyl)-amino]-3-phenyl-propionic acid,
(2s)-2-((2,4-Dichloro-benzoyl)-{2-[5-(2,4-dichloro-phenyl)-furan-2-yl]-2-oxo-ethyl}-amino)-3-phenyl-propionic acid,
(2s)-2-Benzyl-4-(2,4-dichloro-phenyl)-3-[3-(2,6-dichloro-phenyl)-5-methyl-isoxazol-4-ylmethyl]-4-oxo-butyric acid,
(2s)-2-[Allyl-(2,4-dichloro-benzoyl)-amino]-3-phenyl-propionic acid,
(2s)-2-[(2,4-Dichloro-benzoyl)-methyl-amino]-3-phenyl-propionic acid,
(2s)-2-[(2,4-Dichloro-benzoyl)-prop-2-ynyl-amino]-3-phenyl-propionic acid,
(2s)-2-[(2,4-Dichloro-benzoyl)-propyl-amino]-3-phenyl-propionic acid,
(2s)-2-[(3-Benzofuran-2-yl-prop-2-ynyl)-(2,4-dichloro-benzoyl)-amino]-3-phenyl-propionic acid,
(2s)-2-[(4-Benzofuran-2-yl-phenyl)-(2,4-dichloro-benzoyl)-amino]-3-phenyl-propionic acid,
(2s)-2-[(2,4-Dichloro-benzoyl)-(3-methyl-but-2-enyl)-amino]-3-phenyl-propionic acid,
2-[(2-Bromo-allyl)-(2,4-dichloro-benzoyl)-amino]-3-phenyl-propionic acid,
3-{[(1-Carboxy-2-phenyl-ethyl)-(2,4-dichloro-benzoyl)-amino]-methyl}-benzoic acid methyl ester,
3-[[5-(3-Chloro-4-fluoro-phenyl)-thiophen-2-ylmethyl]-(2,4-dichloro-benzoyl)-amino]-5-phenyl-thiophene-2-carboxylic acid,
2-[[5-(3-Cyano-phenyl)-furan-2-ylmethyl]-(2,4-dichloro-benzoyl)-amino]-3-phenyl-propionic acid,
(2s)-2-{(2,4-Dichloro-benzoyl)-[5-(2-trifluoromethyl-phenyl)-furan-2-ylmethyl]-amino}-3-phenyl-propionic acid,
(2s)-2-(5-{[(1s-1-Carboxy-2-phenyl-ethyl)-(2,4-dichloro-benzoyl)-amino]-methyl}-thiophen-2-yl)-benzoic acid ethyl ester,
3-(5-{[1s-1-Carboxy-2-phenyl-ethyl)-(2,4-dichloro-benzoyl)-amino]-methyl}-thiophen-2-yl)-benzoic acid ethyl ester,
(2s)-2-[[5-(3-Chloro-phenyl)-furan-2-ylmethyl]-(2,4-dichloro-benzoyl)-amino]-3-phenyl-propionic acid,
(2s)-2-[(4-Chloro-2-iodo-benzoyl)-(3,5-dibromo-thiophen-2-ylmethyl)-amino]-3-phenyl-propionic acid,
(2s)-3-(5-{[(1-Carboxy-2-phenyl-ethyl)-(2,4-dichloro-benzoyl)-amino]-methyl}-thiophen-2-yl)-benzoic acid,
(2s)-2-[[5-(5-Chloro-thiophen-2-yl)-furan-2-ylmethyl]-(2,4-dichloro-benzoyl)-amino]-3-phenyl-propionic acid,
(2s)-2-[[2,2']Bithiophenyl-5-ylmethyl-(2,4-dichloro-benzoyl)-amino]-3-phenyl-propionic acid,
(2s)-2-[(5'-Chloro-[2,2']bithiophenyl-5-ylmethyl)-(2,4-dichloro-benzoyl)-amino)-3-phenyl-propionic acid,
(2s)-2-{(2,4-Dichloro-benzoyl)-[4-(3,5-difluoro-phenyl)-thiophen-2-ylmethyl]-amino}-3-phenyl-propionic acid,
(2s)-2-{(2,4-Dichloro-benzoyl)-[4-(3-fluoro-phenyl)-thiophen-2-ylmethyl]-amino}-3-phenyl-propionic acid,
(2s)-2-{(4-Chloro-2-iodo-benzoyl)-5-(3-trifluoromethyl-phenyl)-furan-2-ylmethyl]-amino}-3-phenyl-propionic acid,
(2s)-2-{(4-Chloro-2-methyl-benzoyl)-[5-(3-trifluoromethyl-phenyl)-furan-2-ylmethyl]-amino}-3-phenyl-propionic acid,
(2s)-2-[(5-Chloro-[2,3']bithiophenyl-5'-ylmethyl)-(2,4-dichloro-benzoyl)-amino]-3-phenyl-propionic acid,
(2s)-2-{(2,4-Dichloro-benzoyl)-[5-(4-methoxy-phenyl)-furan-2-ylmethyl]-amino)}-3-phenyl-propionic acid,
(2s)-2-{(2,4-Dichloro-benzoyl)-[5-(4-methoxy-phenyl)-thiophen-2-ylmethyl]-amino}-3-phenyl-propionic acid,
(2s)-2-{(2,4-Dichloro-benzoyl)-[4-(4-methoxy-phenyl)-thiophen-2-ylmethyl]-amino}-3-phenyl-propionic acid,
(2s)-2-[(2,4-Dichloro-benzoyl)-(5-pyridin-4-yl-furan-2-ylmethyl)-amino]-3-phenyl-propionic acid,
(2s)-2-[(2,4-Dichloro-benzoyl)-(5-pyridin-4-yl-thiophen-2-ylmethyl)-amino]-3-phenyl-propionic acid,
(2s)-2-[(2,4-Dichloro-benzoyl)-(4-pyridin-4-yl-thiophen-2-ylmethyl)-amino]-3-phenyl-propionic acid,
(2s)-2-[(2-Chloro-thiazol-5-ylmethyl)-(2,4-dichloro-benzoyl)-amino]-3-phenyl-propionic acid,
(2s)-2-{(2,4-Dichloro-benzoyl)-[5-(4-fluoro-phenyl)-thiophen-2-ylmethyl]-amino}-3-phenyl-propionic acid, (2s)-2-[(2,4-Dichloro-benzoyl)-(3,5-dichloro-benzyl)-amino]-3-phenyl-propionic acid,
(2s)-2-[(2,4-Dichloro-benzoyl)-thiophen-3-ylmethyl-amino]-3-phenyl-propionic acid,
(2s)-2-[(2,4-Dichloro-benzoyl)-(3-trifluoromethyl-benzyl)-amino]-3-phenyl-propionic acid,
(2s)-2-[[3-(3-Chloro-4-fluoro-phenyl)-thiophen-2-ylmethyl]-(2,4-dichloro-benzoyl)-amino]-3-phenyl-propionic acid,
(2s)-2-[(3-Bromo-thiophen-2-ylmethyl)-(2,4-dichloro-benzoyl)-amino]-3-phenyl-propionic acid,
(2s)-2-{(2,4-Dichloro-benzoyl)-[5-(3-trifluoromethyl-phenyl)-furan-2-ylmethyl]-amino}-2-methyl-propionic acid,
(2s)-2-{(2,4-Dichloro-benzoyl)-[2-(3-trifluoromethyl-phenyl)-thiazol-5-ylmethyl]-amino}-3-phenyl-propionic acid,
(2s)-2-[(2,4-Dichloro-benzoyl)-(5-nitro-thiophen-3-ylmethyl)-amino]-3-phenyl-propionic acid,
(2s)-2-[(2,4-Dichloro-benzoyl)-(4-methanesulfonyl-benzyl)-amino]-3-phenyl-propionic acid,
(2s)-2-[(2,4-Dichloro-benzoyl)-(3-methoxy-benzyl)-amino]-3-phenyl-propionic acid,
(2s)-2-[(2,4-Dichloro-benzoyl)-(3-methyl-benzyl)-amino]-3-phenyl-propionic acid,
(2s)-2-[[5-(3-Chloro-phenoxy)-1-methyl-3-trifluoromethyl-1h-pyrazol-4-ylmethyl]-(2,4-dichloro-benzoyl)-amino]-3-phenyl-propionic acid,
(2s)-2-{(2,4-Dichloro-benzoyl)-[3-(3,5-difluoro-phenyl)-thiophen-2-ylmethyl]-amino}-3-phenyl-propionic acid,
(2s)-2-{(2,4-Dichloro-benzoyl)-[3-(3,4-dichloro-phenyl)-thiophen-2-ylmethyl]-amino}-3-phenyl-propionic acid,
(2s)-2-[[3-(4-Chloro-3-fluoro-phenyl)-thiophen-2-ylmethyl]-(2,4-dichloro-benzoyl)-amino]-3-phenyl-propionic acid,
(2s)-2-{(2,4-Dichloro-benzoyl)-[3-(2,4-dichloro-phenyl)-thiophen-2-ylmethyl]-amino}-3-phenyl-propionic acid,
(2s)-2-[(2,4-Dichloro-benzoyl)-(3-m-tolyl-thiophen-2-ylmethyl)-amino]-3-phenyl-propionic acid,
(2s)-2-(2-{[(1s-1-Carboxy-2-phenyl-ethyl)-(2,4-dichloro-benzoyl)-amino]-methyl}-thiophen-3-yl)-benzoic acid ethyl ester,
(2s)-4-(2-{[(1s-1-Carboxy-2-phenyl-ethyl)-(2,4-dichloro-benzoyl)-amino]-methyl}-thiophen-3-yl)-benzoic acid ethyl ester,
(2s)-2-{(2,4-Dichloro-benzoyl)-[3-(3-fluoro-phenyl)-thiophen-2-ylmethyl]-amino}-3-phenyl-propionic acid,
(2s)-2-[[3-(3-Cyano-phenyl)-thiophen-2-ylmethyl]-(2,4-dichloro-benzoyl)-amino]-3-phenyl-propionic acid,
{(2,4-Dichloro-benzoyl)-[5-(3-trifluoromethyl-phenyl)-furan-2-ylmethyl]-amino}-thiophen-2-ylacetic acid,
L-2-{[(1-Carboxy-2-phenyl-ethyl)-(2,4-dichloro-benzoyl)-amino]-methyl}-pyrrolidine-1-carboxylic acid #tert!-butyl ester,
d-2-{[(1-carboxy-2-phenyl-ethyl)-(2,4-dichloro-benzoyl)-amino]-methyl}-pyrrolidine-1-carboxylic acid #tert!-butyl ester,
4-[(1-Carboxy-2-phenyl-ethyl)-(2,4-dichloro-benzoyl)-amino]-piperidine-1-carboxylic acid benzyl ester,
1-2-[(2,4-Dichloro-benzoyl)-pyrrolidin-2-ylmethyl-amino]-3-phenyl-propionic acid,
d-2-[(2,4-Dichloro-benzoyl)-pyrrolidin-2-ylmethyl-amino]-3-phenyl-propionic acid,
3-(5-Bromo-thiophen-2-yl)-2-[(2,4-dichloro-benzoyl)-methyl-amino]-propionic acid,
2-[(2,4-Dichloro-benzoyl)-pyridin-3-ylmethyl-amino]-3-phenyl-propionic acid,
2-[(2,4-Dichloro-benzoyl)-(4-trifluoromethyl-benzyl)-amino]-3-phenyl-propionic acid,
2-{(2,4-Dichloro-benzoyl)-[4-(4-fluoro-benzyloxy)-benzyl]-amino}-3-phenyl-propionic acid,
2-[(2,4-Dichloro-benzoyl)-(4-fluoro-3-trifluoromethyl-benzyl)-amino]-3-phenyl-propionic acid,
2-[(1-Benzenesulfonyl-1h-pyrrol-2-ylmethyl)-(2,4-dichloro-benzoyl)-amino]-3-phenyl-propionic acid,
2-[[3-(4-Chloro-phenoxy)-benzyl]-(2,4-dichloro-benzoyl)-amino]-3-phenyl-propionic acid,
2-[(5-Chloro-2-chloromethyl-hepta-2,4,6-trienoyl)-quinolin-3-ylmethyl-amino]-3-phenyl-propionic acid,
2-[(2-Benzyloxy-benzyl)-(2,4-dichloro-benzoyl)-amino]-3-phenyl-propionic acid,
2-{(2,4-Dichloro-benzoyl)-[3-(5-isopropyl-2-methoxy-phenyl)-thiophen-2-ylmethyl]-amino}-3-phenyl-propionic acid,
2-{(2,4-Dichloro-benzoyl)-[3-(4-trifluoromethoxy-phenyl)-thiophen-2ylmethyl]-amino}-3-phenyl-propionic acid,
2-{(2,4-Dichloro-benzoyl)-[3-(3trifluoromethyl-phenyl)-thiophen-2-ylmethyl]-amino}-3-phenyl-propionic acid,
2-[[3-(3,5-Bis-trifluoromethyl-phenyl)-thiophen-2-ylmethyl]-(2,4-dichloro-benzoyl)-amino]-3-phenyl-propionic acid,
2-[(2,4-Dichloro-benzoyl)-(3-pyridin-4-yl-thiophen-2-ylmethyl)-amino]-3-phenyl-propionic acid,
2-{(2,4-Dichloro-benzoyl)-[3-(4-methylsulfanyl-phenyl)-thiophen-2-ylmethyl]-amino}-3-phenyl-propionic acid,
2-{(2,4-Dichloro-benzoyl)-[3-(4-fluoro-phenyl)-thiophen-2-ylmethyl]-amino}-3-phenyl-propionic acid,
2-[(2,4-Dichloro-benzoyl)-(3-pyridin-3-yl-thiophen-2-ylmethyl)-amino]-3-phenyl-propionic acid,
2-{(2,4-Dichloro-benzoyl)-[1-(toluene-2-sulfonyl)-pyrrolidin-2-ylmethyl]-amino}-3-phenyl-propionic acid,
2-[(2-Bromo-benzyl)-(2,4-dichloro-benzoyl)-amino]-3-phenyl-propionic acid,
3(2-Bromo-phenyl)-2-[(2,4-dichloro-benzoyl)-methyl-amino]-propionic acid,
3-(4-Bromo-phenyl)-2-[(2,4-dichloro-benzoyl)-methyl-amino]-propionic acid,
2-[(3-Bromo-phenyl)-(2,4-dichloro-benzoyl)-amino]-3-phenyl-propionic acid,
2-[(4-Bromo-phenyl)-(2,4-dichloro-benzoyl)-amino]-3-phenyl-propionic acid,
2-[[4-(3-Chloro-4-fluoro-phenyl)-thiophen-2-ylmethyl]-(2,4-dimethyl-benzoyl)-amino]-3-phenyl-propionic acid,
3-{[(1-Carboxy-2-phenyl-ethyl)-(2,4-dichloro-benzoyl)-amino]-methyl}-benzoic acid,
2-[(3-Amino-benzyl)-(2,4-dichloro-benzoyl)-amino]-3-phenyl-propionic acid,
3-Phenyl-2-{(2-trifluoromethyl-benzoyl)-[5-(2-trifluoromethyl-phenyl)-furan-2-ylmethyl]-amino}-propionic acid,
2-{(3-Cyano-benzoyl)-[5-(2-trifluoromethyl-phenyl)-furan-2-ylmethyl]-amino}-3-phenyl-propionic acid,
2-{(4-Nitro-benzoyl)-[5-(2-trifluoromethyl-phenyl)-furan-2-ylmethyl]-amino}-3-phenyl-propionic acid,
2-{(2-Fluoro-benzoyl)-[5-(2-trifluoromethyl-phenyl)-furan-2-ylmethyl]-amino}-3-phenyl-propionic acid,
2-[Benzyl-(2,4-dichloro-benzoyl)-amino]-3-phenyl-propionic acid,
2-{(2,4-Dichloro-benzoyl)-[3-(2H-tetrazol-5-yl)-benzyl]-amino}-3-phenyl-propionic acid,
2-[(2,4-Dichloro-benzoyl)-(2-nitro-benzyl)-amino]-3-phenyl-propionic acid,
2-[(2,4-Dichloro-benzoyl)-(4-nitro-benzyl)-amino]-3-phenyl-propionic acid, 2-[(2-Cyano-benzyl)-(2,4-dichloro-benzoyl)-amino]-3-phenyl-propionic acid, 2-[(4-Cyano-benzyl)-(2,4-dichloro-benzoyl)-amino]-3-phenyl-propionic acid, 2-[[1-(3-Cyano-phenyl)-ethyl]-(2,4-dichloro-benzoyl)-amino]-3-phenyl-propionic acid, 3-{[(1-Carboxy-2-phenyl-ethyl)-(2,4-dichloro-benzoyl)-amino]-methyl}-benzoic acid methyl, 3-{[(1-Carboxy-2-phenyl-ethyl)-(2,4-dichloro-benzoyl)-amino]-methyl}-benzoic acid, 2-[(2,4-Dichloro-benzoyl)-(3-methanesulfonyl-benzyl)-amino]-3-phenyl-propionic acid, 2-[(3-Acetyl-benzyl)-(2,4-dichloro-benzoyl)-amino]-3-phenyl-propionic acid, 2-[(2,4-Dichloro-benzoyl)-(1-oxy-pyridin-3-ylmethyl)-amino]-3-phenyl-propionic acid, 2-{(2,4-Dichloro-benzoyl)-[5-(3-trifluoromethyl-phenyl)-thiophen-2-ylmethyl]-amino}-3-phenyl-propionic acid, and pharmaceutically acceptable salts thereof.

10. A compound of formula I:

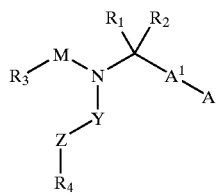

(I)

or a pharmaceutically acceptable salt thereof,
wherein,

M is

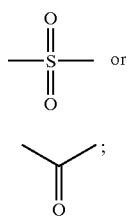

(II)

or (III)

$A^1$ is a bond;

A is COOH;

$R_1$ is benzyl, thiophene, $CH_2$-thiophene, $CH_2$-imidazole, or $CH_2$-cyclohexyl which in each case is unsubstituted or substituted by at least one substituent chosen from halogen, OH or benzyl;

$R_2$ is H or methyl;

$R_3$ is 2,4-dichlorophenyl, 4-methoxy-2,3,6-trimethylphenyl, 2-chlorophenyl, 4-chlorophenyl, 3,4-dichlorophenyl, 4-chloro-2-iodo-phenyl, 2,4-dimethylphenyl, 4-chloro-2-methylphenyl, 4-chloro-2-bromo-phenyl, 4-chloro-2-ethylphenyl or 4-chloro-2-vinyl-phenyl;

Y is —$CH_2$—;

Z is phenyl unsubstituted or substituted by at least one substituent chosen from halogen, $C_{3-10}$ heterocycle, $C_{3-10}$ heterocycle-$COOCH_3$, $NO_2$, CN, CO—$C_{6-12}$ aralkyl, $COOC_{1-6}$ alkyl, $C_{1-6}$ alkyl, O—$C_{1-6}$ alkyl, $C_{6-12}$ aryl, O—$C_{6-12}$ aryl, $C_{6-12}$ aralkyl, or O—$C_{6-12}$ aralkyl;

$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, $COR_7$, $R_5$ is in each case independently H or $C_{1-6}$ alkyl, and $R_7$ is $C_{6-12}$ aryl or $C_{3-10}$ heterocycle.

11. A compound of formula I:

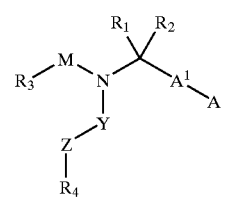

(I)

or a pharmaceutically acceptable salt thereof, wherein,

M is

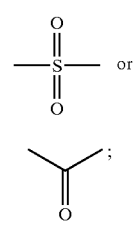

(II)

or (III)

$A^1$ is a bond;

A is COOH;

$R_1$ is benzyl, thiophene, $CH_2$-thiophene, $CH_2$-imidazole, or $CH_2$-cyclohexyl which in each case is unsubstituted or substituted by at least one substituent chosen from halogen, OH or benzyl;

$R_2$ is H or methyl;

$R_3$ is 2,4-dichlorophenyl, 4-methoxy-2,3,6-trimethylphenyl, 2-chlorophenyl, 4-chlorophenyl, 3,4-dichlorophenyl, 4-chloro-2-iodo-phenyl, 2,4-dimethylphenyl, 4-chloro-2-methylphenyl, 4-chloro-2-bromo-phenyl, 4-chloro-2-ethylphenyl or 4-chloro-2-vinyl-phenyl;

Y is —$CH_2$—;

Z is furan unsubstituted or substituted by at least one substituent chosen from halogen, $C_{6-12}$ aryl, or $C_{3-10}$ heterocycle; thiophene unsubstituted or substituted by at least one substituent chosen from halogen, $C_{6-12}$ aryl, $C_{3-10}$ heterocycle, or nitro; or thiazole unsubstituted or substituted by at least one substituent chosen from halogen, $C_{1-6}$ alkyl, $NR_5R_5$, or $C_{3-10}$ heterocycle;

$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, $COR_7$, $R_5$ is in each case independently H or $C_{1-6}$ alkyl, and $R_7$ is $C_{6-12}$ aryl or $C_{3-10}$ heterocycle.

12. A compound of formula I:

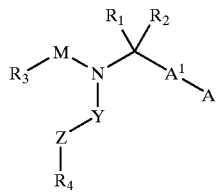
(I)

or a pharmaceutically acceptable salt thereof,
wherein,
M is

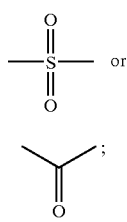
(II)

or (III)

$A^1$ is a bond;

A is COOH;

$R_1$ is benzyl, thiophene, $CH_2$-thiophene, $CH_2$-imidazole, or $CH_2$-cyclohexyl which in each case is unsubstituted or substituted by at least one substituent chosen from halogen, OH or benzyl;

$R_2$ is H or methyl;

$R_3$ is 2,4-dichlorophenyl, 4-methoxy-2,3,6-trimethylphenyl, 2-chlorophenyl, 4-chlorophenyl, 3,4-dichlorophenyl 4-chloro-2-iodo-phenyl, 2,4-dimethylphenyl, 4-chloro-2-methylphenyl, 4-chloro-2-bromo-phenyl, 4-chloro-2-ethylphenyl or 4-chloro-2-vinyl-phenyl;

Y is —$CH_2$—;

Z is vinyl, allyl, methyl, propyl, propynyl, or thiazole unsubstituted or substituted by at least one benzofuran;

$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, $COR_7$, $R_5$ is in each case independently H or $C_{1-6}$ alkyl, and $R_7$ is $C_{6-12}$ aryl or $C_{3-10}$ heterocycle.

13. A compound of formula I:

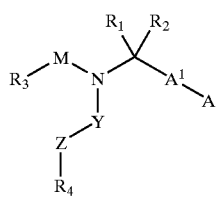
(I)

or a pharmaceutically acceptable salt thereof,
wherein,

M is

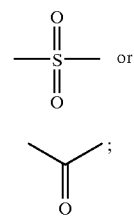
(II)

or (III)

$A^1$ is a bond;

A is COOH;

$R_1$ is benzyl, thiophene, $CH_2$-thiophene, $CH_2$-imidazole, or $CH_2$-cyclohexyl which in each case is unsubstituted or substituted by at least one substituent chosen from halogen, OH or benzyl;

$R_2$ is H or methyl;

$R_3$ is 2,4-dichlorophenyl, 4-methoxy-2,3,6-trimethylphenyl, 2-chlorophenyl, 4-chlorophenyl, 3,4-dichlorophenyl, 4-chloro-2-iodo-phenyl, 2,4-dimethylphenyl, 4-chloro-2-methylphenyl, 4-chloro-2-bromo-phenyl, 4-chloro-2-ethylphenyl or 4-chloro-2-vinyl-phenyl;

Y is —$CH_2$—;

Z is benzofuran, pyrazole, methyl oxazole, pyrrolidine, piperidine, pyridine, pyrrole, or quinolinyl, which in each case is unsubstituted or substituted by at least one substituent chosen from chlorophenyl-ketone, dichlorophenoxy, chlorophenoxy, dichlorophenyl, COO-t-butyl, tolyl-sulfonyl, COO-benzyl and $CF_3$;

$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, $COR_7$, $R_5$ is in each case independently H or $C_{1-6}$ alkyl, and $R_7$ is $C_{6-12}$ aryl or $C_{3-10}$ heterocycle.

14. A compound of formula I:

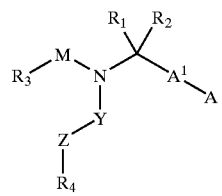
(I)

or a pharmaceutically acceptable salt thereof,
wherein,

M is

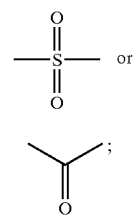
(II)

or (III)

$A^1$ is a bond;

A is COOH;

$R_1$ is benzyl, thiophene, $CH_2$-thiophene, $CH_2$-imidazole, or $CH_2$-cyclohexyl which in each case is unsubstituted or substituted by at least one substituent chosen from halogen, OH or benzyl;

$R_2$ is H or methyl;

$R_3$ is 2,4-dichlorophenyl, 4-methoxy-2,3,6-trimethylphenyl, 2-chlorophenyl, 4-chlorophenyl, 3,4-dichlorophenyl, 4-chloro-2-iodo-phenyl, 2,4-dimethylphenyl, 4-chloro-2-methylphenyl, 4-chloro-2-bromo-phenyl, 4-chloro-2-ethylphenyl or 4-chloro-2-vinyl-phenyl;

Y is —$CH_2$—;

Z is $C_{1-6}$ alkyl which is unsubstituted or substituted substituted by halogen, nitro, $SO_3R'_4$, $PO_3R'_4R'_4$, $CONH_2$, COOH, $SR_5$, O—$C_{1-6}$ alkyl, O—$C_{2-6}$ alkenyl, O—$C_{2-6}$ alkynyl, $C_{6-12}$ aryl, $C_{3-10}$ heterocycle, hydroxyl, amino, $NR_4R_4$, or COOQ, $C_{2-6}$ alkynyl which is unsubstituted or substituted substituted by halogen, nitro, $SO_3R'_4$, $PO_3R'_4R'_4$, $CONH_2$, COOH, $SR_5$, O—$C_{1-6}$ alkyl, O—$C_{2-6}$ alkenyl, O—$C_{2-6}$ alkynyl, $C_{6-12}$ aryl, $C_{3-10}$ heterocycle, hydroxyl, amino, $NR_4R_4$, or COOQ, $C_{6-12}$ aryl which is unsubstituted or substituted by H, $C_{1-6}$ alkyl, $C_{2-6}$ alkenyl, $C_{2-6}$ alkynyl, $C_{3-8}$ heterocycle, halogen, nitro, aminoamidino, amidino, guanido, $CONH_2$, COOH, O—$C_{1-6}$ alkyl, O—$C_{2-6}$ alkenyl, O—$C_{2-6}$ alkynyl, $SCH_3$, $SO_2CH_3$, amino, hydroxyl or COOQ, or $C_{3-10}$ heterocycle which is unsubstituted or mono or di-substituted by a $C_{1-6}$ alkyl, O—$C_{1-6}$ alkyl, O—$C_{6-12}$ aryl, $C_{6-12}$ aryl, $C_{6-12}$ aralkyl, $C_{3-10}$ heterocycle, halogen, amino, COOH, $COOR'_5$ or $NO_2$, $R_4$ is H, halogen, CN, $NO_2$, $C_{1-6}$ alkyl which is unsubstituted or substituted substituted by halogen, nitro, $SO_3R'_4$, $PO_3R'_4R'_4$, $CONH_2$, COOH, $SR_5$, O—$C_{1-6}$ alkyl, O—$C_{2-6}$ alkenyl, O—$C_{2-6}$ alkynyl, $C_{6-12}$ aryl, $C_{3-10}$ heterocycle, hydroxyl, amino, $NR_4R_4$, or COOQ, $C_{6-12}$ aryl which is unsubstituted or substituted by H, $C_{1-6}$ alkyl, $C_{2-6}$ alkenyl, $C_{2-6}$ alkynyl, $C_{3-8}$ heterocycle, halogen, nitro, aminoamidino, amidino, guanido, $CONH_2$, COOH, O—$C_{1-6}$ alkyl, O—$C_{2-6}$ alkenyl, O—$C_{2-6}$ alkynyl, $SCH_3$, $SO_2CH_3$, amino, hydroxyl or COOQ, $C_{3-10}$ heterocycle which is unsubstituted or mono or di-substituted by a $C_{1-6}$ alkyl, O—$C_{1-6}$ alkyl, O—$C_{6-12}$ aryl, $C_{6-12}$ aryl, $C_{6-12}$ aralkyl, $C_{3-10}$ heterocycle, halogen, amino, COOH, $COOR'_5$ or $NO_2$, $C_{6-12}$ aralkyl which is unsubstituted or the aryl group is substituted by H, $C_{1-6}$ alkyl, $C_{2-6}$ alkenyl, $C_{2-6}$ alkynyl, $C_{3-8}$ heterocycle, halogen, nitro, aminoamidino, amidino, guanido, $CONH_2$, COOH, O—$C_{1-6}$ alkyl, O—$C_{2-6}$ alkenyl, O—$C_{2-6}$ alkynyl, $SCH_3$, $SO_2CH_3$, amino, hydroxyl or COOQ, $C_{3-10}$ heteroaralkyl which is unsubstituted or the heterocycle group is mono or di-substituted by a $C_{1-6}$ alkyl, O—$C_{1-6}$ alkyl, O—$C_{6-12}$ aryl, $C_{6-12}$ aryl, $C_{6-12}$ aralkyl, $C_{3-10}$ heterocycle, halogen, amino, COOH, $COOR'_5$ or $NO_2$, $NR_5R_5$, $SO_2CH_3$, O—$C_{1-6}$ alkyl wherein the alkyl group is unsubstituted or substituted substituted by halogen, nitro, $SO_3R'_4$, $PO_3R'_4R'_4$, $CONH_2$, COOH, $SR_5$, O—$C_{1-6}$ alkyl, O—$C_{2-6}$ alkenyl, O—$C_{2-6}$ alkynyl, $C_{6-12}$ aryl, $C_{3-10}$ heterocycle, hydroxyl, amino, $NR_4R_4$, or COOQ, O—$C_{6-12}$ aryl wherein the aryl group is unsubstituted substituted by H, $C_{1-6}$ alkyl, $C_{2-6}$ alkenyl, $C_{2-6}$ alkynyl, $C_{3-8}$ heterocycle, halogen, nitro, aminoamidino, amidino, guanido, $CONH_2$, COOH, O—$C_{1-6}$ alkyl, O—$C_{2-6}$ alkenyl, O—$C_{2-6}$ alkynyl, $SCH_3$, $SO_2CH_3$, amino, hydroxyl or COOQ, O—$C_{6-12}$ aralkyl wherein the aryl group is unsubstituted substituted by H, $C_{1-6}$ alkyl, $C_{2-6}$ alkenyl, $C_{2-6}$ alkynyl, $C_{3-8}$ heterocycle, halogen, nitro, aminoamidino, amidino, guanido, $CONH_2$, COOH, O—$C_{1-6}$ alkyl, O—$C_{2-6}$ alkenyl, O—$C_{2-6}$ alkynyl, $SCH_3$, $SO_2CH_3$, amino, hydroxyl or COOQ, or $COR_7$, $R'_4$ is H, $C_{1-6}$ alkyl $R_5$ is in each case independently H or $C_{1-6}$ alkyl, $R'_5$ is $C_{1-6}$ alkyl, Q is $C_{1-6}$ alkyl, $C_{2-6}$ alkenyl, $C_{2-6}$ alkynyl, or $C_{6-12}$ aryl, and $R_7$ is $C_{6-12}$ aryl which is unsubstituted or substituted by H, $C_{1-6}$ alkyl, $C_{2-6}$ alkenyl, $C_{2-6}$ alkynyl, $C_{3-8}$ heterocycle, halogen, nitro, aminoamidino, amidino, guanido, $CONH_2$, COOH, O—$C_{1-6}$ alkyl, O—$C_{2-6}$ alkenyl, O—$C_{2-6}$ alkynyl, $SCH_3$, $SO_2CH_3$, amino, hydroxyl or COOQ, or $C_{3-10}$ heterocycle which is unsubstituted or mono or di-substituted by a $C_{1-6}$ alkyl, O—$C_{1-6}$ alkyl, O—$C_{6-12}$ aryl, $C_{6-12}$ aryl, $C_{6-12}$ aralkyl, $C_{3-10}$ heterocycle, halogen, amino, COOH, $COOR'_5$ or $NO_2$.

15. A pharmaceutical composition comprising at least one compound according to formula (I):

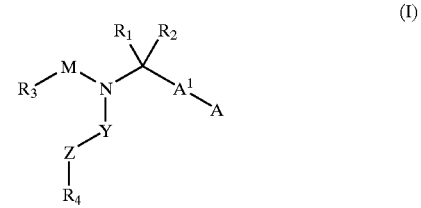

(I)

or a pharmaceutically acceptable salt thereof, wherein,

M is

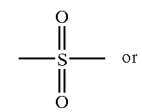 or (II)

(III)

$A^1$ is a bond;

A is COOH;

$R_1$ is benzyl, thiophene, $CH_2$-thiophene, $CH_2$-imidazole, $CH_2$-cyclohexyl which is unsubstituted or substituted by at least one substituent chosen from halogen, OH and benzyl;

$R_2$ is H or methyl;

$R_3$ is chosen from:

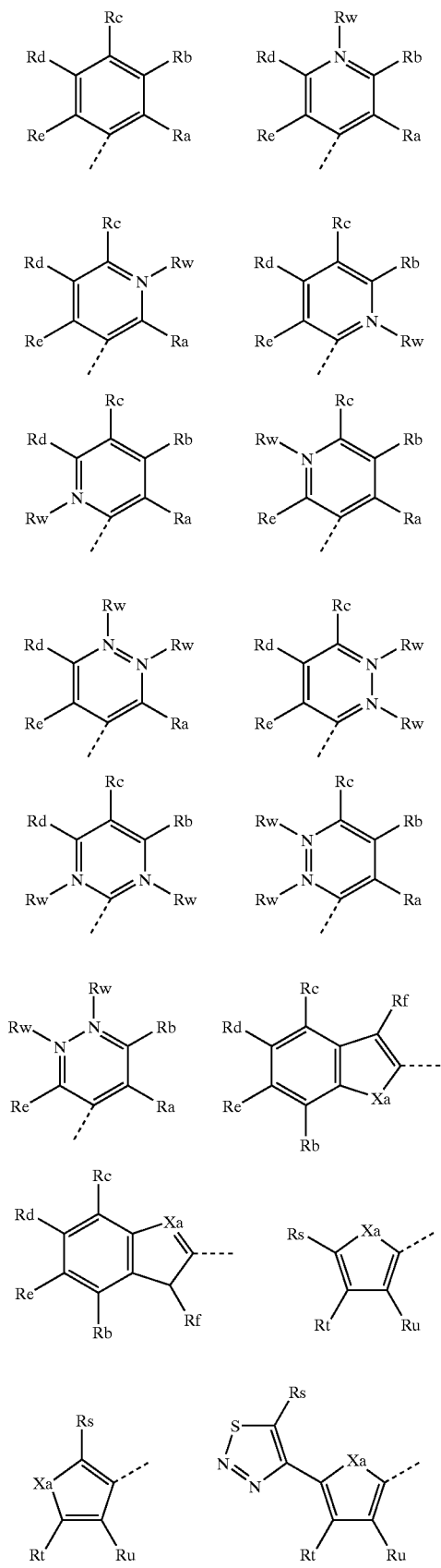

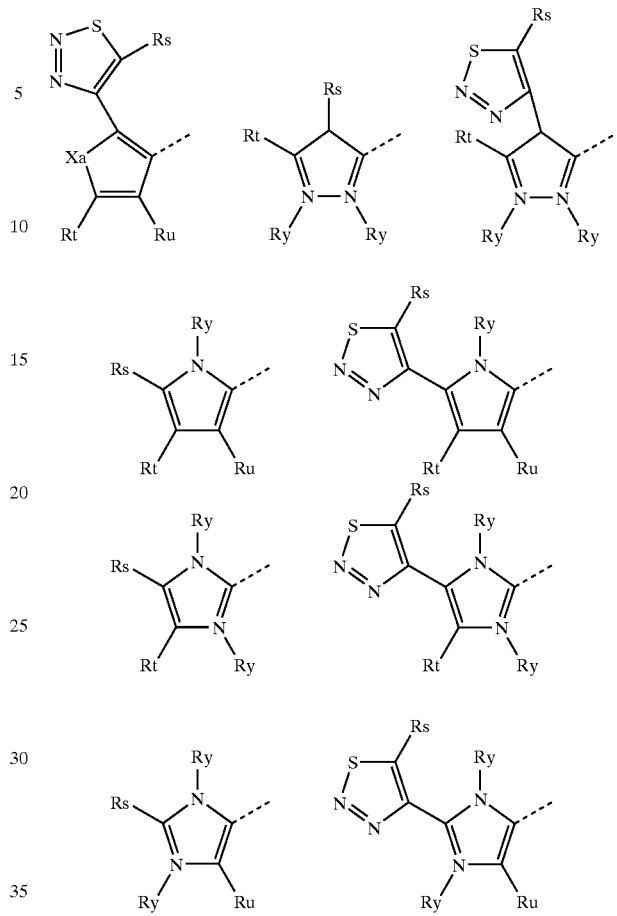

wherein

Rw is H or methyl;

Ry is H or methyl;

Rs, Rt, Ru, are each, independently, H, Cl, Br, I, F, $C_{1-6}$ alkyl, $OC_{1-6}$ alkyl, $CF_3$, COOH, $COOC_{1-6}$ alkyl, CN, $NH_2$, $NO_2$, $NH(C_{1-6}$ alkyl), $N(C_{1-6}$ alkyl$)_2$;

Ra, Rb, Rc, Rd, Re, and Rf are each independently chosen from, H, Cl, Br, I, F, C1–6 alkyl, $C_{2-6}$ alkenyl, $OC_{1-6}$ alkyl, $CF_3$, COOH, OH, $COOC_{1-6}$ alkyl, CN, $NH_2$, $NO_2$, $NH(C_{1-6}$ alkyl), and $N(C_{1-6}$ alkyl$)_2$;

Xa is S, N, O or C;

Y is —$CH_2$—;

Z is $C_{1-6}$ alkyl, $C_{2-6}$ alkenyl, $C_{2-6}$ alkynyl, $C_{6-14}$ aryl, or $C_{3-10}$ heterocycle;

$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$;

$R_5$ is in each case independently H or $C_{1-6}$ alkyl; and $R_7$ is chosen from $C_{6-12}$ aryl or $C_{3-10}$ heterocycle;

together with at least one pharmaceutically acceptable carrier or excipient.

16. A pharmaceutical composition according to claim 15, further comprising one or more additional agent chosen from antiviral agents, immunomudulating agents, antioxydant agents, antibacterial agents and antisense agents.

17. A pharmaceutical composition according to claim 16, wherein the antiviral agent is chosen from a viral serine protease inhibitor, viral polymerase inhibitor and viral helicase inhibitor.

18. A pharmaceutical composition according to claim 16, wherein the antiviral agent is chosen from interferon α and ribavirin.

19. A pharmaceutical composition according to claim 16, wherein said additional agent is chosen from silybum marianum, interleukine-12, amantadine, ribozyme, thymosin, N-acetyl cysteine or cyclosporin.

20. A composition according to claim 15, wherein Ra, Rb, Rc, Rd, Re, and Rf are each, independently, H, Cl, Br, I, F, methyl, O-methyl, $CF_3$, COOH, $COOCH_3$, OH, CN, $NH_2$, or $NO_2$.

21. A composition according to claim 15, wherein Ra, Rb, Rc, Rd, Re, and Rf are each, independently, H, Cl, methyl, O-methyl, $CF_3$, COOH, $COOCH_3$, CN, $NH_2$, or $NO_2$.

22. A composition according to claim 15, wherein Ra, Rb, Rc, Rd, Re, and Rf are each, independently, H, Cl, F, methyl, OH, $CF_3$ or O-methyl.

23. A composition according to claim 15, wherein Rf is H or methyl, and Ra, Rb, Rc, Rd and Re are each, independently, H or Cl.

24. A composition according to claim 15, wherein Rs, Rt and Ru are each, independently, H, Cl, Br, I, F, methyl, O-methyl, $CF_3$, COOH, $COOCH_3$, CN, $NH_2$, $NO_2$, $NH(CH_3)$ or $N(CH_3)_2$.

25. A composition according to claim 15, wherein Rs, Rt, and Ru are each, independently, H, Cl, Br, I, F, methyl, O-methyl, $CF_3$, COOH, $COOCH_3$, CN, $NH_2$, or $NO_2$.

26. A composition according to claim 15, wherein Rs, Rt, and Ru are each, independently, H, Cl, methyl, O-methyl, $CF_3$, COOH, $COOCH_3$, CN, $NH_2$ or $NO_2$.

27. A composition according to claim 15, wherein Rs, Rt, and Ru are each, independently, H, Cl, F, methyl, $CF_3$ or O-methyl.

28. A combination comprising a compound according to formula (I)

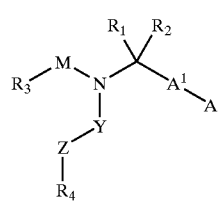
(I)

or a pharmaceutically acceptable salt thereof,
wherein,
M is

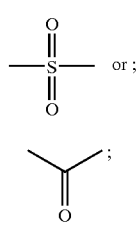
(II)

or;

(III)

$A^1$ is a bond;
A is COOH;
$R_1$ is benzyl, thiophene, $CH_2$-thiophene, methyl, $CH_2$-imidazole, or $CH_2$-cyclohexyl which in each case is unsubstituted or substituted by at least one substituent chosen from halogen, OH or benzyl;

$R_2$ is H or methyl;
$R_3$ is $C_{6-12}$ aryl or $C_{3-10}$ heterocycle;
Y is —$CH_2$—
Z is $C_{1-6}$ alkyl, $C_{2-6}$ alkenyl, $C_{2-6}$ alkynyl, $C_{6-14}$ aryl, or $C_{3-10}$ heterocycle;
$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$;
$R_5$ is in each case independently H or $C_{1-6}$ alkyl; and
$R_7$ is $C_{6-12}$ aryl or $C_{3-10}$ heterocycle;

and one or more additional agent chosen from antiviral agent is chosen from viral serine protease inhibitor, viral polymerase inhibitors, viral helicase inhibitors, immunomudulating agents, antioxydant agents, antibacterial agents, and antisense agents.

29. A combination as defined in claim 28, wherein said additional agent is chosen from silybum marianum, interleukine-12, amantadine, ribozyme, thymosin, N-acetyl cysteine, cyclosporin, interferon α and ribavirin.

30. A combination as defined in claim 28, wherein said compound and said additional agent are administered sequentially.

31. A combination as defined in claim 28, wherein said compound and said additional agent are administered simultaneously.

32. A method for treating a Flaviridae viral infection in a host, wherein the Flavivirus viral infection is hepatitis C virus, bovine viral diarrhea virus, hog cholera virus or yellow fever virus, comprising administering to the host a therapeutically effective amount of at least one compound of formula (I):

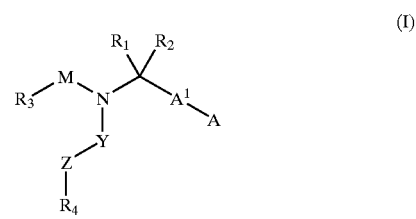
(I)

or a pharmaceutically acceptable salt thereof,
wherein,
M is

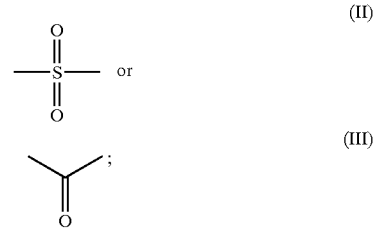
(II)

or (III)

$A^1$ is a bond;
A is COOH;
$R_1$ is benzyl, thiophene, $CH_2$-thiophene, methyl, $CH_2$-imidazole, $CH_2$-cyclohexyl which is unsubstituted or substituted by at least one substituent chosen from halogen, OH or benzyl;

$R_2$ is H or methyl;
$R_3$ is $C_{6-12}$ aryl or $C_{3-10}$ heterocycle;
Y is —$CH_2$—;
Z is $C_{1-6}$ alkyl, $C_{2-6}$ alkenyl, $C_{2-6}$ alkynyl, $C_{6-14}$ aryl, or $C_{3-10}$ heterocycle;
$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$;
$R_5$ is in each case independently H or $C_{1-6}$ alkyl; and
$R_7$ is $C_{6-12}$ aryl or $C_{3-10}$ heterocycle.

33. A method for treating a Flaviridae viral infection in a host, wherein the Flavivirus viral infection is hepatitis C virus, bovine viral diarrhea virus, hog cholera virus or yellow fever virus, comprising administering to the host a therapeutically effective amount of at least one compound selected from:

3-[3-(2,6-Dichloro-pyridin-4-yl)-1-(4-thiophen-2-yl-benzyl)-ureido]-3-thiophen-2-yl-propionic acid,
(2s)-2-[(2,4-Dichloro-benzoyl)-(4-thiazol-2-yl-benzyl)-amino]-3-phenyl-propionic acid,
(2s)-2-[(4-Bromo-benzyl)-(2,4-dichloro-benzoyl)-amino]-3-phenyl-propionic acid,
(2s)-2-[(4-Benzofuran-2-yl-benzyl)-(2,4-dichloro-benzoyl)-amino]-3-phenyl-propionic acid,
(2s)-2-[(4-Benzofuran-2-yl-benzyl)-(4-methoxy-2,3,6-trimethyl-benzenesulfonyl)-amino]-3-phenyl-propionic acid,
(2s)-2-[(4-Benzofuran-2-yl-benzyl)-(4-methoxy-2,3,6-trimethyl-benzenesulfonyl)-amino]-3-phenyl-propionic acid,
(2s)-2-[(3-Benzofuran-2yl-benzyl)-(4-methoxy-2,3,6-trimethyl-benzenesulfonyl)-amino]-3-phenyl-propionic acid,
3-[(4-Iodo-benzyl)-(4-methoxy-2,3,6-trimethyl-benzenesulfonyl)-amino]-3-thiophen-2-yl-propionic acid ethyl ester,
(2s)-2-[(3-Bromo-benzyl)-(2,4-dichloro-benzoyl)-amino]-3-phenyl-propionic acid,
(2s)-2-[(3-Bromo-benzyl)-(2-chloro-benzoyl)-amino]-3-phenyl-propionic acid,
(2s)-2-[(3-Benzofuran-2-yl-benzyl)-(2,4-dichloro-benzoyl)-amino]-3-phenyl-propionic acid,
(2s)-2-[(2,4-Dichloro-benzoyl)-(4-iodo-benzyl)-amino]-3-phenyl-propionic acid,
(2s)-2-[(3-Iodo-benzyl)-(4-methoxy-2,3,6-trimethyl-benzenesulfonyl)-amino]-3-phenyl-propionic acid,
(2s)-2-[(4-Bromo-benzyl)-(4-methoxy-2,3,6-trimethyl-benzenesulfonyl)-amino]-3-phenyl-propionic acid,
(2s)-2-[(3-Bromo-benzyl)-(4-chloro-benzoyl)-amino]-3-phenyl-propionic acid,
(2s)-2-[(4-Iodo-benzyl)-(4-methoxy-2,3,6-trimethyl-benzenesulfonyl)-amino]-3-phenyl-propionic acid,
(2s)-2-[(3-Bromo-benzyl)-(4-methoxy-2,3,6-trimethyl-benzenesulfonyl)-amino]-3-phenyl-propionic acid,
(2s)-5-(4-{[(1s-1-Carboxy-2-phenyl-ethyl)-(4-methoxy-2,3,6-trimethyl-benzenesulfonyl)-amino]-methyl}-phenyl)-furan-2-carboxylic acid methyl ester,
(2s)-2-[(3-Bromo-benzyl)-(3,4-dichloro-benzoyl)-amino]-3-phenyl-propionic acid,
(2s)-2-[(3-Bromo-benzyl)-(2,4-dichloro-benzenesulfonyl)-amino]-3-phenyl-propionic acid,
(2s)-3-(1-Benzyl-1h-imidazol-4-yl)-2-[(3-bromo-benzyl)-(2,4-dichloro-benzoyl)-amino]-propionic acid,
(2s)-2-{(3-Bromo-benzyl)-[(2,4dichloro-phenyl)-acetyl]amino}-3-phenyl-propionic acid,
(2s)-5-(4-{[(1s-1-Carboxy-2-phenyl-ethyl)-(4-methoxy-2,3,6-trimethyl-benzenesulfonyl)-amino]-methyl}-phenyl)-thiophene-2-carboxylic acid methyl ester,
(2s)-2-[(2-Bromo-benzyl)-(4-methoxy-2,3,6-trimethyl-benzenesulfonyl)-amino]-3-phenyl-propionic acid,
(2s)-2-[(3-Bromo-benzyl)-(4-chloro-phenoxycarbonyl)-amino]-3-phenyl-propionic acid,
(2s)-2-[(4-Benzoyl-benzyl)-(4-methoxy-2,3,6-trimethyl-benzenesulfonyl)-amino]-3-phenyl-propionic acid,
(2s)-Triethyl-ammonium; 2-[(3-benzofuran-2-yl-benzyl)-(4-methoxy-2,3,6-trimethyl-benzenesulfonyl)-amino]-3-phenyl-propionate,
2-[Allyl-(4-chloro-2-iodo-benzoyl)-amino]-3-phenyl-propionic acid,
(2s)-2-[(3-Bromo-benzyl)-(2,4-dimethyl-benzoyl)-amino]-3-phenyl-propionic acid,
3-(4-Benzofuran-2-yl-phenyl)-2-[(2,4-dichloro-benzoyl)-methyl-amino]-propionic acid,
(2s)-2-[(3-Bromo-benzyl)-(2,4-dichloro-benzyl)amino]-3-phenyl-propionic acid,
(2s)-2-[(3-Benzofuran-2-yl-benzyl)-(2,4-dimethyl-benzoyl)-amino]-3-phenyl-propionic acid,
(2s)-2-[(4-Benzofuran-2-yl-benzyl)-(4-methoxy-2,3,6-trimethyl-benzenesulfonyl)-amino]-3-(4-hydroxy-phenyl)-propionic acid,
(2s)-2-[(4-Benzofuran-2-yl-benzyl)-(2,4-dichloro-benzoyl)-amino]-3-(4-hydroxy-phenyl)-propionic acid,
(2s)-2-[(3-Bromo-benzyl)-(4-chloro-2-methyl-benzoyl)-amino]-3-phenyl-propionic acid,
(2s)-2-[(3-Bromo-benzyl)-(4-chloro-2-iodo-benzoyl)-amino]-3-phenyl-propionic acid,
(2s)-2-[(3-Bromo-benzyl)-(2-bromo-4-chloro-benzoyl)-amino]-3-phenyl-propionic acid,
(2s)-2-{(3-Benzofuran-2-yl-benzyl)-[(2,4-dichloro-phenyl)-acetyl]-amino}-3-phenyl-propionic acid,
(2s)-2-[(4-Benzofuran-2-yl-benzyl)-(2,4-dichloro-phenyl)-amino]-3-phenyl-propionic acid,
(2s)-2-[(2,4-Dichloro-benzoyl)-naphthalen-2-ylmethyl-amino]-3-phenyl-propionic acid,
(2s)-2-[(2,4-Dichloro-benzoyl)-(9,10-dioxo-9,10-dihydro-anthracen-2-ylmethyl)-amino]-3-phenyl-propionic acid,
(2s)-2-[[3-(3-Chloro-benzoyl)-benzyl]-(2,4-dichloro-benzoyl)-amino]-3-phenyl-propionic acid,
(2s)-2-{(2,4-Dichloro-benzoyl)-[3-(2,4-difluoro-benzoyl)-benzyl]-amino}-3-phenyl-propionic acid,
(2s)-2-[{3-[3-(2-Chloro-phenyl)-5-methyl-isoxazole-4-carbonyl]-benzyl}-(2,4-dichloro-benzoyl)-amino]-3-phenyl-propionic acid,
(2s)-2-{(2,4-Dichloro-benzoyl)-[3-(2,4-dichloro-benzoyl)-benzyl]-amino}-3-phenyl-propionic acid,
(2s)-2-[(3-Benzooxazol-2-yl-benzyl)-(2,4-dichloro-benzoyl)-amino]-3-phenyl-propionic acid,
(2s)-2-[(3-Bromo-benzyl)-(4-chloro-2-ethyl-benzoyl)-amino]-3-phenyl-propionic acid,
(2s)-2-[(4-Benzofuran-2-yl-benzyl)-(2,4-dichloro-benzoyl)-amino]-3-cyclohexyl-propionic acid,
(2s)-2-[(3-Benzofuran-2-yl-benzyl)-(4-chloro-2-methyl-benzoyl)-amino]-3-phenyl-propionic acid,
(2s)-2-[(3-Benzofuran-2-yl-benzyl)-(2-bromo-4-chloro-benzoyl)-amino]-3-phenyl-propionic acid,
(2s)-2-[(3-Bromo-benzyl)-(4-chloro-2-vinyl-benzoyl)-amino]-3-phenyl-propionic acid,
(2s)-2-[(2,4-Dichloro-benzoyl)-(3-fluoro-benzyl)-amino]-3-phenyl-propionic acid,
(2s)-2-[(3-Chloro-benzyl)-(2,4-dichloro-benzoyl)-amino]-3-phenyl-propionic acid,
(2S)-2-[(2,4-Dichloro-benzoyl)-(3-nitro-benzyl)-amino]-3-phenyl-propionic acid, (2S)-2-[(3-Cyano-benzyl)-(2,4-dichloro-benzoyl)-amino]-3-phenyl-propionic acid,
(2s)-2-{(2-Chloro-benzoyl)-[5-(3-chloro-phenyl)-furan-2-ylmethyl]-amino}-3-phenyl-propionic acid,
(2s)-2-{(2,4-Dichloro-benzoyl)-[5-(3-trifluoromethyl-phenyl)-furan-2-ylmethyl]-amino}-3-phenyl-propionic acid,
(2s)-2-[(5-Bromo-furan-2-ylmethyl)-(2,4-dichloro-benzoyl)-amino]-3-phenyl-propionic acid,
(2s)-2-[(5-Benzofuran-2-yl-furan-2-ylmethyl)-(2,4-dichloro-benzoyl)-amino]-3-phenyl-propionic acid,
(2s)-2-[[5-(4-Bromo-phenyl)-furan-2-ylmethyl]-(2,4-dichloro-benzoyl)-amino]-3-phenyl-propionic acid,
(2s)-2-[[5-(2-Chloro-phenyl)-furan-2-ylmethyl]-(2,4-dichloro-benzoyl)-amino]-3-phenyl-propionic acid,
(2s)-2-[[5-(2-Chloro-5-trifluoromethyl-phenyl)-furan-2-ylmethyl]-(2,4-dichloro-benzoyl)-amino]-3-phenyl-propionic acid,
(2s)-2-{(2,4-Dichloro-benzoyl)-[5-(2-nitro-phenyl)-furan-2-ylmethyl]-amino}-3-phenyl-propionic acid,
(3s)-3-{(2,4-Dichloro-benzoyl)-[5-(3-trifluoromethyl-phenyl)-furan-2-ylmethyl]-amino}-4-phenyl-butyric acid,
2-{(2,4-Dichloro-benzoyl)-[2-(3-nitro-phenyl)-thiazol-5-ylmethyl]-amino}-3-phenyl-propionic acid,
(2s)-2-{(2,4-Dichloro-benzoyl)-[5-(3,4-dichloro-phenyl)-furan-2-ylmethyl]-amino}-3-phenyl-propionic acid,
(2s)-2-[Benzofuran-2-ylmethyl-(2,4-dichloro-benzyl)-amino]-3-phenyl-propionic acid,
(2s)-2-{(2,4-Dichloro-benzoyl)-[5-(2,4-dichloro-phenyl)-furan-2-ylmethyl]-amino}-3-phenyl-propionic acid,
(2s)-2-[(2-Bromo-4-chloro-benzoyl)-(5-bromo-furan-2-ylmethyl)-amino]-3-phenyl-propionic acid,
(2s)-2-[[5-(3-Chloro-4-fluoro-phenyl)-furan-2-ylmethyl]-(2,4-dichloro-benzoyl)-amino]-3-phenyl-propionic acid,
(2s)-2-[[5-(4-Chloro-3-fluoro-phenyl)-furan-2-ylmethyl]-(2,4-dichloro-benzoyl)-amino]-3-phenyl-propionic acid,
(2s)-2-[(5-Bromo-furan-2-ylmethyl)-(4-chloro-2-iodo-benzoyl)-amino]-3-phenyl-propionic acid,
(2s)-2-(5-{[(1s-1-Carboxy-2-phenyl-ethyl)-(2,4-dichloro-benzoyl)-amino]-methyl}-furan-2-yl)-benzoic acid ethyl ester,
(2s)-2-(5-{[(1-Carboxy-2-phenyl-ethyl)-(2,4-dichloro-benzoyl)-amino]-methyl}-furan-2-yl)-benzoic acid,
(2s)-2-[(2,4-Dichloro-benzoyl)-(5-thiazol-2-yl-furan-2-ylmethyl)-amino]-3-phenyl-propionic acid,
(2s)-2-[(2,4-Dichloro-benzoyl)-furan-2-ylmethyl-amino]-3-phenyl-propionic acid,
(2s)-3-(5-{[(1s-1-Carboxy-2-phenyl-ethyl)-(2,4-dichloro-benzoyl)-amino]-methyl}-furan-2-yl)-benzoic acid,
(2s)-4-(5-{[(1s-1-Carboxy-2-phenyl-ethyl)-(2,4-dichloro-benzoyl)-amino]-methyl}-furan-2-yl)-benzoic acid,
(2s)-2-{(2-Bromo-4-chloro-benzoyl)-[5-(3-trifluoromethyl-phenyl)-furan-2-ylmethyl]-amino}-3-phenyl-propionic acid,
(2s)-2-{(2,4-Dichloro-benzoyl)-[5-(3,5-difluoro-phenyl)-furan-2-ylmethyl]-amino}-3-phenyl-propionic acid,
(2s)-2-[(2,4-Dichloro-benzoyl)-(5-m-tolyl-furan-2-ylmethyl)-amino]-3-phenyl-propionic acid,
(2s)-2-{(2,4-Dichloro-benzoyl)-[5-(3-fluoro-phenyl)-furan-2-ylmethyl]-amino}-3-phenyl-propionic acid,
(2s)-2-[(5-Bromo-thiophen-2-ylmethyl)-(2,4-dichloro-benzoyl)-amino]-3-phenyl-propionic acid,
(2s)-4-(5-{[(1s-1-Carboxy-2-phenyl-ethyl)-(2,4-dichloro-benzoyl)-amino]-methyl}-thiophen-2-yl)-benzoic acid,
(2s)-4-(5-{[(1-Carboxy-2-phenyl-ethyl)-(2,4-dichloro-benzoyl)-amino]-methyl}-thiophen-2-yl)-benzoic acid methyl ester,
(2s)-2-[(5-Benzofuran-2-yl-thiophen-2-ylmethyl)-(2,4-dichloro-benzoyl)-amino]-3-phenyl-propionic acid,
2-[(2-Benzofuran-2-yl-thiazol-5-ylmethyl)-(2,4-dichloro-benzoyl)-amino]-3-phenyl-propionic acid,
(2s)-2-{(2,4-Dichloro-benzoyl)-[4-(3,4-dichloro-phenyl)-thiophen-2-ylmethyl]-amino}-3-phenyl-propionic acid,
(2s)-2-[[4-(4-Chloro-3-fluoro-phenyl)-thiophen-2-ylmethyl]-(2,4-dichloro-benzoyl)-amino]-3-phenyl-propionic acid,
(2s)-2-[[4-(3-Chloro-4-fluoro-phenyl)-thiophen-2-ylmethyl]-(2,4-dichloro-benzoyl)-amino]-3-phenyl-propionic acid,
(2s)-2-{(2,4-Dichloro-benzoyl)-[4-(2,4-dichloro-phenyl)-thiophen-2-ylmethyl]-amino}-3-phenyl-propionic acid,
(2s)-2-[[5-(3-Chloro-4-fluoro-phenyl)-thiophen-2-ylmethyl]-(2,4-dichloro-benzoyl)-amino]-3-phenyl-propionic acid,
(2s)-2-[[5-(4-chloro-3-fluoro-phenyl)-thiophen-2-ylmethyl]-(2,4-dichloro-benzoyl)-amino]-3-phenyl-propionic acid,
(2s)-2-{(2,4-Dichloro-benzoyl)-[5-(2,4-dichloro-phenyl)-thiophen-2-ylmethyl]-amino}-3-phenyl-propionic acid,
(2s)-2-[(2,4-Dichloro-benzoyl)-(5-thiazol-2-yl-thiophen-2-ylmethyl)-amino]-3-phenyl-propionic acid,
(2s)-2-{(2,4-Dichloro-benzoyl)-[5-(3,5-difluoro-phenyl)-thiophen-2-ylmethyl]-amino}-3-phenyl-propionic acid,
(2s)-2-{(2,4-Dichloro-benzoyl)-[5-(3-methoxy-phenyl)-thiophen-2-ylmethyl]-amino}-3-phenyl-propionic acid,
(2s)-2-{(2,4-Dichloro-benzoyl)-[5-(3-fluoro-phenyl)-thiophen-2-ylmethyl]-amino}-3-phenyl-propionic acid,
(2s)-2-[(2,4-Dichloro-benzoyl)-thiophen-2-ylmethyl-amino]-3-phenyl-propionic acid,
(2s)-2-[(4-Bromo-thiophen-2-ylmethyl)-(2,4-dichloro-benzoyl)-amino]-3-phenyl-propionic acid,
(2s)-2-{(2,4-Dichloro-benzoyl)-[2-(4-phenyl-piperazin-1-yl)-thiazol-5-ylmethyl]-amino}-3-phenyl-propionic acid,
(2s)-1-(5-{[(1s-1-Carboxy-2-phenyl-ethyl)-(2,4-dichloro-benzoyl)-amino]-methyl}-thiazol-2-yl)-piperidine-4-carboxylic acid,
(2s)-2-[[2-(4-Benzyl-piperazin-1-yl)-thiazol-5-ylmethyl]-(2,4-dichloro-benzoyl)-amino]-3-phenyl-propionic acid,
(2s)-2-[(2,4-Dichloro-benzoyl)-(2-piperidin-1-yl-thiazol-5-ylmethyl)-amino]-3-phenyl-propionic acid,
(2s)-2-[(2,4-Dichloro-benzoyl)-(2-diethylamino-thiazol-5-ylmethyl)-amino]-3-phenyl-propionic acid,
(2s)-2-[[2-(4-Chloro-benzoyl)-benzofuran-3-ylmethyl]-(4-methoxy-2,3,6-trimethyl-benzenesulfonyl)-amino]-3-phenyl-propionic acid,
(2s)-2-[[5-(2,4-Dichloro-phenoxy)-1-methyl-3-trifluoromethyl-1h-pyrazol-4-ylmethyl]-(4-methoxy-2,3,6-trimethyl-benzenesulfonyl)-amino]-3-phenyl-propionic acid,
(2s)-2-((2,4-Dichloro-benzoyl)-{2-[5-(2,4-dichloro-phenyl)-furan-2-yl]-2-oxo-ethyl}-amino)-3-phenyl-propionic acid,
(2s)-2-Benzyl-4-(2,4-dichloro-phenyl)-3-[3-(2,6-dichloro-phenyl)-5-methyl-isoxazol-4-ylmethyl]-4-oxo-butyric acid,
(2s)-2-[Allyl-(2,4-dichloro-benzoyl)-amino]-3-phenyl-propionic acid,
(2s)-2-[(2,4-Dichloro-benzoyl)-methyl-amino]-3-phenyl-propionic acid,
(2s)-2-[(2,4-Dichloro-benzoyl)-prop-2-ynyl-amino]-3-phenyl-propionic acid
(2s)-2-[(2,4-Dichloro-benzoyl)-propyl-amino]-3-phenyl-propionic acid,
(2s)-2-[(3-Benzofuran-2-yl-prop-2-ynyl)-(2,4-dichloro-benzoyl)-amino]-3-phenyl-propionic acid, (2s)-2-[(4-Benzofuran-2-yl-phenyl)-(2,4-dichloro-benzoyl)-amino]-3-phenyl-propionic acid,
(2s)-2-[(2,4-Dichloro-benzoyl)-(3-methyl-but-2-enyl)-amino]-3-phenyl-propionic acid,
2-[(2-Bromo-allyl)-(2,4-dichloro-benzoyl)-amino]-3-phenyl-propionic acid,
3-{[(1-Carboxy-2-phenyl-ethyl)-(2,4-dichloro-benzoyl)-amino]-methyl}-benzoic acid methyl ester,
3-[[5-(3-Chloro-4-fluoro-phenyl)-thiophen-2-ylmethyl]-(2,4-dichloro-benzoyl)-amino]-5-phenyl-thiophene-2-carboxylic acid,
2-[[5-(3-Cyano-phenyl)-furan-2-ylmethyl]-(2,4-dichloro-benzoyl)-amino]-3-phenyl-propionic acid,
(2s)-2-{(2,4-Dichloro-benzoyl)-[5-(2-trifluoromethyl-phenyl)-furan-2-ylmethyl]-amino}-3-phenyl-propionic acid,
(2s)-2-(5-{[(1s-1-Carboxy-2-phenyl-ethyl)-(2,4-dichloro-benzoyl)-amino]-methyl}-thiophen-2-yl)-benzoic acid ethyl ester,
3-(5-{[(1s-1-Carboxy-2-phenyl-ethyl)-(2,4-dichloro-benzoyl)-amino]-methyl}-thiophen-2-yl)-benzoic acid ethyl ester,
(2s)-2-[[5-(3-Chloro-phenyl)-furan-2-ylmethyl]-(2,4-dichloro-benzoyl)-amino]-3-phenyl-propionic acid,
(2s)-2-[(4-Chloro-2-iodo-benzoyl)-(3,5-dibromo-thiophen-2-ylmethyl)-amino]-3-phenyl-propionic acid,
(2s)-3-(5-{[(1-Carboxy-2-phenyl-ethyl)-(2,4-dichloro-benzoyl)-amino]-methyl}-thiophen-2-yl)-benzoic acid,
(2s)-2-[[5-(5-Chloro-thiophen-2-yl)-furan-2-ylmethyl]-(2,4-dichloro-benzoyl)-amino]-3-phenyl-propionic acid,
(2s)-2-[[2,2']Bithiophenyl-5-ylmethyl-(2,4-dichloro-benzoyl)-amino]-3-phenyl-propionic acid,
(2s)-2-[(5'-Chloro-[2,2']bithiophenyl-5-ylmethyl)-(2,4-dichloro-benzoyl)-amino]-3-phenyl-propionic acid,
(2s)-2-{(2,4-Dichloro-benzoyl)-[4-(3,5-difluoro-phenyl)-thiophen-2-ylmethyl]-amino}-3-phenyl-propionic acid,
(2s)-2-{(2,4-Dichloro-benzoyl)-[4-(3-fluoro-phenyl)-thiophen-2-ylmethyl]-amino}-3-phenyl-propionic acid,
(2s)-2-{(4-Chloro-2-iodo-benzoyl)-[5-(3-trifluoromethyl-phenyl)-furan-2-ylmethyl]-amino}-3-phenyl-propionic acid,
(2s)-2-{(4-Chloro-2-methyl-benzoyl)-[5-(3-trifluoromethyl-phenyl)-furan-2-ylmethyl]-amino}-3-phenyl-propionic acid,
(2s)-2-[(5-Chloro-[2,3']bithiophenyl-5'-ylmethyl)-(2,4-dichloro-benzoyl)-amino]-3-phenyl-propionic acid,
(2s)-2-{(2,4-Dichloro-benzoyl)-[5-(4-methoxy-phenyl)-furan-2-ylmethyl]-amino}-3-phenyl-propionic acid,
(2s)-2-{(2,4-Dichloro-benzoyl)-[5-(4-methoxy-phenyl)-thiophen-2-ylmethyl]-amino}-3-phenyl-propionic acid,
(2s)-2-{(2,4-Dichloro-benzoyl)-[4-(4-methoxy-phenyl)-thiophen-2-ylmethyl]-amino}-3-phenyl-propionic acid,
(2s)-2-[(2,4-Dichloro-benzoyl)-(5-pyridin-4-yl-furan-2-ylmethyl)-amino]-3-phenyl-propionic acid,
(2s)-2-[(2,4-Dichloro-benzoyl)-(5-pyridin-4-yl-thiophen-2-ylmethyl)-amino]-3-phenyl-propionic acid,
(2s)-2-[(2,4-Dichloro-benzoyl)-(4-pyridin-4-yl-thiophen-2-ylmethyl)-amino]-3-phenyl-propionic acid,
(2s)-2-[(2-Chloro-thiazol-5-ylmethyl)-(2,4-dichloro-benzoyl)-amino]-3-phenyl-propionic acid
(2s)-2-{(2,4-Dichloro-benzoyl)-[5-(4-fluoro-phenyl)-thiophen-2-ylmethyl]-amino}-3-phenyl-propionic acid,
(2s)-2-[(2,4-Dichloro-benzoyl)-(3,5-dichloro-benzyl)-amino]-3-phenyl-propionic acid,
(2s)-2-[(2,4-Dichloro-benzoyl)-thiophen-3-ylmethyl-amino]-3-phenyl-propionic acid,
(2s)-2-[(2,4-Dichloro-benzoyl)-(3-trifluoromethyl-benzyl)-amino]-3-phenyl-propionic acid,
(2s)-2-[[3-(3-Chloro-4-fluoro-phenyl)-thiophen-2-ylmethyl]-(2,4-dichloro-benzoyl)-amino]-3-phenyl-propionic acid,
(2s)-2-[(3-Bromo-thiophen-2-ylmethyl)-(2,4-dichloro-benzoyl)-amino]-3-phenyl-propionic acid,
(2s)-2-{(2,4-Dichloro-benzoyl)-[5-(3-trifluoromethyl-phenyl)-furan-2-ylmethyl]-amino}-2-methyl-propionic acid,
(2s)-2-{(2,4-Dichloro-benzoyl)-[2-(3-trifluoromethyl-phenyl)-thiazol-5-ylmethyl]-amino}-3-phenyl-propionic acid,
(2s)-2-[(2,4-Dichloro-benzoyl)-(5-nitro-thiophen-3-ylmethyl)-amino]-3-phenyl-propionic acid,
(2s)-2-[(2,4-Dichloro-benzoyl)-(4-methanesulfonyl-benzyl)-amino]-3-phenyl-propionic acid,
(2s)-2-[(2,4-Dichloro-benzoyl)-(3-methoxy-benzyl)-amino]-3-phenyl-propionic acid,
(2s)-2-[(2,4-Dichloro-benzoyl)-(3-methyl-benzyl)-amino]-3-phenyl-propionic acid,
(2s)-2-[[5-(3-Chloro-phenoxy)-1-methyl-3-trifluoromethyl-1h-pyrazol-4-ylmethyl]-(2,4-dichloro-benzoyl)-amino]-3-phenyl-propionic acid,
(2s)-2-{(2,4-Dichloro-benzoyl)-[3-(3,5-difluoro-phenyl)-thiophen-2-ylmethyl]-amino}-3-phenyl-propionic acid,
(2s)-2-{(2,4-Dichloro-benzoyl)-[3-(3,4-dichloro-phenyl)-thiophen-2-ylmethyl]-amino}-3-phenyl-propionic acid,
(2s)-2-[[3-(4-Chloro-3-fluoro-phenyl)-thiophen-2-ylmethyl]-(2,4-dichloro-benzoyl)-amino]-3-phenyl-propionic acid,
(2s)-2-{(2,4-Dichloro-benzoyl)-[3-(2,4-dichloro-phenyl)-thiophen-2-ylmethyl]-amino}-3-phenyl-propionic acid,
(2s)-2-[(2,4-Dichloro-benzoyl)-(3-m-tolyl-thiophen-2-ylmethyl)-amino]-3-phenyl-propionic acid,
(2s)-2-(2-{[(1s-1-Carboxy-2-phenyl-ethyl)-(2,4-dichloro-benzoyl)-amino]-methyl}-thiophen-3-yl)-benzoic acid ethyl ester,
(2s)-4-(2-{[(1s-1-Carboxy-2-phenyl-ethyl)-(2,4-dichloro-benzoyl)-amino]-methyl}-thiophen-3-yl)-benzoic acid ethyl ester,
(2s)-2-{(2,4-Dichloro-benzoyl)-[3-(3-fluoro-phenyl)-thiophen-2-ylmethyl]-amino}-3-phenyl-propionic acid,
(2s)-2-[[3-(3-Cyano-phenyl)-thiophen-2-ylmethyl]-(2,4-dichloro-benzoyl)-amino]-3-phenyl-propionic acid,
{(2,4-Dichloro-benzoyl)-[5-(3-trifluoromethyl-phenyl)-furan-2-ylmethyl]-amino}-thiophen-2-yl-acetic acid,
L-2-{[(1-Carboxy-2-phenyl-ethyl)-(2,4-dichloro-benzoyl)-amino]-methyl}-pyrrolidine-1-carboxylic acid #tert!-butyl ester,
d-2-{[(1-carboxy-2-phenyl-ethyl)-(2,4-dichloro-benzoyl)-amino]-methyl}-pyrrolidine-1-carboxylic acid #tert!-butyl ester,
4-[(1-Carboxy-2-phenyl-ethyl)-(2,4-dichloro-benzoyl)-amino]-piperidine-1-carboxylic acid benzyl ester,
1-2-[(2,4-Dichloro-benzoyl)-pyrrolidin-2-ylmethyl-amino]-3-phenyl-propionic acid,
d-2-[(2,4-Dichloro-benzoyl)-pyrrolidin-2-ylmethyl-amino]-3-phenyl-propionic acid,
3-(5-Bromo-thiophen-2-yl)-2-[(2,4-dichloro-benzoyl)-methyl-amino]-propionic acid,
2-[(2,4-Dichloro-benzoyl)-pyridin-3-ylmethyl-amino]-3-phenyl-propionic acid,
2-[(2,4-Dichloro-benzoyl)-(4-trifluoromethyl-benzyl)-amino]-3-phenyl-propionic acid,
2-{(2,4-Dichloro-benzoyl)-[4-(4-fluoro-benzyloxy)-benzyl]-amino}-3-phenyl-propionic acid,
2-[(2,4-Dichloro-benzoyl)-(4-fluoro-3-trifluoromethyl-benzyl)-amino]-3-phenyl-propionic acid, 2-[(1-Benzenesulfonyl-1h-pyrrol-2-ylmethyl)-(2,4-dichloro-benzoyl)-amino]-3-phenyl-propionic acid,
2-[[3-(4-Chloro-phenoxy)-benzyl-]-(2,4-dichloro-benzoyl)-amino]-3-phenyl-propionic acid,
2-[(5-Chloro-2-chloromethyl-hepta-2,4,6-trienoyl)-quinolin-3-ylmethyl-amino]-3-phenyl-propionic acid,
2-[(2-Benzyloxy-benzyl)-(2,4-dichloro-benzoyl)-amino]-3-phenyl-propionic acid,
2-{(2,4-Dichloro-benzoyl)-[3-(5-isopropyl-2-methoxy-phenyl)-thiophen-2-ylmethyl]-amino}-3-phenyl-propionic acid,
2-{(2,4-Dichloro-benzoyl)-[3-(4-trifluoromethoxy-phenyl)-thiophen-2-ylmethyl]-amino}-3-phenyl-propionic acid,
2-{(2,4-Dichloro-benzoyl)-[3-(3-trifluoromethyl-phenyl)-thiophen-2-ylmethyl]-amino}-3-phenyl-propionic acid,
2-[[3-(3,5-Bis-trifluoromethyl-phenyl)-thiophen-2-ylmethyl]-(2,4-dichloro-benzoyl)-amino]-3-phenyl-propionic acid,
2-[(2,4-Dichloro-benzoyl)-(3-pyridin-4-yl-thiophen-2-ylmethyl)-amino]-3-phenyl-propionic acid,
2-{(2,4-Dichloro-benzoyl)-[3-(4-methylsulfanyl-phenyl)-thiophen-2-ylmethyl]-amino}-3-phenyl-propionic acid,
2-{(2,4-Dichloro-benzoyl)-[3-(4-fluoro-phenyl)-thiophen-2-ylmethyl]-amino}-3-phenyl-propionic acid,
2-[(2,4-Dichloro-benzoyl)-(3-pyridin-3-yl-thiophen-2-ylmethyl)-amino]-3-phenyl-propionic acid,
2-{(2,4-Dichloro-benzoyl)-[1-(toluene-2-sulfonyl)-pyrrolidin-2-ylmethyl]-amino}-3-phenyl-propionic acid,
2-[(2-Bromo-benzyl)-(2,4-dichloro-benzoyl)-amino]-3-phenyl-propionic acid,
3-(2-Bromo-phenyl)-2-[(2,4-dichloro-benzoyl)-methyl-amino]-propionic acid,
3-(4-Bromo-phenyl)-2-[(2,4-dichloro-benzoyl)-methyl-amino]-propionic acid,
2-[(3-Bromo-phenyl)-(2,4-dichloro-benzoyl)-amino]-3-phenyl-propionic acid,
2-[(4-Bromo-phenyl)-(2,4-dichloro-benzoyl)-amino]-3-phenyl-propionic acid,
2-[[4-(3-Chloro-4-fluoro-phenyl)-thiophen-2-ylmethyl]-(2,4-dimethyl-benzoyl)-amino]-3-phenyl-propionic acid,
3-{[(1-Carboxy-2-phenyl-ethyl)-(2,4-dichloro-benzoyl)-amino]-methyl}-benzoic acid,
2-[(3-Amino-benzyl)-(2,4-dichloro-benzoyl)-amino]-3-phenyl-propionic acid,
3-Phenyl-2-{(2-trifluoromethyl-benzoyl)-[5-(2-trifluoromethyl-phenyl)-furan-2-ylmethyl]-amino}-propionic acid,
2-{(3-Cyano-benzoyl)-[5-(2-trifluoromethyl-phenyl)-furan-2-ylmethyl]-amino}-3-phenyl-propionic acid,
2-{(4-Nitro-benzoyl)-[5-(2-trifluoromethyl-phenyl)-furan-2-ylmethyl]-amino}-3-phenyl-propionic acid,
2-{(2-Fluoro-benzoyl)-[5-(2-trifluoromethyl-phenyl)-furan-2-ylmethyl]-amino}-3-phenyl-propionic acid,
2-[Benzyl-(2,4-dichloro-benzoyl)-amino]-3-phenyl-propionic acid,
2-{(2,4-Dichloro-benzoyl)-[3-(2H-tetrazol-5-yl)-benzyl]-amino}-3-phenyl-propionic acid,
2-[(2,4-Dichloro-benzoyl)-(2-nitro-benzyl)-amino]-3-phenyl-propionic acid,
2-[(2,4-Dichloro-benzoyl)-(4-nitro-benzyl)-amino]-3-phenyl-propionic acid,
2-[(2-Cyano-benzyl)-(2,4-dichloro-benzoyl)-amino]-3-phenyl-propionic acid,
2-[(4-Cyano-benzyl)-(2,4-dichloro-benzoyl)-amino]-3-phenyl-propionic acid,
2-[[1-(3-Cyano-phenyl)-ethyl]-(2,4-dichloro-benzoyl)-amino]-3-phenyl-propionic acid,
3-{[(1-Carboxy-2-phenyl-ethyl)-(2,4-dichloro-benzoyl)-amino]-methyl}-benzoic acid methyl,
3-{[(1-Carboxy-2-phenyl-ethyl)-(2,4-dichloro-benzoyl)-amino]-methyl}-benzoic acid,
2-[(2,4-Dichloro-benzoyl)-(3-methanesulfonyl-benzyl)-amino]-3-phenyl-propionic acid,
2-[(3-Acetyl-benzyl)-(2,4-dichloro-benzoyl)-amino]-3-phenyl-propionic acid,
2-[(2,4-Dichloro-benzoyl)-(1-oxy-pyridin-3-ylmethyl)-amino]-3-phenyl-propionic acid,
2-{(2,4-Dichloro-benzoyl)-[5-(3-trifluoromethyl-phenyl)-thiophen-2-ylmethyl]-amino}-3-phenyl-propionic acid, and pharmaceutically acceptable salts thereof.

34. A method according to claim 32, further comprising administering at least one further antiviral agent.

35. A method according to claim 33, further comprising administering at least one further antiviral agent.

36. A method according to claim 34, wherein the antiviral agent is chosen from a viral serine protease inhibitor, viral polymerase inhibitor and viral helicase inhibitor.

37. A method according to claim 34, wherein the antiviral agent is chosen from interferon α and ribavirin.

38. A method according to claim 34, wherein said compound and said antiviral agent are administered sequentially.

39. A method according to claim 34, wherein said compound and said antiviral agent are administered simultaneously.

40. A method of claim 32, further comprising at least one additional agent chosen from immunomudulating agent, antioxydant agent, antibacterial agent or antisense agent.

41. A method of claim 40, wherein said additional agent is chosen from silybum marianum, interleukine-12, amantadine, ribozyme, thymosin, N-acetyl cysteine or cyclosporin.

42. A method according to claim 40, wherein said compound and said additional agent are administered sequentially.

43. A method according to claim 40, wherein said compound and said additional agent are administered simultaneously.

44. A method as defined in claim 32, wherein said Flaviridae infection is hepatitis C.

45. A method for inhibiting or reducing the activity of viral polymerase in a host comprising administering a therapeutically effective amount of a compound having the formula (I):

(I)

$$\begin{array}{c} R_1 \quad R_2 \\ R_3 \diagdown M \diagdown N \diagup A^1 \diagdown A \\ | \\ Y \\ | \\ Z \\ | \\ R_4 \end{array}$$

or a pharmaceutically acceptable salt thereof,
wherein,

M is

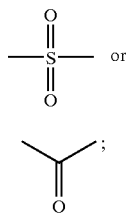

$A^1$ is a bond;
A is COOH;
$R_1$ is benzyl, thiophene, $CH_2$-thiophene, $CH_2$-imidazole, $CH_2$-cyclohexyl which in each case is unsubstituted or substituted by at least one substituent chosen from halogen, OH or benzyl;
$R_2$ is H or methyl;
$R_3$ is $C_{6-12}$ aryl or $C_{3-10}$ heterocycle;
Y is —$CH_2$—;
Z is $C_{1-6}$ alkyl, $C_{2-6}$ alkenyl, $C_{2-6}$ alkynyl, $C_{6-14}$ aryl, or $C_{3-10}$ heterocycle;
$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, $COR_7$,
$R_5$ is in each case independently H or $C_{1-6}$ alkyl, and
$R_7$ is $C_{6-12}$ aryl or $C_{3-10}$ heterocycle.

46. A method as defined in claim 45, further comprising one or more viral polymerase inhibitors.
47. A method as defined in claim 45, wherein said viral polymerase is a Flaviridae viral polymerase.
48. A method as defined in claim 45, wherein said viral polymerase is a RNA-dependant RNA-polymerase.
49. A method as defined in claim 45, wherein said viral polymerase is HCV polymerase.
50. A method for inhibiting or reducing the activity of viral helicase in a host comprising administering a therapeutically effective amount of a compound having the formula (I):

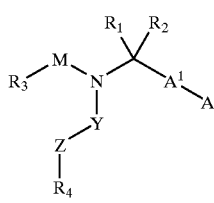

or a pharmaceutically acceptable salt thereof,
wherein,
M is

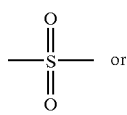

$A^1$ is a bond;
A is COOH;
$R_1$ is benzyl, thiophene, $CH_2$-thiophene, methyl, $CH_2$-imidazole, or $C_2$-cyclohexyl which in each case is unsubstituted or substituted by at least one substituent chosen from halogen, OH or benzyl;
$R_2$ is H or methyl;
$R_3$ is $C_{6-2}$ aryl or $C_{3-10}$ heterocycle;
Y is —$CR_2$—;
Z is $C_{1-6}$ alkyl, $C_{2-6}$ alkenyl, $C_{2-6}$ alkynyl, $C_{6-14}$ aryl, or $C_{3-10}$ heterocycle;
$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$,
$R_5$ is in each case independently H or $C_{1-6}$ alkyl, and
$R_7$ is $C_{6-12}$ aryl or $C_{3-10}$ heterocycle.

51. A method as defined in claim 50, wherein said viral helicase is a flaviviridea helicase.
52. A method as defined in claim 50, wherein said viral helicase is a HCV helicase.
53. A method according to claim 32, wherein $R_2$ is H.
54. A method for treating a Flaviridae viral infection in a host, wherein the Flavivirus viral infection is hepatitis C virus (HCV), bovine viral diarrhea virus (BVDV), hog cholera virus or yellow fever virus, comprising administering to the host a therapeutically effective amount of at least one compound of formula (I);

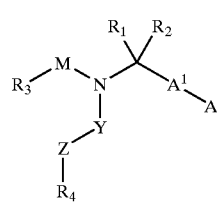

or a pharmaceutically acceptable salt thereof,
wherein,
M is

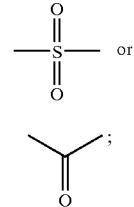

$A^1$ is a bond;
A is COOH;
$R_1$ is benzyl, thiophene, $CH_2$-thiophene, methyl, $CH_2$-imidazole, $CH_2$-cyclohexyl which is unsubstituted or substituted by at least one substituent chosen from halogen, OH or benzyl;

$R_2$ is H or methyl;

$R_3$ is phenyl, pyridinyl, thiophenyl, benzofuran, thiazole, or pyrazole, which in each case is unsubstituted or substituted with at least one substituent chosen from halogen, $C_{1-6}$ alkyl, $C_{2-6}$ alkenyl, $OC_{1-6}$ alkyl, $CF_3$, COOH, OH, $COOC_{1-6}$ alkyl, CN, $NH_2$, $NO_2$, $NH(C_{1-6}$ alkyl), $N(C_{1-6}$ alkyl)$_2$;

Y is —$CH_2$—;

Z is $C_{1-6}$ alkyl, $C_{2-6}$ alkenyl, $C_{2-6}$ alkynyl, $C_{6-14}$ aryl, or $C_{3-10}$ heterocycle;

$R_4$ is H, halogen CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$;

$R_5$ is in each case independently H or $C_{1-6}$ alkyl; and $R_7$ is $C_{6-12}$ aryl or $C_{3-10}$ heterocycle.

55. A method according to claim 54, wherein $R_3$ is 2,4-dichlorophenyl, 4-methoxy-2,3,6-trimethylphenyl, 2-chlorophenyl, 4-chlorophenyl, 3,4-dichlorophenyl, 4-chloro-2-iodo-phenyl, 2,4-dimethylphenyl, 4-chloro-2-methylphenyl, 4-chloro-2-bromo-phenyl, 4-chloro-2-ethylphenyl or 4-chloro-2-vinyl-phenyl.

56. A method according to claim 54, wherein $R_3$ is 2,4-dichlorophenyl.

57. A method for treating a Flaviridae viral infection in a host, wherein the Flavivirus viral infection is hepatitis C virus (HCV), bovine viral diarrhea virus (BVDV), hog cholera virus or yellow fever virus, comprising administering to the host a therapeutically effective amount of at least one compound of formula (I):

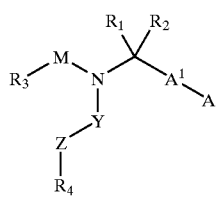

(I)

or a pharmaceutically acceptable salt thereof, wherein,

M is

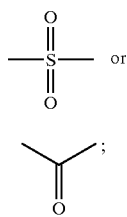

(II)

(III)

$A^1$ is a bond;

A is COOH;

$R_1$ is benzyl, thiophene, $CH_2$-thiophene, methyl, $CH_2$-imidazole, $CH_2$-cyclohexyl which is unsubstituted or substituted by at least one substituent chosen from halogen, OH or benzyl;

$R_2$ is H or methyl;

$R_3$ is a $C_{6-12}$ aryl or $C_{3-10}$ heterocycle;

Y is —$CH_2$—;

Z is phenyl unsubstituted or substituted by at least one substituent chosen from halogen, $C_{3-10}$ heterocycle, $C_{3-10}$ heterocycle-$COOCH_3$, $NO_2$, CN, CO—$C_{6-12}$ aralkyl, $COOC_{1-6}$ alkyl, $C_{1-6}$ alkyl, O—$C_{1-6}$ alkyl, $C_{6-12}$ aryl, O—$C_{6-12}$ aryl, $C_{6-12}$ aralkyl, and O—$C_{6-12}$ aralkyl;

$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$;

$R_5$ is in each case independently H or $C_{1-6}$ alkyl; and $R_7$ is $C_{6-12}$ aryl or $C_{3-10}$ heterocycle.

58. A method for treating a Flaviridae viral infection in a host, wherein the Flavivirus viral infection is from hepatitis C virus (HCV), bovine viral diarrhea virus (BVDV), hog cholera virus or yellow fever virus, comprising administering to the host a therapeutically effective amount of at least one compound of formula (I):

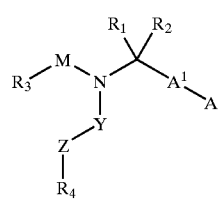

(I)

or a pharmaceutically acceptable salt thereof, wherein,

M is

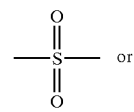

(II)

(III)

$A^1$ is a bond;

A is COOH;

$R_1$ is benzyl, thiophene, $CH_2$-thiophene, methyl, $CH_2$-imidazole, $CH_2$-cyclohexyl which is unsubstituted or substituted by at least one substituent chosen from halogen, OH or benzyl;

$R_2$ is H or methyl;

$R_3$ is a $C_{6-12}$ aryl or $C_{3-10}$ heterocycle;

Y is —$CH_2$—;

Z is furan unsubstituted or substituted by at least one substituent chosen from halogen, $C_{6-12}$ aryl, or $C_{3-10}$ heterocycle; thiophene unsubstituted or substituted by at least one substituent chosen from halogen, $C_{6-12}$ aryl, $C_{3-10}$ heterocycle, or nitro; or thiazole unsubstituted or substituted by at least one substituent chosen from halogen, $C_{1-6}$ alkyl, $NR_5R_5$, or $C_{3-10}$ heterocycle;

$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$;

$R_5$ is in each case independently H or $C_{1-6}$ alkyl; and $R_7$ is $C_{6-12}$ aryl or $C_{3-10}$ heterocycle.

59. A method for treating a Flaviridae viral infection in a host, wherein the Flavivirus viral infection is from hepatitis C virus (HCV), bovine viral diarrhea virus (BVDV), hog cholera virus or yellow fever virus, comprising administering to the host a therapeutically effective amount of at least one compound of formula (I):

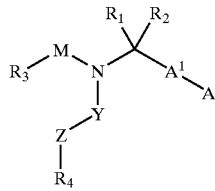

or a pharmaceutically acceptable salt thereof,
wherein,
M is

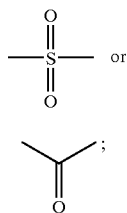

A¹ is a bond;
A is COOH;
R₁ is benzyl, thiophene, CH₂-thiophene, methyl, CH₂-imidazole, CH₂-cyclohexyl which is unsubstituted or substituted by at least one substituent chosen from halogen, OH or benzyl;
R₂ is H or methyl;
R₃ is a $C_{6-12}$ aryl or $C_{3-10}$ heterocycle;
Y is —CH₂—;
Z is vinyl, allyl, methyl, propyl, propynyl, or thiazole unsubstituted or substituted by at least one benzofuran;
R₄ is H, halogen, CN, NO₂, $C_{1-6}$ alkyl, $C_{6-12}$ aryl, $C_{3-10}$ heterocycle, $C_{6-12}$ aralkyl, $C_{3-10}$ heteroaralkyl, NR₅R₅, SO₂CH₃, O—$C_{1-6}$ alkyl, O—$C_{6-12}$ aryl, O—$C_{6-12}$ aralkyl, or COR₇;
R₅ is in each case independently H or $C_{1-6}$ alkyl; and
R₇ is $C_{6-12}$ aryl or $C_{3-10}$ heterocycle.

60. A method for treating a Flaviridae viral infection in a host, wherein the Flavivirus viral infection is from hepatitis C virus (HCV), bovine viral diarrhea virus (BVDV), hog cholera virus or yellow fever virus, comprising administering to the host a therapeutically effective amount of at least one compound of formula (I);

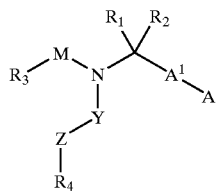

or a pharmaceutically acceptable salt thereof,
wherein,
M is

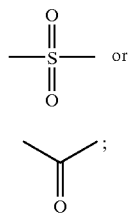

A¹ is a bond;
A is COOH;
R₁ is benzyl, thiophene, CH₂-thiophene, methyl, CH₂-imidazole, CH₂-cyclohexyl which is unsubstituted or substituted by at least one substituent chosen from halogen, OH or benzyl;
R₂ is H or methyl;
R₃ is a $C_{6-12}$ aryl or $C_{3-10}$ heterocycle;
Y is —CH₂—;
Z is benzofuran, pyrazole, methyl oxazole, pyrrolidine, piperidine, pyridine, pyrrole, or quinolinyl, which in each case is unsubstituted or substituted by at least one substituent chosen from chlorophenyl-ketone, dichlorophenoxy, chlorophenoxy, dichlorophenyl, COO-t-butyl, tolyl-sulfonyl, COO-benzyl and CF₃;
R₄ is H, halogen, CN, NO₂, $C_{1-6}$ alkyl, $C_{6-12}$ aryl, $C_{3-10}$ heterocycle, $C_{6-12}$ aralkyl, $C_{3-10}$ heteroaralkyl, NR₅R₅, SO₂CH₃, O—$C_{1-6}$ alkyl, O—$C_{6-12}$ aryl, O—$C_{6-12}$ aralkyl, or COR₇;
R₅ is in each case independently H or $C_{1-6}$ alkyl; and
R₇ is $C_{6-12}$ aryl or $C_{3-10}$ heterocycle.

61. A method according to claim 32, wherein M is:

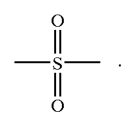

62. A method according to claim 32, wherein M is:

63. A method according to claim 35, wherein the antiviral agent is chosen from a viral serine protease inhibitor, viral polymerase inhibitor and viral helicase inhibitor.

64. A method according to claim 35, wherein the antiviral agent is chosen from interferon α and ribavirin.

65. A method according to claim 35, wherein said compound and said antiviral agent are administered sequentially.

66. A method according to claim 35, wherein said compound and said antiviral agent are administered simultaneously.

67. A method of claim 33, further comprising at least one additional agent chosen from immunomudulating agents, antioxydant agents, antibacterial agents and antisense agents.

68. A method of claim 67, wherein said additional agent is chosen from silybum marianum, interleukine-12, amantadine, ribozyme, thymosin, N-acetyl cysteine and cyclosporin.

69. A method according to claim 67, wherein said compound and said additional agent are administered sequentially.

70. A method according to claim 67, wherein said compound and said additional agent are administered simultaneously.

71. A method as defined in claim 33, wherein said Flaviridae infection is hepatitis C.

72. A method for treating a Flaviridae viral infection in a host, wherein the Flavivirus viral infection is from hepatitis C virus, bovine viral diarrhea virus, hog cholera virus or yellow fever virus, comprising administering to the host a therapeutically effective amount of at least one compound of formula (I):

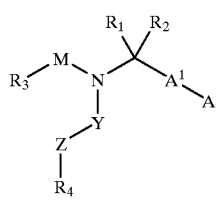

(I)

or a pharmaceutically acceptable salt thereof,
wherein,
M is

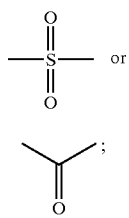

(II)

or (III)

$A^1$ is a bond;

A is COOH;

$R_1$ is benzyl, thiophene, $CH_2$-thiophene, methyl, $CH_2$-imidazole, or $CH_2$-cyclohexyl which is unsubstituted or substituted by at least one substituent chosen from halogen, OH or benzyl;

$R_2$ is H or methyl;

$R_3$ is chosen from:

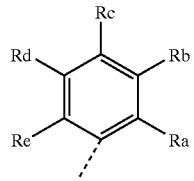
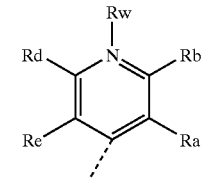
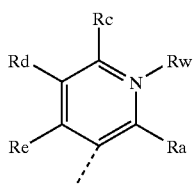
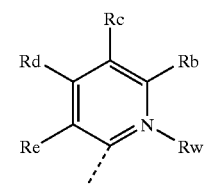

-continued

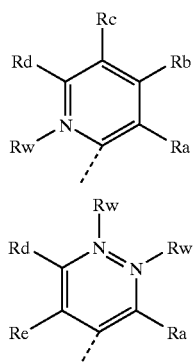
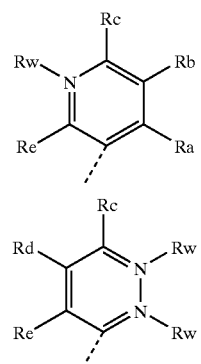
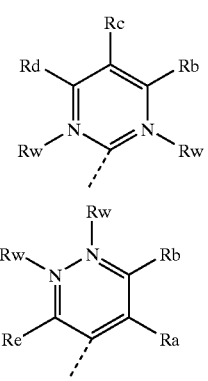
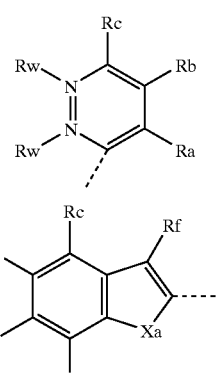
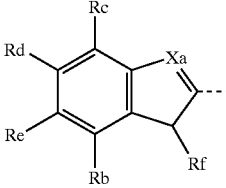
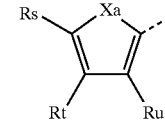
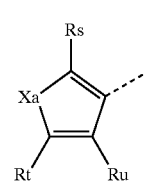
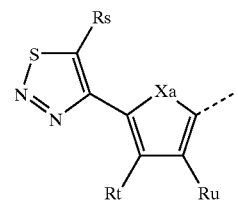
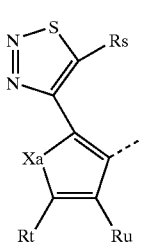
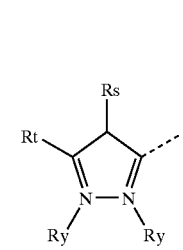
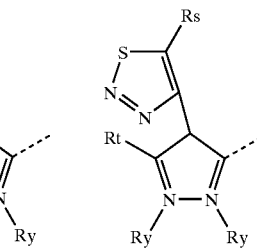
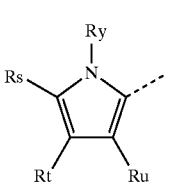
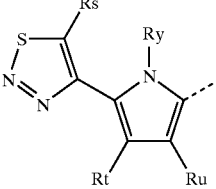

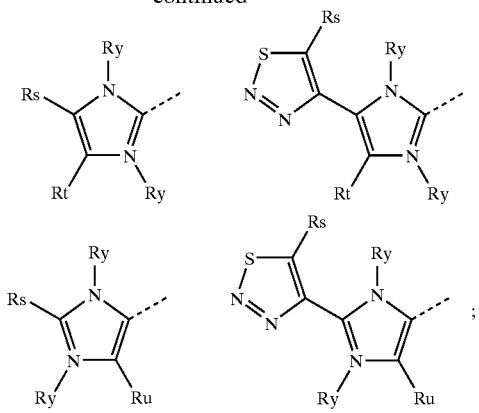

Rw is H or methyl;
Ry is H or methyl;
Rs, Rt, Ru, are each, independently, H, Cl, Br, I, F, $C_{1-6}$ alkyl, $OC_{1-6}$ $CF_3$, COOH, $COOC_{1-6}$ alkyl, CN, $NH_2$, $NO_2$, $NH(C_{1-6}$ alkyl), $N(C_{1-6}$ alkyl$)_2$;
Xa is S, N,O or C;
Ra, Rb, Rc, Rd, Re, and Rf are each independently chosen from, H, Cl, Br, I, F, C1–6 alkyl, alkyl, $C_{2-6}$ alkenyl, $OC_{1-6}$ alkyl, $CF_3$, COOH, OH, $COOC_{1-6}$ alkyl, CN, $NH_2$, $NO_2$, $NH(C_{1-6}$ alkyl), and $N(C_{1-6}$ alkyl$)_2$;
Y is —$CH_2$—;
Z is $C_{1-6}$ alkyl, $C_{2-6}$ alkenyl, $C_{2-6}$ alkynyl, $C_{6-14}$ aryl, or $C_{3-10}$ heterocycle;
$R_4$ is H, halogen, CN, $NO_2$, $C_{1-6}$ alkyl, $C_{6-12}$ aryl, $C_{3-10}$ heterocycle, $C_{6-12}$ aralkyl, $C_{3-10}$ heteroaralkyl, $NR_5R_5$, $SO_2CH_3$, O—$C_{1-6}$ alkyl, O—$C_{6-12}$ aryl, O—$C_{6-12}$ aralkyl, or $COR_7$;
$R_5$ is in each case independently H or $C_{1-6}$ alkyl; and
$R_7$ is $C_{6-12}$ aryl or $C_{3-10}$ heterocycle.

73. A method according to claim 32, wherein said Flavivirus viral infection is from bovine viral diarrhea virus.
74. A method according to claim 32, wherein said Flavivirus viral infection is from hog cholera virus.
75. A method according to claim 32, wherein said Flavivirus viral infection is from yellow fever virus.
76. A method according to claim 32, wherein said Flavivirus viral infection is from hepatitis C virus, hog cholera virus or yellow fever virus.
77. A method according to claim 74, wherein said compound is administered in an amount of 0.1 to 750 mg/kg of body weight per day.
78. A method according to claim 75, wherein said compound is administered in an amount of 0.1 to 750 mg/kg of body weight per day.
79. A method according to claim 76, wherein said compound is administered in an amount of 0.1 to 750 mg/kg of body weight per day.
80. A method according to claim 44, wherein said compound is administered in an amount of 0.1 to 750 mg/kg of body weight per day.
81. A method according to claim 33, wherein said Flavivirus viral infection is from bovine viral diarrhea virus.
82. A method according to claim 33, wherein said Flavivirus viral infection is from hog cholera virus.
83. A method according to claim 33, wherein said Flavivirus viral infection is from yellow fever virus.
84. A method according to claim 33, wherein said Flavivirus viral infection is from hepatitis C virus, hog cholera virus or yellow fever virus.
85. A method according to claim 82, wherein said compound is administered in an amount of 0.1 to 750 mg/kg of body weight per day.
86. A method according to claim 83, wherein said compound is administered in an amount of 0.1 to 750 mg/kg of body weight per day.
87. A method according to claim 84, wherein said compound is administered in an amount of 0.1 to 750 mg/kg of body weight per day.
88. A method according to claim 71, wherein said compound is administered in an amount of 0.1 to 750 mg/kg of body weight per day.
89. A method according to claim 72, wherein Ra, Rb, Rc, Rd, Re, and Rf are each, independently, H, Cl, Br, I, F, methyl, O-methyl, $CF_3$, COOH, $COOCH_3$, OH, CN, $NH_2$, or $NO_2$.
90. A method according to claim 72, wherein Ra, Rb, Rc, Rd, Re, and Rf are each, independently, H, Cl, methyl, O-methyl, $CF_3$, COOH, $COOCH_3$, CN, $NH_2$, or $NO_2$.
91. A method according to claim 72, wherein Ra, Rb, Rc, Rd, Re, and Rf are each, independently, H, Cl, F, methyl, OH, $CF_3$ or O-methyl.
92. A method according to claim 72, wherein Rf is H or methyl, and Ra, Rb, Rc, Rd and Re are each, independently, H or Cl.
93. A method according to claim 72, wherein Rs, Rt, an Ru are each, independently, H, Cl, Br, I, F, methyl, O-methyl, $CF_3$, COOH, $COOCH_3$, CN, $NH_2$, $NO_2$, $NH(CH_3)$ or $N(CH_3)_2$.
94. A method according to claim 72, wherein Rs, Rt, an Ru are each, independently, H, Cl, Br, I, F, methyl, O-methyl, $CF_3$, COOH, $COOCH_3$, CN, $NH_2$, or $NO_2$.
95. A method according to claim 72, wherein Rs, Rt, and Ru are each, independently, H, Cl, methyl, O-methyl, $CF_3$, COOH, $COOCH_3$, CN, $NH_2$, or $NO_2$.
96. A method according to claim 72, wherein Rs, Rt, and Ru are each, independently, H, Cl, F, methyl, $CF_3$ or O-methyl.

* * * * *